US008309718B2

(12) United States Patent
Li et al.

(10) Patent No.: US 8,309,718 B2
(45) Date of Patent: Nov. 13, 2012

(54) 4-PYRAZOLYL-N-ARYLPYRIMIDIN-2-AMINES AND 4-PYRAZOLYL-N-HETEROARYLPYRIMIDIN-2-AMINES AS JANUS KINASE INHIBITORS

(75) Inventors: Yun-Long Li, Chadds Ford, PA (US); Wenqing Yao, Kennett Square, PA (US); James D. Rodgers, Landenberg, PA (US)

(73) Assignee: Incyte Corporation, Wilmington, DE (US)

( * ) Notice: Subject to any disclaimer, the term of this patent is extended or adjusted under 35 U.S.C. 154(b) by 682 days.

(21) Appl. No.: 12/270,135

(22) Filed: Nov. 13, 2008

(65) Prior Publication Data

US 2009/0318405 A1  Dec. 24, 2009

Related U.S. Application Data

(60) Provisional application No. 60/988,606, filed on Nov. 16, 2007.

(51) Int. Cl.
*C07D 473/00* (2006.01)
(52) U.S. Cl. ...................... 544/295; 514/275
(58) Field of Classification Search ................ 544/122, 544/295, 296, 331
See application file for complete search history.

(56) References Cited

U.S. PATENT DOCUMENTS

| 5,521,184 | A | 5/1996 | Zimmermann |
| 7,820,821 | B2 * | 10/2010 | Mjalli et al. ................ 544/370 |
| 7,834,022 | B2 | 11/2010 | Rodgers et al. |
| 2002/0111353 | A1 * | 8/2002 | Ledeboer et al. .......... 514/235.8 |
| 2003/0144309 | A1 | 7/2003 | Choon-Moon |
| 2004/0198737 | A1 | 10/2004 | Cox et al. |
| 2006/0106020 | A1 | 5/2006 | Rodgers et al. |
| 2006/0106027 | A1 * | 5/2006 | Furet et al. ............... 514/252.19 |
| 2006/0135537 | A1 * | 6/2006 | Knegtel et al. ............ 514/259.3 |
| 2006/0183906 | A1 | 8/2006 | Rodgers et al. |
| 2007/0135461 | A1 | 6/2007 | Rodgers et al. |
| 2007/0149506 | A1 | 6/2007 | Arvanitis et al. |
| 2008/0188500 | A1 | 8/2008 | Arvanitis et al. |
| 2008/0312259 | A1 | 12/2008 | Rodgers et al. |
| 2009/0233903 | A1 | 9/2009 | Rodgers et al. |
| 2010/0113416 | A1 | 5/2010 | Friedman et al. |
| 2010/0190981 | A1 | 7/2010 | Zhou et al. |
| 2010/0298334 | A1 | 11/2010 | Rodgers et al. |
| 2010/0298355 | A1 | 11/2010 | Li et al. |

FOREIGN PATENT DOCUMENTS

| WO | WO 99/62908 | 12/1999 |
| WO | WO 99/65909 | 12/1999 |
| WO | WO 00/09495 | 2/2000 |
| WO | WO 00/53595 | 9/2000 |
| WO | WO 01/14402 | 3/2001 |
| WO | WO 01/42246 | 6/2001 |
| WO | WO 01/64655 | 9/2001 |
| WO | WO 02/00196 | 1/2002 |
| WO | WO 02/46184 | 6/2002 |
| WO | WO 02/092573 | 11/2002 |
| WO | WO 02092573 A2 * | 11/2002 |
| WO | WO 03/024967 | 3/2003 |
| WO | WO 03/037347 | 5/2003 |
| WO | WO 03/099771 | 12/2003 |
| WO | WO 2004/005281 | 1/2004 |
| WO | WO 2004/005282 | 1/2004 |
| WO | WO 2004/046120 | 6/2004 |
| WO | WO 2004/056786 | 7/2004 |
| WO | WO 2004/072063 | 8/2004 |
| WO | WO 2004/080980 | 9/2004 |
| WO | WO 2004/099204 | 11/2004 |
| WO | WO 2004/099205 | 11/2004 |
| WO | WO 2005/028444 | 3/2005 |
| WO | WO 2005/049033 A1 | 6/2005 |
| WO | WO 2007/049041 A1 | 5/2007 |
| WO | WO2007/105058 | 9/2007 |
| WO | WO 2007/129195 | 11/2007 |
| WO | WO 2007129195 A2 * | 11/2007 |

OTHER PUBLICATIONS

C. Pillonel, Pest Management Science, 61(11), 1069-1076 (2005).*
Pillonel, C., "Evaluation of phenylaminopyrimidines as antifungal protein kinase Inhibitors", *Pest Management Science*, Wiley & Sons, Bognor Regis, GB, vol. 61, pp. 1069-1076, 2005, XP002429106.
European Examiner Sahagun Krause, International Search Report and Written Opinion for Application PCT/US2008/083319, dated Mar. 5, 2009, 11 pages.
Adv Pharmacol. 2000;47:113-74.
Agents Actions. Jan. 1993;38(1-2):116-21.
Blume-Jensen P et al, Nature 2001, 411(6835):355-365.
Bolen JB. Nonreceptor tyrosine protein kinases. Oncogene. 1993, 8(8):2025-31.
Boudny, V., and Kovarik, J., Neoplasm. 49:349-355, 2002.
Bowman, T., et al. Oncogene 19:2474-2488, 2000.
Burger, R., et al. Hematol J. 2:42-53, 2001.
Candotti, F., L. Notarangelo, et al. (2002). "Molecular aspects of primary immunodeficiencies: lessons from cytokine and other signaling pathways." J Clin Invest 109(10): 1261-9.
Candotti, F., S. A. Oakes, et al. (1997). "Structural and functional basis for JAK3-deficient severe combined immunodeficiency." Blood 90(10): 3996-4003.
Cetkovic-Cvrlje, M., A. L. Dragt, et al. (2003). "Targeting JAK3 with JANEX-1 for prevention of autoimmune type 1 diabetes in NOD mice." Clin Immunol 106(3): 213-25.
Chalandon, Yves, and Schwaller, Jürg, "Targeting mutated protein tyrosine kinases and their signaling pathways in hematologic malignancies." Hematologica, 90:949-968, 2005.
Chen et al., (2007). British Journal of Cancer 96: 591-599).
Current Protocols in Immunology, vol. 3., Coligan, J.E. et al, Wiley Press*, (2005).

(Continued)

*Primary Examiner* — James O. Wilson
*Assistant Examiner* — Alexander R Pagano
(74) *Attorney, Agent, or Firm* — Fish & Richardson P.C.

(57) ABSTRACT

The present invention provides substituted bicyclic heteroaryl compounds, including, for example, 4-pyrazolyl-N-arylpyrimidin-2-amines and 4-pyrazolyl-N-heteroarylpyrimidin-2-amines that modulate the activity of kinases and are useful in the treatment of diseases related to activity of kinases including, for example, immune-related diseases, skin disorders, myeloid proliferative disorders, cancer, and other diseases.

35 Claims, No Drawings

OTHER PUBLICATIONS

Daniels et al., "Imatinib mesylate inhibits the profibrogenic activity of TGF-β and prevents bleomycinmediated lung fibrosis." J. Clin. Invest., 114(9):1308-1316, Nov. 2004.

De Vos, J., M. Jourdan, et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells." Br J Haematol 109(4): 823-8.

Dudley, A.C. et al. Biochem. J. 2005, 390(Pt 2):427-36.

Gorre, M.E. et al., "Clinical Resistance to STI-571 Cancer Therapy Caused by BCR-ABL Gene Mutation or Amplification." Science, 293:876, 2001.

Gottlieb, A.B., et al, Nat Rev Drug Disc., 4:19-34, 2008.

Immunol Today. Jan. 1998;19(1):37-44.

James, C., et al. Nature 434:1144-1148, 2005.

Journal of Pharmaceutical Science, 66, 2 (1977).

Kruh et al., "The complete coding sequence of arg defines the Abelson subfamily of cytoplasmic tyrosine kinases." Proc. Natl. Acad. Sci., 87:5802-5806, Aug. 1990.

Levine, et al., Cancer Cell, vol. 7, 2005: 387-397.

Manning, G. et al., Science. 2002, 298(5600):1912-1934.

Methods in Molecular Biology: vol. 225, Inflammation Protocols., Winyard, P.G. and Willoughby, D.A., Humana Press, 2003*.

Nakagawara, Akira, "Trk receptor tyrosine kinases: A bridge between cancer and neural development." Cancer Letters, 169:107-114, 2001.

Neubauer, H., A. Cumano, et al. (1998). Cell 93(3): 397-409.

Ortmann, R. A., T. Cheng, et al. (2000). "Janus kinases and signal transducers and activators of transcription: their roles in cytokine signaling, development and immunoregulation." Arthritis Res 2(1): 16-32.

Parganas, E., D. Wang, et al. (1998). Cell 93(3): 385-95.

Palmer, Amparo, and Klein, Rudiger, "Multiple roles of ephrins in morphogenesis, neuronal networking, and brain function." *Genes & Dev.*, 17:1429-1450, 2003.

Pernis, A. B. and P. B. Rothman (2002). "JAK-STAT signaling in asthma." J Clin Invest 109(10): 1279-83.

Peters, K.G.et al., "Functional Significance of Tie2 Signaling in the Adult Vasculature", 2004, © The Endocrine Society.

Remington's Pharmaceutical Sciences, 17th ed., Mack Publishing Company, Easton, Pa., 1985, p. 1418.

Rodig, S. J., M. A. Meraz, et al. (1998). "Disruption of the Jak1 gene demonstrates obligatory and nonredundant roles of the Jaks in cytokine-induced biologic responses." Cell 93(3): 373-83.

Saemann, M. D., C. Diakos, et al. (2003). "Prevention of CD40-triggered dendritic cell maturation and induction of T-cell hyporeactivity by targeting of Janus kinase 3." Am J Transplant 3(11): 1341-9.

Scott, M. J., C. J. Godshall, et al. (2002). "Jaks, STATs, Cytokines, and Sepsis." Clin Diagn Lab Immunol 9(6): 1153-9.

Seto, Y., H. Nakajima, et al. (2003). "Enhanced Th2 cell-mediated allergic inflammation in Tyk2-deficient mice." J Immunol 170(2): 1077-83.

Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.

Sriram, K. et al. J. Biol. Chem. 2004, 279(19):19936-47. Epub Mar. 2, 2004.

Staerk, J., et al. JBC 280:41893-41899, (2005).

T.W. Green and P.G.M. Wuts, Protective Groups in Organic Synthesis, 3rd. Ed., Wiley & Sons, Inc., New York (1999).

Takemoto, S., J. C. Mulloy, et al. (1997). "Proliferation of adult T cell leukemia/lymphoma cells is associated with the constitutive activation of JAK/STAT proteins." Proc Natl Acad Sci U S A 94(25): 13897-902.

Zou, Xiaoming, and Calame, Kathryn, "Signaling Pathways Activated by Oncogenic Forms of Abl Tyrosine Kinase." Journal of Biological Chemistry, 274(26):18141-18144, 1999.

EPO Office Action dated Aug. 8, 2011 in EP Application No. 08848610.5 (4 pages).

* cited by examiner

4-PYRAZOLYL-N-ARYLPYRIMIDIN-2-AMINES AND 4-PYRAZOLYL-N-HETEROARYLPYRIMIDIN-2-AMINES AS JANUS KINASE INHIBITORS

CROSS REFERENCE TO RELATED APPLICATIONS

This application claims the benefit of U.S. Provisional Patent Application Ser. No. 60/988,606, filed Nov. 16, 2007, which is incorporated herein by reference in its entirety.

FIELD OF THE INVENTION

The present invention provides substituted bicyclic heteroaryl compounds, including, for example, 4-pyrazolyl-N-arylpyrimidin-2-amines and 4-pyrazolyl-N-heteroarylpyrimidin-2-amines that modulate the activity of kinases and are useful in the treatment of diseases related to activity of kinases including, for example, immune-related diseases, skin disorders, myeloid proliferative disorders, cancer, and other diseases.

BACKGROUND OF THE INVENTION

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression (Blume-Jensen P et al, Nature 2001, 411(6835):355-365). Thus far, oncogenic protein kinases represent one of the largest and most attractive groups of protein targets for cancer intervention and drug development.

Protein kinases can be categorized as receptor type and non-receptor type and may show specificity for phosphorylating either a Ser/Thr residue or a Tyr residue. Thus, a kinase may be described as a Ser/Thr kinase (e.g., a receptor Ser/Thr kinase or a non-receptor Ser/Thr kinase) or a Tyr kinase (e.g., a receptor Tyr kinase or a non-receptor Tyr kinase). Receptors that bind to ligands from the TGFβ family of growth factors are Ser/Thr kinases and are termed TGFβR. Examples of non-receptor Ser/Thr kinases include PKA, PKG, PKC, CaM-kinase, phosphorylase kinase, MAPK (ERK), MEKK, Akt, and mTOR.

Receptor Tyr kinases (RTKs) have an extracellular portion, a transmembrane domain, and an intracellular portion, while non-receptor tyrosine kinases are entirely intracellular. RTK mediated signal transduction is typically initiated by extracellular interaction with a specific growth factor (ligand), typically followed by receptor dimerization, stimulation of the intrinsic protein tyrosine kinase activity, and receptor transphosphorylation. Binding sites are thereby created for intracellular signal transduction molecules and lead to the formation of complexes with a spectrum of cytoplasmic signaling molecules that facilitate the appropriate cellular response such as cell division, differentiation, metabolic effects, and changes in the extracellular microenvironment At present, at least nineteen (19) distinct RTK subfamilies have been identified. One RTK subfamily, designated the HER subfamily, includes EGFR, HER2, HER3 and HER4. A second family of RTKs, designated the insulin subfamily, includes the INS-R, the IGF-1R and the IR-R. A third family, the "PDGF" subfamily, includes the PDGF alpha and beta receptors, CSFIR, c-kit and FLK-II. Another subfamily of RTKs, referred to as the FLK subfamily, encompasses the Kinase insert Domain-Receptor fetal liver kinase-1 (KDR/FLK-1), the fetal liver kinase 4 (FLK-4) and the fins-like tyrosine kinase 1 (flt-1). Two other subfamilies of RTKs have been designated as the FGF receptor family (FGFR1, FGFR2, FGFR3 and FGFR4) and the Met subfamily (c-Met, Ron and Sea). Additional RTKs are VEGFR/Flt2, FLT4, Eph family RTKs (A1, A2, A3, B2, B4), and Tie2. For a detailed discussion of protein kinases, see for example, Blume-Jensen, P. et al., Nature. 2001, 411(6835):355-365, and Manning, G. et al., Science. 2002, 298(5600):1912-1934. A review of TRK family kinases can be found in Cancer Letter 169 (2001) 107-114 which is herein incorporated by reference. A review of Eph family kinases can be found in Genes & Development, 17:1429-1450 and is herein incorporated by reference. Information on Tie2 kinase can be found in K. G. Peters et al. "Functional Significance of Tie2 Signaling in the Adult Vasculature", 2004,© The Endocrine Society.

The non-receptor Tyr kinases can be divided into numerous subfamilies, including Src, Btk, ABL, Fak, and JAK. Each of these subfamilies can be further subdivided into multiple members that have been frequently linked to oncogenesis. The ABL family includes ABL1 and ARG (ABL2). The JAK family includes JAK1, JAK2, JAK3, and TYK2. The Src family, is the largest and includes Src, Fyn, Lck and Fgr among others. For a detailed discussion of these kinases, see Bolen J B. Nonreceptor tyrosine protein kinases. Oncogene. 1993, 8(8):2025-31.

The inappropriate regulation of kinase activity can contribute to disease states. Deregulated kinase activity is known to occur through mutations (i.e. gene fusions resulting from chromosomal translocations, point mutations that effect kinase activity) or changes to expression of the kinase gene (i.e. increased expression through gene amplification). Over 40 chromosomal translocations, leading to gene fusions and the deregulation of 12 different Tyr kinases, are associated with various hematologic malignancies. The protein tyrosine kinases involved in hematologic malignancies include, ABL (ABL1), ARG (ABL2), PDGFβR, PDGFαR, JAK2, SYK, TRKC, FGFR1, FGFR3, FLT3, and FRK. The range of diseases associated with mutations in these kinases include myeloproliferative disorder, MPD; chronic myeloid leukemia, CML; acute myeloid leukemia, AML; acute lymphoblastic leukemia, ALL; chronic myelomonocytic leukemia, DMML; 8p13 myeloproliferative syndrome, EMS; anaplastic large cell lymphoma, ALCL; inflammatory myofibroblastic tumor, IMF; peripheral T-cell lymphoma, PTL; polycythemia vera, PV; and essential thrombocythemia, ET (Y. Chalandon and J. Schwaller, Haematologica, 2005; 90(7):949-968). Small molecule inhibitors of various kinases have been successfully employed to treat disease states. Small molecule inhibitors for the protein tyrosine kinases ABL, ALK, PDGFαR, PDGFβR, KIT, FLT3, FGFR1, and FGFR3 are used to treat hematologic malignancies (Y. Chalandon and J. Schwaller, Haematologica, 2005; 90(7):949-968).

Specifically, inappropriate activity of the ABL and JAK non-receptor Tyr kinases are implicated in human disease. Inappropriate ABL kinase activity is a hallmark of cancer and may contribute to myeloproliferative disorders and fibrotic conditions such as pulmonary fibrosis (Daniels C E et al., J Clin Invest, 2004 November; 114(9):1308-16). Inappropriate JAK kinase activity contributes to cancer, myeloid proliferative disorders and immune system disorders.

The ABL family of non-receptor Tyr kinases includes ABL1 and ARG (ABL2) (Kruh G D et al., PNAS, 1990 August; 87(15)5802-6). Henceforth, the ABL family will be referred to simply as ABL. Studies of ABL1 have demonstrated involvement in multiple signaling pathways, including Ras-dependent, Rac-dependent, JNK-dependent, PI3K-dependent, PKC-dependent, mTOR, and JAK/STAT. These signaling pathways regulate processes including cell cycle progression, cell cycle arrest, cell growth, cell differentiation and apoptosis (M G Kharas and D A Fruman, Cancer Research, 65:2047-2053; X. Zou and K. Calame, J. Biol. Chem., 274(26):18141-18144).

Deregulation of ABL kinase activity are linked to disease and may occur through gene amplification and mutations. For example, Gene fusions of ABL kinases are linked to blood cancers. ABL1 fusions with TEL, NUP214, EMS, and SFQ have been correlated with CML and ALL and fusions of ARG (ABL2) with BCR and TEL have been correlated with CML (Y. Chalandon and J. Schwaller, Haematologica, 2005; 90(7): 949-968). The BCR/ABL1 fusion gene, which results from a chromosomal translocation generating the Philadelphia chromosome (Ph), is widely thought to be a causative factor in leukemia: the Philadelphia chromosome, is associated with 95% of CML cases and 10% of ALL cases (X. Zou and K. Calame, J. Biol. Chem., 274(26):18141-18144).

The small molecule inhibitor Imatinib mesylate (Gleevec™), a small molecular inhibitor of ABL1 kinase activity, has been widely used to treat CML. However, clinical resistance to Imatinib is increasingly problematic. Resistance occurs most commonly through clonal expansion of mutants in the kinase domain of BCR/ABL1 (Gorre M E et al., Science, 293(5531):876-80). Numerous mutations have been mapped from clinical isolates, including T315D, F359D, D276G, E255K, M351T, G250E, H396R, Q252H, Y253H, E355G, F317L, G250E, Y253F, F359V, Q252R, L387M, M244V, M343T/F382L, and V379I (Shah N P et al., Cancer Cell, 2:117-25). Thus, alternative small molecule inhibitors are needed to target Imatinib resistant ABL1 mutants. In addition, combination therapy with multiple small molecule inhibitors targeting ABL1 are expected to reduce the likelihood of resistance arising in a single cell, through mutation of ABL 1, and subsequent clonal expansion.

The pathway involving the Janus kinase family of protein tyrosine kinases (JAKs) and Signal Transducers and Activators of Transcription (STATs) is engaged in the signaling of a wide range of cytokines and growth factors. Cytokines are low-molecular weight polypeptides or glycoproteins that stimulate biological responses in virtually all cell types. For example, cytokines regulate many of the pathways involved in the host inflammatory response to sepsis. Cytokines influence cell differentiation, proliferation and activation, and they can modulate both proinflammatory and anti-inflammatory responses to allow the host to react appropriately to pathogens. Generally, cytokine receptors do not have intrinsic tyrosine kinase activity, and thus require receptor-associated kinases to propagate a phosphorylation cascade. JAKs fulfill this function. Cytokines bind to their receptors, causing receptor dimerization, and this enables JAKs to phosphorylate each other as well as specific tyrosine motifs within the cytokine receptors. STATs that recognize these phosphotyrosine motifs are recruited to the receptor, and are then themselves activated by a JAK-dependent tyrosine phosphorylation event. Upon activation, STATs dissociate from the receptors, dimerize, and translocate to the nucleus to bind to specific DNA sites and alter transcription (Scott, M. J., C. J. Godshall, et al. (2002). "JAKs, STATs, Cytokines, and Sepsis." *Clin Diagn Lab Immunol* 9(6): 1153-9).

The JAK family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs (Scott, Godshall et al. 2002, supra). While JAK1, JAK2 and TYK2 are ubiquitously expressed, JAK3 is reported to be preferentially expressed in lymphocytes.

Not only do the cytokine-stimulated immune and inflammatory responses contribute to normal host defense, they also play roles in the pathogenesis of diseases: pathologies such as severe combined immunodeficiency (SCID) arise from hypoactivity and suppression of the immune system, and a hyperactive or inappropriate immune/inflammatory response contributes to the pathology of autoimmune diseases such as rheumatoid and psoriatic arthritis, asthma and systemic lupus erythematosus, inflammatory bowel disease, multiple sclerosis, type I diabetes mellitus, myasthenia gravis, thyroiditis, immunoglobulin nephropathies, myocarditis as well as illnesses such as scleroderma and osteoarthritis (Ortmann, R. A., T. Cheng, et al. (2000). "Janus kinases and signal transducers and activators of transcription: their roles in cytokine signaling, development and immunoregulation." *Arthritis Res* 2(1): 16-32). Furthermore, syndromes with a mixed presentation of autoimmune and immunodeficiency disease are quite common (Candotti, F., L. Notarangelo, et al. (2002). "Molecular aspects of primary immunodeficiencies: lessons from cytokine and other signaling pathways." *J Clin Invest* 109(10): 1261-9). Thus, therapeutic agents are typically aimed at augmentation or suppression of the immune and inflammatory pathways, accordingly.

Deficiencies in expression of JAK family members are associated with disease states. JAK1−/− mice are runted at birth, fail to nurse, and die perinatally (Rodig, S. J., M. A. Meraz, et al (1998). "Disruption of the JAK1 gene demonstrates obligatory and nonredundant roles of the JAKs in cytokine-induced biologic responses." *Cell* 93(3): 373-83). JAK2−/− mouse embryos are anemic and die around day 12.5 postcoitum due to the absence of definitive erythropoiesis. JAK2-deficient fibroblasts do not respond to IFN gamma, although responses to IFNalpha/beta and IL-6 are unaffected. JAK2 functions in signal transduction of a specific group of cytokine receptors required in definitive erythropoiesis (Neubauer, H., A. Cumano, et al. (1998). *Cell* 93(3): 397-409; Parganas, E., D. Wang, et al. (1998). *Cell* 93(3): 385-95). JAK3 appears to play a role in normal development and function of B and T lymphocytes. Mutations of JAK3 are reported to be responsible for autosomal recessive severe combined immunodeficiency (SCID) in humans (Candotti, F., S. A. Oakes, et al. (1997). "Structural and functional basis for JAK3-deficient severe combined immunodeficiency." *Blood* 90(10): 3996-4003).

The JAK/STAT pathway, and in particular all four members of the JAK family, are believed to play a role in the pathogenesis of the asthmatic response, chronic obstructive pulmonary disease, bronchitis, and other related inflammatory diseases of the lower respiratory tract. For instance, the inappropriate immune responses that characterize asthma are orchestrated by a subset of CD4+ T helper cells termed T helper 2 (Th2) cells. Signaling through the cytokine receptor IL-4 stimulates JAK1 and JAK3 to activate STAT6, and signaling through IL-12 stimulates activation of JAK2 and TYK2, and subsequent phosphorylation of STAT4. STAT4 and STAT6 control multiple aspects of CD4+ T helper cell differentiation (Pernis, A. B. and P. B. Rothman (2002). "JAK-STAT signaling in asthma." J Clin Invest 109(10): 1279-83). Furthermore, TYK2-deficient mice were found to have enhanced Th2 cell-mediated allergic airway inflammation (Seto, Y., H. Nakajima, et al. (2003). "Enhanced Th2 cell-mediated allergic inflammation in Tyk2-deficient mice." J Immunol 170(2): 1077-83). Moreover, multiple cytokines that signal through JAK kinases have been linked to inflammatory diseases or conditions of the upper respiratory tract such as those affecting the nose and sinuses (e.g. rhinitis, sinusitis) whether classically allergic reactions or not.

The JAK/STAT pathway has also been implicated to play a role in inflammatory diseases/conditions of the eye including, but not limited to, iritis, uveitis, scleritis, conjunctivitis, as well as chronic allergic responses. Therefore, inhibition of JAK kinases may have a beneficial role in the therapeutic treatment of these diseases.

The JAK/STAT pathway has also been implicated in cancers. Activation of STAT3 has been reported for endometrial and cervical cancers (C. L. Chen et al. (2007). British Journal of Cancer 96: 591-599). In addition, JAK/STAT pathway components, in particular JAK3, play a role in cancers of the immune system. In adult T cell leukemia/lymphoma (ATLL), human CD4+ T cells acquire a transformed phenotype, an event that correlates with acquisition of constitutive phosphorylation of JAKs and STATs. Furthermore, an association between JAK3 and STAT-1, STAT-3, and STAT-5 activation and cell-cycle progression was demonstrated by both propidium iodide staining and bromodeoxyuridine incorporation in cells of four ATLL patients tested. These results imply that JAK/STAT activation is associated with replication of leukemic cells and that therapeutic approaches aimed at JAK/STAT inhibition may be considered to halt neoplastic growth (Takemoto, S., J. C. Mulloy, et al. (1997). "Proliferation of adult T cell leukemia/lymphoma cells is associated with the constitutive activation of JAK/STAT proteins." *Proc Natl Acad Sci USA* 94(25): 13897-902).

Blocking signal transduction at the level of the JAK kinases holds promise for developing treatments for human cancers. Cytokines of the interleukin 6 (IL-6) family, which activate the signal transducer gp130, are major survival and growth factors for human multiple myeloma (MM) cells. The signal transduction of gp130 is believed to involve JAK1, JAK2 and Tyk2 and the downstream effectors STAT3 and the mitogen-activated protein kinase (MAPK) pathways. In IL-6-dependent MM cell lines treated with the JAK2 inhibitor tyrphostin AG490, JAK2 kinase activity and ERK2 and STAT3 phosphorylation were inhibited. Furthermore, cell proliferation was suppressed and apoptosis was induced (De Vos, J., M. Jourdan, et al (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells." *Br J Haematol* 109(4): 823-8). However, in some cases, AG490 can induce dormancy of tumor cells and actually then protect them from death.

Activation of JAK/STAT in cancers may occur by multiple mechanisms including cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Importantly, activation of STAT signaling, as well as other pathways downstream of JAKs (e.g. Akt), has been correlated with poor prognosis in many cancer types (Bowman, T., et al *Oncogene* 19:2474-2488, 2000). Moreover, elevated levels of circulating cytokines that signal through JAK/STAT may adversely impact patient health as they are thought to play a causal role in cachexia and/or chronic fatigue. As such, JAK inhibition may be therapeutic for the treatment of cancer patients for reasons that extend beyond potential anti-tumor activity. The cachexia indication may gain further mechanistic support with realization that the satiety factor leptin signals through JAKs.

Pharmacological targeting of Janus kinase 3 (JAK3) has been employed successfully to control allograft rejection and graft versus host disease (GVHD). In addition to its involvement in signaling of cytokine receptors, JAK3 is also engaged in the CD40 signaling pathway of peripheral blood monocytes. During CD40-induced maturation of myeloid dendritic cells (DCs), JAK3 activity is induced, and increases in costimulatory molecule expression, IL-12 production, and potent allogeneic stimulatory capacity are observed. A rationally designed JAK3 inhibitor WHI-P-154 prevented these effects arresting the DCs at an immature level, suggesting that immunosuppressive therapies targeting the tyrosine kinase JAK3 may also affect the function of myeloid cells (Saemann, M. D., C. Diakos, et al. (2003). "Prevention of CD40-triggered dendritic cell maturation and induction of T-cell hyporeactivity by targeting of Janus kinase 3." *Am J Transplant* 3(11): 1341-9). In the mouse model system, JAK3 was also shown to be an important molecular target for treatment of autoimmune insulin-dependent (type 1) diabetes mellitus. The rationally designed JAK3 inhibitor JANEX-1 exhibited potent immunomodulatory activity and delayed the onset of diabetes in the NOD mouse model of autoimmune type 1 diabetes (Cetkovic-Cvrlje, M., A. L. Dragt, et al. (2003). "Targeting JAK3 with JANEX-1 for prevention of autoimmune type 1 diabetes in NOD mice." *Clin Immunol* 106(3): 213-25).

It has been suggested that inhibition of JAK2 tyrosine kinase can be beneficial for patients with myeloproliferative disorder. (Levine, et al, *Cancer Cell, vol.* 7, 2005: 387-397) Myeloproliferative disorder (MPD) includes polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES) and systemic mast cell disease (SMCD). Although the myeloproliferative disorder (such as PV, ET and MMM) are thought to be caused by acquired somatic mutation in hematopoietic progenitors, the genetic basis for these diseases has not been known. However, it has been reported that hematopoietic cells from a majority of patients with PV and a significant number of patients with ET and MMM possess a recurrent somatic activating mutation in the JAK2 tyrosine kinase. It has also been reported that inhibition of the JAK2V617F kinase with a small molecule inhibitor leads to inhibition of proliferation of hematopoietic cells, suggesting that the JAK2 tyrosine kinase is a potential target for pharmacologic inhibition in patients with PV, ET and MMM.

Inhibition of the JAK kinases is also envisioned to have therapeutic benefits in patients suffering from skin immune disorders such as psoriasis, and skin sensitization. In psoriasis vulgaris, the most common form of psoriasis, it has been generally accepted that activated T lymphocytes are important for the maintenance of the disease and its associated psoriatic plaques (Gottlieb, A. B., et al, *Nat Rev Drug Disc.*, 4:19-34). Psoriatic plaques contain a significant immune infiltrate, including leukocytes and monocytes, as well as multiple epidermal layers with increased keratinocyte proliferation. While the initial activation of immune cells in psoriasis occurs by an ill defined mechanism, the maintenance is believed to be dependent on a number of inflammatory cytokines, in addition to various chemokines and growth factors (JCI, 113:1664-1675). Many of these, including interleukins-2, -4, -6, -7, -12, -15, -18, and -23 as well as GM-CSF and IFNg, signal through the Janus (JAK) kinases (*Adv Pharmacol.* 2000; 47:113-74). As such, blocking signal transduction at the level of JAK kinases may result in therapeutic benefits in patients suffering from psoriasis or other immune disorders of the skin.

It has been known that certain therapeutics can cause immune reactions such as skin rash or diarrhea in some patients. For instance, administration of some of the new targeted anti-cancer agents such as Iressa, Erbitux, and Tarceva has induced acneiform rash with some patients. Another example is that some therapeutics used topically induce skin irritation, skin rash, contact dermatitis or allergic contact sensitization. For some patients, these immune reactions may be bothersome, but for others, the immune reactions such as rash or diarrhea may result in inability to continue the treatment. Although the driving force behind these immune reactions has not been elucidated completely at the present time, these immune reactions are likely linked to immune infiltrate.

Inhibitors of Janus kinases or related kinases are widely sought and several publications report effective classes of compounds. For example, certain inhibitors are reported in WO 99/65909, US 2004/0198737; WO 2004/099204; WO 2004/099205; and WO 01/42246. Heteroaryl substituted pyrroles and other compounds are reported in WO 2004/72063 and WO 99/62908.

Thus, new or improved agents which inhibit kinases are continually needed, in part, to cope with resistant mutants. Combination therapy (using newly identified agents), may decrease the odds of developing drug resistant kinase mutants and new agents are needed to treat existing drug-resistant kinase mutants (i.e. ABL1 mutants which are resistant to Imatinib). Agents that inhibit JAK kinases are continually needed, that act as immunosuppressive agents for organ transplants, as well as agents for the prevention and treatment of autoimmune diseases (e.g., multiple sclerosis, rheumatoid arthritis, asthma, type I diabetes, inflammatory bowel disease, Crohn's disease, autoimmune thyroid disorders, Alzheimer's disease), diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics, to name a few. The compounds, compositions and methods described herein are directed toward these needs and other ends.

SUMMARY OF THE INVENTION

The present invention provides compounds of Formula I:

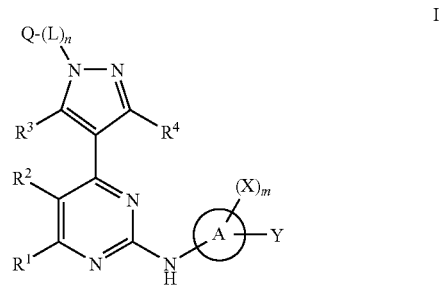

or pharmaceutically acceptable salt forms, wherein constituent members are defined herein.

The present invention further provides compositions comprising a compound of Formula I, or pharmaceutically acceptable salt thereof, and at least one pharmaceutically acceptable carrier.

The present invention further provides methods of modulating an activity of one or more kinases comprising contacting the kinase with a compound of Formula I, or pharmaceutically acceptable salt thereof.

The present invention further provides methods of modulating an activity of JAK comprising contacting JAK with a compound of Formula I, or pharmaceutically acceptable salt thereof.

The present invention further provides methods of treating a disease in a patient, wherein the disease is associated with abnormal JAK activity, comprising administering to the patient a therapeutically effective amount of a compound of Formula I, or pharmaceutically acceptable salt thereof.

DETAILED DESCRIPTION

The present invention provides, inter alia, compounds that modulate the activity of one or more JAKs and are useful, for example, in the treatment of various diseases such as those associated with JAK expression or activity. The compounds of the invention have Formula I:

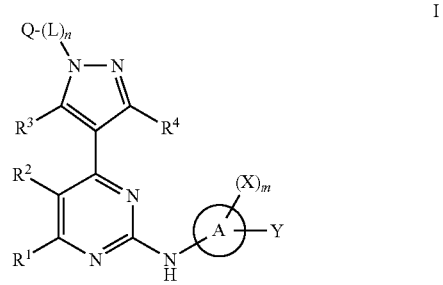

including pharmaceutically acceptable salt forms or prodrugs thereof, wherein:

Ring A is aryl or heteroaryl;

L is $C_{1-8}$ alkylene, $C_{2-8}$ alkenylene, $C_{2-8}$ alkynylene, $(CR^5R^6)_p$—$(C_{3-10}$ cycloalkylene$)$-$(CR^5R^6)_q$, $(CR^5R^6)_p$-

(arylene)-(CR$^5$R$^6$)$_q$, (CR$^5$R$^6$)$_p$—(C$_{1-10}$ heterocycloalkylene)-(CR$^5$R$^6$)$_q$, (CR$^5$R$^6$)$_p$-(heteroarylene)-(CR$^5$R$^6$)$_q$, (CR$^5$R$^6$)$_p$O(CR$^5$R$^6$)$_q$, (CR$^5$R$^6$)$_p$S(CR$^5$R$^6$)$_q$, (CR$^5$R$^6$)$_p$C(O) (CR$^5$R$^6$)$_q$, (CR$^5$R$^6$)$_p$C(O)NR$^c$(CR$^5$R$^6$)$_q$, (CR$^5$R$^6$)$_p$C(O)O (CR$^5$R$^6$)$_q$, (CR$^5$R$^6$)$_p$OC(O)(CR$^5$R$^6$)$_q$, (CR$^5$R$^6$)$_p$OC(O)NR$^c$ (CR$^5$R$^6$)$_q$, (CR$^5$R$^6$)$_p$NR$^c$(CR$^5$R$^6$)$_q$, (CR$^5$R$^6$)$_p$NR$^c$C(O)NR$^d$ (CR$^5$R$^6$)$_q$, (CR$^5$R$^6$)$_p$S(O)(CR$^5$R$^6$)$_q$, (CR$^5$R$^6$)$_p$S(O)NR$^c$ (CR$^5$R$^6$)$_q$, (CR$^5$R$^6$)$_p$S(O)$_2$(CR$^5$R$^6$)$_q$, or (CR$^5$R$^6$)$_p$S(O)$_2$NR$^c$ (CR$^5$R$^6$)$_q$, wherein said C$_{1-8}$ alkylene, C$_{2-8}$ alkenylene, C$_{2-8}$ alkynylene, C$_{3-10}$ cycloalkylene, arylene, C$_{1-10}$ heterocycloalkylene, or heteroarylene, is optionally substituted with 1, 2, or 3 substituents independently selected from halo, C$_{1-6}$ alkyl, C$_{2-6}$ alkenyl, C$_{2-6}$ alkynyl, C$_{1-6}$ haloalkyl, CN, OR$^a$, SR$^a$, C(O)R$^b$, C(O)NR$^c$R$^d$, C(O)OR$^a$, OC(O)R$^b$, OC(O)NR$^c$ R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, S(O)R$^b$, S(O)NR$^c$ R$^d$, S(O)$_2$R$^b$, NR$^c$S(O)$_2$R$^b$, and S(O)$_2$NR$^c$R$^d$;

Q is H, Cy$^1$, halo, C$_{1-6}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{b1}$, C(O) NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein said C$_{1-6}$ alkyl, C$_{2-6}$ alkenyl, or C$_{2-6}$ alkynyl, are optionally substituted by 1, 2, 3, 4 or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a1}$, SR$^{a1}$, C(O) R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O) OR$^{a1}$, C(=NR$^g$)NR$^{c1}$R$^{d1}$, NR$^{c1}$C(=NR$^g$)NR$^{c1}$R$^{d1}$, S(O) R$^{b1}$, S(O)NR$^{c1}$R$^{d1}$, S(O)$_2$R$^{b1}$, NR$^{c1}$S(O)$_2$R$^{b1}$, and S(O)$_2$ NR$^{c1}$R$^{d1}$;

X is H, halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O) OR$^a$, OC(O)R$^b$, OC(O)NR$^c$R$^d$, NR$^c$R$^d$, NR$^c$C(O)R$^b$, NR$^c$C (O)NR$^c$R$^d$, NR$^c$C(O)OR$^a$, C(=NR$^g$)NR$^c$R$^d$, NR$^c$C(=NR$^g$) NR$^c$R$^d$, S(O)R$^b$, S(O)NR$^c$R$^d$, S(O)$_2$R$^b$, NR$^c$S(O)$_2$R$^b$, or S(O)$_2$ NR$^c$R$^d$;

Y is H, Cy$^2$, halo, C$_{1-6}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{b1}$, C(O) NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein said C$_{1-6}$ alkyl, C$_{2-6}$ alkenyl, C$_{2-6}$ alkynyl, or C$_{1-6}$ haloalkyl, is optionally substituted by 1, 2, 3, 4 or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O) NR$^{c1}$R$^{d1}$, NR$^{c1}$C(O)OR$^{a1}$, C(=NR$^g$)NR$^{c1}$R$^{d1}$, NR$^{c1}$C (=NR$^g$)NR$^{c1}$R$^{d1}$, S(O)R$^{b1}$, S(O)NR$^{c1}$R$^{d1}$, S(O)$_2$R$^{b1}$, NR$^{c1}$S (O)$_2$R$^{b1}$, and S(O)$_2$NR$^{c1}$R$^{d1}$;

R$^1$, R$^2$, R$^3$, R$^4$, R$^5$, and R$^6$ are independently selected from H, halo, C$_{1-6}$ alkyl, C$_{2-6}$ alkenyl, C$_{2-6}$ alkynyl, C$_{1-6}$ haloalkyl, CN, (CH$_2$)$_m$CN, NO$_2$, OR$^a$, (CH$_2$)$_m$OR$^a$, SR$^a$, C(O)R$^b$, C(O) NR$^c$R$^d$, C(O)OR$^a$, NR$^c$R$^d$, (CH$_2$)$_m$NR$^c$R$^d$, NR$^c$C(O)R$^b$, NR$^c$S(O)$_2$R$^b$, and S(O)$_2$NR$^c$R$^d$;

Cy$^1$ and Cy$^2$ are independently selected from aryl, cycloalkyl, heteroaryl, and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, aryl, cycloalkyl, heteroaryl, heterocycloalkyl, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C (O)R$^{b1}$, NR$^{c1}$C(O)NR$^{c1}$R$^{d1}$, NR$^{c1}$C(O)OR$^{a1}$, C(=NR$^g$) NR$^{c1}$R$^{d1}$, NR$^{c1}$C(=NR$^g$)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, and S(O)$_2$NR$^{c1}$R$^{d1}$, wherein said C$_{1-6}$ alkyl, C$_{2-6}$ alkenyl, C$_{2-6}$ alkynyl, aryl, cycloalkyl, heteroaryl, or heterocycloalkyl that is substituted on Cy$^1$ or Cy$^2$ is further optionally substituted by 1, 2, or 3 substituents independently selected from halo, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O) OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, and S(O)$_2$NR$^{c1}$R$^{d1}$;

R$^a$, R$^b$, R$^c$, and R$^d$ are independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, CN, amino, halo, C$_{1-6}$ alkyl, C$_{1-6}$alkoxy, C$_{1-6}$haloalkyl, and C$_{1-6}$haloalkoxy;

or R$^c$ and R$^d$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, C$_{1-6}$ alkyl, C$_{1-6}$ alkoxy, C$_{1-6}$ haloalkyl, and C$_{1-6}$ haloalkoxy;

R$^{a1}$, R$^{b1}$, R$^{c1}$, and R$^{d1}$ are independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from C$_{1-6}$ alkyl, halo, CN, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^g$)NR$^{c2}$R$^{d2}$, NR$^{c2}$C(=NR$^g$)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

or R$^{c1}$ and R$^{d1}$ together with the N atom to which they are attached form a 4-, 5-, 6- or 7-membered heterocycloalkyl group or heteroaryl group, each optionally substituted with 1, 2, or 3 substituents independently selected from C$_{1-6}$ alkyl, halo, CN, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)N$^{c2}$R$^{d2}$, NR$^{c2}$C(O)OR$^{a2}$, C(=NR$^g$)NR$^{c2}$R$^{d2}$, NR$^{c2}$C(=NR$^g$)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^{a2}$, R$^{b2}$, R$^{c2}$, and R$^{d2}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, C$_{1-6}$ alkyl, C$_{1-6}$ alkoxy, C$_{1-6}$ haloalkyl, and C$_{1-6}$ haloalkoxy;

or R$^{c2}$ and R$^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, C$_{1-6}$ alkyl, C$_{1-6}$ alkoxy, C$_{1-6}$ haloalkyl, and C$_{1-6}$ haloalkoxy;

R$^g$ is H, CN, or NO$_2$;

m is 0, 1, 2, or 3;

n is 0 or 1;

p is 0, 1, 2, 3, 4, 5, or 6; and q is 0, 1, 2, 3, 4, 5 or 6.

In some embodiments, A is aryl.

In some embodiments, A is phenyl.

In some embodiments, A is heteroaryl.

In some embodiments, A is pyrazolyl.

In some embodiments, A is pyridyl.

In some embodiments, L is $C_{1-8}$ alkylene, $C_{2-8}$ alkenylene, $C_{2-8}$ alkynylene, $(CR^5R^6)_p$—$(C_{3-10}$ cycloalkylene)-$(CR^5R^6)_q$, $(CR^5R^6)_p$-(arylene)-$(CR^5R^6)_q$, $(CR^5R^6)_p$—$(C_{1-10}$ heterocycloalkylene)-$(CR^5R^6)_q$, $(CR^5R^6)_p$-(heteroarylene)-$(CR^5R^6)_q$, $(CR^5R^6)_pO(CR^5R^6)_q$, $(CR^5R^6)_pS(CR^5R^6)_q$, wherein said $C_{1-8}$ alkylene, $C_{2-8}$ alkenylene, $C_{2-8}$ alkynylene, $C_{3-10}$ cycloalkylene, arylene, $C_{1-10}$ heterocycloalkylene, or heteroarylene, is optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $S(O)R^b$, $S(O)NR^cR^d$, $S(O)_2R^b$, $NR^cS(O)_2R^b$, and $S(O)_2NR^cR^d$.

In some embodiments, L is $C_{1-8}$ alkylene, $C_{2-8}$ alkenylene, $C_{2-8}$ alkynylene, $(CR^5R^6)_p$—$(C_{3-10}$ cycloalkylene)-$(CR^5R^6)_q$, $(CR^5R^6)_p$-(arylene)-$(CR^5R^6)_q$, $(CR^5R^6)_p$—$(C_{1-10}$ heterocycloalkylene)-$(CR^5R^6)_q$, $(CR^5R^6)_p$-(heteroarylene)-$(CR^5R^6)_q$, wherein said $C_{1-8}$ alkylene, $C_{2-8}$ alkenylene, $C_{2-8}$ alkynylene, $C_{3-10}$ cycloalkylene, arylene, $C_{1-10}$ heterocycloalkylene, or heteroarylene, is optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $S(O)R^b$, $S(O)NR^cR^d$, $S(O)_2R^b$, $NR^cS(O)_2R^b$, and $S(O)_2NR^cR^d$.

In some embodiments, L is $C_{1-8}$ alkylene, $C_{2-8}$ alkenylene, $C_{2-8}$ alkynylene, $(CR^5R^6)_p$—$(C_{3-10}$ cycloalkylene)-$(CR^5R^6)_q$, $(CR^5R^6)_p$—$(C_{1-10}$ heterocycloalkylene)-$(CR^5R^6)_q$, wherein said $C_{1-8}$ alkylene, $C_{2-8}$ alkenylene, $C_{2-8}$ alkynylene, $C_{3-10}$ cycloalkylene, or $C_{1-10}$ heterocycloalkylene, is optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $S(O)R^b$, $S(O)NR^cR^d$, $S(O)_2R^b$, $NR^cS(O)_2R^b$, and $S(O)_2NR^cR^d$.

In some embodiments, L is $C_{1-8}$ alkylene or $(CR^5R^6)_p$—$(C_{1-10}$ heterocycloalkylene)-$(CR^5R^6)_q$, wherein said $C_{1-8}$ alkylene or $C_{1-10}$ heterocycloalkylene, is optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $S(O)R^b$, $S(O)NR^cR^d$, $S(O)_2R^b$, $NR^cS(O)_2R^b$, and $S(O)_2NR^cR^d$.

In some embodiments, L is $C_{1-8}$ alkylene optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)N$-$R^cR^d$, $NR^cC(O)OR^a$, $C(=NR^g)NR^cR^d$, $NR^cC(=NR^g)NR^cR^d$, $S(O)R^b$, $S(O)NR^cR^d$, $S(O)_2R^b$, $NR^cS(O)_2R^b$, and $S(O)_2NR^cR^d$.

In some embodiments, L is $(CR^5R^6)_p$—$(C_{1-10}$ heterocycloalkylene)-$(CR^5R^6)_q$ optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $S(O)R^b$, $S(O)NR^cR^d$, $S(O)_2R^b$, $NR^cS(O)_2R^b$, and $S(O)_2NR^cR^d$.

In some embodiments, L is $(CR^5R^6)_pC(O)(CR^5R^6)_q$, $(CR^5R^6)_pC(O)NR^c(CR^5R^6)_q$, $(CR^5R^6)_pC(O)O(CR^5R^6)_q$, $(CR^5R^6)_pOC(O)(CR^5R^6)_q$, $(CR^5R^6)_pOC(O)NR^c(CR^5R^6)_q$, $(CR^5R^6)_pNR^c(CR^5R^6)_q$, $(CR^5R^6)_pNR^cC(O)NR^d(CR^5R^6)_q$, $(CR^5R^6)_pS(O)(CR^5R^6)_q$, $(CR^5R^6)_pS(O)NR^c(CR^5R^6)_q$, $(CR^5R^6)_pS(O)_2(CR^5R^6)_q$, or $(CR^5R^6)_pS(O)_2NR^c(CR^5R^6)_q$.

In some embodiments, Q is H, $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, or $SR^{a1}$, wherein said $C_{1-6}$ alkyl, $C_{2-6}$ alkenyl, or $C_{2-6}$ alkynyl, are optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

In some embodiments, Q is $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$.

In some embodiments, Q is $Cy^1$, $C(O)R^{b1}$, $S(O)_2R^{b1}$, or $OR^{a1}$.

In some embodiments, $Cy^1$ is aryl or cycloalkyl, each optionally substituted by 1, 2, 3, 4, or 5 substituents independently selected from halo, $C_{1-6}$ alkyl, $C_{2-6}$ alkenyl, $C_{2-6}$ alkynyl, aryl, cycloalkyl, heteroaryl, heterocycloalkyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

In some embodiments, $Cy^1$ is heteroaryl or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, aryl, cycloalkyl, heteroaryl, heterocycloalkyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}S(O)_2R^{b1}$, $NR^{c1}S(O)_2R^{b1}$, and $S(O)_2NR^{c1}R^{d1}$.

In some embodiments, $R_1$ is H.

In some embodiments, $R_2$ is H.

In some embodiments, $R_2$ is $C_{1-6}$ alkyl.

In some embodiments, $R_2$ is methyl.

In some embodiments, $R_2$ is $C_{1-6}$ alkoxy.

In some embodiments, $R_2$ is methoxy.

In some embodiments, wherein $R_3$ is H.

In some embodiments, $R_4$ is H.

In some embodiments, $R_5$ is H.

In some embodiments, $R_6$ is H.

In some embodiments, the compound has Formula IIa, IIb, IIc, IId, IIe, IIf, or IIg:

IIa
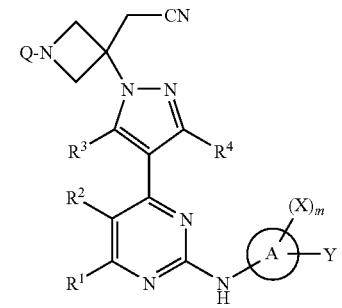

IIb
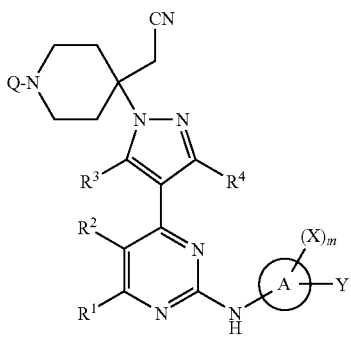

IIc
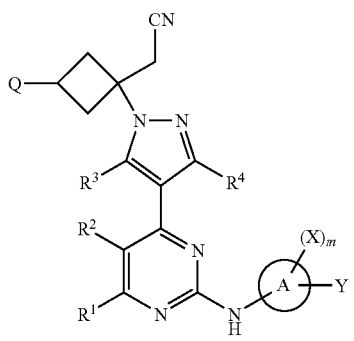

IId
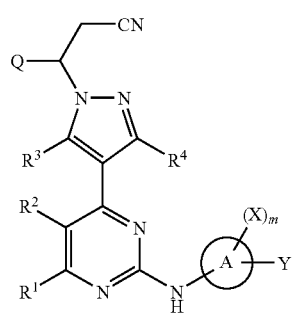

IIe
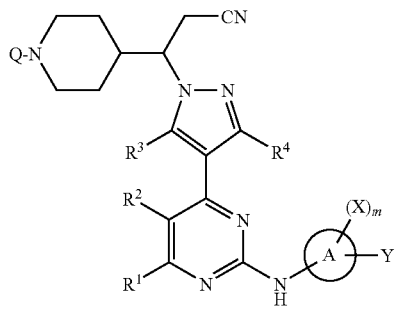

IIf
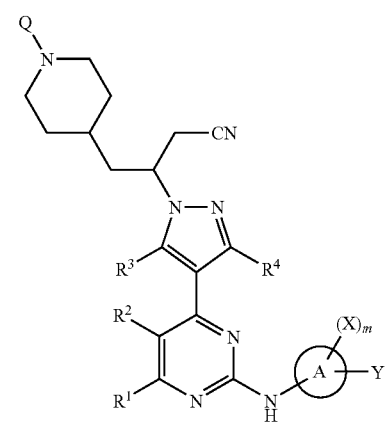

IIg
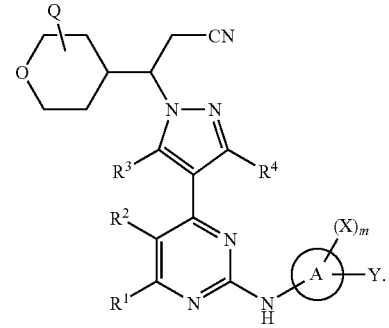

In some embodiments, X is H, halo, $C_{1-6}$ alkyl, $C_{2-6}$ alkenyl, $C_{2-6}$ alkynyl, $C_{1-6}$ haloalkyl, CN, $SR^a$, $C(O)R^b$, $C(O)OR^a$, $OC(O)R^b$, $OC(O)NR^cR^d$, $NR^cC(O)NR^cR^d$, $C(=NR^g)NR^cR^d$, $NR^cC(=NR^g)NR^cR^d$, $S(O)R^b$, $S(O)NR^cR^d$, or $S(O)_2R^b$.

In some embodiments, X is $NO_2$, $OR^a$, $C(O)NR^cR^d$, $NR^cR^d$, $NR^cC(O)R^b$, $NR^cC(O)OR^a$, $NR^cS(O)_2R^b$, or $S(O)_2NR^cR^d$.

In some embodiments, X is $OCH_3$, $OC_6H_5$, $NO_2$, $NH_2$, or $N(CH_2CH_3)_2$ In some embodiments, X is H.

In some embodiments, Y is $C_{1-6}$ alkyl, $C_{2-6}$ alkenyl, $C_{2-6}$ alkynyl, or $C_{1-6}$ haloalkyl, wherein said $C_{1-6}$ alkyl, $C_{2-6}$ alkenyl, or $C_{2-6}$ alkynyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

In some embodiments, Y is H, $Cy^2$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$.

In some embodiments, Y is H.

In some embodiments, Cy$^2$ is aryl or cycloalkyl, each optionally substituted by 1, 2, 3, 4, or 5 substituents independently selected from halo, C$_{1-6}$ alkyl, C$_{2-6}$ alkenyl, C$_{2-6}$ alkynyl, aryl, cycloalkyl, heteroaryl, heterocycloalkyl, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, and S(O)$_2$NR$^{c1}$R$^{d1}$.

In some embodiments, Cy$^2$ is heteroaryl or heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, aryl, cycloalkyl, heteroaryl, heterocycloalkyl, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, and S(O)$_2$NR$^{c1}$R$^{d1}$.

In some embodiments the compound has the Formula IIIa, IIIb, or IIIc:

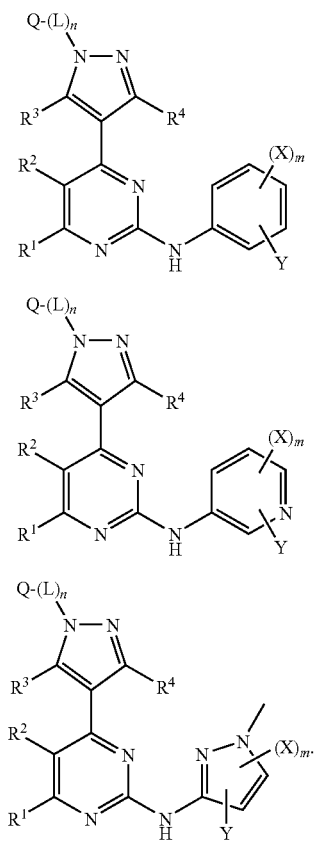

At various places in the present specification, substituents of compounds of the invention are disclosed in groups or in ranges. It is specifically intended that the invention include each and every individual subcombination of the members of such groups and ranges. For example, the term "C$_{1-6}$ alkyl" is specifically intended to individually disclose methyl, ethyl, C$_3$ alkyl, C$_4$ alkyl, C$_5$ alkyl, and C$_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, linking substituents are described. It is specifically intended that each linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, sec-butyl, t-butyl), pentyl (e.g., n-pentyl, isopentyl, sec-pentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. A linking alkyl group is referred to herein as "alkylene."

As used herein, "alkenyl" refers to an alkyl group having one or more carbon-carbon double bonds. Example alkenyl groups include ethenyl, propenyl, cyclohexenyl, and the like. An alkenyl group can contain from 2 to about 20, from 3 to about 15, from 2 to about 10, from 2 to about 8, from 2 to about 6, from 2 to about 4, or from 2 to about 3 carbon atoms. A linking alkenyl group is referred to herein as "alkenylene."

As used herein, "alkynyl" refers to an alkyl group having one or more carbon-carbon triple bonds. Example alkynyl groups include ethynyl, propynyl, and the like. An alkynyl group can contain from 2 to about 20, from 3 to about 15, from 2 to about 10, from 2 to about 8, from 2 to about 6, from 2 to about 4, or from 2 to about 3 carbon atoms. A linking alkynyl group is referred to herein as "alkynylene."

As used herein, "haloalkyl" refers to an alkyl group having one or more halogen substituents. Example haloalkyl groups include CF$_3$, C$_2$F$_5$, CHF$_2$, CCl$_3$, CHCl$_2$, C$_2$Cl$_5$, and the like.

As used herein, "halosulfanyl" refers to a sulfur group having one or more halogen substituents. Example halosulfanyl groups include pentahalosulfanyl groups such as SF$_5$.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. A linking aryl group is referred to herein as "arylene."

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of cyclopentane, cyclopentene, cyclohexane, and the like. A cycloalkyl group containing a fused aromatic ring can be attached through any ring-forming atom including a ring-forming atom of the fused aromatic ring. A cycloalkyl group can contain from 3 to about 20, from 3 to about 15, from 3 to about 10, from 3 to about 8, from 3 to about 7, from 3 to about 6, or from 4 to about 7 carbon atoms. A linking cycloalkyl group is referred to herein as "cycloalkylene."

As used herein, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, any ring-forming N in a heteroaryl moiety can be substituted by oxo. In some embodiments, the heteroaryl group has from 1 to about 20 carbon atoms, and in further embodiments from about 3 to about 20 carbon atoms, from about 3 to about 10 carbon atoms, from about 3 to about 5 carbon atoms. In some embodiments, the heteroaryl group contains 3 to about 14, 4 to about 14, 3 to about 7, or 5 to 6 ring-forming atoms. In some embodiments, the heteroaryl group has 1 to about 4, 1 to about 3, or 1 to 2 heteroatoms. A linking heteroaryl group is referred to herein as "heteroarylene."

As used herein, "heterocycloalkyl" refers to non-aromatic heterocycles having one or more ring-forming heteroatoms such as an O, N, or S atom. Heterocycloalkyl groups include monocyclic and polycyclic (e.g., having 2, 3 or 4 fused rings) systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. The heterocycloalkyl group can be attached through a ring-forming carbon atom or a ring-forming heteroatom. The heterocycloalkyl group containing a fused aromatic ring can be attached through any ring-forming atom including a ring-forming atom of the fused aromatic ring. In some embodiments, the heterocycloalkyl group has from 1 to about 20 carbon atoms, and in further embodiments from about 3 to about 20 carbon atoms. In some embodiments, the heterocycloalkyl group contains 3 to about 14, 4 to about 14, 3 to about 7, or 5 to 6 ring-forming atoms. In some embodiments, the heterocycloalkyl group has 1 to about 4, 1 to about 3, or 1 to 2 heteroatoms. A heterocycloalkyl group can contain from 1 to about 20, from 1 to about 15, from 1 to about 10, from 1 to about 8, from 1 to about 7, from 1 to about 6, or from 1 to about 5 carbon atoms. In some embodiments, the heterocycloalkyl group contains 0 to 3 double or triple bonds. In some embodiments, the heterocycloalkyl group contains 0 to 2 double or triple bonds. A linking heterocycloalkyl group is referred to herein as "heterocycloalkylene."

As used herein, "halo" or "halogen" includes fluoro, chloro, bromo, and iodo.

As used herein, "arylalkyl" refers to alkyl substituted by aryl and "cycloalkylalkyl" refers to alkyl substituted by cycloalkyl. An example arylalkyl group is benzyl.

As used herein, "heteroarylalkyl" refers to alkyl substituted by heteroaryl and "heterocycloalkylalkyl" refers to alkyl substituted by heterocycloalkyl.

As used herein, "amino" refers to NH$_2$.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-(haloalkyl) group.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention further include hydrates and solvates, as well as anhydrous and non-solvated forms.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers, and isotopes of the structures depicted.

All compounds, and pharmaceutically acceptable salts thereof, can be found together with other substances such as water and solvents (e.g. hydrates and solvates) or can be isolated.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of Compounds of the Invention can Involve the Protection and Deprotection of Various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Example synthetic methods for preparing compounds of the invention are provided in the Schemes below. For instance, compounds of the invention can be prepared by the general synthetic procedure shown in Scheme 1. Pyrazole-4-boronic acid pinacol esters of formula 1 reacts with 5-substituted-2,4-dichloropyrimidine under Suzuki coupling conditions to yield 4-pyrazole-substituted-2-chloropyrimidines of formula 2. The latter can be subjected to acid catalyzed chlorine replacement with aniline of formula $NH_2$-A-D-E-G to generate compounds of formula 3. When $NH_2$-A-D-E-G is amines, the replacement reaction can be achieved directly by heating up mixture of 2 and the amine, without the presence of an acid catalyst.

Scheme 1

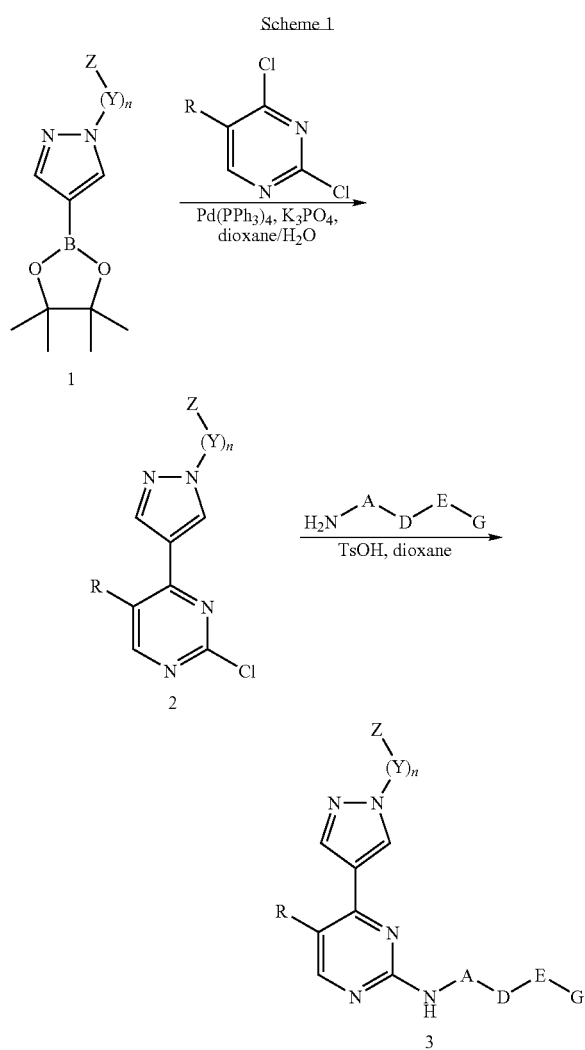

Scheme 2

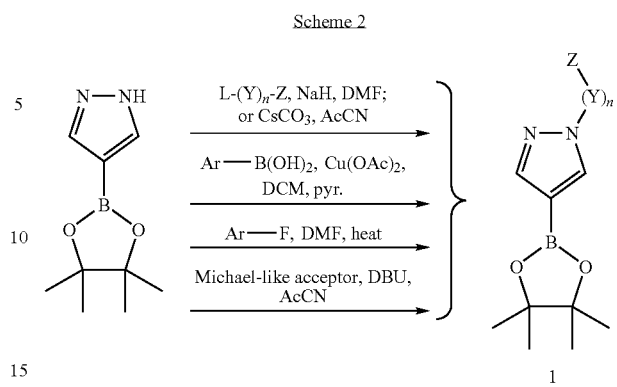

As shown in Scheme 2, pyrazole-4-boronic acid pinacol esters of formula 1 can be prepared by reaction of commercially available pyrazole-4-boronic acid pinacol esters with L-(Y)$_n$—Z where L represents a leaving group such as halide, triflate or the like under basic condition.

The N-aryl pyrazole of formula 1 (wherein Y is aromatic) may be prepared by reacting 4-pyrazole-4-boronic acid pinacol esters with an appropriately substituted aryl boronic acid in a solvent such as dichloromethane (DCM), in the presence of copper acetate and pyridine. Alternatively the N-aryl pyrazole of formula 1 (wherein Y is aromatic) can be prepared by reacting pyrazole-4-boronic acid pinacol esters with an appropriately substituted aryl-fluoride in a solvent such as DMF at elevated temperature.

The substituted pyrazole compounds of formula 1 (wherein Z is a group such as nitrile or ester and Y is at least two carbons) can also be prepared by the reaction of pyrazole-4-boronic acid pinacol esters with an appropriately substituted acrylate, acrylonitrile or other Michael-like acceptors in a solvent such as acetonitrile (ACN) in the presence of a base such as 1,8-diazabicyclo[5.4.0]undec-7-ene (DBU) or triethylamine (TEA) and at a temperature below the boiling point of the solvent.

It should noted that in all of the Schemes described herein, if there are functional groups present on a substituent group such as Y, Z, R, $R^1$, $R^5$, etc., further modification can be made if appropriate and desired. For example, a CN group can be hydrolyzed to afford an amide group; a carboxylic acid can be converted to a ester, which in turn can be reduced to an alcohol, which in turn can be further modified. In another example, an OH group can be converted into a better leaving group such as mesylate, which in turn is suitable for nucleophilic substitution, such as by CN. Furthermore, an OH group can be subjected to Mitsunobu reaction conditions with phenol, or heteroaryl alcohol, to afford aryl or heteroaryl ether compounds. One skilled in the art will recognize further modifications.

It should be further noted that the reaction sequences described above can be modified to suit different target molecules. For instance, 4-pyrazoleboronic acid pinacol esters can be reacted with substituted-1,4-dichloropyrimidine to generate the Suzuki product first. The pyrazole NH group of the Suzuki product can then be further functionalized as described in Scheme 2.

Methods

Compounds of the invention can modulate activity of one or more various kinases including, for example, Janus kinases (JAKs). The term "modulate" is meant to refer to an ability to increase or decrease the activity of the kinase. Accordingly, compounds of the invention can be used in methods of modulating kinases, such as a JAK kinase, by contacting the kinase with any one or more of the compounds or compositions described herein. In some embodiments, compounds of the present invention can act as inhibitors of one or more kinases. In further embodiments, the compounds of the invention can be used to modulate activity of a kinase in an individual in need of modulation of the receptor by administering a modulating amount of a compound of the invention.

Given that cancer cell growth and survival can be impacted by multiple signaling pathways, the present invention can be useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

Kinases to which the present compounds bind and/or modulate include receptor and non-receptor Ser/Thr kinases such as TGF-βR, PKA, PKG, PKC, CaM-kinase, phosphorylase kinase, MEKK, ERK, MAPK, Akt, and mTOR; receptor Tyr kinases such as EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2; and non-receptor Tyr kinases such as Src, Fyn, Lck, Fgr, Btk, Fak, SYK, FRK, JAK, or ABL. Certain JAKs include JAK1, JAK2, JAK3 or TYK2. In some embodiments, the JAK is JAK1 or JAK2. In some embodiments, the JAK is JAK2. In some embodiments, the JAK is mutant. In some embodiments, the mutant JAK carries the V617F, F537-K539delinsL, H538QK539L, K539L, or N542-E543del mutations in JAK2. In some embodiments, the non-receptor Tyr kinase is ABL such as ABL1 or ARG (ABL2). In some embodiments, the ABL is mutant. In some embodiments, the mutant ABL carries the T315I mutation. In some embodiments, the mutant ABL carries the T315D, F359D, D276G, E255K, M351T, G250E, H396R, Q252H, Y253H, E355G, F317L, G250E, Y253F, F359V, Q252R, L387M, M244V, M343T/F382L, or V379I mutation. In some embodiments, both JAK and ABL kinase activities are modulated. In some embodiments, the kinase results from the fusion of multiple genes such as where the fusion occurs between two genes as follows: BCR/ABL1, TEL/ABL1, NUP214/ABL1, EMS/ABL1, SFQ/ABL1, BCR/ARG, TEL/ARG, TEL/PDGFβR, HIP1/PDGFβR, RAB5/PDGFβR, H4/PDGFβR, Myomegalin/PDGFβR, CEV14/PDGFβR, NIN1/PDGFβR, HCMOGT/PDGFβR, KIAA1509/PDGFβR, TP53BP1/PDGFβR, FIIP1L1/PDGFβR, BCR/PDGFβR, BCR/JAK2, TEL/JAK2, PCM1/JAK2, TEL/SYK, TEL/TRKC, ZNF198/FGFR1, FOP/FGFR1, CEP110/FGFR1, HERVK/FGFR1, BCR/FGFR1, FGFR1OP2/FGFR1, TIF1/FGFR1, TEL/FGFR3, TEL/FLT3, TEL/FRK, NPM/ALK, TPM3/ALK, TFG/ALK, ATIC/ALK, CLTC/ALK, MSN/ALK, TPM4/ALK, ALO17/ALK, RANBP2/ALK, MYH9/ALK, CARS/ALK Kinases to which the present compounds bind and/or modulate include any member of the JAK family. In some embodiments, the JAK is JAK1, JAK2, JAK3 or TYK2. In some embodiments, the JAK is JAK1 or JAK2. In some embodiments, the JAK is JAK2. In some embodiments, the JAK is JAK3.

In some embodiments, more than one compound of the invention can be used to inhibit the activity of one kinase (e.g., JAK2).

In some embodiments, more than one compound of the invention can be used to inhibit more than one kinase (e.g., JAK2), such as at least two kinases (e.g., ABL1 and JAK2).

In some embodiments, the compound can be used in combination with another kinase inhibitor to inhibit the activity of one kinase (e.g., JAK2).

In some embodiments, the compound can be used in combination with another kinase inhibitor to inhibit the activities of more than one kinase (e.g., JAK2), such as at least two kinases.

The compounds of the invention can be selective. By "selective" is meant that the compound binds to or inhibits a kinase with greater affinity or potency, respectively, compared to at least one other kinase. In some embodiments, the compounds of the invention are selective inhibitors of JAK1 or JAK2 over JAK3 and/or TYK2. In some embodiments, the compounds of the invention are selective inhibitors of JAK2 (e.g., over JAK1, JAK3 and TYK2). Without wishing to be bound by theory, because inhibitors of JAK3 can lead to immunosuppressive effects, a compound which is selective for JAK2 over JAK3 and which is useful in the treatment of cancer (such as multiple myeloma, for example) can offer the additional advantage of having fewer immunosuppressive side effects. Selectivity can be at least about 5-fold, at least about 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, selectivity of compounds of the invention for JAK2 over JAK3 can be determined at the cellular ATP concentration. In some embodiments, the selectivity of compounds of the invention can be determined by cellular assays associated with particular JAK kinase activity.

Another aspect of the present invention pertains to methods of treating a kinase-associated disease or disorder in an individual (e.g., patient) by administering to the individual in need of such treatment a therapeutically effective amount or dose of a compound of the present invention or a pharmaceutical composition thereof. A kinase-associated disease can include any disease, disorder or condition that is directly or indirectly linked to expression or activity of the kinase, including over-expression and/or abnormal activity levels. Abnormal activity levels can be determined by comparing activity level in normal, healthy tissue or cells with activity level in diseased cells. A kinase-associated disease can also include any disease, disorder or condition that can be prevented, ameliorated, or cured by modulating kinase activity. In some embodiments, the disease is characterized by the abnormal activity of JAK, ABL, or both. In some embodiments, the disease is characterized by mutant JAK2, such as where the mutation resides in the pseudo-kinase domain. In some embodiments, the disease is characterized by mutant ABL, such as where the mutation resides in the kinase domain.

Examples of kinase-associated diseases include diseases involving the immune system including, for example, organ transplant rejection (e.g., allograft rejection and graft versus host disease).

Further examples of kinase-associated diseases include autoimmune diseases such as skin disorders, multiple sclerosis, rheumatoid arthritis, juvenile arthritis, type I diabetes, lupus, psoriasis, inflammatory bowel disease, ulcerative colitis, Crohn's disease, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP).

Further examples of kinase-associated diseases include allergic conditions such as asthma, food allergies, atopic dermatitis and rhinitis. Further examples of kinase-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of kinase-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one kinase inhibitor of the invention together with the agent causing unwanted sensitization can be helpful in treating such unwanted sensitization or dermatitis. In some embodiments, the skin disorder can be treated by topical administration of at least one kinase inhibitor of the invention.

In further embodiments, the kinase-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma etc.), hematological cancers (e.g., lymphoma, leukemia such as acute lymphoblastic leukemia, or multiple myeloma), and skin cancer such as cutaneous T-cell lymphoma (CTCL) and cutaneous B-cell lymphoma. Examples of cutaneous T-cell lymphomas include Sezary syndrome and mycosis fungoides. In further embodiments, the kinase-associated disease is endometrial and cervical cancer.

Kinase-associated diseases can further include those characterized by the presence of a mutation (genetic or epi-genetic) resulting in increased signaling from JAK kinases. These include diseases with mutated cytokine and growth factor receptors (e.g. mutant EpoR or MPL). Further, mutations downstream of JAKs which may result in a net increase in JAK pathway activation (e.g. SOCS or PIAS proteins) should also be considered kinase-associated.

Kinase-associated diseases can further include those characterized by expression of a mutant kinase. These include diseases characterized by expression of a mutant JAK2 such as those having at least one mutation in the pseudo-kinase domain (e.g., JAK2V617F) or near the pseudo-kinase domain (exon 12) (NEJM, 356:459-468; 2007)) and diseases characterized by expression of mutant ABL1 (e.g. BCR-ABL or ABL1T315I).

Kinase-associated diseases can further include myeloproliferative disorders (MPDs) such as polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), systemic mast cell disease (SMCD), and the like.

Further kinase-associated diseases include inflammation and inflammatory diseases. Example inflammatory diseases include inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases.

The kinase inhibitors described herein can further be used to treat ischemia reperfusion injuries or a disease or condition related to an inflammatory ischemic event such as stroke or cardiac arrest. The kinase inhibitors described herein can further be used to treat anorexia, cachexia, or fatigue such as that resulting from or associated with cancer. The kinase inhibitors described herein can further be used to treat restenosis, sclerodermitis, or fibrosis. Examples of fibrosis are renal fibrogenesis and pulmonary fibrosis. The kinase inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub 2004 Mar. 2.

Further provided are methods of treating an autoimmune disease, skin disorder, viral disease, cancer, or myeloproliferative disorder in a patient by administering to the patient a therapeutically effective amount of a compound of the invention (e.g., more than one compound). In some embodiments, a compound of the invention can be administered in combination with a further kinase inhibitor.

Further provided are methods of treating gout, systemic inflammatory response syndrome (SIRS), and septic shock by administering a compound of the invention. The present invention also provides methods of treating increased prostate size due to, e.g., benign prostatic hypertrophy or benign prostatic hyperplasia by administering a compound of the invention.

As used herein, the term "contacting" refers to the bringing together of indicated moieties in an in vitro system or an in vivo system. For example, "contacting" a kinase with a compound of the invention includes the administration of a compound of the present invention to an individual or patient, such as a human, having a kinase, as well as, for example, introducing a compound of the invention into a sample containing a cellular or purified preparation containing the kinase.

As used herein, the terms "individual" or "patient," used interchangeably, refer to any animal, including mammals, preferably mice, rats, other rodents, rabbits, dogs, cats, swine, cattle, sheep, horses, or primates, and most preferably humans. As used herein, the term "juvenile" refers to a human patient in which onset of the disease state or disorder occurs prior to the age of 18.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomotology of the disease; 2) inhibiting the disease; for example, inhibiting a disease, condition or disorder in an individual who is experiencing or displaying the pathology or symptomotology of the disease, condition or disorder (i.e., arresting further development of the pathology and/or symptomotology), or 3) ameliorating the disease; for example, ameliorating a disease, condition or disorder in an individual who is experiencing or displaying the pathology or symptomotology of the disease, condition or disorder (i.e., reversing the pathology and/or symptomotology).

Combination Therapies

One or more additional pharmaceutical agents such as, for example, chemotherapeutics, anti-inflammatory agents, steroids, immunosuppressants, as well as BCR-ABL1, Flt-3, EGFR, HER2, c-MET, VEGFR, PDGFR, cKit, IGF-1R, RAF and FAK kinase inhibitors such as, for example, those described in WO 2006/056399, or other agents can be used in combination with the compounds of the present invention for treatment of kinase-associated diseases, disorders or conditions. The one or more additional pharmaceutical agents can be administered to a patient simultaneously or sequentially. Therapeutic antibodies may be used in combination with the compounds of the present invention for treatment of kinase-associated diseases, disorders or conditions.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), and antibodies directed to c-MET.

Example chemotherapeutic include proteosome inhibitors (e.g., bortezomib), thalidomide, revlimid, and DNA-damaging agents such as melphalan, doxorubicin, cyclophosphamide, vincristine, etoposide, carmustine, and the like.

One or more of the following agents may be used in combination with the compounds of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methotrexate, temozolomide, cyclophosphamide, SCH 66336, R115777, L778,123, BMS 214662, Iressa, Tarceva, antibodies to EGFR, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycofor-mycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sm11, fludarabine, pentostatin, triapine, didox, trimidox, amidox, 3-AP, and MDL-101,731.

Example chemotherapeutic include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-ABL1 inhibitors include the compounds, and pharmaceutically acceptable salts thereof, of the genera and species disclosed in U.S. Pat. No. 5,521,184, WO 04/005281, EP2005/009967, EP2005/010408, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, one or more kinase inhibitors of the invention can be used in combination with a chemotherapeutic in the treatment of cancer and may improve the treatment response as compared to the response to the chemotherapeutic agent alone, without exacerbation of its toxic effects. Examples of additional pharmaceutical agents used in the treatment of cancers such as multiple myeloma, for example, can include without limitation, melphalan, melphalan plus prednisone [MP], doxorubicin, dexamethasone, and Velcade (bortezomib). Further additional agents used in the treatment of multiple myeloma include Bcr-ABL1, Flt-3, RAF and FAK kinase inhibitors. Additive or synergistic effects are desirable outcomes of combining a kinase inhibitor of the present invention with an additional agent. Furthermore, resistance of cancer cells (e.g. multiple myeloma, lung cancer, etc) to therapeutic agents (e.g. dexamethasone, melphalan, erlotinib/Tarceva, imatinib, dasatinib, etc.) may be reversible upon treatment with a kinase inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one kinase inhibitor where the dexamethasone, or other therapeutic, is administered intermittently as opposed to continuously.

In some further embodiments, combinations of one or more kinase inhibitors of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, for example see International Patent Pub. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The compounds of the Examples have been found to be JAK inhibitors according to at least one assay described herein.

EXAMPLES

In general, the exemplified compounds were purified on Waters XBridge reversed phase HPLC (RP-HPLC) column (C18, 19×100 mm, 5 μM), with an injection volume 2 mL and flow rate 30 mL/min, eluting with a gradient acetonitrile/water containing 0.15% NH$_4$OH. In cases where acidic preparative HPLC conditions were specified, the products were eluted with a gradient acetonitrile/water containing 0.01% trifluoroacetic acid (TFA).

Analytical LCMS were performed on Waters SunFire RP-HPLC column (C18, 2.1×50 mm, 5 μM), with an injection volume 2 μL, flow rate 3 mL/min, eluting with a gradient from 2 to 80% B in 3 minutes (A=water with 0.025% TFA; B=acetonitrile).

(3-Endo)-8-azabicyclo[3.2.1]octan-3-ol hydrochloride and 2-oxa-6-azatricyclo[3.3.1.13,7]decane hydrochloride were prepared according to procedures described in WO 2007/089683. 4,4-Dimethyl-1-oxa-7-azaspiro[4.4]nonane TFA salt was prepared according to procedures described in WO 2005/110992.

Example 1

3-(4-(2-(4-(1H-imidazol-1-yl)phenylamino)pyrimidin-4-yl)-1H-pyrazol-1-yl)-4-(1-(2,4-difluorobenzoyl)piperidin-4-yl)butanenitrile

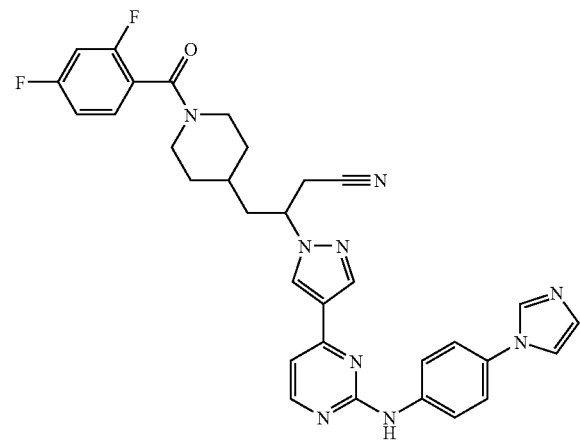

Step 1: tert-butyl 4-(2-oxoethyl)piperidine-1-carboxylate

Dimethyl sulfoxide (7.43 mL, 0.105 mol) was added to oxalyl chloride (5.53 mL, 0.0654 mol) in methylene chloride (244.2 mL) at −78° C. After 10 min, tert-butyl 4-(2-hydroxyethyl)piperidine-1-carboxylate (10.0 g, 0.0436 mol) in methylene chloride (488.4 mL) was added and the resultant mixture was stirred at −78° C. for 30 min. Triethylamine (30.4 mL, 0.218 mol) was then added and the mixture was stirred for 5 h with the temperature allowed to gradually warm up to room temperature. After being quenched with water, the mixture was extracted with methylene chloride. The organic layers were combined, washed with brine, dried over MgSO$_4$, evaporated to dryness and used directly in next step. LCMS (M+Na) 250.0.

Step 2: tert-butyl 4-(3-cyanoprop-2-en-1-yl)piperidine-1-carboxylate

To a solution of 1.0 M of potassium tert-butoxide in tetrahydrofuran (45.8 mL) at 0° C. was added dropwise a solution of diethyl cyanomethylphosphonate (7.77 mL, 0.0480 mol) in tetrahydrofuran (58.39 mL). The reaction was warmed to room temperature and then cooled at 0° C. again. To the reaction mixture was added a solution of tert-butyl 4-(2-oxoethyl)piperidine-1-carboxylate (9.91 g, 0.0436 mol) in tetrahydrofuran (11.7 mL). The reaction was allowed to warm up to room temperature and stirred at room temperature overnight. After being quenched with water, the mixture was extracted with EtOAc. The combined organic layers were washed with brine, dried and evaporated to dryness. The crude mixture was purified on silica gel, eluting with 0 to 40% EtOAc in hexanes, to give the desired product (8.22 g, 75% in 2 steps). LCMS (M+Na) 273.0.

Step 3: tert-butyl 4-(3-cyano-2-(4-(4,4,5,5-tetramethyl-1,3,2-dioxaborolan-2-yl)-1H-pyrazol-1-yl)propyl)piperidine-1-carboxylate To a solution of 4-(4,4,5,5-tetramethyl-1,3,2-dioxaborolan-2-yl)-1H-pyrazole (1.28 g, 6.60 mmol) in acetonitrile (33.0 mL) was added tert-butyl 4-(3-cyanoprop-2-en-1-yl)piperidine-1-carboxylate (3.30 g, 13.2 mmol), followed by 1,8-diazabicyclo[5.4.0]undec-7-ene (0.987 mL, 6.60 mmol). The resulting mixture was stirred at room temperature overnight. After evaporating the reaction mixture to dryness, the residue was purified on silica gel, eluting with 0-50% EtOAc in hexanes, to give the desired product (2.35 g, 80%). LCMS (M+H) 445.2

Step 4: tert-butyl 4-(2-(4-(2-chloropyrimidin-4-yl)-1H-pyrazol-1-yl)-3-cyanopropyl)piperidine-1-carboxylate A mixture of 2,4-dichloropyrimidine (0.26 g, 1.7 mmol), tert-butyl 4-3-cyano-2-(4-(4,4,5,5-tetramethyl-1,3,2-dioxaborolan-2-yl)-1H-pyrazol-1-yl)propylpiperidine-1-carboxylate (0.76 g, 1.7 mmol), tetrakis(triphenylphosphine) palladium (0.1 g, 0.1 mmol), and potassium phosphate (1.1 g, 5.2 mmol) in 1,4-dioxane (5 mL) and water (0.5 mL) was heated at 100° C. overnight. After cooling to room temperature, the mixture was diluted with EtOAc, washed with water, brine, dried over MgSO$_4$ and evaporated to dryness. The residue was purified on silica gel, eluting with 0 to 100% EtOAc in hexanes, to give the desired product (277 mg, 37%). LCMS (M+Na) 453.0.

Step 5: 3-(4-(2-chloropyrimidin-4-yl)-1H-pyrazol-1-yl)-4-(1-(2,4-difluorobenzoyl)piperidin-4-yl)butanenitrile To a mixture of tert-butyl 4-2-(4-(2-chloropyrimidin-4-yl)-1H-pyrazol-1-yl)-3-cyanopropylpiperidine-1-carboxylate (0.277 g, 0.643 mmol) in 2 mL of dioxane was added 4 mL of 4 M HCl in dioxane. The reaction was stirred at room temperature for 30 min, then evaporated to dryness. To the resulting crude HCl salt in methylene chloride (5.0 mL) was added triethylamine (0.269 mL, 1.93 mmol) followed by 2,4-difluorobenzoyl chloride (0.0948 mL, 0.771 mmol). The mixture was stirred at room temperature for 30 min, washed with saturated sodium bicarbonate, dried, and evaporated to dryness. The crude product obtained was used directly in next step (300 mg, 99%). LCMS (M+H) 471.0.

Step 6: 3-(4-(2-(4-(4H-imidazol-1-yl)phenylamino)pyrimidin-4-yl)-1H-pyrazol-1-yl)-4-(1-(2,4-difluorobenzoyl)piperidin-4-yl)butanenitrile A mixture of 3-(4-(2-chloropyrimidin-4-yl)-1H-pyrazol-1-yl)-4-(1-(2,4-difluorobenzoyl)piperidin-4-yl)butanenitrile (30 mg, 0.06 mmol), 4-(1H-imidazol-1-yl)aniline (15.2 mg, 0.0956 mmol), and p-toluenesulfonic acid (9.3 mg, 0.054 mmol) in dry 1,4-dioxane (0.5 mL) was refluxed overnight. The mixture was diluted with acetonitrile and water, purified on RP-HPLC to give the desired product as a racemic mixture (25 mg, 71%). LCMS (M+H) 594.1.

Example 2

4-(1-(2,4-difluorobenzoyl)piperidin-4-yl)-3-(4-(2-(4-(piperazin-1-yl)phenylamino)pyrimidin-4-yl)-1H-pyrazol-1-yl)butanenitrile

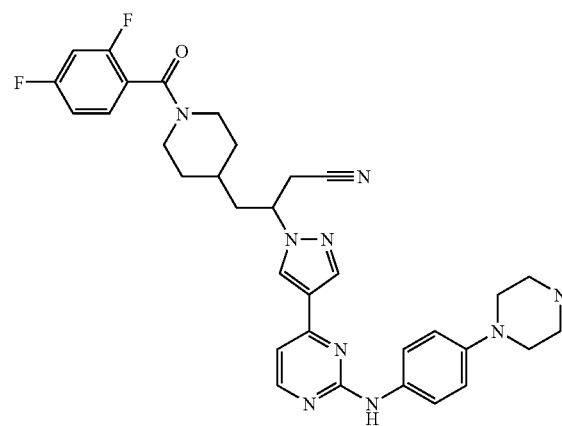

This compound was prepared as a racemic mixture according to the procedure described in example 1, replacing 4-(1H-imidazol-1-yl)aniline with 1-(4-amino-phenyl)-piperazine-4-carboxylic acid tert-butyl ester in step 6. LCMS (M+H) 611.2.

Example 3

4-(1-(2,4-difluorobenzoyl)piperidin-4-yl)-3-(4-(2-(4-methoxyphenylamino)pyrimidin-4-yl)-1H-pyrazol-1-yl)butanenitrile

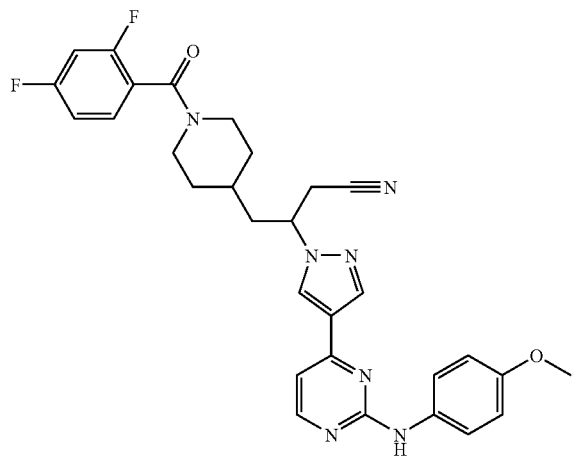

This compound was prepared as a racemic mixture according to the procedure described in example 1, using p-methoxyaniline instead of 4-(1H-imidazol-1-yl)aniline in step 6. LCMS (M+H) 558.2.

Example 4

4-(1-(2,4-difluorobenzoyl)piperidin-4-yl)-3-(4-(2-(phenylamino)pyrimidin-4-yl)-1H-pyrazol-1-yl)butanenitrile

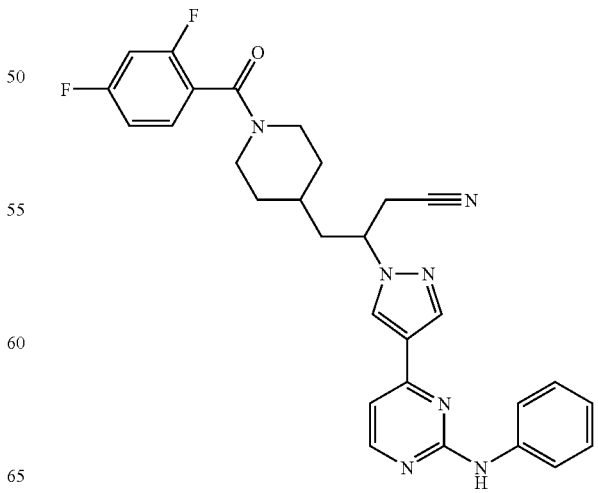

This compound was prepared as a racemic mixture according to the procedure described in example 1, using aniline instead of 4-(1H-imidazol-1-yl)aniline in step 6. LCMS (M+H) 528.1.

Example 5

4-(1-(2,4-difluorobenzoyl)piperidin-4-yl)-3-(4-(2-(4-morpholinophenylamino)pyrimidin-4-yl)-1H-pyrazol-1-yl)butanenitrile

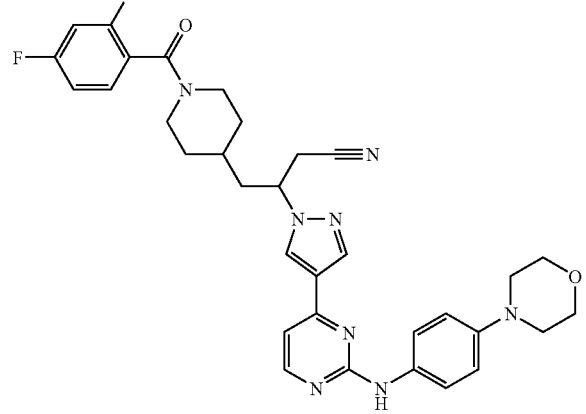

This compound was prepared as a racemic mixture according to the procedure described in example 1, using 4-(4-morpholinyl)-benzenamine instead of 4-(1H-imidazol-1-yl) aniline in step 6. LCMS (M+H) 613.3.

Example 6

3-(4-(2-(4-(1H-pyrazol-1-yl)phenylamino)pyrimidin-4-yl)-1H-pyrazol-1-yl)-4-(1-(2,4-difluorobenzoyl) piperidin-4-yl)butanenitrile

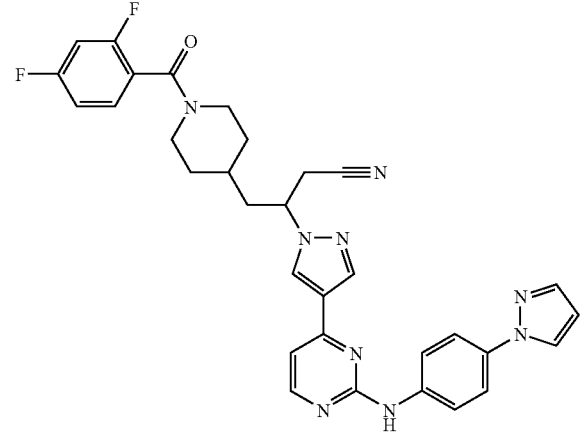

This compound was prepared as a racemic mixture according to the procedure described in example 1, using 4-(1H-pyrazol-1-yl)aniline instead of 4-(1H-imidazol-1-yl)aniline in step 6. LCMS (M+H) 594.2.

Example 7

4-(1-(2,4-difluorobenzoyl)piperidin-4-yl)-3-(4-(2-(3-(oxazol-5-yl)phenylamino)pyrimidin-4-yl)-1H-pyrazol-1-yl)butanenitrile

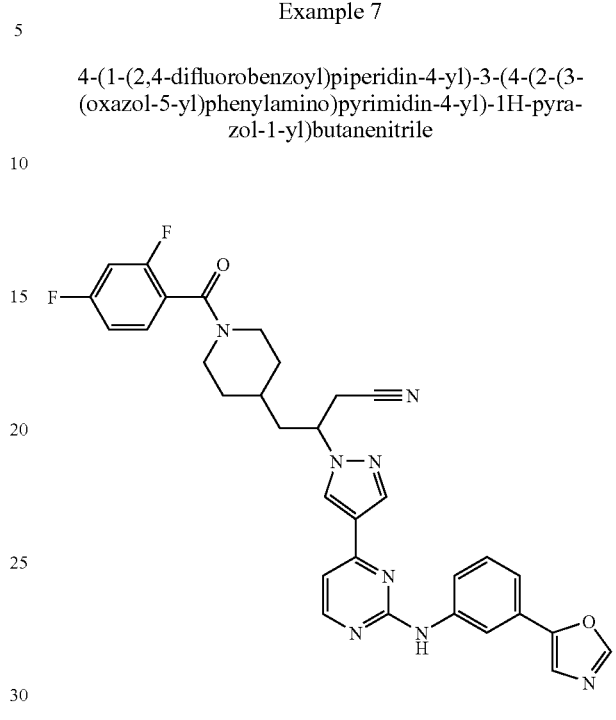

This compound was prepared as a racemic mixture according to the procedure described in example 1, using 3-(5-oxazolyl)-benzenamine instead of 4-(1H-imidazol-1-yl) aniline in step 6. LCMS (M+H) 595.2.

Example 8

4-(1-(2,4-difluorobenzoyl)piperidin-4-yl)-3-(4-(2-(1-methyl-1H-pyrazol-3-ylamino)pyrimidin-4-yl)-1H-pyrazol-1-yl)butanenitrile

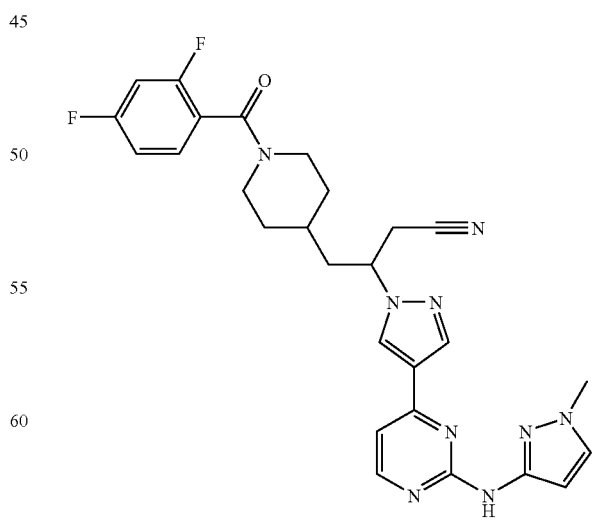

This compound was prepared as a racemic mixture according to the procedure described in example 1, using 1-methyl- 1H-pyrazol-3-amine instead of 4-(1H-imidazol-1-yl)aniline in step 6. LCMS (M+H) 532.1.

Example 11

4-(1-(2,4-difluorobenzoyl)piperidin-4-yl)-3-(4-(2-(4-phenoxyphenylamino)pyrimidin-4-yl)-1H-pyrazol-1-yl)butanenitrile

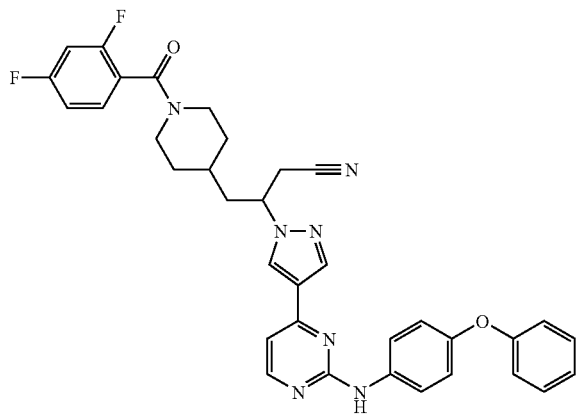

This compound was prepared as a racemic mixture according to the procedure described in example 1 using p-phenoxyaniline instead of 4-(1H-imidazol-1-yl)aniline in step 6. LCMS (M+H) 620.2.

Example 12

2-(4-(4-(2-(4-(1H-pyrazol-1-yl)phenylamino)pyrimidin-4-yl)-1H-pyrazol-1-yl)-1-(isoxazole-5-carbonyl)piperidin-4-yl)acetonitrile

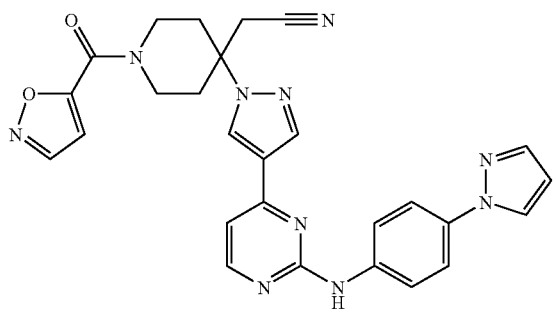

Step 1: tert-butyl 4-(cyanomethylene)piperidine-1-carboxylate

To a solution of 1.0 M of potassium tert-butoxide in tetrahydrofuran (26.3 mL) at 0° C. was added dropwise a solution of diethyl cyanomethylphosphonate (4.47 mL, 0.0276 mol) in tetrahydrofuran (33.61 mL). The reaction was warmed to room temperature and then cooled to 0° C. again. To the reaction mixture was added a solution of tert-butyl 4-oxo-1-piperidinecarboxylate (5.0 g, 0.025 mol) in tetrahydrofuran (6.72 mL). The reaction was allowed to warm up to room temperature and stirred at room temperature overnight. After being quenched with water, the mixture was extracted with EtOAc. The combined organic layers were washed with brine, dried and evaporated to dryness. The crude mixture was purified on silica gel, eluting with 0 to 60% EtOAc in hexanes, to give the desired product (5.40 g, 97%). LCMS (M+Na) 244.9.

Step 2: tert-butyl 4-(cyanomethyl)-4-(4-(4,4,5,5-tetramethyl-1,3,2-dioxaborolan-2-yl)-1H-pyrazol-1-yl)piperidine-1-carboxylate To a solution of 4-(4,4,5,5-tetramethyl-1,3,2-dioxaborolan-2-yl)-1H-pyrazole (4.3 g, 0.022 mol) in acetonitrile (50 mL) was added tert-butyl 4-(cyanomethylene)piperidine-1-carboxylate (4.9 g, 0.022 mol), followed by 1,8-diazabicyclo[5.4.0]undec-7-ene (3.3 mL, 0.022 mol). The resulting mixture was stirred at room temperature overnight. After being evaporated to dryness, the residue was purified on silica gel, eluting with 0-100% EtOAc in hexanes, to give the desired product (5.62 g, 61%). LCMS (M+H) 417.1.

Step 3: tert-butyl 4-(4-(2-chloropyrimidin-4-yl)-1H-pyrazol-1-yl)-4-(cyanomethyl)piperidine-1-carboxylate A mixture of 2,4-dichloropyrimidine (1.00 g, 6.71 mmol), tert-butyl 4-(cyanomethyl)-4-(4-(4,4,5,5-tetramethyl-1,3,2-dioxaborolan-2-yl)-1H-pyrazol-1-yl)piperidine-1-carboxylate (2.8 g, 6.7 mol), tetrakis(triphenylphosphine)palladium (0.5 g, 0.4 mmol), and potassium phosphate (4.3 g, 20 mmol) in 1,4-dioxane (20 mL) and water (2 mL) was heated at 100° C. overnight. After cooling to room temperature, the mixture was diluted with EtOAc, washed with water, brine, dried over $MgSO_4$, and concentrated. The residue was purified on silica gel, eluting with 0 to 100% EtOAc in hexanes, to give the desired product (2.19 g, 82%). LCMS (M+H) 403.0.

Step 4: (4-(4-(2-chloropyrimidin-4-yl)-1H-pyrazol-1-yl)-1-(isoxazol-5-ylcarbonyl)piperidin-4-yl)acetonitrile To a mixture of tert-butyl 4-(4-(2-chloropyrimidin-4-yl)-1H-pyrazol-1-yl)-4-(cyanomethyl)piperidine-1-carboxylate (0.259 g, 0.643 mmol) in 2 mL of dioxane was added 4 M HCl in dioxane (4.0 mL). The reaction was stirred at room temperature for 30 min, then evaporated to dryness. To the resulting crude HCl salt in methylene chloride (5.0 mL) was added triethylamine (0.269 mL, 1.93 mmol) followed by isoxazole-5-carbonyl chloride (0.0744 mL, 0.771 mmol). The mixture was stirred at room temperature for 30 min, washed with saturated sodium bicarbonate, dried, and evaporated to dryness. The residue was used directly in next step (233 mg, 91%). LCMS (M+H) 398.0.

Step 5: 1-(isoxazol-5-ylcarbonyl)-4-(4-(2-(4-(1H-pyrazol-1-yl)phenyl)aminopyrimidin-4-yl)-1H-pyrazol-1-yl)piperidin-4-ylacetonitrile A mixture of (4-(4-(2-chloropyrimidin-4-yl)-1H-pyrazol-1-yl)-1-(isoxazol-5-ylcarbonyl)piperidin-4-yl)acetonitrile (30 mg, 0.08 mmol), 4-(1H-pyrazol-1-yl)aniline (18.9 mg, 0.119 mmol), and p-toluenesulfonic acid (12 mg, 0.067 mmol) in dry 1,4-dioxane (0.6 mL) was refluxed overnight. The mixture was diluted with acetonitrile and water, purified on RP-HPLC to give the desired product as a racemic mixture (22 mg, 52%). LCMS (M+H) 521.1.

Example 13

2-(1-(isoxazole-5-carbonyl)-4-(4-(2-(3-(oxazol-5-yl)phenylamino)pyrimidin-4-yl)-1H-pyrazol-1-yl)piperidin-4-yl)acetonitrile

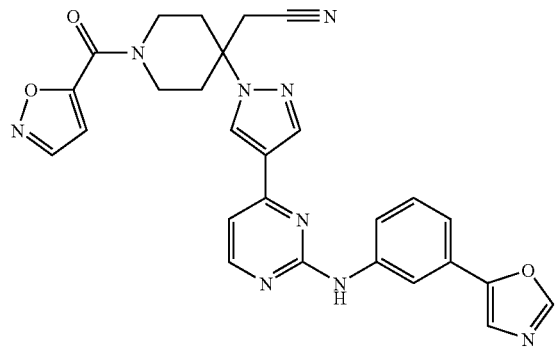

This compound was prepared as a racemic mixture according to the procedure described in example 12, using 3-(5-oxazolyl)-benzenamine instead of 4-(1H-pyrazol-1-yl)aniline in step 5. LCMS (M+H) 522.1.

Example 14

2-(4-(4-(2-(3-(1H-tetrazol-5-yl)phenylamino)pyrimidin-4-yl)-1H-pyrazol-1-yl)-1-(isoxazole-5-carbonyl)piperidin-4-yl)acetonitrile

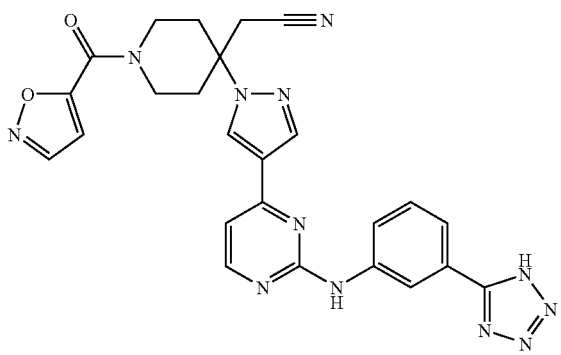

This compound was prepared as a racemic mixture according to the procedure described in example 12, using 3-(2H-tetrazol-5-yl)-benzenamine instead of 4-(1H-pyrazol-1-yl)aniline in step 5. LCMS (M+H) 523.0.

Example 15

2-(1-(isoxazole-5-carbonyl)-4-(4-(2-(4-(morpholinosulfonyl)phenylamino)pyrimidin-4-yl)-1H-pyrazol-1-yl)piperidin-4-yl)acetonitrile

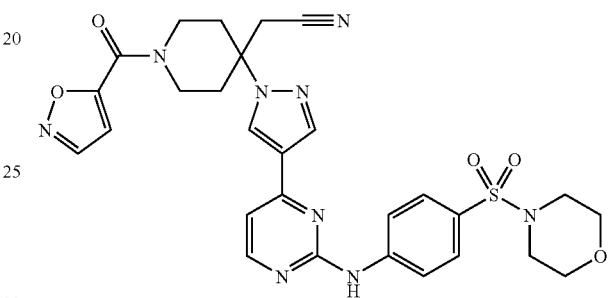

This compound was prepared as a racemic mixture according to the procedure described in example 12, using 4-(4-morpholinylsulfonyl)-benzenamine instead of 4-(1H-pyrazol-1-yl)aniline in step 5. LCMS (M+H) 604.2.

Example 16

2-(1-(isoxazole-5-carbonyl)-4-(4-(2-(6-methoxypyridin-3-ylamino)pyrimidin-4-yl)-1H-pyrazol-1-yl)piperidin-4-yl)acetonitrile

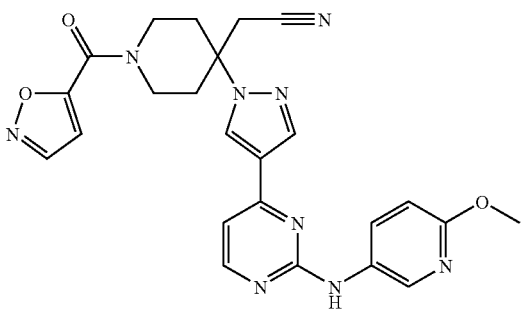

This compound was prepared as a racemic mixture according to the procedure described in example 12, using 6-methoxy-3-pyridinamine instead of 4-(1H-pyrazol-1-yl)aniline in step 5. LCMS (M+H) 486.1.

Example 17

2-(3-(4-(2-(4-(1H-pyrazol-1-yl)phenylamino)pyrimidin-4-yl)-1H-pyrazol-1-yl)-1-(cyclopropylsulfonyl)azetidin-3-yl)acetonitrile

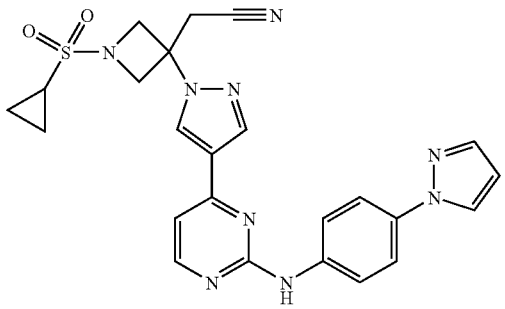

Step 1: tert-butyl 3-(cyanomethylene)azetidine-1-carboxylate

To a solution of 1.0 M of potassium tert-butoxide in tetrahydrofuran (30.7 mL) at 0° C. was added dropwise a solution of diethyl cyanomethylphosphonate (5.20 mL, 0.0322 mol) in tetrahydrofuran (39.12 mL). The reaction was warmed to room temperature and then cooled to 0° C. again. To the reaction mixture was added a solution of tert-butyl 3-oxoazetidine-1-carboxylate (5.0 g, 0.029 mol) in tetrahydrofuran (7.82 mL). The reaction was allowed to warm up to room temperature and stirred at room temperature overnight. After being quenched with water, the mixture was extracted with EtOAc. The combined organic layers were washed with brine, dried and evaporated to dryness. The crude mixture was purified on silica gel, eluting with 0 to 70% EtOAc in hexanes, to give the desired product (5.40 g, 95%). LCMS (M+Na) 217.1.

Step 2: tert-butyl 3-(cyanomethyl)-3-(4-(4,4,5,5-tetramethyl-1,3,2-dioxaborolan-2-yl)-1H-pyrazol-1-yl)azetidine-1-carboxylate To a solution of 4-(4,4,5,5-tetramethyl-1,3,2-dioxaborolan-2-yl)-1H-pyrazole (3.06 g, 0.0158 mol) in acetonitrile (50 mL) was added tert-butyl 3-(cyanomethylene)azetidine-1-carboxylate (3.06 g, 0.0158 mol), followed by 1,8-diazabicyclo[5.4.0]undec-7-ene (2.36 mL, 0.0158 mol). The resulting mixture was stirred at room temperature overnight. After evaporating to dryness, the residue was purified on silica gel, eluting with 0-100% EtOAc in hexanes, to give the desired product (5.40 g, 88%). LCMS (M+H) 389.1.

Step 3: tert-butyl 3-(4-(2-chloropyrimidin-4-yl)-1H-pyrazol-1-yl)-3-(cyanomethyl)azetidine-3-carboxylate A mixture of 2,4-dichloropyrimidine (1.0 g, 6.7 mmol), tert-butyl 3-(cyanomethyl)-3-(4-(4,4,5,5-tetramethyl-1,3,2-dioxaborolan-2-yl)-1H-pyrazol-1-yl)azetidine-1-carboxylate (2.6 g, 6.7 mmol), tetrakis(triphenylphosphine)palladium (0.5 g, 0.4 mmol), and potassium phosphate (4.3 g, 20 mmol) in 1,4-dioxane (20 mL) and water (2 mL) was heated at 100° C. overnight. After cooling to room temperature, the mixture was diluted with EtOAc, washed with water, brine, dried over MgSO$_4$, and concentrated. The residue was purified on silica gel, eluting with 0 to 100% EtOAc in hexanes, to give the desired product. (2.10 g, 83%). LCMS (M+H) 375.0.

Step 4: (3-(4-(2-chloropyrimidin-4-yl)-1H-pyrazol-1-yl)-1-(cyclopropylsulfonyl)azetidin-3-yl)acetonitrile To a mixture of tert-butyl 3-(4-(2-chloropyrimidin-4-yl)-1H-pyrazol-1-yl)-3-(cyanomethyl)azetidine-1-carboxylate (0.241 g, 0.643 mmol) in 2 mL of dioxane was added 4 M HCl in dioxane (4.0 mL). The reaction was stirred at room temperature for 30 min, then evaporated to dryness. To the resulting crude HCl salt in methylene chloride (5.0 mL) was added triethylamine (0.269 mL, 1.93 mmol) followed by cyclopropanesulfonyl chloride (0.0786 mL, 0.771 mmol). The mixture was stirred at room temperature for 30 min, washed with saturated sodium bicarbonate, dried, and evaporated to dryness. The residue was used directly in next step (229 mg, 94%). LCMS (M+H) 379.0.

Step 5: 1-(cyclopropylsulfonyl)-3-(4-(2-(4-(1H-pyrazol-1-yl)phenyl)aminopyrimidin-4-yl)-1H-pyrazol-1-yl)azetidin-3-ylacetonitrile A mixture of (3-(4-(2-chloropyrimidin-4-yl)-1H-pyrazol-1-yl)-1-(cyclopropylsulfonyl)azetidin-3-yl)acetonitrile (30 mg, 0.08 mmol), 4-(1H-pyrazol-1-yl)aniline (18.9 mg, 0.119 mmol), and p-toluenesulfonic acid (12 mg, 0.067 mmol) in dry 1,4-dioxane (0.6 mL) was refluxed overnight. The mixture was diluted with acetonitrile and water, purified on RP-HPLC to give the desired product as a racemic mixture (17.6 mg, 44%). LCMS (M+H) 502.0.

Example 18

2-(1-(cyclopropylsulfonyl)-3-(4-(2-(3-(oxazol-5-yl)phenylamino)pyrimidin-4-yl)-1H-pyrazol-1-yl)azetidin-3-yl)acetonitrile

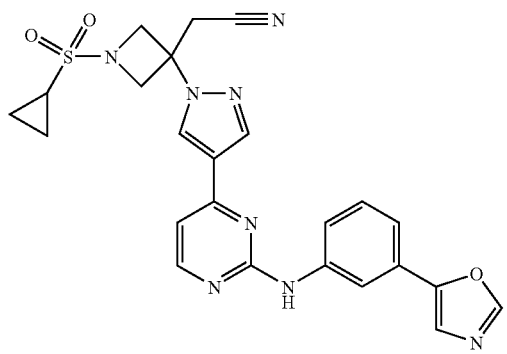

This compound was prepared according to the procedure described in example 17, using 3-(5-oxazolyl)-benzenamine instead of 4-(1H-pyrazol-1-yl)aniline in step 5. LCMS (M+H) 503.1.

Example 19

N-(4-(4-(1-(3-(cyanomethyl)-1-(cyclopropylsulfonyl)azetidin-3-yl)-1H-pyrazol-4-yl)pyrimidin-2-ylamino)phenyl)acetamide

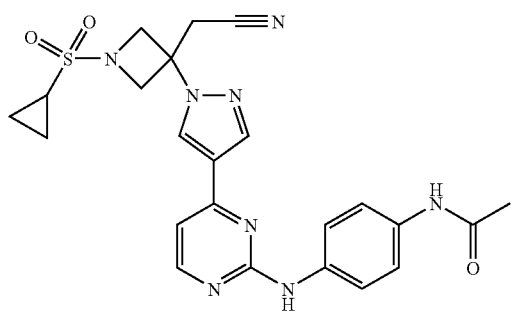

This compound was prepared according to the procedure described in example 17, using N-(4-aminophenyl)-acetamide instead of 4-(1H-pyrazol-1-yl)aniline in step 5. LCMS (M+H) 493.0.

Example 20

2-(1-(cyclopropylsulfonyl)-3-(4-(2-(3-(2-methylpyrimidin-4-yl)phenylamino)pyrimidin-4-yl)-1H-pyrazol-1-yl)azetidin-3-yl)acetonitrile

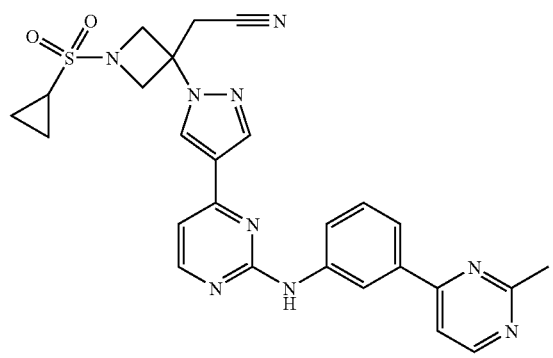

This compound was prepared according to the procedure described in example 17, using 3-(2-methyl-4-pyrimidinyl)-benzenamine instead of 4-(1H-pyrazol-1-yl)aniline in step 5. LCMS (M+H) 528.2.

Example 21

2-(1-(cyclopropylsulfonyl)-3-(4-(2-(4-(oxazol-5-yl)phenylamino)pyrimidin-4-yl)-1H-pyrazol-1-yl)azetidin-3-yl)acetonitrile

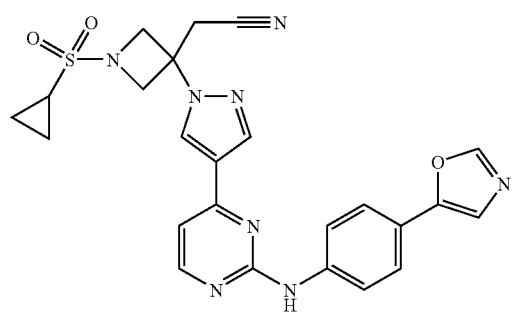

This compound was prepared according to the procedure described in example 17, using 4-(5-oxazolyl)-benzenamine instead of 4-(1H-pyrazol-1-yl)aniline in step 5. LCMS (M+H) 503.0.

Example 22

3-(4-(2-(4-morpholinophenylamino)pyrimidin-4-yl)-1H-pyrazol-1-yl)-3-(piperidin-4-yl)propanenitrile

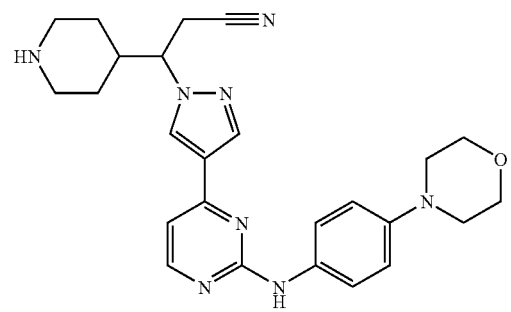

Step 1: tert-butyl 4-(2-cyanovinyl)piperidine-1-carboxylate

To a solution of 1.0 M of potassium tert-butoxide in tetrahydrofuran (24.6 mL) at 0° C. was added dropwise a solution of diethyl cyanomethylphosphonate (4.18 mL, 0.0258 mol) in tetrahydrofuran (31.40 mL). The reaction was warmed to room temperature and then cooled to 0° C. again. To the reaction mixture was added a solution of tert-butyl 4-formylpiperidine-1-carboxylate (5.0 g, 0.023 mol) in tetrahydrofuran (6.28 mL). The reaction was allowed to warm up to room temperature and stirred at room temperature overnight. After being quenched with water, the mixture was extracted with EtOAc. The combined organic layers were washed with brine, dried and evaporated to dryness. The crude mixture was purified on silica gel, eluting with 0 to 50% EtOAc in hexanes, to give the desired product (5.10 g, 92%). LCMS (M+Na) 259.0.

Step 2: tert-butyl 4-2-cyano-1-(4-(4,4,5,5-tetramethyl-1,3,2-dioxaborolan-2-yl)-1H-pyrazol-1-yl) ethylpiperidine-1-carboxylate To a solution of 4-(4,4,5,5-tetramethyl-1,3,2-dioxaborolan-2-yl)-1H-pyrazole (4.11 g, 0.0212 mol) in acetonitrile (70 mL) was added tert-butyl 4-(2-cyanovinyl)piperidine-1-carboxylate (5.00 g, 0.0212 mol), followed by 1,8-diazabicyclo[5.4.0]undec-7-ene (3.16 mL, 0.0212 mol). The resulting mixture was stirred at room temperature overnight. After evaporating to dryness, the residue was purified on silica gel, eluting with 0-100% EtOAc in hexanes, to give the desired product. (6.11 g, 67%). LCMS (M+H) 431.2.

Step 3: tert-butyl 4-1-(4-(2-chloropyrimidin-4-yl)-1H-pyrazol-1-yl)-2-cyanoethylpiperidine-1-carboxylate A mixture of 2,4-dichloropyrimidine (1.04 g, 6.98 mmol), tert-butyl 4-2-cyano-1-(4-(4,4,5,5-tetramethyl-1,3,2-dioxaborolan-2-yl)-1H-pyrazol-1-yl)ethylpiperidine-1-carboxylate (2.98 g, 6.93 mmol), tetrakis(triphenylphosphine)palladium (0.5 g, 0.4 mmol), and potassium phosphate (4.4 g, 0.021 mol) in 1,4-dioxane (20 mL) and water (2 mL) was heated at 100° C. overnight. After cooling to room temperature, the mixture was dilute with EtOAc, washed with water, brine, dried over MgSO$_4$, and concentrated. The residue was purified on silica gel, eluting with 0 to 100% EtOAc in hexanes, to give the desired product. (2.23 g, 77%). LCMS (M+H) 417.1.

Step 4. 3-(4-2-((4-morpholin-4-ylphenyl)amino)pyrimidin-4-yl-3H-pyrazol-1-yl)-3-piperidin-4-yl-propanenitrile A mixture of tert-butyl 4-1-(4-(2-chloropyrimidin-4-yl)-1H-pyrazol-1-yl)-2-cyanoethylpiperidine-1-carboxylate (800 mg, 0.002 mol), 4-morpholin-4-ylaniline (500 mg, 0.003 mol), and p-toluenesulfonic acid (270 mg, 0.0016 mol) in dry 1,4-dioxane (10 mL) was refluxed overnight. The mixture was diluted with water, extracted with EtOAc and the combined organic layers were washed with brine, dried and evaporated to dryness. The residue was purified on silica gel, eluting with 0 to 20% MeOH in dichloromethane, to give the desired product as a racemic mixture (30 mg, 4%). LCMS (M+H) 459.1.

Example 23

3-(1-(5-fluoropyrimidin-2-yl)piperidin-4-yl)-3-(4-(2-(4-morpholinophenylamino)pyrimidin-4-yl)-1H-pyrazol-1-yl)propanenitrile

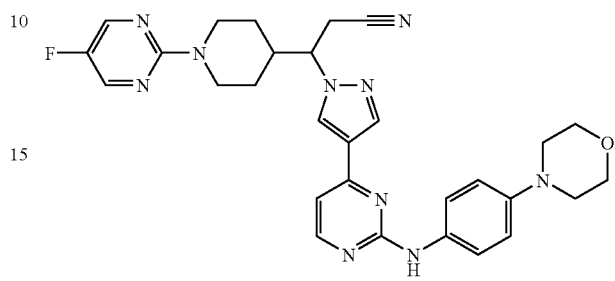

A mixture of 3-(4-2-((4-morpholin-4-ylphenyl)amino)pyrimidin-4-yl-1H-pyrazol-1-yl)-3-piperidin-4-ylpropanenitrile (0.030 g, 0.065 mmol), 2-chloro-5-fluoropyrimidine (0.013 g, 0.098 mmol), and N,N-diisopropylethylamine (0.023 mL, 0.13 mmol) in ethanol (0.5 mL) was heated at 120° C. in a sealed tube for 2 h. After evaporating to dryness, the residue was purified on RP-HPLC to give the desired product as a racemic mixture (12 mg, 33%), LCMS (M+H) 555.2.

Example 24

3-(1-(methylsulfonyl)piperidin-4-yl)-3-(4-(2-(4-morpholinophenylamino)pyrimidin-4-yl)-1H-pyrazol-1-yl)propanenitrile

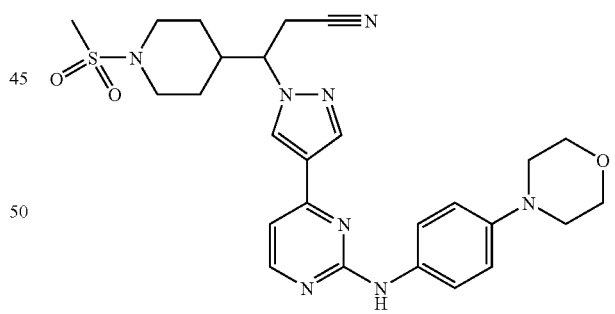

To a mixture of 3-(4-2-((4-morpholin-4-ylphenyl)amino)pyrimidin-4-yl-1H-pyrazol-1-yl)-3-piperidin-4-ylpropanenitrile trihydrochloride (30 mg, 0.05 mmol) in 1.0 M sodium carbonate in water (0.25 mL) and tetrahydrofuran (0.25 mL) was added methanesulfonyl chloride (6.1 μL, 0.079 mmol). The reaction was shaken at room temperature for 30 min. The mixture was diluted with water and acetonitrile, purified on RP-HPLC to give the desired product as a racemic mixture (TFA salt). LCMS (M+H) 537.1.

Example 25

3-(4-(2-(4-morpholinophenylamino)pyrimidin-4-yl)-1H-pyrazol-1-yl)-3-(1-(phenylsulfonyl)piperidin-4-yl)propanenitrile

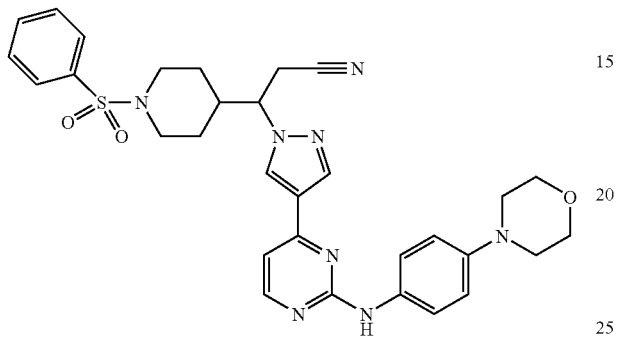

This compound was prepared as a racemic mixture according to the procedure described in example 24, using benzenesulfonyl chloride instead of methanesulfonyl chloride. LCMS (M+H) 599.1.

Example 26

3-(1-acetylpiperidin-4-yl)-3-(4-(2-(4-morpholinophenylamino)pyrimidin-4-yl)-1H-pyrazol-1-yl)propanenitrile

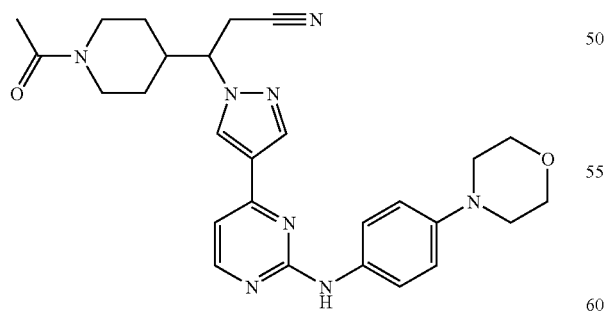

This compound was prepared as a racemic mixture according to the procedure described in example 24, using acetyl chloride instead of methanesulfonyl chloride. LCMS (M+H) 501.2.

Example 27

3-(1-benzoylpiperidin-4-yl)-3-(4-(2-(4-morpholinophenylamino)pyrimidin-4-yl)-1H-pyrazol-1-yl)propanenitrile

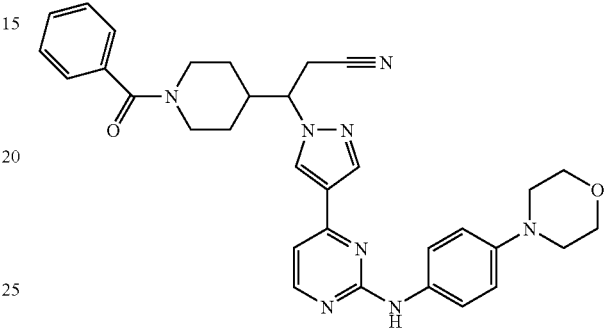

This compound was prepared as a racemic mixture according to the procedure described in example 24, using benzoyl chloride instead of methanesulfonyl chloride. LCMS (M+H) 563.2.

Example 28

2-(4-(4-(2-(4-(1H-pyrazol-1-yl)phenylamino)pyrimidin-4-yl)-1H-pyrazol-1-yl)-1-(cyclopropylsulfonyl)piperidin-4-yl)acetonitrile

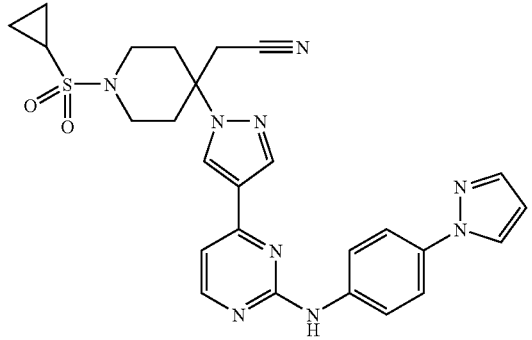

Step 1: (4-(4-(2-chloropyrimidin-4-yl)-1H-pyrazol-1-yl)-1-(cyclopropylsulfonyl)piperidin-4-yl)acetonitrile To a mixture of tert-butyl 4-(4-(2-chloropyrimidin-4-yl)-1H-pyrazol-1-yl)-4-(cyanomethyl)piperidine-1-carboxylate (0.487 g, 1.21 mmol) in 2 mL of dioxane was added 4 M HCl in dioxane (4.0 mL). The reaction was stirred at room temperature for 30 min, then evaporated to dryness. To the resulting crude HCl salt in methylene chloride (9.4 mL) was added triethylamine (0.505 mL, 3.62 mmol) followed by cyclopropanesulfonyl chloride (0.148 mL, 1.45 mmol). The mixture was stirred at room temperature for 30 min, washed with saturated sodium bicarbonate, dried, and evaporated to dryness. The residue was used directly in next step (402 mg, 82%). LCMS (M+H) 407.0.

Step 2: 1-(cyclopropylsulfonyl)-4-(4-(2-(4-(1H-pyrazol-1-yl)phenyl)aminopyrimidin-4-yl)-1H-pyrazol-1-yl)piperidin-4-ylacetonitrile A mixture of (4-(4-(2-chloropyrimidin-4-yl)-1H-pyrazol-1-yl)-1-(cyclopropylsulfonyl)piperidin-4-yl)acetonitrile (30 mg, 0.08 mmol), 4-(1H-pyrazol-1-yl)aniline (18.9 mg, 0.119 mol), and p-toluenesulfonic acid (12 mg, 0.067 mmol) in dry 1,4-dioxane (0.6 mL) was refluxed overnight. The mixture was diluted with acetonitrile and water, purified on RP-HPLC at pH 10 to give the desired product as free base (30 mg, 72%). LCMS (M+H) 530.1.

Example 29

2-(1-(cyclopropylsulfonyl)-4-(4-(2-(4-morpholinophenylamino)pyrimidin-4-yl)-1H-pyrazol-1-yl)piperidin-4-yl)acetonitrile

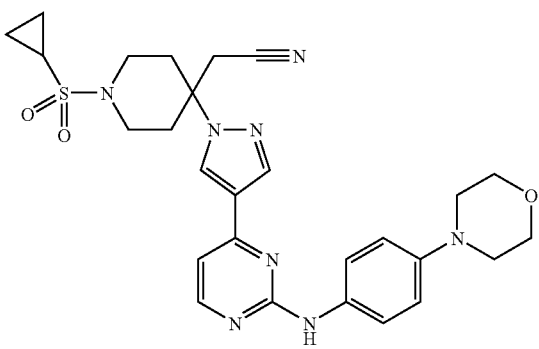

This compound was prepared according to the procedure described in example 28, using 4-morpholin-4-ylaniline instead of 4-(1H-pyrazol-1-yl)aniline in step 2. LCMS (M+H) 549.1.

Example 30

4-(4-(1-(4-(cyanomethyl)-1-(cyclopropylsulfonyl)piperidin-4-yl)-1H-pyrazol-4-yl)pyrimidin-2-ylamino)benzamide

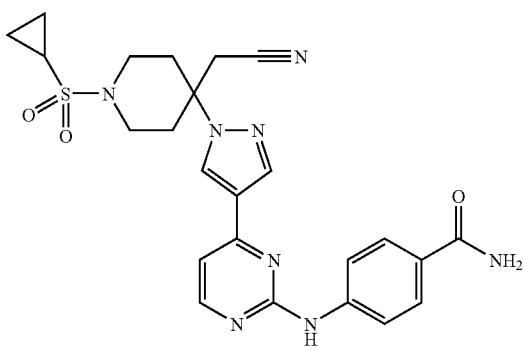

This compound was prepared according to the procedure described in example 28, using 4-amino-benzamide instead of 4-(1H-pyrazol-1-yl)aniline in step 2. LCMS (M+H) 507.0.

Example 31

4-(4-(1-(4-(cyanomethyl)-1-(cyclopropylsulfonyl)piperidin-4-yl)-1H-pyrazol-4-yl)pyrimidin-2-ylamino)-N-(2-hydroxyethyl)benzamide

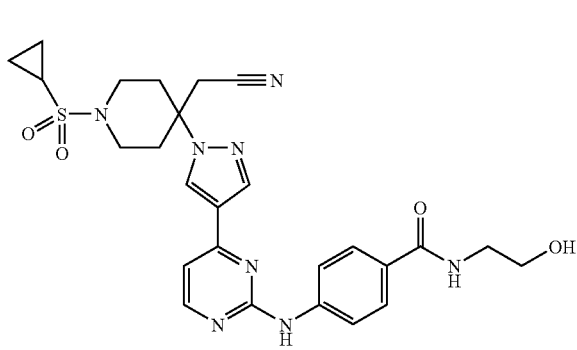

This compound was prepared according to the procedure described in example 28, using 4-amino-N-(2-hydroxyethyl)-benzamide instead of 4-(1H-pyrazol-1-yl)aniline in step 2. LCMS (M+H) 551.0.

Example 32

4-(4-(1-(4-(cyanomethyl)-1-(cyclopropylsulfonyl)piperidin-4-yl)-1H-pyrazol-4-yl)pyrimidin-2-ylamino)-N,N-dimethylbenzamide

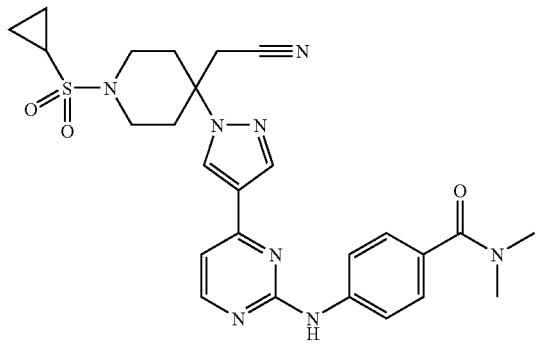

This compound was prepared according to the procedure described in example 28, using 4-amino-N,N-dimethyl-benzamide instead of 4-(1H-pyrazol-1-yl)aniline in step 2. LCMS (M+H) 535.2.

Example 33

4-(4-(1-(2-cyano-1-cyclopentylethyl)-1H-pyrazol-4-yl)pyrimidin-2-ylamino)benzamide

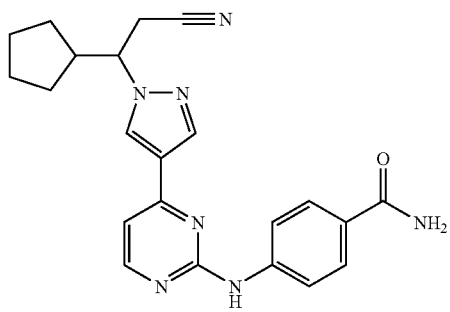

Step 1: 3-cyclopentyl-3-(4-(4,4,5,5-tetramethyl-1,3,2-dioxaborolan-2-yl)-1H-pyrazol-1-yl)propanenitrile To a solution of 4-(4,4,5,5-tetramethyl-1,3,2-dioxaborolan-2-yl)-1H-pyrazole (2.00 g, 0.0103 mol) in acetonitrile (30 mL) was added 3-cyclopentylacrylonitrile (1.25 g, 0.0103 mol), followed by 1,8-diazabicyclo[5.4.0]undec-7-ene (1.54 mL, 0.0103 mol). The resulting mixture was stirred at 60° C. overnight, then evaporated to dryness. The residue was purified on silica gel, eluting with 0 to 50% EtOAc in hexanes, to give the desired product (2.36 g, 73%). LCMS (M+H) 316.1.

Step 2: 3-(4-(2-chloropyrimidin-4-yl)-1H-pyrazol-1-yl)-3-cyclopentylpropanenitrile A mixture of 2,4-dichloropyrimidine (0.28 g, 1.9 mmol), 3-cyclopentyl-3-(4-(4,4,5,5-tetramethyl-1,3,2-dioxaborolan-2-yl)-1H-pyrazol-1-yl)propanenitrile (0.500 g, 1.59 mmol), tetrakis(triphenylphosphine)palladium (100 mg, 0.1 mmol), and potassium phosphate (1.0 g, 4.8 mmol) in 1,4-dioxane (5 mL) and water (0.5 mL) was heated at 100° C. overnight. After cooling to room temperature, the mixture was diluted with EtOAc, washed with water, brine, dried over MgSO$_4$, concentrated. The residue was purified on silica gel, eluting with 0 to 80% EtOAc in hexanes, to give the desired product (323 mg, 67%). LCMS (M+H) 302.0.

Step 3: 4-(4-(1-(2-cyano-1-cyclopentylethyl)-1H-pyrazol-4-yl)pyrimidin-2-ylamino)benzamide A mixture of 3-(4-(2-chloropyrimidin-4-yl)-1H-pyrazol-1-yl)-3-cyclopentylpropanenitrile (30 mg, 0.1 mmol), 4-amino-benzamide (20.3 mg, 0.149 mmol), and p-toluenesulfonic acid (14 mg, 0.084 mmol) in dry 1,4-dioxane (0.8 mL) was refluxed overnight. The mixture was diluted with acetonitrile and water, purified on RP-HPLC at pH 1 to give the desired product as a racemic mixture (TFA salt, 38 mg, 75%). LCMS (M+H) 402.1.

Example 34

3-(4-(2-(4-(1H-pyrazol-1-yl)phenylamino)pyrimidin-4-yl)-1H-pyrazol-1-yl)-3-cyclopentylpropanenitrile

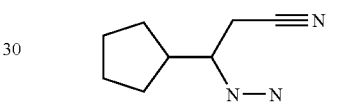

This compound was prepared as a racemic mixture according to the procedure described in example 33, using 4-(1H-pyrazol-1-yl)aniline instead of 4-amino-benzamide in step 3. LCMS (M+H) 425.0.

Example 35

3-cyclopentyl-3-(4-(2-(4-morpholinophenylamino)pyrimidin-4-yl)-1H-pyrazol-1-yl)propanenitrile

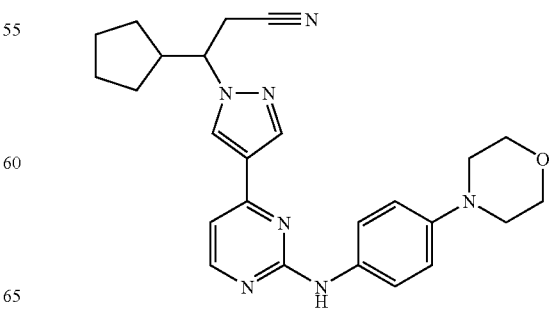

This compound was prepared as a racemic mixture according to the procedure described in example 33, using 4-morpholin-4-yl aniline instead of 4-amino-benzamide in step 3. LCMS (M+H) 444.1.

Example 36

3-cyclopentyl-3-(4-(2-(phenylamino)pyrimidin-4-yl)-1H-pyrazol-1-yl)propanenitrile

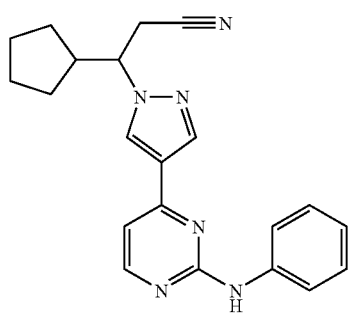

This compound was prepared as a racemic mixture according to the procedure described in example 33, using aniline instead of 4-amino-benzamide in step 3. LCMS (M+H) 359.0.

Example 37

3-cyclopentyl-3-(4-(2-(3-(oxazol-5-yl)phenylamino)pyrimidin-4-yl)-1H-pyrazol-1-yl)propanenitrile

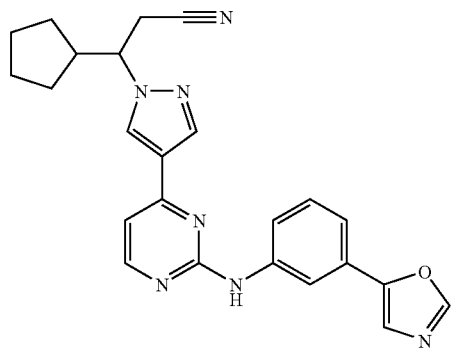

This compound was prepared as a racemic mixture according to the procedure described in example 33, using 3-(5-oxazolyl)-benzenamine instead of 4-amino-benzamide in step 3. LCMS (M+H) 426.0.

Example 38

3-cyclopentyl-3-(4-(2-(4-methoxyphenylamino)pyrimidin-4-yl)-1H-pyrazol-1-yl)propanenitrile

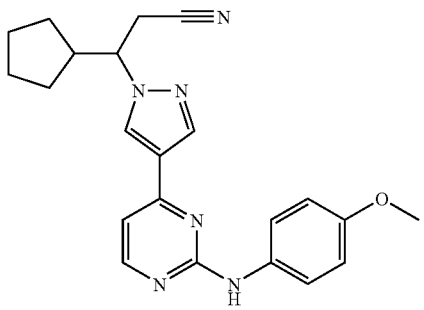

This compound was prepared as a racemic mixture according to the procedure described in example 33, using p-methoxyaniline instead of 4-amino-benzamide in step 3. LCMS (M+H) 389.1.

Example 39

N-(4-(4-(1-(2-cyano-1-cyclopentylethyl)-1H-pyrazol-4-yl)pyrimidin-2-ylamino)phenyl)acetamide

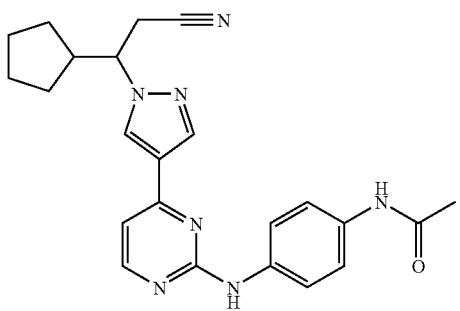

This compound was prepared as a racemic mixture according to the procedure described in example 33, using N-(4-aminophenyl)-acetamide instead of 4-amino-benzamide in step 3. LCMS (M+H) 416.0.

Example 40

4-(4-(1-(2-cyano-1-cyclopentylethyl)-1H-pyrazol-4-yl)pyrimidin-2-ylamino)-N,N-dimethylbenzamide

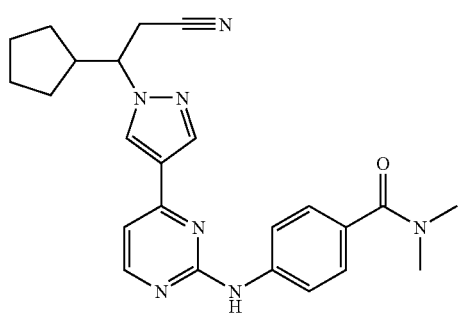

This compound was prepared as a racemic mixture according to the procedure described in example 33, using 4-amino-N,N-dimethyl-benzamide instead of 4-amino-benzamide in step 3. LCMS (M+H) 430.1.

Example 41

3-cyclopentyl-3-(4-(2-(4-(piperazin-1-yl)phenylamino)pyrimidin-4-yl)-1H-pyrazol-1-yl)propanenitrile

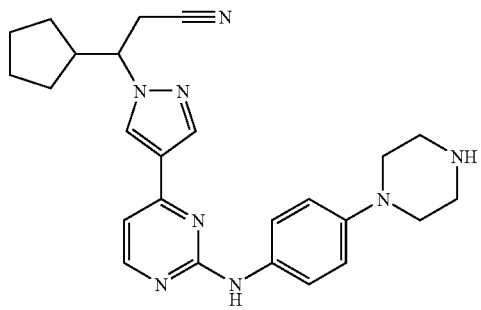

This compound was prepared as a racemic mixture according to the procedure described in example 33, using 1-(4-amino-phenyl)-piperazine-4-carboxylic acid tert-butyl ester instead of 4-amino-benzamide in step 3. LCMS (M+H) 443.1.

Example 42

4-(1-(ethylsulfonyl)piperidin-4-yl)-3-(4-(2-(4-morpholinophenylamino)pyrimidin-4-yl)-1H-pyrazol-1-yl)butanenitrile

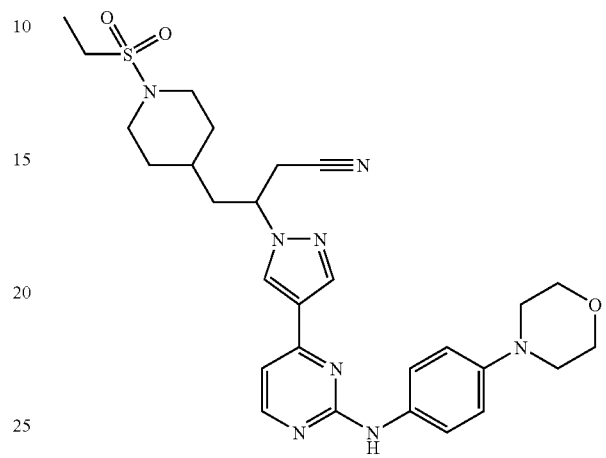

This compound was prepared as a racemic mixture according to the procedure described in example 1, using ethanesulfonyl chloride instead of 2,4-difluorobenzoyl chloride in step 5 and 4-morpholin-4-ylaniline instead of 4-(1H-imidazoyl-1-yl)aniline in step 6. LCMS (M+H) 565.1.

Example 43

3-(4-(2-(4-(1H-pyrazol-1-yl)phenylamino)pyrimidin-4-yl)-1H-pyrazol-1-yl)-4-(1-(ethylsulfonyl)piperidin-4-yl)butanenitrile

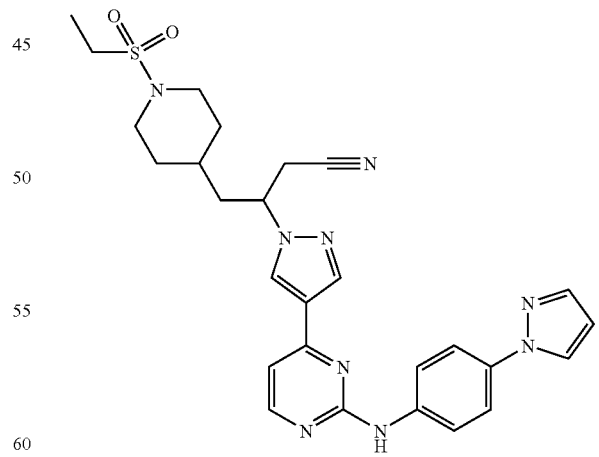

This compound was prepared as a racemic mixture according to the procedure described in example 1, using ethanesulfonyl chloride instead of 2,4-difluorobenzoyl chloride in step 5 and 4-(1H-pyrazol-1-yl)aniline instead of 4-(1H-imidazoyl-1-yl)aniline in step 6. LCMS (M+H) 546.2.

Example 44

4-(1-(ethylsulfonyl)piperidin-4-yl)-3-(4-(2-(phenylamino)pyrimidin-4-yl)-1H-pyrazol-1-yl)butanenitrile

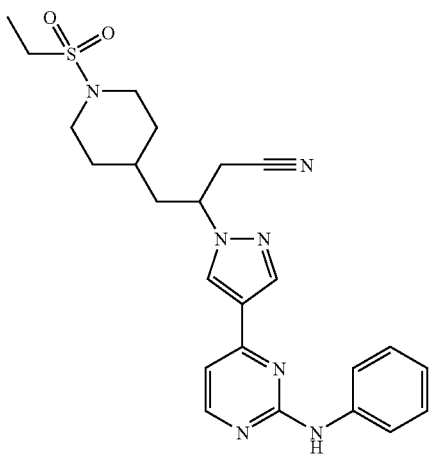

This compound was prepared as a racemic mixture according to the procedure described in example 1, using ethanesulfonyl chloride instead of 2,4-difluorobenzoyl chloride in step 5 and aniline instead of 4-(1H-imidazoyl-1-yl)aniline in step 6. LCMS (M+H) 480.1.

Example 45

N-(4-(4-(1-(1-cyano-3-(1-(1-methyl-1H-pyrazol-3-ylsulfonyl)piperidin-4-yl)propan-2-yl)-1H-pyrazol-4-yl)pyrimidin-2-ylamino)phenyl)acetamide

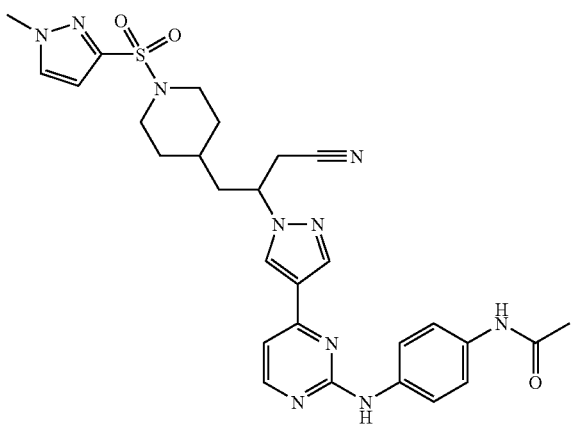

This compound was prepared as a racemic mixture according to the procedure described in example 1, using 1-methyl-1H-pyrazole-3-sulfonyl chloride instead of 2,4-difluorobenzoyl chloride in step 5 and N-(4-aminophenyl)-acetamide instead of 4-(1H-imidazoyl-1-yl)aniline in step 6. LCMS (M+H) 589.1.

Example 46

4-(4-(1-(1-cyano-3-(1-(ethylsulfonyl)piperidin-4-yl)propan-2-yl)-1H-pyrazol-4-yl)pyrimidin-2-ylamino)-N,N-dimethylbenzamide

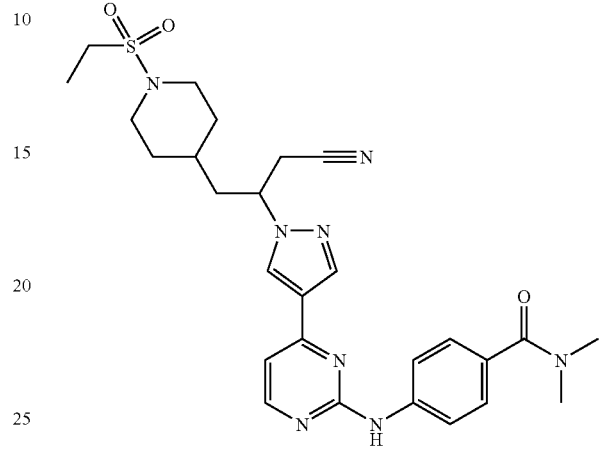

This compound was prepared as a racemic mixture according to the procedure described in example 1, using ethanesulfonyl chloride instead of 2,4-difluorobenzoyl chloride in step 5 and 4-amino-N,N-dimethyl-benzamide instead of 4-(1H-imidazoyl-1-yl)aniline in step 6. LCMS (M+H) 551.2.

Example 47

4-(4-(1-(1-cyano-3-(1-(1-methyl-1H-pyrazol-3-ylsulfonyl)piperidin-4-yl)propan-2-yl)-1H-pyrazol-4-yl)pyrimidin-2-ylamino)benzamide

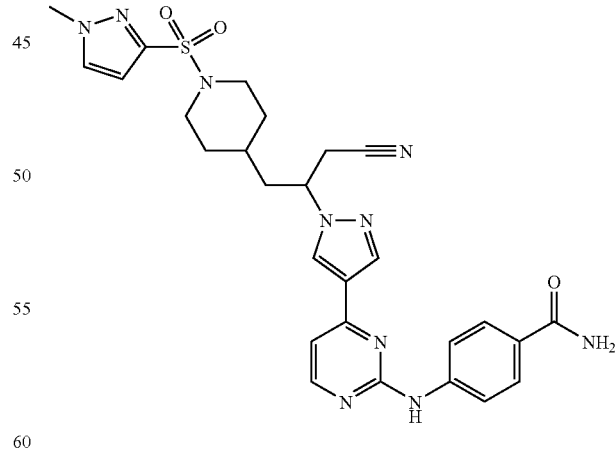

This compound was prepared as a racemic mixture according to the procedure described in example 1, using 1-methyl-1H-pyrazole-3-sulfonyl chloride instead of 2,4-difluorobenzoyl chloride in step 5 and 4-aminobenzamide instead of 4-(1H-imidazoyl-1-yl)aniline in step 6. LCMS (M+H) 575.1.

Example 48

4-(1-(ethylsulfonyl)piperidin-4-yl)-3-(4-(5-methyl-2-(4-morpholinophenylamino)pyrimidin-4-yl)-1H-pyrazol-1-yl)butanenitrile

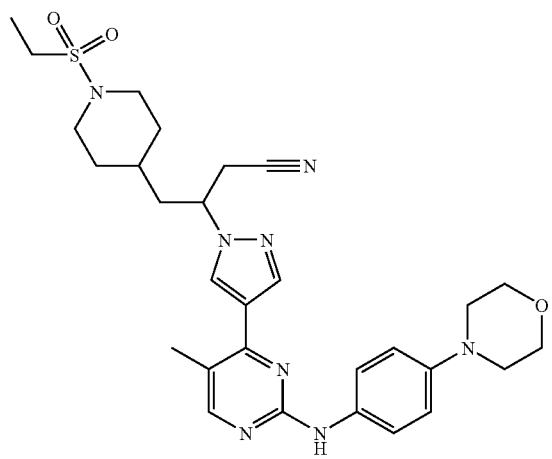

Step 1: tert-butyl 4-(2-(4-(2-chloro-5-methylpyrimidin-4-yl)-1H-pyrazol-1-yl)-3-cyanopropyl)piperidine-1-carboxylate A mixture of 2,4-dichloro-5-methylpyrimidine (0.44 g, 2.7 mmol), tert-butyl 4-3-cyano-2-(4-(4,4,5,5-tetramethyl-1,3,2-dioxaborolan-2-yl)-1H-pyrazol-1-yl)propylpiperidine-1-carboxylate (1.00 g, 2.25 mol), tetrakis(triphenylphosphine) palladium (0.2 g, 0.1 mmol), and potassium phosphate (1.4 g, 6.8 mmol) in 1,4-dioxane (7 mL) and water (0.7 mL) was heated at 100° C. overnight. After cooling to room temperature, the mixture was diluted with EtOAc, washed with water, brine, dried over MgSO$_4$, concentrated. The residue was purified on silica gel, eluting with 0 to 100%, to give the desired product (652 mg, 65%). LCMS (M+Na) 467.0.

Step 2: 4-(1-(ethylsulfonyl)piperidin-4-yl)-3-(4-(5-ethyl-2-(4-morpholinophenylamino)pyrimidin-4-yl)-1H-pyrazol-1-yl)butanenitrile A mixture of tert-butyl 4-(2-(4-(2-chloro-5-methylpyrimidin-4-yl)-1H-pyrazol-1-yl)-3-cyanopropyl)piperidine-1-carboxylate (30 mg, 0.07 mmol), 4-morpholin-4-ylaniline (18.0 mg, 0.101 mmol), and p-toluenesulfonic acid (9.9 mg, 0.057 mmol) in dry 1,4-dioxane (0.5 mL) was refluxed overnight, to give amination product with loss of Boc group. LCMS (M+H) 487.2.

To the mixture from above was added 1.0 M sodium carbonate in water (0.5 mL) followed by ethanesulfonyl chloride (0.013 mL, 0.13 mmol). The reaction was stirred at room temperature for 1 h. The organic phase was separated and purified on RP-HPLC to give the desired product as a racemic mixture (TFA salt, 30 mg, 62%). LCMS (M+H) 579.2.

Example 49

3-(4-(2-(4-(1H-pyrazol-1-yl)phenylamino)-5-methylpyrimidin-4-yl)-1H-pyrazol-1-yl)-4-(1-(ethylsulfonyl)piperidin-4-yl)butanenitrile

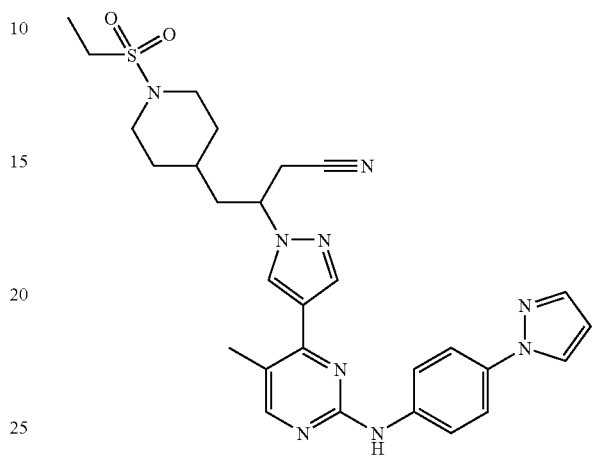

This compound was prepared as a racemic mixture according to the procedure described in example 48, using 4-(1H-pyrazol-1-yl)aniline instead of 4-morpholin-4-ylaniline in step 2. LCMS (M+H) 560.1.

Example 50

4-(1-(ethylsulfonyl)piperidin-4-yl)-3-(4-(5-methyl-2-(phenylamino)pyrimidin-4-yl)-1H-pyrazol-1-yl)butanenitrile

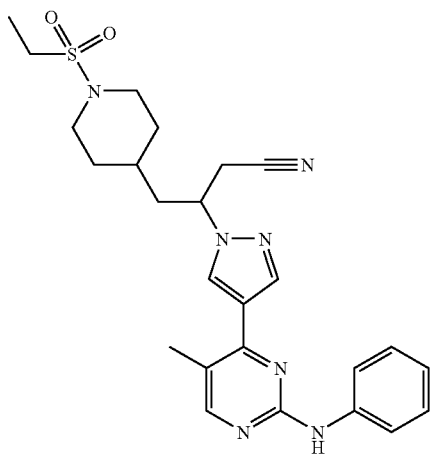

This compound was prepared as a racemic mixture according to the procedure described in example 48, using aniline instead of 4-morpholin-4-ylaniline in step 2. LCMS (M+H) 494.1.

Example 51

N-(4-(4-(1-(1-cyano-3-(1-(1-methyl-1H-pyrazol-3-ylsulfonyl)piperidin-4-yl)propan-2-yl)-1H-pyrazol-4-yl)-5-methylpyrimidin-2-ylamino)phenyl)acetamide

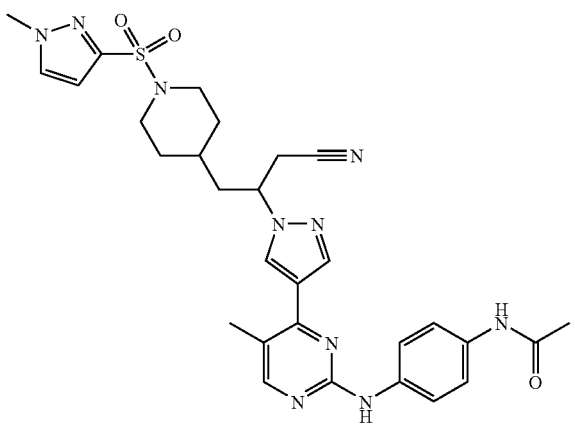

This compound was prepared as a racemic mixture according to the procedure described in example 48, using 1-methyl-1H-pyrazole-3-sulfonyl chloride instead of ethanesulfonyl chloride in step 1 and N-(4-aminophenyl)-acetamide instead of 4-morpholin-4-ylaniline in step 2. LCMS (M+H) 603.0.

Example 52

4-(4-(1-(1-cyano-3-(1-(ethylsulfonyl)piperidin-4-yl)propan-2-yl)-1H-pyrazol-4-yl)-5-methylpyrimidin-2-ylamino)-N,N-dimethylbenzamide

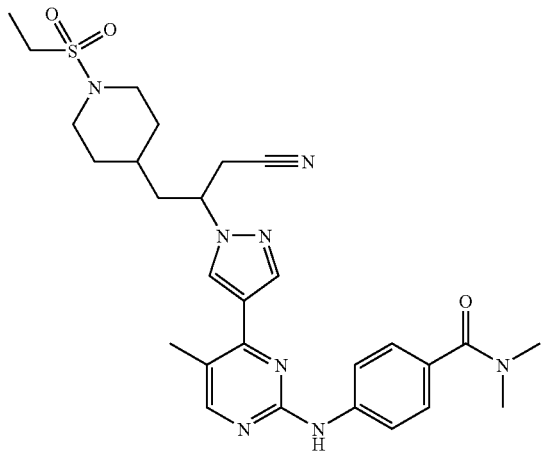

This compound was prepared as a racemic mixture according to the procedure described in example 48, using 4-amino-N,N-dimethyl-benzamide instead of 4-morpholin-4-ylaniline in step 2. LCMS (M+H) 565.1.

Example 53

4-(4-(1-(1-cyano-3-(1-(1-methyl-1H-pyrazol-3-ylsulfonyl)piperidin-4-yl)propan-2-yl)-1H-pyrazol-4-yl)-5-methylpyrimidin-2-ylamino)benzamide

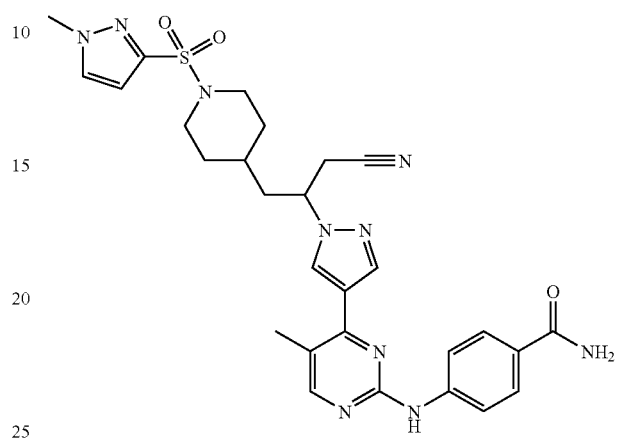

This compound was prepared as a racemic mixture according to the procedure described in example 48, using 1-methyl-1H-pyrazole-3-sulfonyl chloride instead of ethanesulfonyl chloride in step 1 and 4-aminobenzamide instead of 4-morpholin-4-ylaniline in step 2. LCMS (M+H) 589.2.

Example 54

3-cyclopentyl-3-(4-(2-(4-(4-(methylsulfonyl)piperazin-1-yl)phenylamino)pyrimidin-4-yl)-1H-pyrazol-1-yl)propanenitrile

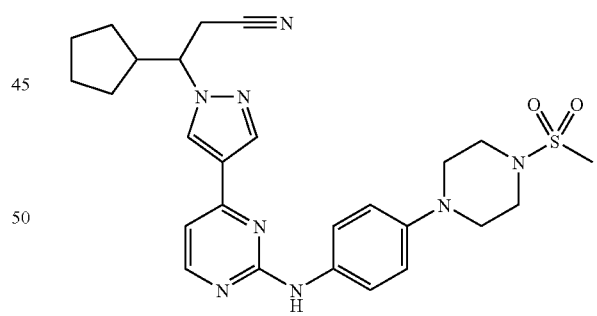

A mixture of 3-(4-(2-chloropyrimidin-4-yl)-1H-pyrazol-1-yl)-3-cyclopentylpropanenitrile (30 mg, 0.1 mmol), 4-(piperazin-1-yl)aniline (28.5 mg, 0.149 mmol), and p-toluenesulfonic acid (14 mg, 0.084 mmol) in dry 1,4-dioxane (0.8 mL) was refluxed overnight, then cooled to room temperature. To the resulting mixture was added 1.0 M sodium carbonate in water (0.8 mL), followed by methanesulfonyl chloride (0.015 mL, 0.20 mmol). The reaction was stirred at room temperature for 30 min and the phases were separated. The organic phase was purified on RP-HPLC at pH 10 to give the desired product as a racemic mixture (33 mg, 63%). LCMS (M+H) 521.1.

Example 55

4-(1-(1-methyl-1H-pyrazol-3-ylsulfonyl)piperidin-4-yl)-3-(4-(2-(4-morpholinophenylamino)pyrimidin-4-yl)-1H-pyrazol-1-yl)butanenitrile

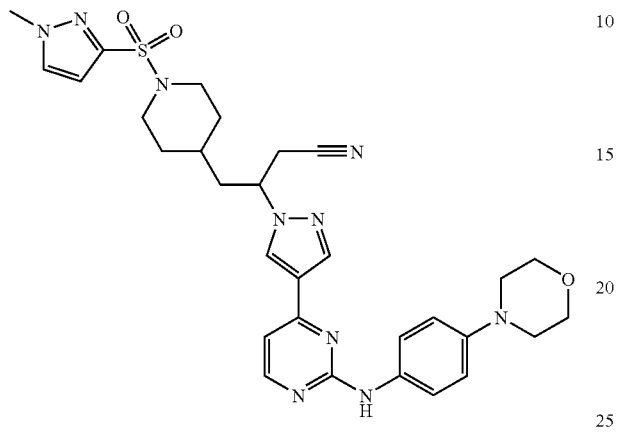

This compound was prepared as a racemic mixture according to the procedure described in example 1, using 1-methyl-1H-pyrazole-3-sulfonyl chloride instead of 2,4-difluorobenzoyl chloride in step 5 and 4-morpholin-4-ylaniline instead of 4-(1H-imidazoyl-1-yl)aniline in step 6. LCMS (M+H) 617.2.

Example 56

3-(4-(2-(4-(1H-pyrazol-1-yl)phenylamino)pyrimidin-4-yl)-1H-pyrazol-1-yl)-4-(1-(1-methyl-1H-pyrazol-3-ylsulfonyl)piperidin-4-yl)butanenitrile

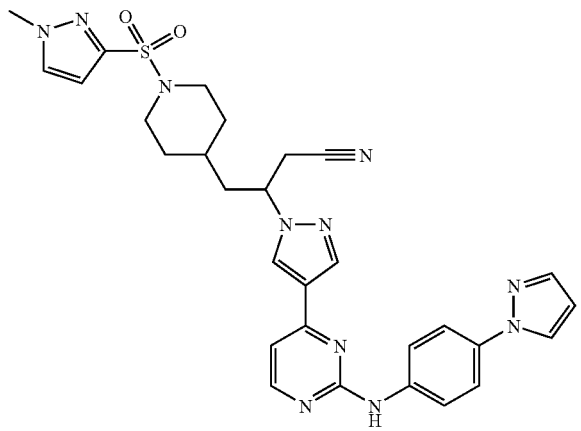

This compound was prepared as a racemic mixture according to the procedure described in example 1, using 1-methyl-1H-pyrazole-3-sulfonyl chloride instead of 2,4-difluorobenzoyl chloride in step 5 and 4-(1H-pyrazol-1-yl)aniline instead of 4-(1H-imidazoyl-1-yl)aniline in step 6. LCMS (M+H) 598.1.

Example 57

4-(1-(1-methyl-1H-pyrazol-3-ylsulfonyl)piperidin-4-yl)-3-(4-(2-(phenylamino)pyrimidin-4-yl)-1H-pyrazol-1-yl)butanenitrile

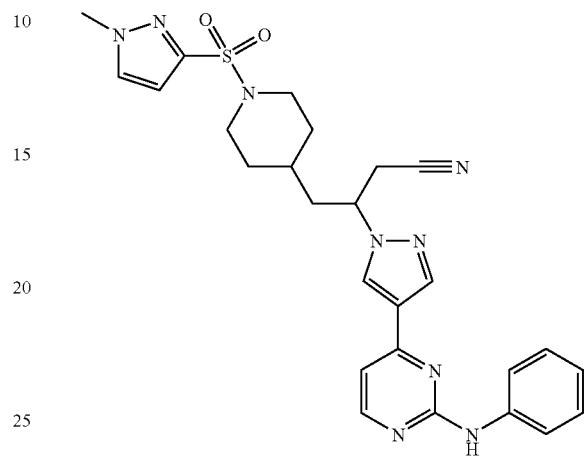

This compound was prepared as a racemic mixture according to the procedure described in example 1, using 1-methyl-1H-pyrazole-3-sulfonyl chloride instead of 2,4-difluorobenzoyl chloride in step 5 and aniline instead of 4-(1H-imidazoyl-1-yl)aniline in step 6. LCMS (M+H) 532.1.

Example 58

4-(4-(1-(1-cyano-3-(1-(1-methyl-1H-pyrazol-3-ylsulfonyl)piperidin-4-yl)propan-2-yl)-1H-pyrazol-4-yl)pyrimidin-2-ylamino)-N,N-dimethylbenzamide

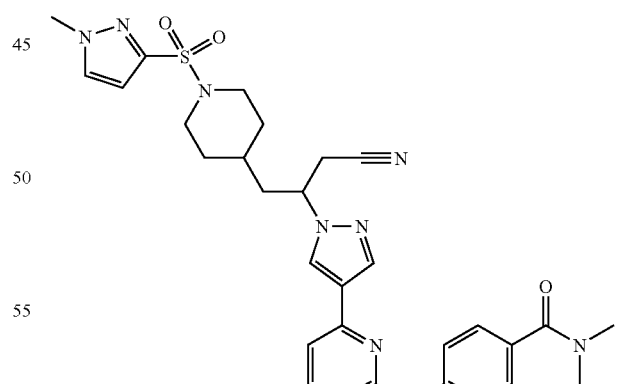

This compound was prepared as a racemic mixture according to the procedure described in example 1, using 1-methyl-1H-pyrazole-3-sulfonyl chloride instead of 2,4-difluorobenzoyl chloride in step 5 and 4-amino-N,N-dimethylbenzamide instead of 4-(1H-imidazoyl-1-yl)aniline in step 6. LCMS (M+H) 603.1.

Example 59

4-(4-(1-(1-cyano-3-(1-(2,4-difluorobenzoyl)piperidin-4-yl)propan-2-yl)-1H-pyrazol-4-yl)pyrimidin-2-ylamino)-N,N-dimethylbenzamide

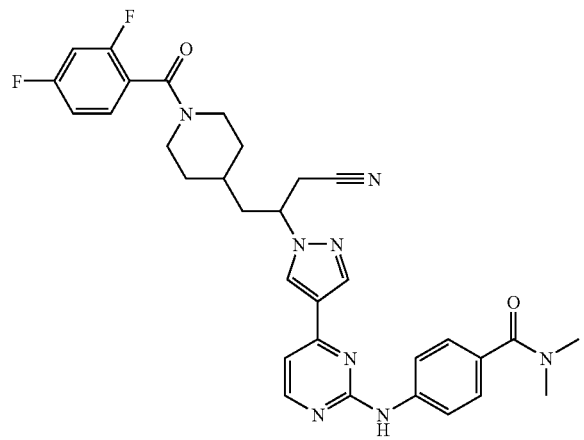

This compound was prepared as a racemic mixture according to the procedure described in example 1, using 4-amino-N,N-dimethyl-benzamide instead of 4-(1H-imidazoyl-1-yl) aniline in step 6. LCMS (M+H) 599.1.

Example 60

N-(4-(4-(1-(1-cyano-3-(1-(2,4-difluorobenzoyl)piperidin-4-yl)propan-2-yl)-1H-pyrazol-4-yl)pyrimidin-2-ylamino)phenyl)acetamide

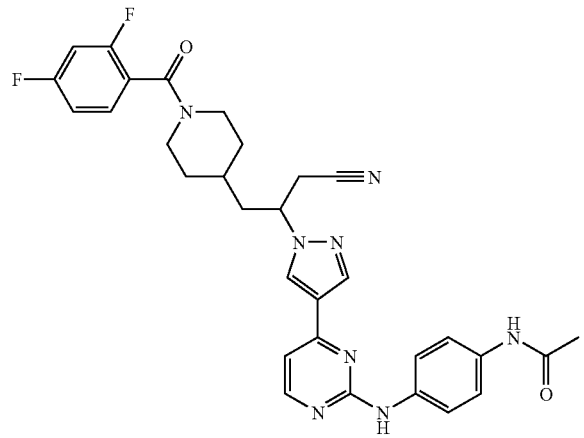

This compound was prepared as a racemic mixture according to the procedure described in example 1, using N-(4-aminophenyl)-acetamide instead of 4-(1H-imidazoyl-1-yl) aniline in step 6. LCMS (M+H) 585.1.

Example 61

4-(1-(1-methyl-1H-pyrazol-3-ylsulfonyl)piperidin-4-yl)-3-(4-(5-methyl-2-(4-morpholinophenylamino) pyrimidin-4-yl)-1H-pyrazol-1-yl)butanenitrile

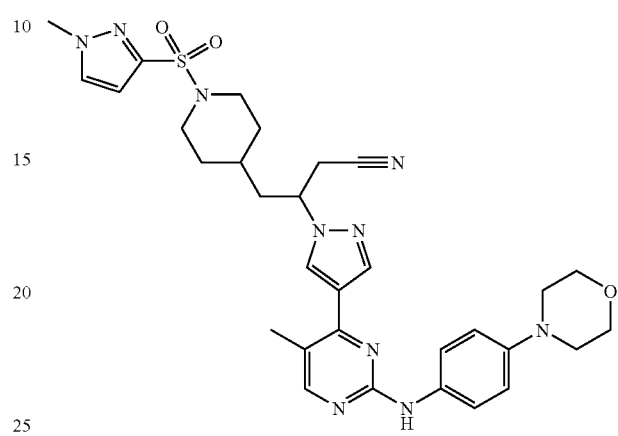

This compound was prepared as a racemic mixture according to the procedure described in example 48, using 1-methyl-1H-pyrazole-3-sulfonyl chloride instead of ethanesulfonyl chloride in step 1. LCMS (M+H) 631.1.

Example 62

4-(1-(2,4-difluorobenzoyl)piperidin-4-yl)-3-(4-(5-methyl-2-(4-morpholinophenylamino)pyrimidin-4-yl)-1H-pyrazol-1-yl)butanenitrile

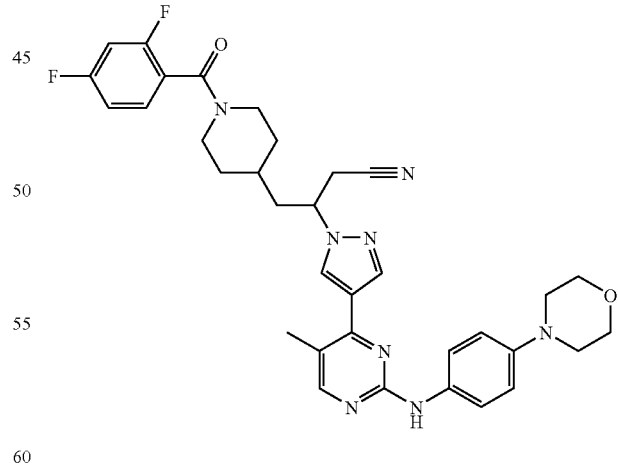

This compound was prepared as a racemic mixture according to the procedure described in example 48, using 2,4-difluorobenzoyl chloride instead of ethanesulfonyl chloride in step 1. LCMS (M+H) 627.1.

Example 63

3-(4-(2-(4-(1H-pyrazol-1-yl)phenylamino)-5-methylpyrimidin-4-yl)-1H-pyrazol-1-yl)-4-(1-(1-methyl-1H-pyrazol-3-ylsulfonyl)piperidin-4-yl)butanenitrile

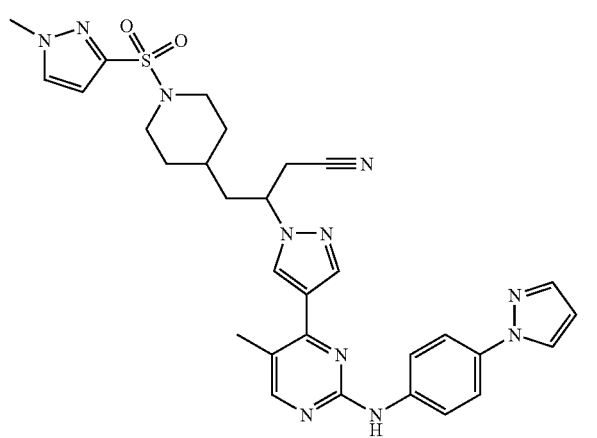

This compound was prepared as a racemic mixture according to the procedure described in example 48, using 1-methyl-1H-pyrazole-3-sulfonyl chloride instead of ethanesulfonyl chloride in step 1 and 4-(1H-pyrazol-1-yl)aniline instead of 4-morpholin-4-ylaniline in step 2. LCMS (M+H) 612.1.

Example 64

3-(4-(2-(4-(1H-pyrazol-1-yl)phenylamino)-5-methylpyrimidin-4-yl)-1H-pyrazol-1-yl)-4-(1-(2,4-difluorobenzoyl)piperidin-4-yl)butanenitrile

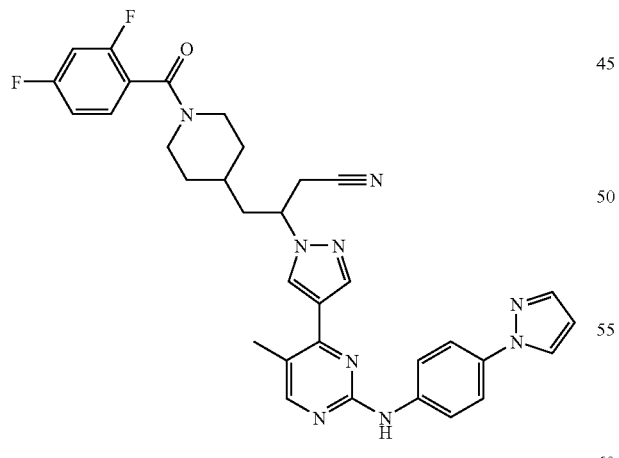

This compound was prepared as a racemic mixture according to the procedure described in example 48, using 2,4-difluorobenzoyl chloride instead of ethanesulfonyl chloride in step 1 and 4-(1H-pyrazol-1-yl)aniline instead of 4-morpholin-4-ylaniline in step 2. LCMS (M+H) 608.1.

Example 65

4-(1-(1-methyl-1H-pyrazol-3-ylsulfonyl)piperidin-4-yl)-3-(4-(5-methyl-2-(phenylamino)pyrimidin-4-yl)-1H-pyrazol-1-yl)butanenitrile

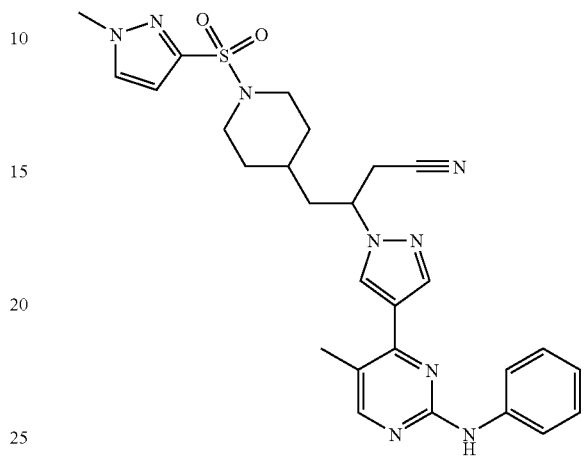

This compound was prepared as a racemic mixture according to the procedure described in example 48, using 1-methyl-1H-Pyrazole-3-sulfonyl chloride instead of ethanesulfonyl chloride in step 1 and aniline instead of 4-morpholin-4-ylaniline in step 2. LCMS (M+H) 546.1.

Example 66

4-(1-(2,4-difluorobenzoyl)piperidin-4-yl)-3-(4-(5-methyl-2-(phenylamino)pyrimidin-4-yl)-1H-pyrazol-1-yl)butanenitrile

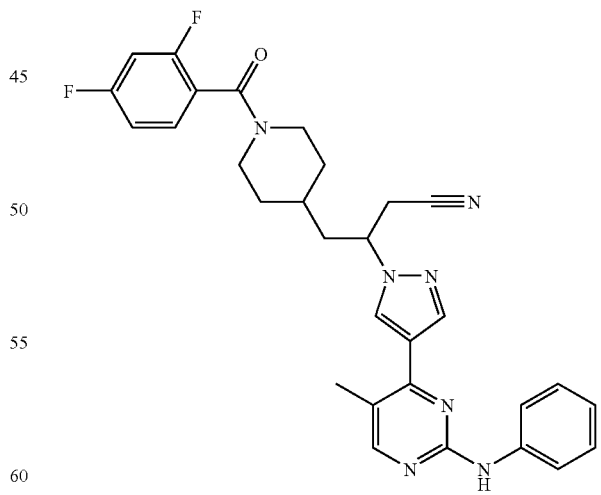

This compound was prepared as a racemic mixture according to the procedure described in example 48, using 2,4-difluorobenzoyl chloride instead of ethanesulfonyl chloride in step 1 and aniline instead of 4-morpholin-4-ylaniline in step 2. LCMS (M+H) 542.1.

Example 67

4-(4-(1-(1-cyano-3-(1-(1-methyl-1H-pyrazol-3-ylsulfonyl)piperidin-4-yl)propan-2-yl)-1H-pyrazol-4-yl)-5-methylpyrimidin-2-ylamino)-N,N-dimethylbenzamide

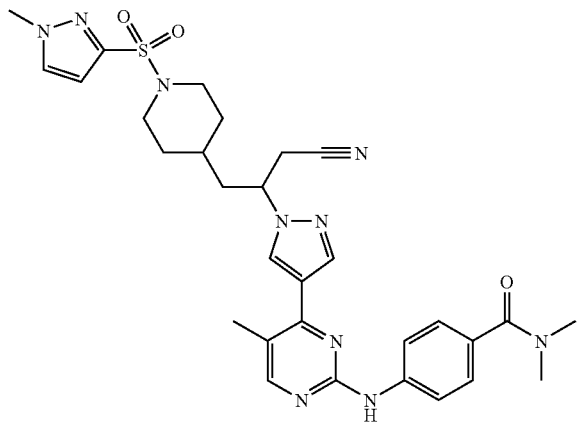

This compound was prepared as a racemic mixture according to the procedure described in example 48, using 1-methyl-1H-Pyrazole-3-sulfonyl chloride instead of ethanesulfonyl chloride in step 1 and 4-amino-N,N-dimethyl-benzamide instead of 4-morpholin-4-ylaniline in step 2. LCMS (M+H) 617.2.

Example 68

4-(4-(1-(1-cyano-3-(1-(2,4-difluorobenzoyl)piperidin-4-yl)propan-2-yl)-1H-pyrazol-4-yl)-5-methylpyrimidin-2-ylamino)-N,N-dimethylbenzamide

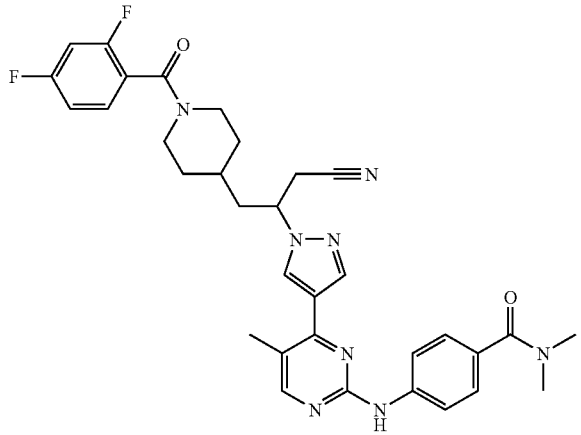

This compound was prepared as a racemic mixture according to the procedure described in example 48, using 2,4-difluorobenzoyl chloride instead of ethanesulfonyl chloride in step 1 and 4-amino-N,N-dimethyl-benzamide instead of 4-morpholin-4-ylaniline in step 2. LCMS (M+H) 613.1.

Example 69

N-(4-(4-(1-(1-cyano-3-(1-(2,4-difluorobenzoyl)piperidin-4-yl)propan-2-yl)-1H-pyrazol-4-yl)-5-methylpyrimidin-2-ylamino)phenyl)acetamide

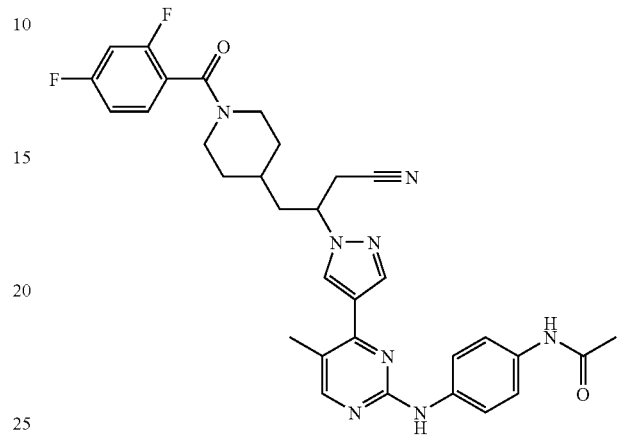

This compound was prepared as a racemic mixture according to the procedure described in example 48, using 2,4-difluorobenzoyl chloride instead of ethanesulfonyl chloride in step 1 and N-(4-aminophenyl)-acetamide instead of 4-morpholin-4-ylaniline in step 2. LCMS (M+H) 599.1.

Example 70

4-(4-(1-(2-cyano-1-cyclopentylethyl)-1H-pyrazol-4-yl)-5-methylpyrimidin-2-ylamino)benzamide

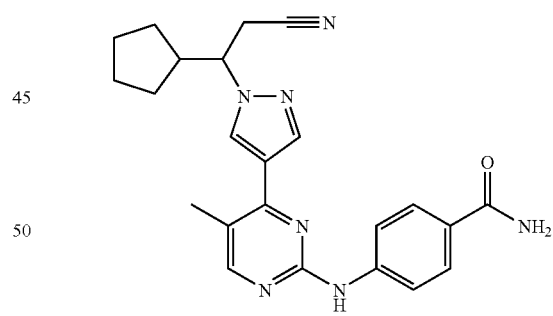

Step 1: 3-(4-(2-chloro-5-ethylpyrimidin-4-yl)-1H-pyrazol-1-yl)-3-cyclopentylpropanenitrile A mixture of 2,4-dichloro-5-methylpyrimidine (0.62 g, 3.8 mmol), 3-cyclopentyl-3-(4-(4,4,5,5-tetramethyl-1,3,2-dioxaborolan-2-yl)-1H-pyrazol-1-yl)propanenitrile (1.0 g, 3.17 mmol), tetrakis(triphenylphosphine)palladium (200 mg, 0.2 mmol), and potassium phosphate (2.0 g, 9.6 mmol) in 1,4-dioxane (9 mL) and water (0.9 mL) was heated at 100° C. overnight. After cooling to room temperature, the mixture was diluted with EtOAc, washed with water, brine, dried over MgSO₄, concentrated. The residue was purified on silica gel, eluting with 0 to 80% EtOAc-hexanes, to give the desired product (780 mg, 78%). LCMS (M+H) 316.0.

Step 2: 4-(4-(1-(2-cyano-1-cyclopentylethyl)-1H-pyrazol-4-yl)-5-ethylpyrimidin-2-ylamino)benzamide A mixture of 3-(4-(2-chloro-5-methylpyrimidin-4-yl)-1H-pyrazol-1-yl)-3-cyclopentylpropanenitrile (30 mg, 0.1 mmol), 4-amino-benzamide (20.3 mg, 0.149 mmol), and p-toluenesulfonic acid (14 mg, 0.084 mmol) in dry 1,4-dioxane (0.8 mL) was refluxed overnight. The mixture was diluted with acetonitrile and water, purified on RP-HPLC at pH 1 to give the desired product as a racemic mixture (TFA salt, 32 mg, 60%). LCMS (M+H) 416.0.

Example 71

3-(4-(2-(4-(1H-pyrazol-1-yl)phenylamino)-5-methylpyrimidin-4-yl)-1H-pyrazol-1-yl)-3-cyclopentylpropanenitrile

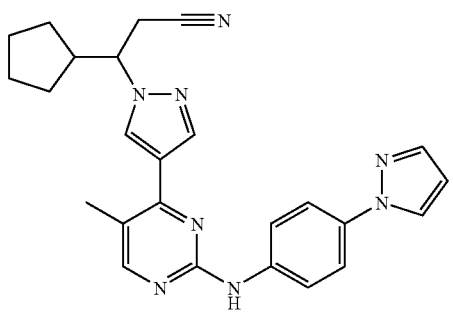

This compound was prepared as a racemic mixture according to the procedure described in example 70, using 4-(1H-pyrazol-1-yl)aniline instead of 4-amino-benzamide in step 2. LCMS (M+H) 439.1.

Example 72

3-cyclopentyl-3-(4-(5-methyl-2-(4-morpholinophenylamino)pyrimidin-4-yl)-1H-pyrazol-1-yl)propanenitrile

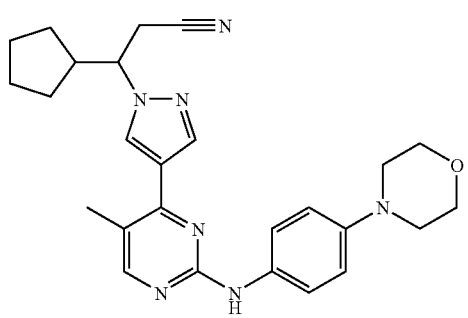

This compound was prepared as a racemic mixture according to the procedure described in example 70, using 4-morpholin-4-ylaniline instead of 4-amino-benzamide in step 2. LCMS (M+H) 458.1.

Example 73

3-cyclopentyl-3-(4-(5-methyl-2-(phenylamino)pyrimidin-4-yl)-1H-pyrazol-1-yl)propanenitrile

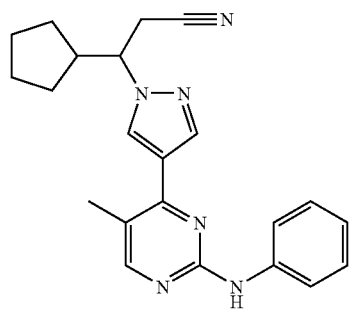

This compound was prepared as a racemic mixture according to the procedure described in example 70, using aniline instead of 4-amino-benzamide in step 2. LCMS (M+H) 373.0.

Example 74

3-cyclopentyl-3-(4-(5-methyl-2-(4-(oxazol-5-yl)phenylamino)pyrimidin-4-yl)-1H-pyrazol-1-yl)propanenitrile

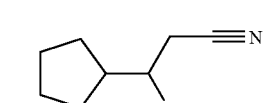

This compound was prepared as a racemic mixture according to the procedure described in example 70, using 4-(5-oxazolyl)-benzenamine instead of 4-amino-benzamide in step 2. LCMS (M+H) 440.0.

Example 75

3-cyclopentyl-3-(4-(2-(4-methoxyphenylamino)-5-methylpyrimidin-4-yl)-1H-pyrazol-1-yl)propanenitrile

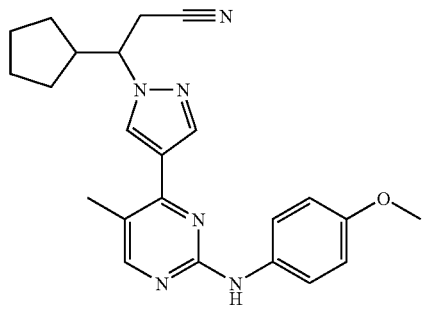

This compound was prepared as a racemic mixture according to the procedure described in example 70, using 4-methoxyaniline instead of 4-amino-benzamide in step 2. LCMS (M+H) 403.1.

Example 76

N-(4-(4-(1-(2-cyano-1-cyclopentylethyl)-1H-pyrazol-4-yl)-5-methylpyrimidin-2-ylamino)phenyl)acetamide This compound was prepared as a racemic mixture according to the procedure described in example 70, using N-(4-aminophenyl)-acetamide instead of 4-amino-benzamide in step 2. LCMS (M+H) 430.1.

Example 77

4-(4-(1-(2-cyano-1-cyclopentylethyl)-1H-pyrazol-4-yl)-5-methylpyrimidin-2-ylamino)-N,N-dimethyl-benzamide This compound was prepared as a racemic mixture according to the procedure described in example 70, using 4-amino-N,N-dimethyl-benzamide instead of 4-amino-benzamide in step 2. LCMS (M+H) 444.1.

Example 78

3-cyclopentyl-3-(4-(5-methyl-2-(4-(piperazin-1-yl)phenylamino)pyrimidin-4-yl)-1H-pyrazol-1-yl)propanenitrile This compound was prepared as a racemic mixture according to the procedure described in example 70, using 1-(4-amino-phenyl)-piperazine-4-carboxylic acid tert-butyl ester instead of 4-amino-benzamide in step 2. LCMS (M+H) 457.1.

Example 79

3-cyclopentyl-3-(4-(2-(4-(diethylamino)phenylamino)-5-methylpyrimidin-4-yl)-1H-pyrazol-1-yl)propanenitrile

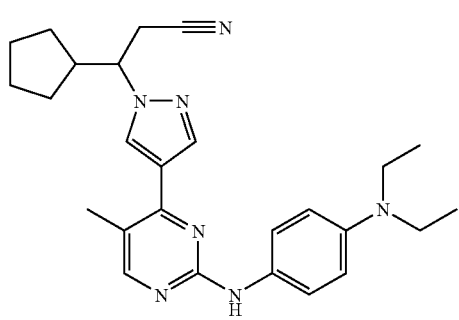

This compound was prepared as a racemic mixture according to the procedure described in example 70, using $N^1,N^1$-diethyl-1,4-benzenediamine instead of 4-amino-benzamide in step 2. LCMS (M+H) 444.1.

Example 80

3-cyclopentyl-3-(4-(2-(4-(ethyl(3-hydroxypropyl)amino)phenylamino)-5-methylpyrimidin-4-yl)-1H-pyrazol-1-yl)propanenitrile

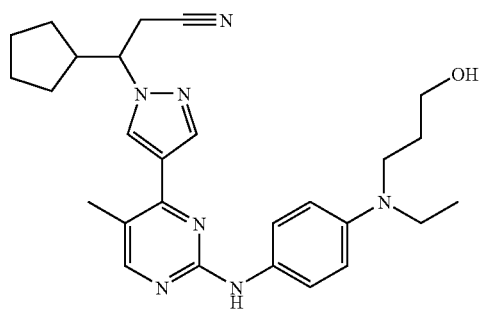

This compound was prepared as a racemic mixture according to the procedure described in example 70, using 2-[(4-aminophenyl)ethylamino]-ethanol instead of 4-amino-benzamide in step 2. LCMS (M+H) 460.1.

Example 81

4-(4-(1-(2-cyano-1-cyclopentylethyl)-1H-pyrazol-4-yl)-5-methylpyrimidin-2-ylamino)benzoic acid

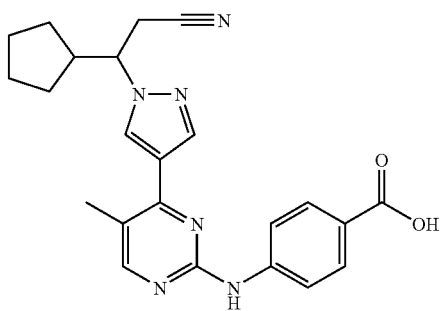

This compound was prepared as a racemic mixture according to the procedure described in example 70, using 4-aminobenzoic acid instead of 4-amino-benzamide in step 2. LCMS (M+H) 417.2.

Example 82

3-cyclopentyl-3-(4-(5-methyl-2-(4-nitrophenylamino)pyrimidin-4-yl)-1H-pyrazol-1-yl)propanenitrile

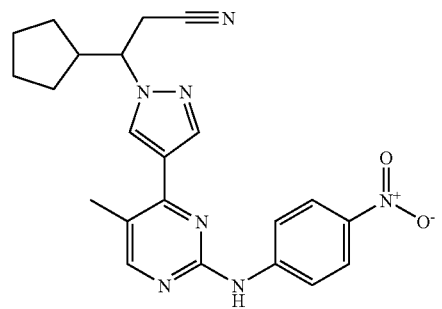

This compound was prepared as a racemic mixture according to the procedure described in example 70, using 4-nitrobenzenamine instead of 4-amino-benzamide in step 2. LCMS (M+H) 418.1.

Example 83

4-(4-(1-(2-cyano-1-cyclopentylethyl)-1H-pyrazol-4-yl)-5-methylpyrimidin-2-ylamino)-N-(2-hydroxyethyl)benzamide

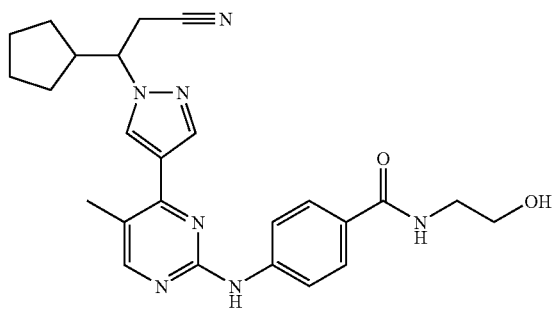

This compound was prepared as a racemic mixture according to the procedure described in example 70, using 4-amino-N-(2-hydroxyethyl)-benzamide instead of 4-amino-benzamide in step 2. LCMS (M+H) 460.2.

Example 84

3-cyclopentyl-3-(4-(5-methyl-2-(3-(oxazol-5-yl)phenylamino)pyrimidin-4-yl)-1H-pyrazol-1-yl)propanenitrile

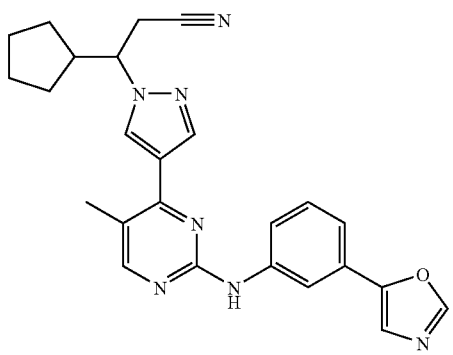

This compound was prepared as a racemic mixture according to the procedure described in example 70, using 3-(5-oxazolyl)-benzenamine instead of 4-amino-benzamide in step 2. LCMS (M+H) 440.0.

Example 85

3-(4-(2-(4-aminophenylamino)-5-methylpyrimidin-4-yl)-1H-pyrazol-1-yl)-3-cyclopentylpropanenitrile

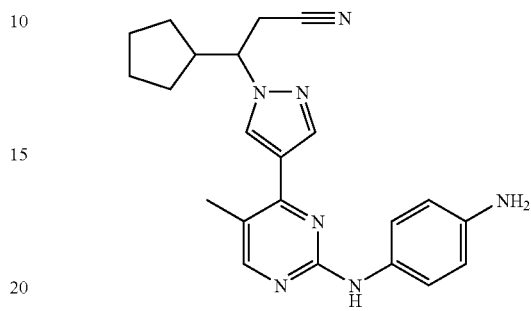

A mixture of 3-cyclopentyl-3-(4-5-methyl-2-((4-nitrophenyl)amino)pyrimidin-4-yl-1H-pyrazol-1-yl)propanenitrile (0.020 g, 0.048 mmol) (free base) in 10 mL of methanol was hydrogenated, in the presence of 10% Pd/C, under balloon pressure of hydrogen, overnight. After the catalyst was filtered off, the filtrate was evaporated to dryness to give the desired product as a racemic mixture (18 mg, 97%). LCMS (M+H) 388.0.

Example 86

4-(4-(1-(2-cyano-1-cyclopentylethyl)-1H-pyrazol-4-yl)-5-methylpyrimidin-2-ylamino)-N-methylbenzamide

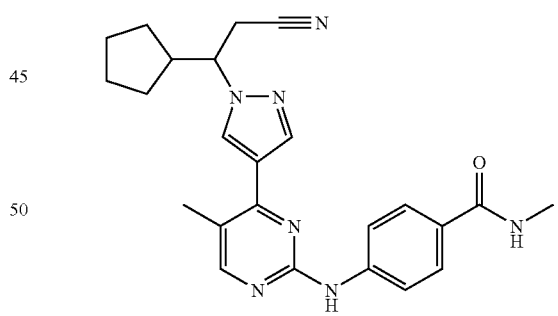

To a mixture of 4-(4-(1-(2-cyano-1-cyclopentylethyl)-1H-pyrazol-4-yl)-5-methylpyrimidin-2-ylamino)benzoic acid (10 mg, 0.02 mmol), methylammonium chloride (2.4 mg, 0.036 mmol) and benzotriazol-1-yloxytris(dimethylamino)phosphonium hexafluorophosphate (16 mg, 0.036 mmol) in N,N-dimethylformamide (0.5 mL) was added N,N-diisopropylethylamine (0.019 mL, 0.11 mmol). The mixture was stirred at room temperature overnight, quenched with 1 N HCl, purified on RP-HPLC to give the desired product as a racemic mixture (TFA salt, 9 mg, 85%). LCMS (M+H) 430.1.

Example 87

4-(4-(1-(2-cyano-1-cyclopentylethyl)-1H-pyrazol-4-yl)-5-methylpyrimidin-2-ylamino)-N-(1-methoxypropan-2-yl)benzamie

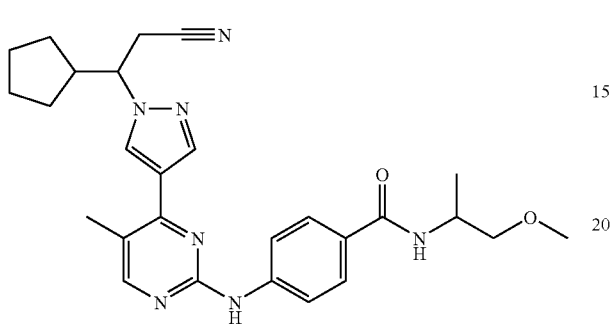

This compound was prepared as a diastereoisomeric mixture according to the procedure described in example 86, using 1-methoxy-2-propylamine instead of methylammonium chloride. LCMS (M+H) 488.1.

Example 88

3-cyclopentyl-3-(4-(2-(4-(4-hydroxypiperidine-1-carbonyl)phenylamino)-5-methylpyrimidin-4-yl)-1H-pyrazol-1-yl)propanenitrile

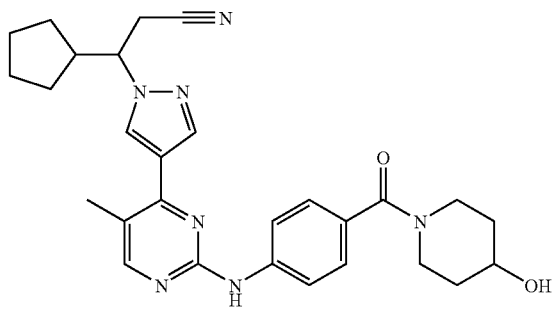

This compound was prepared as a racemic mixture according to the procedure described in example 86, using 4-hydroxypiperidine instead of methylammonium chloride. LCMS (M+H) 500.1.

Example 89

N-(4-(4-(1-(2-cyano-1-cyclopentylethyl)-1H-pyrazol-4-yl)-5-methylpyrimidin-2-ylamino)phenyl)methanesulfonamide

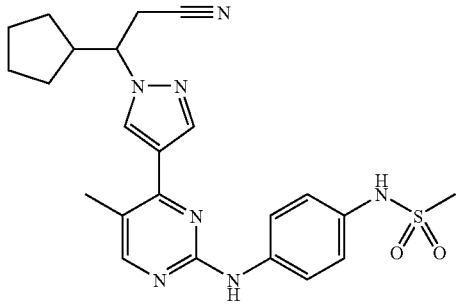

To a mixture of 3-(4-2-((4-aminophenyl)amino)-5-methylpyrimidin-4-yl-1H-pyrazol-1-yl)-3-cyclopentylpropanenitrile (10 mg, 0.02 mmol) in tetrahydrofuran (0.5 mL) was added triethylamine (7.2 μL, 0.052 mmol), followed by methanesulfonyl chloride (3.0 μL, 0.039 mmol). The reaction was stirred at room temperature for 1 h, purified on RP-HPLC to give the desired product as a racemic mixture (TFA, 9 mg, 80%). LCMS (M+H) 466.1.

Example 90

Methyl 4-(4-(1-(2-cyano-1-cyclopentylethyl)-1H-pyrazol-4-yl)-5-methylpyrimidin-2-ylamino)phenylcarbamate

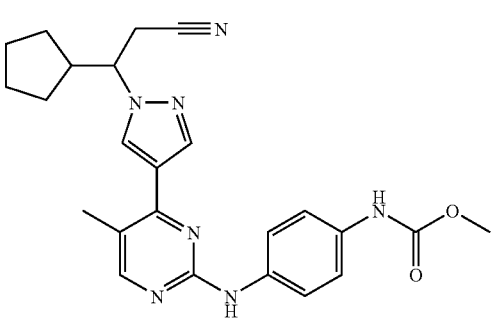

This compound was prepared as a racemic mixture according to the procedure described in example 89, using methyl chloroformate instead of methanesulfonyl chloride. LCMS (M+H) 446.1.

Example 91

N-(4-(4-(1-(2-cyano-1-cyclopentylethyl)-1H-pyrazol-4-yl)-5-methylpyrimidin-2-ylamino)phenyl)-2-(pyrrolidin-1-yl)acetamide

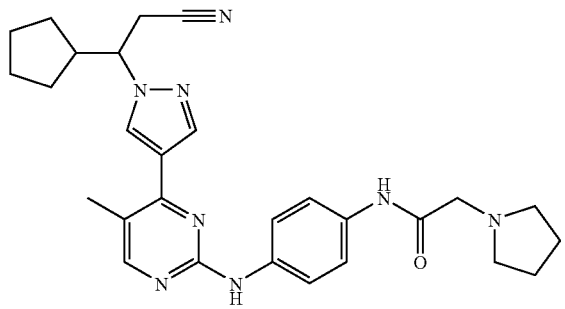

To a mixture of 3-(4-2-((4-aminophenyl)amino)-5-methylpyrimidin-4-yl-1H-pyrazol-1-yl)-3-cyclopentylpropanenitrile (10 mg, 0.02 mmol) in tetrahydrofuran (0.5 mL) was added triethylamine (7.2 µL, 0.052 mmol), followed by chloroacetyl chloride (3.1 µL, 0.039 mmol). The reaction was stirred at room temperature for 1 h, then treated with pyrrolidine (4.3 µL, 0.052 mmol) at room temperature for an additional 1 h. The resulting mixture was quenched with 1 N HCl, purified on RP-HPLC to give the desired product as a racemic mixture (TFA salt, 6 mg, 54%). LCMS (M+H) 499.1.

Example 92

3-(4-(2-(4-(3-oxomorpholino)phenylamino)pyrimidin-4-yl)-1H-pyrazol-1-yl)-4-(piperidin-4-yl)butanenitrile

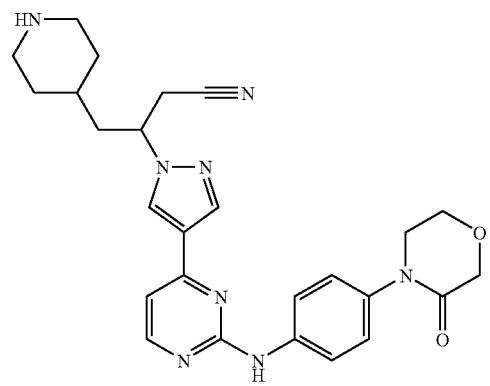

This compound was prepared as a racemic mixture, by coupling of tert-butyl 4-(2-(4-(2-chloropyrimidin-4-yl)-1H-pyrazol-1-yl)-3-cyanopropylpiperidine-1-carboxylate (from example 1, step 4) with 4-(4-aminophenyl)-3-morpholinone (from Affinitis Pharma) according to the procedure described in example 1, step 6. LCMS (M+H) 487.1.

Example 93

2-(1-(cyclopropylsulfonyl)-3-(4-(2-(4-morpholinophenylamino)pyrimidin-4-yl)-1H-pyrazol-1-yl)azetidin-3-yl)acetonitrile

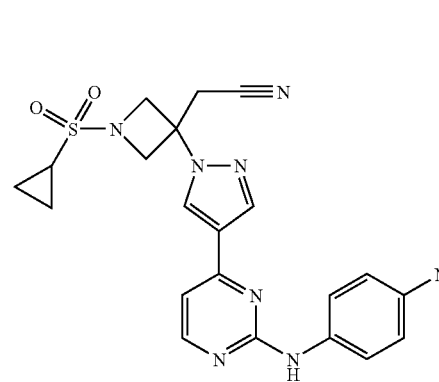

This compound was prepared according to the procedure described in example 17, using 4-morpholin-4-ylaniline instead of 4-(1H-pyrazol-1-yl)aniline in step 5. LCMS (M+H) 521.0.

Example 94

2-(1-(isoxazole-5-carbonyl)-4-(4-(2-(4-morpholinophenylamino)pyrimidin-4-yl)-1H-pyrazol-1-yl)piperidin-4-yl)acetonitrile This compound was prepared according to the procedure described in example 12, using 4-morpholin-4-ylaniline instead of 4-(1H-pyrazol-1-yl)aniline in step 5. LCMS (M+H) 540.1.

Example 95

4-(1-(methylsulfonyl)piperidin-4-yl)-3-(4-(2-(4-(3-oxomorpholino)phenylamino)pyrimidin-4-yl)-1H-pyrazol-1-yl)butanenitrile

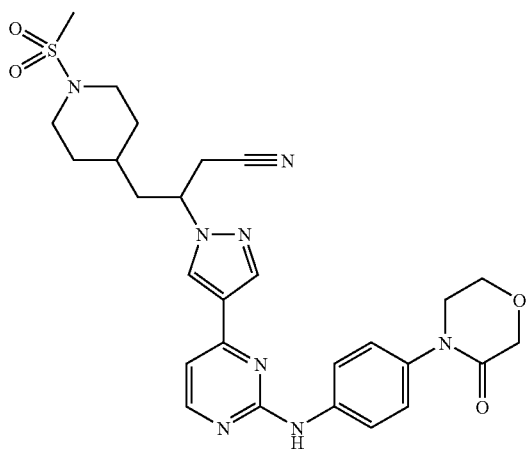

This compound was prepared as a racemic mixture according to the procedure described in example 1, using methanesulfonyl chloride instead of 2,4-difluorobenzoyl chloride in step 5; and 4-(4-aminophenyl)-3-morpholinone instead of 4-(1H-imidazol-1-yl)aniline in step 6. LCMS (M+H) 565.2.

Example 96

4-(1-(ethylsulfonyl)piperidin-4-yl)-3-(4-(2-(4-(3-oxomorpholino)phenylamino)pyrimidin-4-yl)-1H-pyrazol-1-yl)butanenitrile

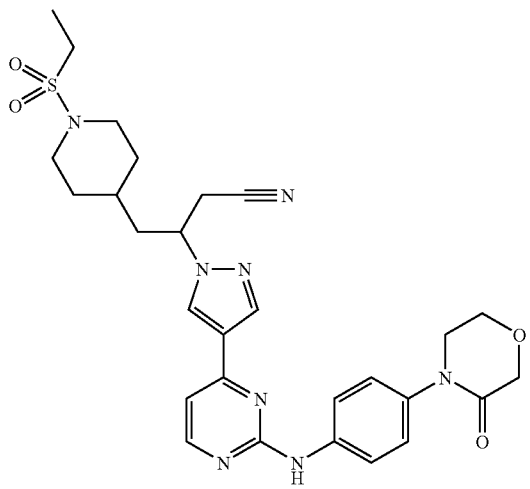

This compound was prepared as a racemic mixture according to the procedure described in example 1, using ethanesulfonyl chloride instead of 2,4-difluorobenzoyl chloride in step 5; and 4-(4-aminophenyl)-3-morpholinone instead of 4-(1H-imidazol-1-yl)aniline in step 6. LCMS (M+H) 579.1.

Example 97

4-(1-(cyclopropylsulfonyl)piperidin-4-yl)-3-(4-(2-(4-(3-oxomorpholino)phenylamino)pyrimidin-4-yl)-1H-pyrazol-1-yl)butanenitrile

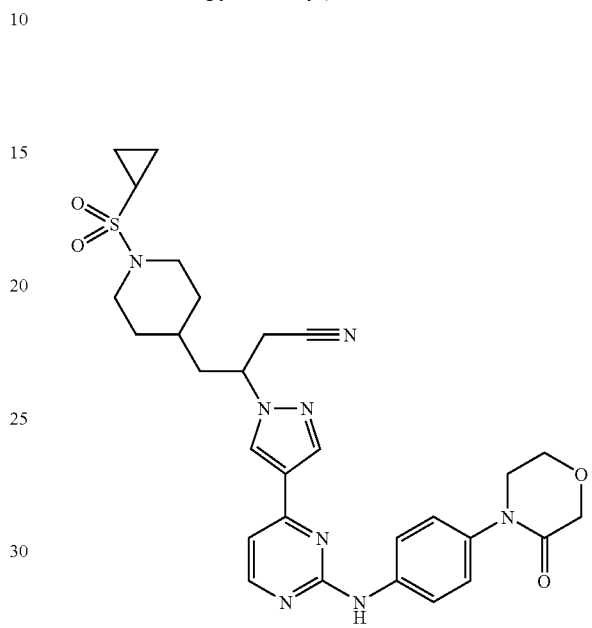

This compound was prepared as a racemic mixture according to the procedure described in example 1, using cyclopropylsulfonyl chloride instead of 2,4-difluorobenzoyl chloride in step 5; and 4-(4-aminophenyl)-3-morpholinone instead of 4-(1H-imidazol-1-yl)aniline in step 6. LCMS (M+H) 591.1.

Example 98

3-cyclopentyl-3-(4-(2-(4-(3-oxomorpholino)phenylamino)pyrimidin-4-yl)-1H-pyrazol-1-yl)propanenitrile

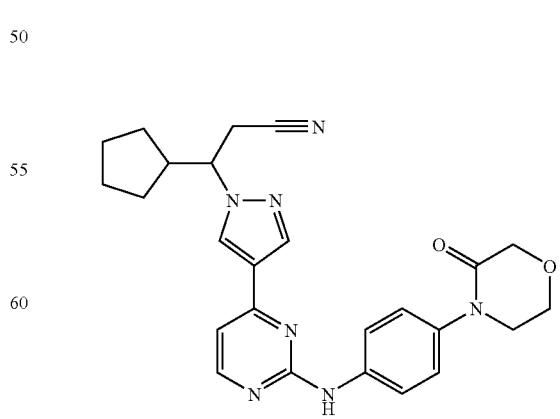

This compound was prepared as a racemic mixture according to the procedure described in example 33, using 4-(4-aminophenyl)-3-morpholinone instead of 4-aminobenzamide in step 3. LCMS (M+H) 458.0.

Example 99

3-cyclopentyl-3-(4-(2-(3-(2-methylpyrimidin-4-yl)phenylamino)pyrimidin-4-yl)-1H-pyrazol-1-yl)propanenitrile

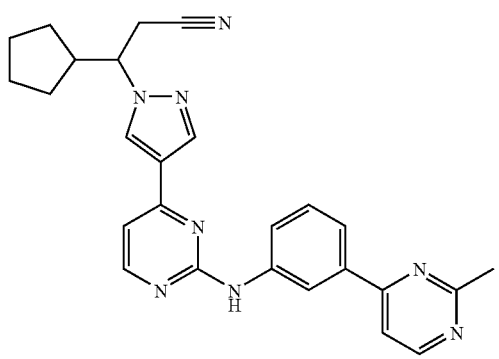

This compound was prepared as a racemic mixture according to the procedure described in example 33, using 3-(2-methyl-4-pyrimidinyl)-benzenamine instead of 4-aminobenzamide in step 3. LCMS (M+H) 454.1.

Example 100

3-(4-(1-(2-cyano-1-cyclopentylethyl)-1H-pyrazol-4-yl)pyrimidin-2-ylamino)benzoic Acid

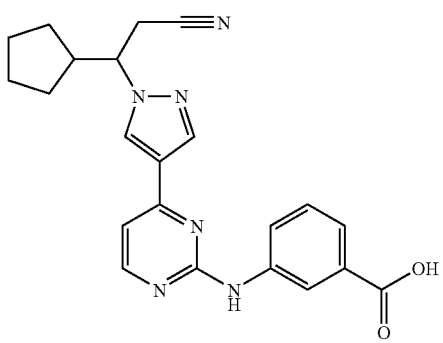

This compound was prepared as a racemic mixture according to the procedure described in example 33, using 3-aminobenzoic acid instead of 4-aminobenzamide in step 3. LCMS (M+H) 403.1.

Example 101

3-cyclopentyl-3-(4-(5-methoxy-2-(4-morpholinophenylamino)pyrimidin-4-yl)-1H-pyrazol-1-yl)propanenitrile

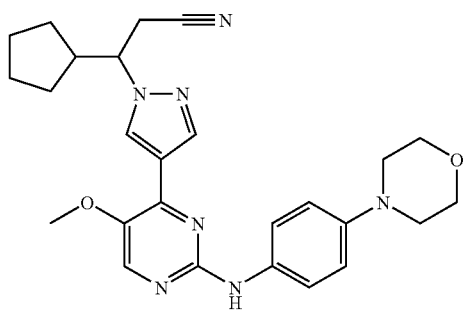

Step 1: 3-(4-(2-chloro-5-methoxypyrimidin-4-yl)-1H-pyrazol-1-yl)-3-cyclopentylpropanenitrile A mixture of 2,4-dichloro-5-methoxypyrimidine (0.68 g, 3.8 mmol), 3-cyclopentyl-3-(4-(4,4,5,5-tetramethyl-1,3,2-dioxaborolan-2-yl)-1H-pyrazol-1-yl)propanenitrile (1.0 g, 3.17 mmol), tetrakis(triphenylphosphine)palladium (200 mg, 0.2 mmol), and potassium phosphate (2.0 g, 9.6 mmol) in 1,4-dioxane (9 mL) and water (0.9 mL) was heated at 100° C. overnight. After cooling to room temperature, the mixture was diluted with EtOAc, washed with water, brine, dried over MgSO$_4$, concentrated. The residue was purified on silica gel, eluting with 0 to 60% EtOAc-hexanes, to give the desired product (860 mg, 82%). LCMS (M+H) 331.9.

Step 2: 3-cyclopentyl-3-(4-5-ethoxy-2-((4morpholin-4-ylphenyl)amino)pyrimidin-4-yl-1H-pyrazol-1-yl)propanenitrile A mixture of 3-(4-(2-chloro-5-methoxypyrimidin-4-yl)-1H-pyrazol-1-yl)-3-cyclopentylpropanenitrile (20 mg, 0.06 mmol), 4-morpholin-4-ylaniline (16.1 mg, 0.0904 mmol), and p-toluenesulfonic acid (8.8 mg, 0.051 mmol) in dry 1,4-dioxane (0.5 mL) was refluxed overnight. The mixture was diluted with acetonitrile and water, purified on RP-HPLC at pH 1 to give the desired product as a racemic mixture (TFA salt, 16 mg, 45%). LCMS (M+H) 474.2.

Example 102

3-(4-(2-(4-(1H-pyrazol-1-yl)phenylamino)-5-methoxypyrimidin-4-yl)-1H-pyrazol-1-yl)-3-cyclopentylpropanenitrile

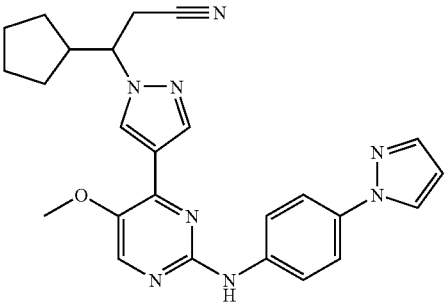

This compound was prepared as a racemic mixture according to the procedure described in example 101, replacing 4-morpholin-4-ylaniline with 4-(1H-pyrazol-1-yl)aniline in step 2. LCMS (M+H) 455.0.

Example 103

N-(4-(4-(1-(2-cyano-1-cyclopentylethyl)-1H-pyrazol-4-yl)-5-methoxydin-2-ylamino)phenyl)acetamide

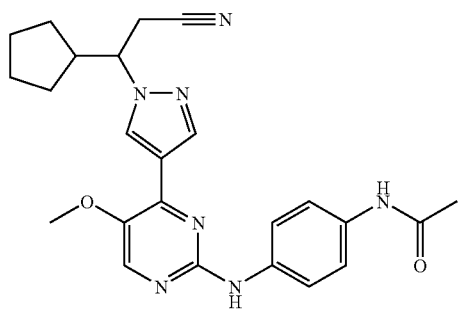

This compound was prepared as a racemic mixture according to the procedure described in example 101, replacing 4-morpholin-4-ylaniline with N-(4-aminophenyl)-acetamide in step 2. LCMS (M+H) 446.0.

Example 104

4-(4-(1-(2-cyano-1-cyclopentylethyl)-1H-pyrazol-4-yl)-5-methoxypyrimidin-2-ylamino)-N,N-dimethyl-benzamide

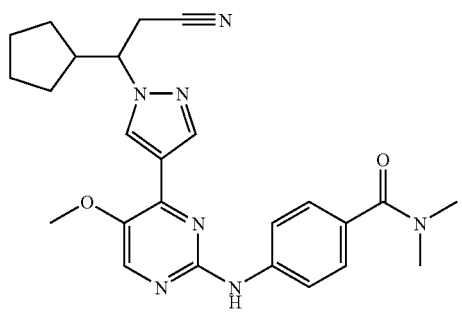

This compound was prepared as a racemic mixture according to the procedure described in example 101, replacing 4-morpholin-4-ylaniline with 4-amino-N,N-dimethyl-benzamide in step 2. LCMS (M+H) 460.0.

Example 105

3-cyclopentyl-3-(4-(2-(4-(2-oxopiperidin-1-yl)phenylamino)pyrimidin-4-yl)-1H-pyrazol-1-yl)propanenitrile

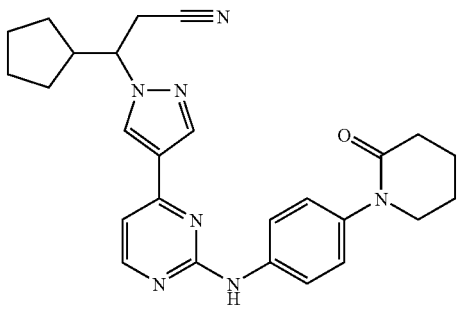

This compound was prepared as a racemic mixture according to the procedure described in example 33, replacing 4-aminobenzamide with 1-(4-aminophenyl)-2-piperidinone (from Aurora Fine Chemicals) in step 3. LCMS (M+H) 456.1.

Example 106

3-cyclopentyl-3-(4-(2-(4-(2-oxo-1,3-oxazinan-3-yl)phenylamino)pyrimidin-4-yl)-1H-pyrazol-1-yl)propanenitrile

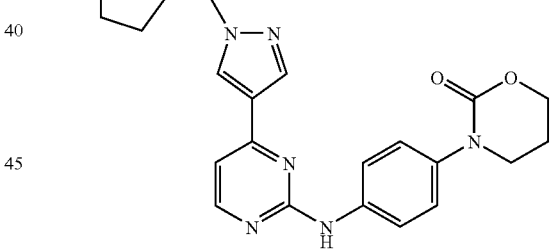

Step 1. 3-(4-nitrophenyl)-1,3-oxazinan-2-one

To a mixture of p-nitroaniline (0.50 g, 0.0036 mol) and 4-dimethylaminopyridine (DMAP, 0.531 g, 0.00434 mol) in tetrahydrofuran (10 mL, 0.1 mol) was added 3-chloropropyl chloridocarbonate (0.480 mL, 0.00398 mol). The mixture was stirred at room temperature for 1 h, then treated with 1.0 M of potassium tert-butoxide in tetrahydrofuran (7.96 mL, 0.00796 mol) at room temperature for 2 h, then quenched with aqueous ammonium chloride, extracted with EtOAc. The combined organic layers were washed with water, brine, dried and evaporated to dryness. The residue was purified on silica gel, eluting with 0 to 10% MeOH in dichloromethane, to provide the product (260 mg, 32.32%). LCMS (M+H) 222.9.

Step 2. 3-(4-aminophenyl)-1,3-oxazinan-2-one

A mixture of 3-(4-nitrophenyl)-1,3-oxazinan-2-one (0.10 g, 0.00045 mol) in 5 mL of methanol was hydrogenated, in the presence of 10% Pd/C, under balloon pressure of hydrogen, overnight. After filtering off the catalyst, the filtrate was evaporated to dryness and used directly in next step. LCMS (M+H) 193.0.

Step 3. 3-cyclopentyl-3-(4-(2-(4-(2-oxo-1,3-oxazinan-3-yl)phenylamino)pyrimidin-4-yl)-1H-pyrazol-1-yl)propanenitrile This compound was prepared as a racemic mixture according to the procedure described in example 33, replacing 4-aminobenzamide with 3-(4-aminophenyl)-1,3-oxazinan-2-one in step 3. LCMS (M+H) 458.0.

Example 107

3-cyclopentyl-3-(4-(2-(4-(2-oxooxazolidin-3-yl)phenylamino)pyrimidin-4-yl)-1H-pyrazol-1-yl)propanenitrile

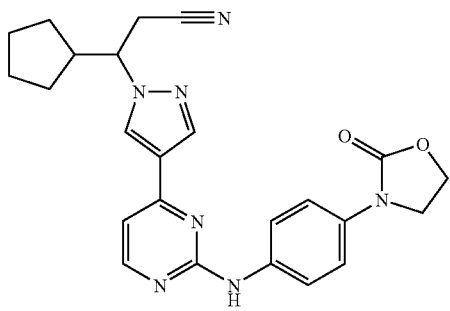

This compound was prepared as a racemic mixture according to the procedure described in example 33, replacing 4-aminobenzamide with 3-(4-aminophenyl)-2-oxazolidinone in step 3. LCMS (M+H) 444.0.

Example 108

3-(4-(2-(3-aminophenylamino)pyrimidin-4-yl)-1H-pyrazol-1-yl)-3-cyclopentylpropanenitrile

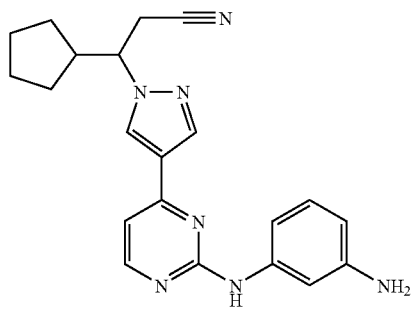

A mixture of 3-(4-(1-(2-cyano-1-cyclopentylethyl)-1H-pyrazol-4-yl)pyrimidin-2-ylamino)benzoic acid (228 mg, 0.566 mmol), and diphenylphosphonic azide (0.18 mL, 0.85 mmol), triethylamine (0.16 mL, 1.1 mmol) in 1,4-dioxane (4.2 mL) was stirred at room temperature overnight. To the resulting mixture was added water (0.36 mL). The reaction was refluxed overnight. The crude racemic mixture was used directly in next step. An analytically pure sample was obtained by RP-HPLC (pH 2). LCMS (M+H) 374.1.

Example 109

3-(4-(1-(2-cyano-1-cyclopentylethyl)-1H-pyrazol-4-yl)pyrimidin-2-ylamino)-N-methylbenzamide

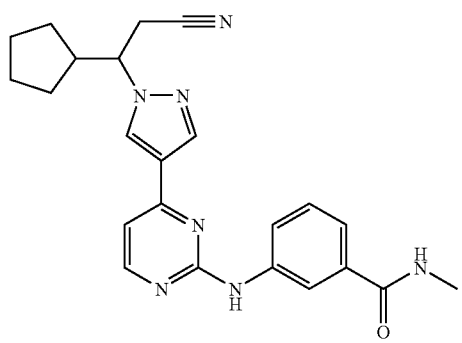

To a mixture of 3-(4-(1-(2-cyano-1-cyclopentylethyl)-1H-pyrazol-4-yl)pyrimidin-2-ylamino)benzoic acid (20 mg, 0.05 mmol) and methylammonium chloride (5.0 mg, 0.074 mmol) and benzotriazol-1-yloxytris(dimethylamino)phosphonium hexafluorophosphate (33 mg, 0.074 mmol) in N,N-dimethylformamide (0.5 mL) was added N,N-diisopropylethylamine (0.039 mL, 0.22 mol). The reaction was stirred at room temperature for 2 h, quenched with 1 N HCl, purified on RP-HPLC to give the desired product as a racemic mixture (TFA salt, 22 mg, 82%). LCMS (M+H) 416.0.

Example 110

3-(4-(1-(2-cyano-1-cyclopentylethyl)-1H-pyrazol-4-yl)pyrimidin-2-ylamino)-N,N-dimethylbenzamide

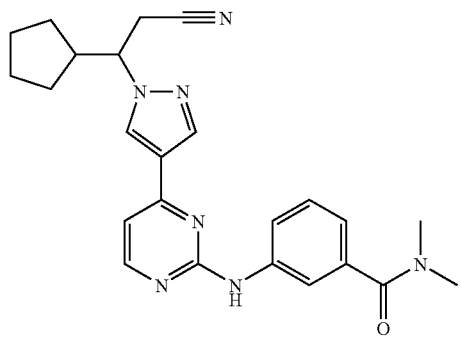

91

This compound was prepared as a racemic mixture according to the procedure described in example 109, replacing methylammonium chloride with dimethylamine HCl salt. LCMS (M+H) 430.1.

Example 111

3-cyclopentyl-3-(4-(2-(3-(4-hydroxypiperidine-1-carbonyl)phenylamino)pyrimidin-4-yl)-1H-pyrazol-1-yl)propanenitrile

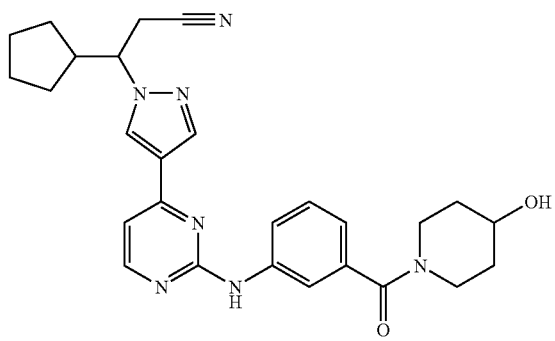

This compound was prepared as a racemic mixture according to the procedure described in example 109, replacing methylammonium chloride with 4-hydroxypiperidine. LCMS (M+H) 486.1.

Example 112

3-(4-(1-(2-cyano-1-cyclopentylethyl)-1H-pyrazol-4-yl)pyrimidin-2-ylamino)-N-(2-hydroxyethyl)benzamide

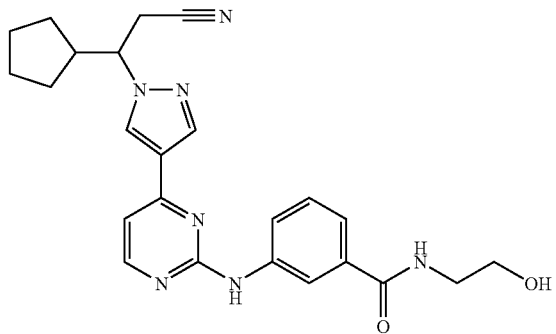

92

This compound was prepared as a racemic mixture according to the procedure described in example 109, replacing methylammonium chloride with 2-aminoethanol. LCMS (M+H) 446.1.

Example 113

3-(4-(1-(2-cyano-1-cyclopentylethyl)-1H-pyrazol-4-yl)pyrimidin-2-ylamino)-N-(1-methoxypropan-2-yl)benzamide

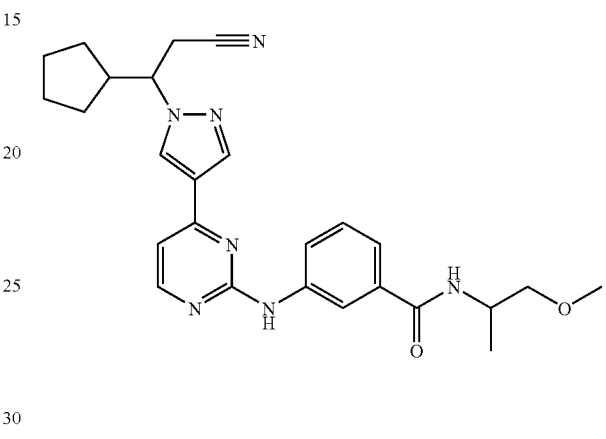

This compound was prepared as a diastereoisomeric mixture according to the procedure described in example 109, replacing methylammonium chloride with 1-methoxy-2-propylamine. LCMS (M+H) 474.1.

Example 114

N-(3-(4-(1-(2-cyano-1-cyclopentylethyl)-1H-pyrazol-4-yl)pyrimidin-2-ylamino)phenyl)ethanesulfonamide

To a mixture of 3-(4-(2-(3-aminophenyl)amino)pyrimidin-4-yl-1H-pyrazol-1-yl)-3-cyclopentylpropanenitrile (30 mg, 0.08 mmol) in 1,4-dioxane (0.5 mL) was added 1.0 M sodium carbonate in water (0.5 mL), followed by ethanesulfonyl chloride (20 µL, 0.2 mmol). The reaction was stirred at room temperature for 1 h, then purified on RP-HPLC to give the desired product as a racemic mixture (TFA salt, 38 mg, 84%). LCMS (M+H) 466.0.

Example 115

N-(3-(4-(1-(2-cyano-1-cyclopentylethyl)-1H-pyrazol-4-yl)pyrimidin-2-ylamino)phenyl)methanesulfonamide

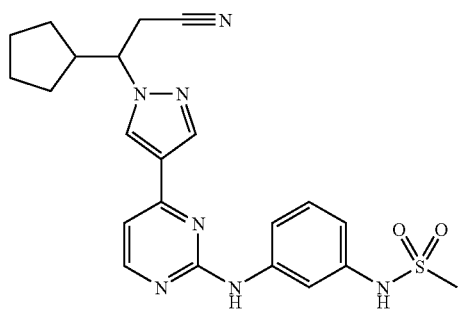

This compound was prepared as a racemic mixture according to the procedure described in example 114, using methanesulfonyl chloride instead of ethanesulfonyl chloride. LCMS (M+H) 452.1.

Example 116

Methyl 3-(4-(1-(2-cyano-1-cyclopentylethyl)-1H-pyrazol-4-yl)pyrimidin-2-ylamino)phenylcarbamate

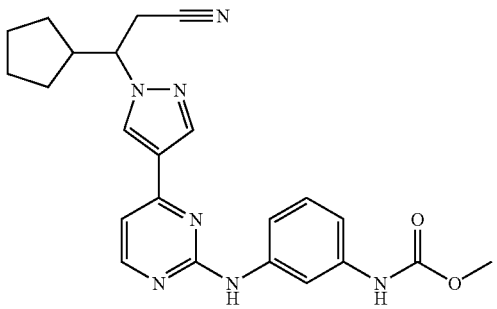

This compound was prepared as a racemic mixture according to the procedure described in example 114, using methyl chloroformate instead of ethanesulfonyl chloride. LCMS (M+H) 432.1.

Example 117

N-(3-(4-(1-(2-cyano-1-cyclopentylethyl)-1H-pyrazol-4-yl)pyrimidin-2-ylamino)phenyl)acetamide

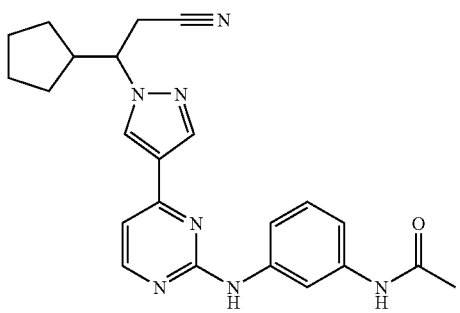

This compound was prepared as a racemic mixture according to the procedure described in example 114, using acetyl chloride instead of ethanesulfonyl chloride. LCMS (M+H) 416.1.

Example 118

N-(3-(4-(1-(2-cyano-1-cyclopentylethyl)-1H-pyrazol-4-yl)pyrimidin-2-ylamino)phenyl)-2-(pyrrolidin-1-yl)acetamide

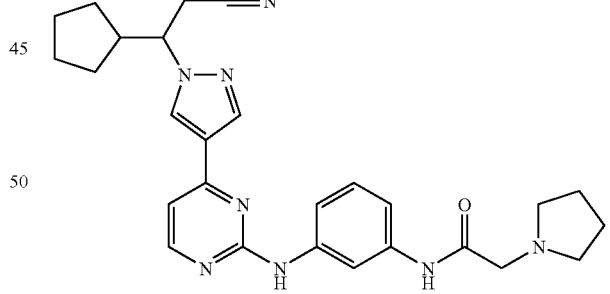

To a mixture of 3-(4-(2-(3-aminophenyl)amino)pyrimidin-4-yl-1H-pyrazol-1-yl)-3-cyclopentylpropanenitrile (30 mg, 0.08 mmol) in 1,4-dioxane (0.5 mL) was added 1.0 M sodium carbonate in water (0.5 mL), followed by chloroacetyl chloride (9.6 µL, 0.12 mmol). The mixture was stirred at room temperature for 1 h, then treated with pyrrolidine (0.017 g, 0.24 mmol) at room temperature overnight. The resulting mixture was purified on RP-HPLC at pH 10 to give the desired product as a racemic mixture (20 mg, 52%). LCMS (M+H) 485.2.

Example 119

4-(4-(1-(2-cyano-1-cyclopentylethyl)-1H-pyrazol-4-yl)pyrimidin-2-ylamino)benzoic Acid

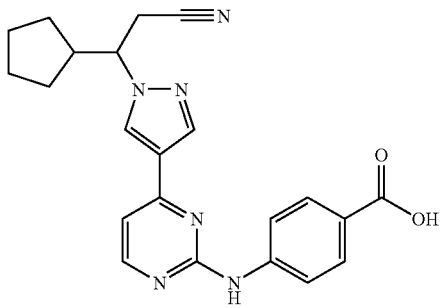

A mixture of 3-(4-(2-chloropyrimidin-4-yl)-1H-pyrazol-1-yl)-3-cyclopentylpropanenitrile (500.0 mg, 0.001657 mol), p-aminobenzoic acid (341 mg, 0.00248 mol), and p-toluenesulfonic acid (240 mg, 0.0014 mol) in dry 1,4-dioxane (10 mL) was refluxed overnight. The mixture was cooled to room temperature. The resulting solid was filtered, washed with dioxane, and air dried to yield the desired product as a racemic mixture (460 mg, 69%). LCMS (M+H) 403.1.

Example 120

3-cyclopentyl-3-(4-(2-(4-(4-methylpiperazine-1-carbonyl)phenylamino)pyrimidin-4-yl)-1H-pyrazol-1-yl)propanenitrile

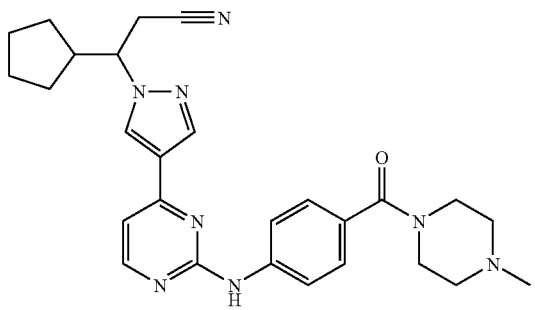

To a mixture of 4-(4-(1-(2-cyano-1-cyclopentylethyl)-1H-pyrazol-4-yl)pyrimidin-2-ylamino)benzoic acid (30 mg, 0.07 mmol), 1-methyl-piperazine (8.3 µL, 0.074 mmol) and benzotriazol-1-yloxytris(dimethylamino)phosphonium hexafluorophosphate (0.4 mg, 0.089 mmol) in N,N-dimethylformamide (0.5 mL) was added N,N-diisopropylethylamine (31 µL, 0.18 mmol). The reaction was stirred at room temperature for 1 h, quenched with water, purified on HPLC to give the desired product as a racemic mixture (28 mg, 82%). LCMS (M+H) 485.5.

Example 121

3-cyclopentyl-3-(4-(2-(4-(4-(2-hydroxyethyl)piperazine-1-carbonyl)phenylamino)pyrimidin-4-yl)-1H-pyrazol-1-yl)propanenitrile

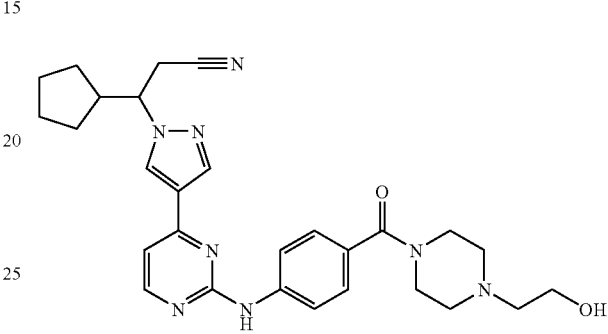

This compound was prepared as a racemic mixture according to the procedure described in example 120, replacing 1-methyl-piperazine with 1-piperazineethanol. LCMS (M+H) 515.5.

Example 122

3-cyclopentyl-3-(4-(2-(4-(pyrrolidine-1-carbonyl)phenylamino)pyrimidin-4-yl)-1H-pyrazol-1-yl)propanenitrile

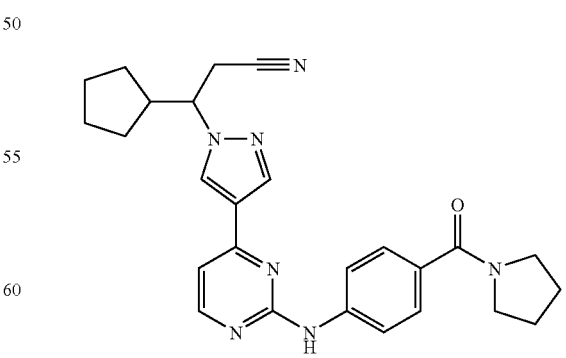

This compound was prepared as a racemic mixture according to the procedure described in example 120, replacing 1-methyl-piperazine with pyrrolidine. LCMS (M+H) 456.45

Example 123

3-cyclopentyl-3-(4-(2-(4-(3-oxopiperazine-1-carbonyl)phenylamino)pyrimidin-4-yl)-1H-pyrazol-1-yl)propanenitrile

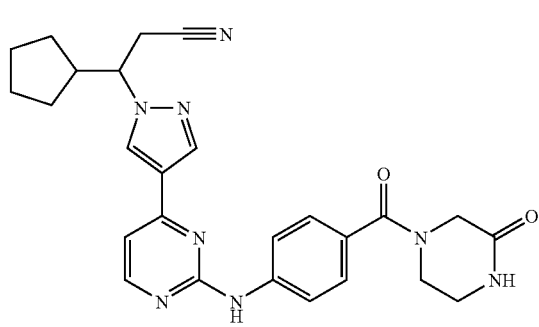

This compound was prepared as a racemic mixture according to the procedure described in example 120, replacing 1-methyl-piperazine with 3-oxopiperazine. LCMS (M+H) 485.4.

Example 124

3-cyclopentyl-3-(4-(2-(4-(4-hydroxypiperidine-1-carbonyl)phenylamino)pyrimidin-4-yl)-1H-pyrazol-1-yl)propanenitrile

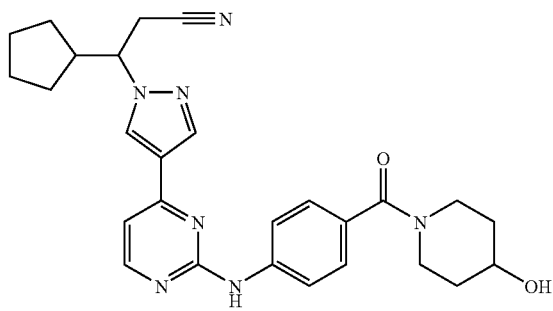

This compound was prepared as a racemic mixture according to the procedure described in example 120, replacing 1-methyl-piperazine with 4-hydroxypiperidine. LCMS (M+H) 486.5.

Example 125

4-(4-(1-(2-cyano-1-cyclopentylethyl)-1H-pyrazol-4-yl)pyrimidin-2-ylamino)-N-(cyclopropylmethyl)-N-propylbenzamie

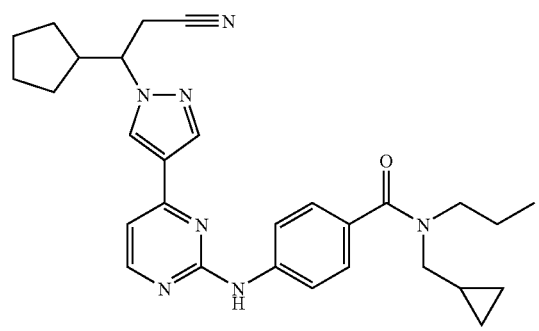

This compound was prepared as a racemic mixture according to the procedure described in example 120, replacing 1-methyl-piperazine with N-propyl cyclopropanemethylamine. LCMS (M+H) 498.5.

Example 126

4-(4-(1-(2-cyano-1-cyclopentylethyl)-1H-pyrazol-4-yl)pyrimidin-2-ylamino)-N-(cyclopropylmethyl)benzamide

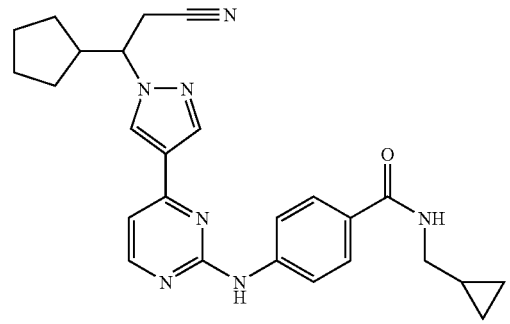

This compound was prepared as a racemic mixture according to the procedure described in example 120, replacing 1-methyl-piperazine with cyclopropanemethylamine. LCMS (M+H) 456.4.

Example 127

3-cyclopentyl-3-(4-(2-(4-((R)-3-hydroxypyrrolidine-1-carbonyl)phenylamino)pyrimidin-4-yl)-1H-pyrazol-1-yl)propanenitrile

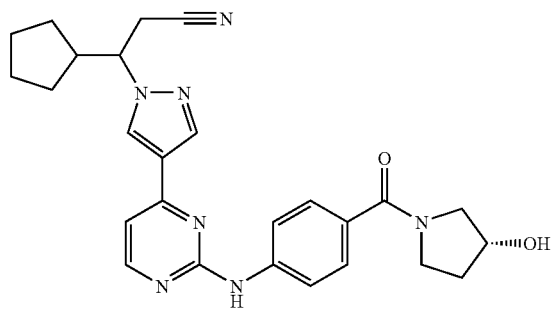

This compound was prepared as a diastereoisomeric mixture according to the procedure described in example 120, replacing 1-methyl-piperazine with (R)-3-hydroxypyrrolidine. LCMS (M+H) 472.45

Example 128

3-(4-(2-(4-(azetidine-1-carbonyl)phenylamino)pyrimidin-4-yl)-1H-pyrazol-1-yl)-3-cyclopentylpropanenitrile

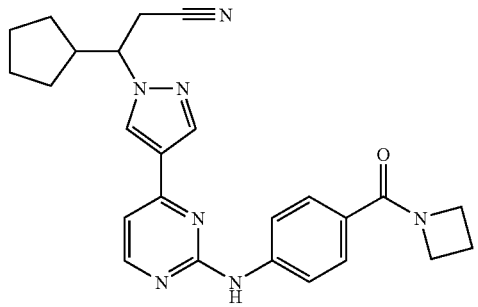

This compound was prepared as a racemic mixture according to the procedure described in example 120, replacing 1-methyl-piperazine with azetidine HCl salt. LCMS (M+H) 442.4.

Example 129

3-cyclopentyl-3-(4-(2-(4-(2-oxopyrrolidin-1-yl)phenylamino)pyrimidin-4-yl)-1H-pyrazol-1-yl)propanenitrile

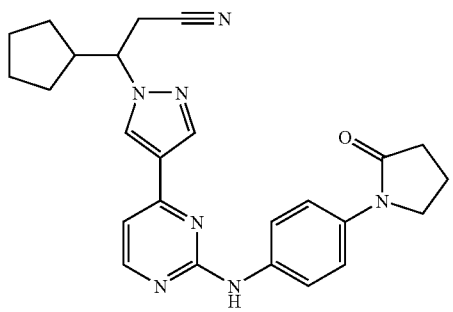

This compound was prepared as a racemic mixture according to the procedure described in example 33, replacing 4-aminobenzamide with 1-(4-aminophenyl)-2-pyrrolidinone (from Ryan Scientific) in step 3. LCMS (M+H) 442.4.

Example 130

3-cyclopentyl-3-(4-(5-methoxy-2-(4-(2-oxopyrrolidin-1-yl)phenylamino)pyrimidin-4-yl)-1H-pyrazol-1-yl)propanenitrile

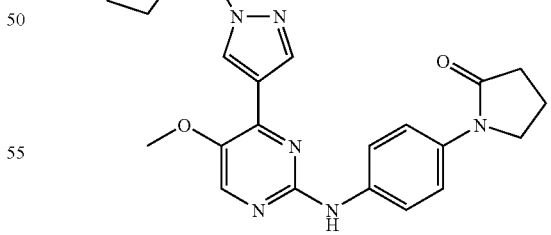

This compound was prepared as a racemic mixture according to the procedure described in example 101, replacing 4-morpholin-4-ylaniline with 1-(4-aminophenyl)-2-pyrrolidinone in step 2. LCMS (M+H) 472.4.

Example 131

3-cyclopentyl-3-(4-(5-methoxy-2-(4-(oxazol-5-yl)phenylamino)pyrimidin-4-yl)-1H-pyrazol-1-yl)propanenitrile

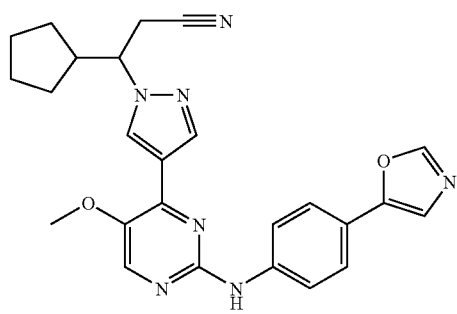

This compound was prepared as a racemic mixture according to the procedure described in example 101, replacing 4-morpholin-4-ylaniline with 4-(5-oxazolyl)-benzenamine in step 2. LCMS (M+H) 456.4.

Example 132

3-cyclopentyl-3-(4-(5-methoxy-2-(3-(oxazol-5-yl)phenylamino)pyrimidin-4-yl)-1H-pyrazol-1-yl)propanenitrile

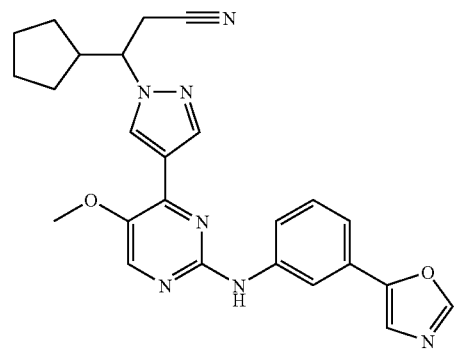

This compound was prepared as a racemic mixture according to the procedure described in example 101, replacing 4-morpholin-4-ylaniline with 3-(5-oxazolyl)-benzenamine in step 2. LCMS (M+H) 456.4.

Example 133

3-cyclopentyl-3-(4-(5-methoxy-2-(4-(3-oxomorpholino)phenylamino)pyrimidin-4-yl)-1H-pyrazol-1-yl)propanenitrile

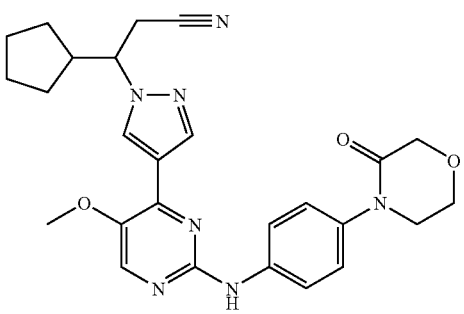

This compound was prepared as a racemic mixture according to the procedure described in example 101, replacing 4-morpholin-4-ylaniline with 4-(4-aminophenyl)-3-morpholinone in step 2. LCMS (M+H) 488.4.

Example 134

3-cyclopentyl-3-(4-(5-methoxy-2-(3-(2-methylpyrimidin-4-yl)phenylamino)pyrimidin-4-yl)-1H-pyrazol-1-yl)propanenitrile

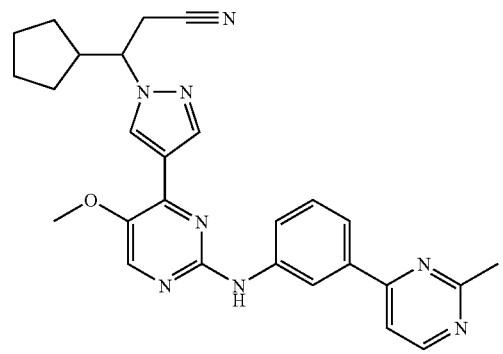

This compound was prepared as a racemic mixture according to the procedure described in example 101, replacing 4-morpholin-4-ylaniline with 3-(2-methyl-4-pyrimidinyl)-benzenamine in step 2. LCMS (M+H) 481.4.

Example 135

3-cyclopentyl-3-(4-(5-methoxy-2-(4-(2-oxopiperidin-1-yl)phenylamino)pyrimidin-4-yl)-1H-pyrazol-1-yl)propanenitrile

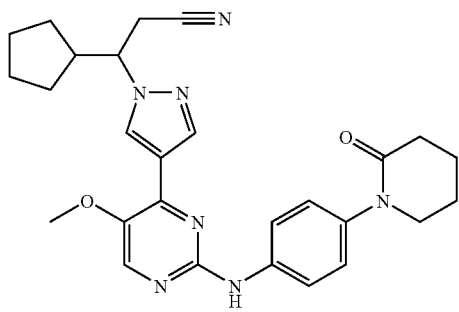

This compound was prepared as a racemic mixture according to the procedure described in example 101, replacing 4-morpholin-4-ylaniline with 1-(4-aminophenyl)-2-piperidinone in step 2. LCMS (M+H) 486.45

Example 136

3-cyclopentyl-3-(4-(5-methoxy-2-(4-(2-oxooxazolidin-3-yl)phenylamino)pyrimidin-4-yl)-1H-pyrazol-1-yl)propanenitrile

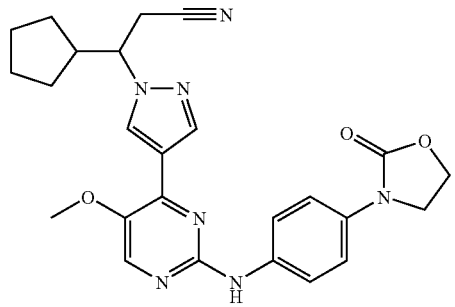

This compound was prepared as a racemic mixture according to the procedure described in example 101, replacing 4-morpholin-4-ylaniline with 3-(4-aminophenyl)-2-oxazolidinone in step 2. LCMS (M+H) 474.4.

Example 137

3-cyclopentyl-3-(4-(2-(3-(4-methylpiperazine-1-carbonyl)phenylamino)pyrimidin-4-yl)-1H-pyrazol-1-yl)propanenitrile

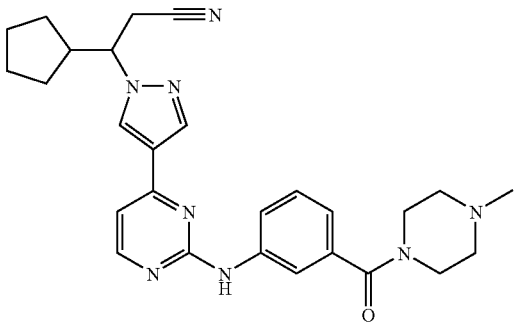

This compound was prepared as a racemic mixture according to the procedure described in example 109, replacing methylammonium chloride with 1-methylpiperazine. LCMS (M+H) 485.2.

Example 138

3-cyclopentyl-3-(4-(2-(3-(4-(2-hydroxyethyl)piperazine-1-carbonyl)phenylamino)pyrimidin-4-yl)-1H-pyrazol-1-yl)propanenitrile

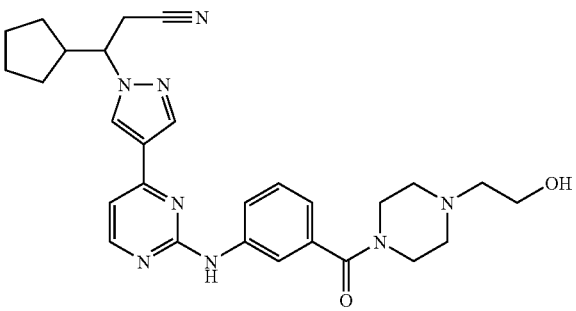

This compound was prepared as a racemic mixture according to the procedure described in example 109, replacing methylammonium chloride with 1-piperazineethanol. LCMS (M+H) 515.5.

Example 139

3-cyclopentyl-3-(4-(2-(3-(pyrrolidine-1-carbonyl)phenylamino)pyrimidin-4-yl)-1H-pyrazol-1-yl)propanenitrile

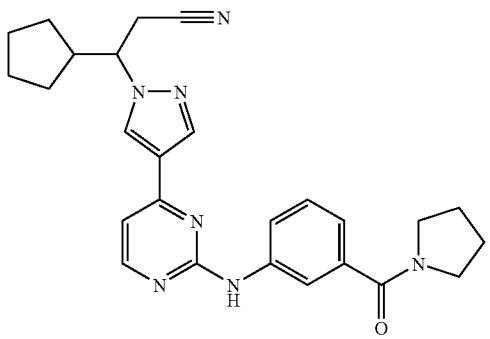

This compound was prepared as a racemic mixture according to the procedure described in example 109, replacing methylammonium chloride with pyrrolidine. LCMS (M+H) 456.2.

Example 140

3-cyclopentyl-3-(4-(2-(3-(3-oxopiperazine-1-carbonyl)phenylamino)pyrimidin-4-yl)-1H-pyrazol-1-yl)propanenitrile

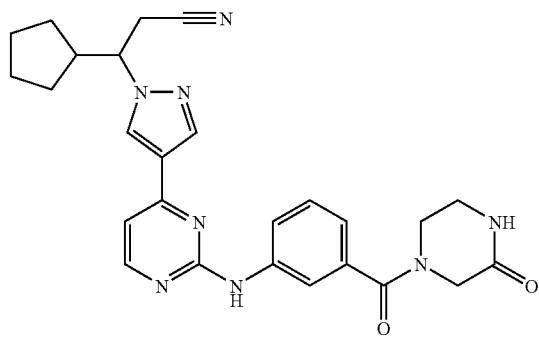

This compound was prepared as a racemic mixture according to the procedure described in example 109, replacing methylammonium chloride with 3-oxopiperazine. LCMS (M+H) 485.4.

Example 141

3-cyclopentyl-3-(4-(2-(3-((R)-3-hydroxypyrrolidine-1-carbonyl)phenylamino)pyrimidin-4-yl)-1H-pyrazol-1-yl)propanenitrile

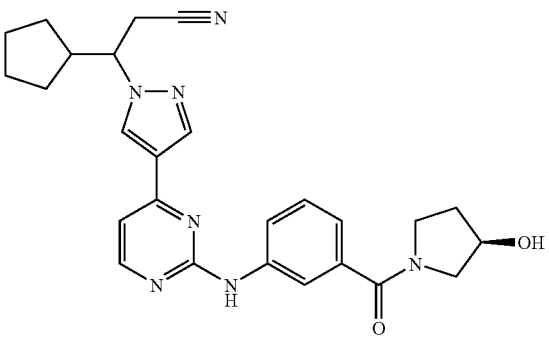

This compound was prepared as a diastereoisomeric mixture according to the procedure described in example 109, replacing methylammonium chloride with 3-(R)-hydroxypyrrolidine. LCMS (M+H) 472.2.

Example 142

3-(4-(2-(3-(azetidine-1-carbonyl)phenylamino)pyrimidin-4-yl)-1H-pyrazol-1-yl)-3-cyclopentylpropanenitrile

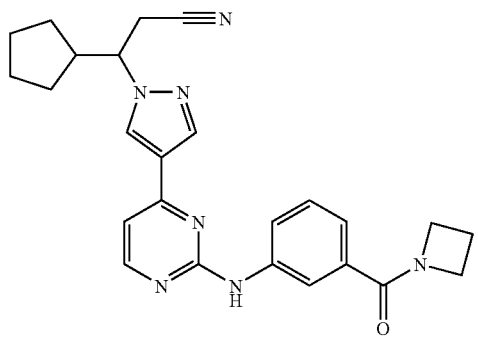

This compound was prepared as a racemic mixture according to the procedure described in example 109, replacing methylammonium chloride with azetidine HCl salt. LCMS (M+H) 442.2.

Example 143

3-(4-(2-(3-(4-acetylpiperazine-1-carbonyl)phenylamino)pyrimidin-4-yl)-1H-pyrazol-1-yl)-3-cyclopentylpropanenitrile

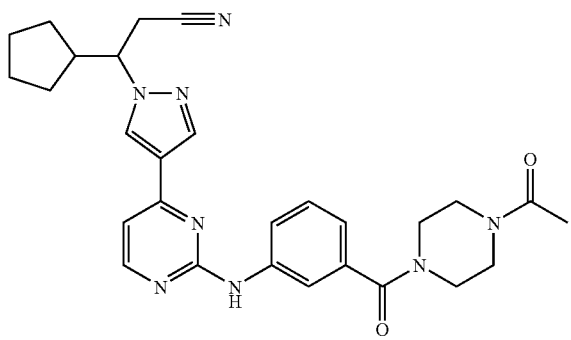

This compound was prepared as a racemic mixture according to the procedure described in example 109, replacing methylammonium chloride with 1-acetylpiperazine. LCMS (M+H) 513.2.

Example 144

3-cyclopentyl-3-(4-(2-(3-(4-(pyridin-3-ylmethyl)piperidine-1-carbonyl)phenylamino)pyrimidin-4-yl)-1H-pyrazol-1-yl)propanenitrile

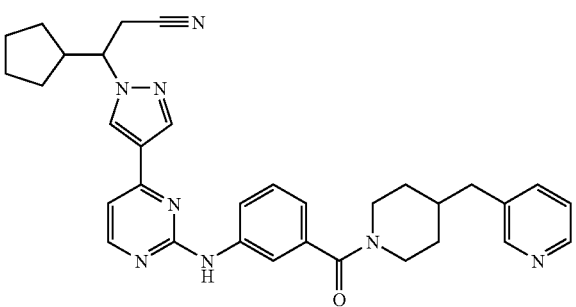

This compound was prepared as a racemic mixture according to the procedure described in example 109, replacing methylammonium chloride with 3-(4-piperidinylmethyl)-pyridine. LCMS (M+H) 561.2.

Example 145

3-(4-(1-(2-cyano-1-cyclopentylethyl)-1H-pyrazol-4-yl)pyrimidin-2-ylamino)-N—((R)-1-(3-methoxyphenyl)ethyl)benzaide

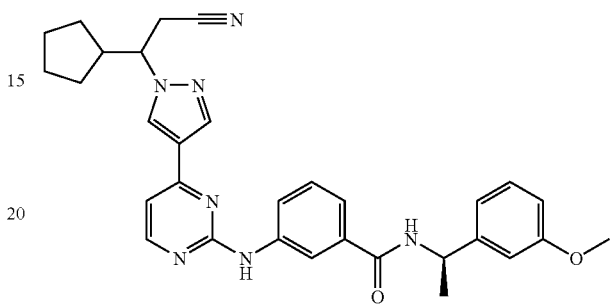

This compound was prepared as a diastereoisomeric mixture according to the procedure described in example 109, replacing methylammonium chloride with (αR)-3-methoxy-α-methyl-benzenemethanamine. LCMS (M+H) 536.2.

Example 146

3-(4-(1-(2-cyano-1-cyclopentylethyl)-1H-pyrazol-4-yl)pyrimidin-2-ylamino)-N-(pyridin-3-ylmethyl)benzamide

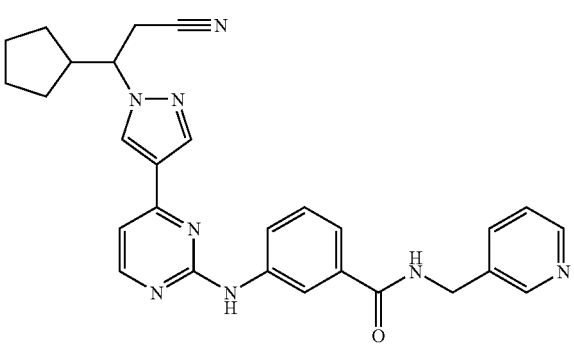

This compound was prepared as a racemic mixture according to the procedure described in example 109, replacing methylammonium chloride with 3-pyridinemethanamine. LCMS (M+H) 493.2.

Example 147

3-cyclopentyl-3-(4-(2-(3-(morpholine-4-carbonyl)phenylamino)pyrimidin-4-yl)-1H-pyrazol-1-ylropanenitrile

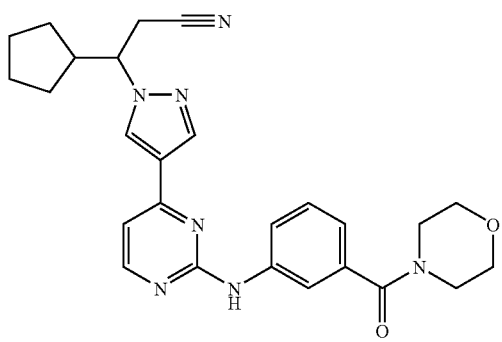

This compound was prepared as a racemic mixture according to the procedure described in example 109, replacing methylammonium chloride with morpholine. LCMS (M+H) 472.5.

Example 148

3-(4-(1-(2-cyano-1-cyclopentylethyl)-1H-pyrazol-4-yl)pyrimidin-2-ylamino)-N-((5-methylisoxazol-3-yl)methyl)benzamide

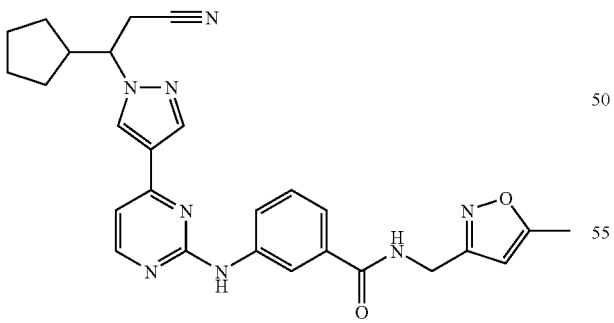

This compound was prepared as a racemic mixture according to the procedure described in example 109, replacing methylammonium chloride with 5-methyl-3-isoxazolemethanamine. LCMS (M+H) 497.4.

Example 149

3-(4-(1-(2-cyano-1-cyclopentylethyl)-1H-pyrazol-4-yl)pyrimidin-2-ylamino)-N-(2-(1-methylpyrrolidin-2-yl)ethyl)benzamide

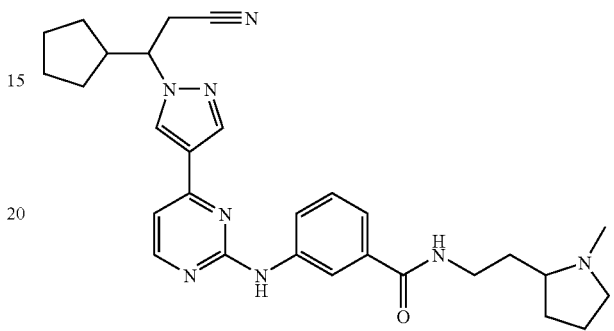

This compound was prepared as a diastereoisomeric mixture according to the procedure described in example 109, replacing methylammonium chloride with 1-methyl-2-pyrrolidineethanamine. LCMS (M+H) 513.2.

Example 150

3-cyclopentyl-3-(4-(2-(3-(4-hydroxy-4-phenylpiperidine-1-carbonyl)phenylamino)pyrimidin-4-yl)-1H-pyrazol-1-yl)propanenitrile

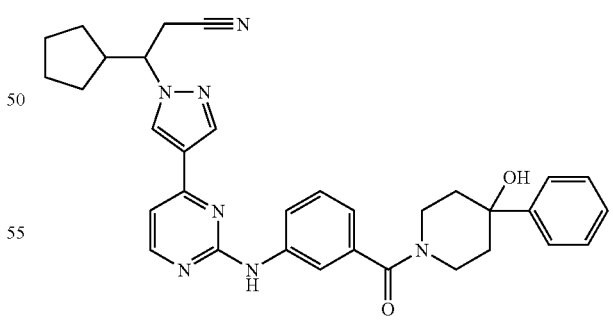

This compound was prepared as a racemic mixture according to the procedure described in example 109, using 4-phenyl-4-piperidinol instead of methylammonium chloride. LCMS (M+H) 562.2.

Example 151

3-(4-(2-(3-(4-benzyl-4-hydroxypiperidine-1-carbonyl)phenylamino)pyrimidin-4-yl)-1H-pyrazol-1-yl)-3-cyclopentylpropanenitrile

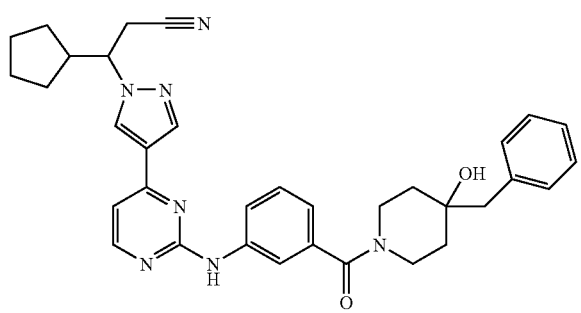

This compound was prepared as a racemic mixture according to the procedure described in example 109, using 4-benzyl-4-piperidinol instead of methylammonium chloride. LCMS (M+H) 576.2.

Example 152

3-cyclopentyl-3-(4-(2-(3-(3-(pyridin-2-yl)pyrrolidine-1-carbonyl)phenylamino)pyrimidin-4-yl)-1H-pyrazol-1-yl)propanenitrile

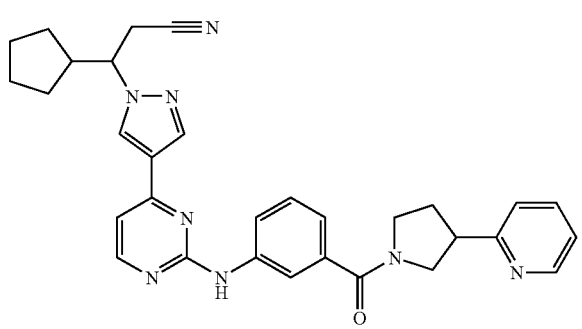

This compound was prepared as a diastereoisomeric mixture according to the procedure described in example 109, using 2-(3-pyrrolidinyl)-pyridine instead of methylammonium chloride. LCMS (M+H) 533.5.

Example 153

3-(4-(1-(2-cyano-1-cyclopentylethyl)-1H-pyrazol-4-yl)pyrimidin-2-ylamino)-N-((tetrahydro-2H-pyran-4-yl)methyl)benzamide

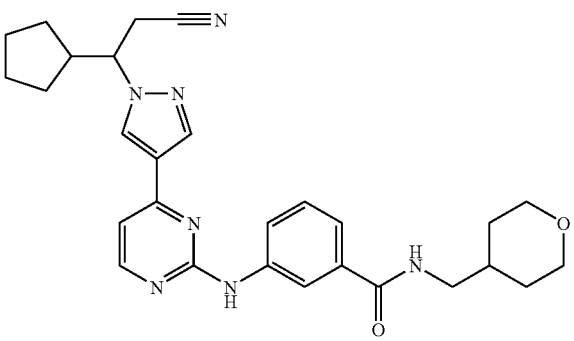

This compound was prepared as a racemic mixture according to the procedure described in example 109, using 4-aminomethyltetrahydropyran instead of methylammonium chloride. LCMS (M+H) 500.5.

Example 154

3-(4-(1-(2-cyano-1-cyclopentylethyl)-1H-pyrazol-4-yl)pyrimidin-2-ylamino)-N-(1-methylpiperidin-4-yl)benzamide

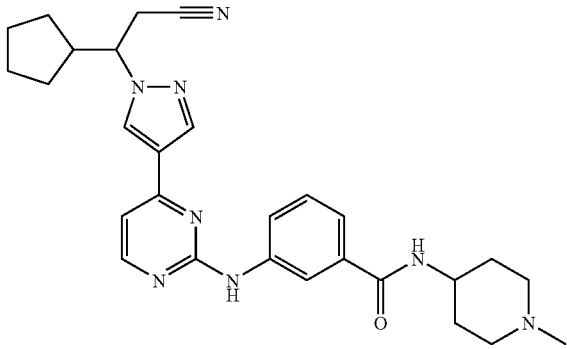

This compound was prepared as a racemic mixture according to the procedure described in example 109, using 1-methyl-4-piperidinamine instead of methylammonium chloride. LCMS (M+H) 499.5.

Example 155

3-cyclopentyl-3-(4-(2-(3-(4-phenylpiperidine-1-carbonyl)phenylamino)pyrimidin-4-yl)-1H-pyrazol-1-yl)propanenitrile

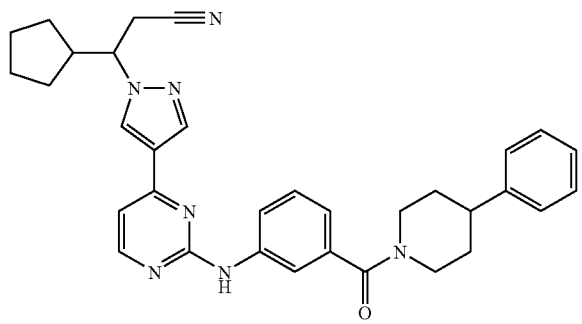

This compound was prepared as a racemic mixture according to the procedure described in example 109, using 4-phenylpiperidine instead of methylammonium chloride. LCMS (M+H) 546.5.

Example 156

3-(4-(1-(2-cyano-1-cyclopentylethyl)-1H-pyrazol-4-yl)pyrimidin-2-ylamino)-N-(1-(pyridin-2-yl)ethyl)benzamide

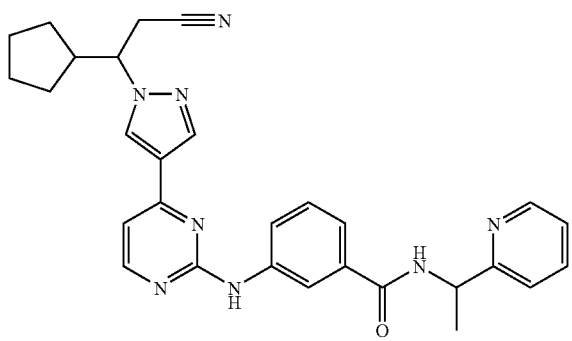

This compound was prepared as a diastereoisomeric mixture according to the procedure described in example 109, using α-methyl-2-pyridinemethanamine instead of methylammonium chloride. LCMS (M+H) 507.5.

Example 157

3-cyclopentyl-3-(4-(2-(3-(3-(3-fluorophenyl)pyrrolidine-1-carbonyl)phenylamino)pyrimidin-4-yl)-1H-pyrazol-1-yl)propanenitrile

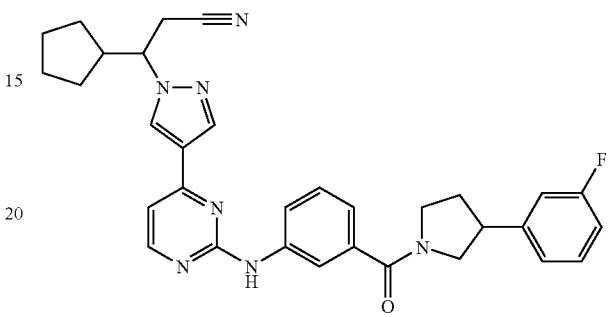

This compound was prepared as a diastereoisomeric mixture according to the procedure described in example 109, using 3-(3-fluorophenyl)-pyrrolidine instead of methylammonium chloride. LCMS (M+H) 550.5.

Example 158

N-((3R)-1-(3-(4-(1-(2-cyano-1-cyclopentylethyl)-1H-pyrazol-4-yl)pyrimidin-2-ylamino)benzoyl)pyrrolidin-3-yl)acetamide

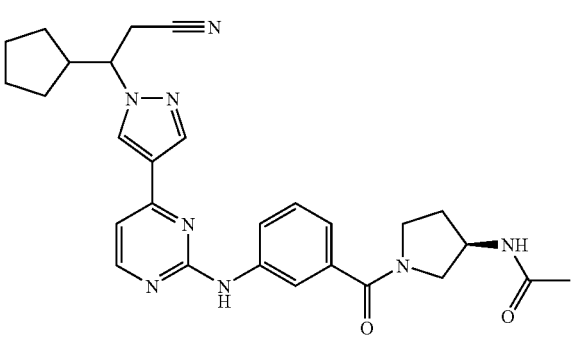

This compound was prepared as a diastereoisomeric mixture according to the procedure described in example 109, using N-(3R)-3-pyrrolidinyl-acetamide instead of methylammonium chloride. LCMS (M+H) 513.5.

Example 159

3-(4-(1-(2-cyano-1-cyclopentylethyl)-1H-pyrazol-4-yl)pyrimidin-2-ylamino)-N-(2-(2-oxoimidazolidin-1-yl)ethyl)benzamide

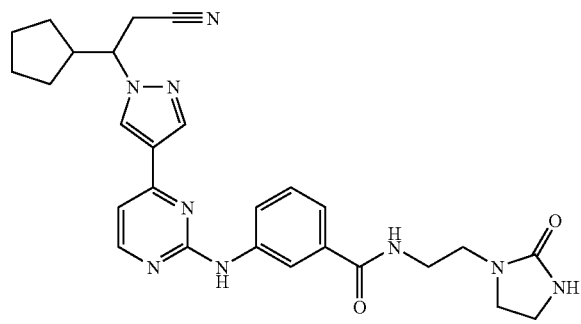

This compound was prepared as a racemic mixture according to the procedure described in example 109, using 1-(2-aminoethyl)-2-imidazolidinone instead of methylammonium chloride. LCMS (M+H) 514.5.

Example 160

3-cyclopentyl-3-(4-(2-(3-(4-(pyrimidin-2-yl)piperazine-1-carbonyl)phenylamino)pyrimidin-4-yl)-1H-pyrazol-1-yl)propanenitrile

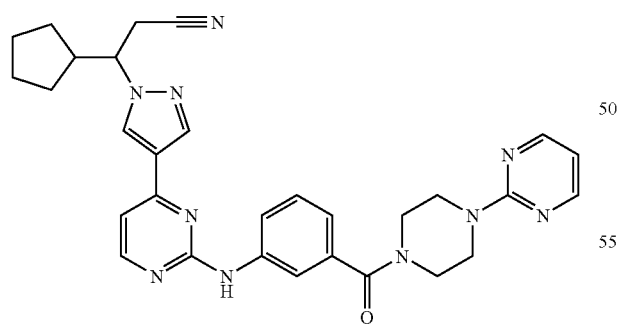

This compound was prepared as a racemic mixture according to the procedure described in example 109, using 2-(1-piperazinyl)-pyrimidine instead of methylammonium chloride. LCMS (M+H) 549.2.

Example 161

3-(4-(1-(2-cyano-1-cyclopentylethyl)-1H-pyrazol-4-yl)pyrimidin-2-ylamino)-N-(2-(pyridin-3-yl)ethyl)benzamide

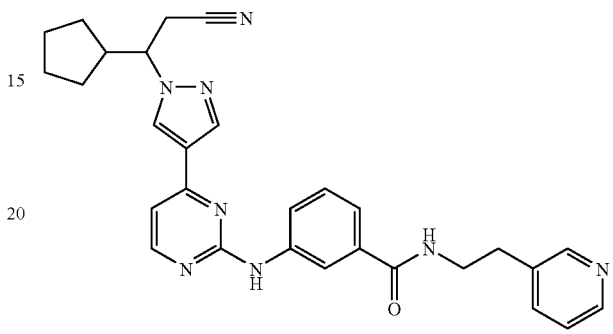

This compound was prepared as a racemic mixture according to the procedure described in example 109, using 3-pyridineethanamine instead of methylammonium chloride. LCMS (M+H) 507.2.

Example 162

3-cyclopentyl-3-(4-(2-(3-((R)-2-(methoxymethyl)pyrrolidine-1-carbonyl)phenylamino)pyrimidin-4-yl)-1H-pyrazol-1-yl)propanenitrile

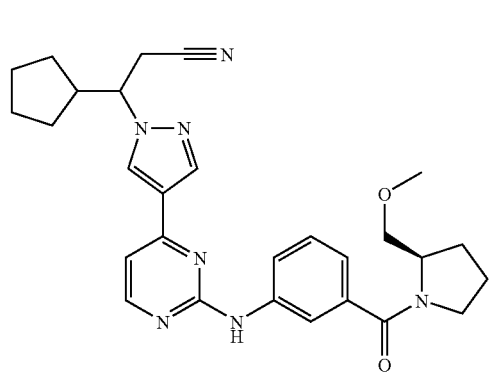

This compound was prepared as a diastereoisomeric mixture according to the procedure described in example 109, using (R)-2-methoxymethyl-pyrrolidine instead of methylammonium chloride. LCMS (M+H) 500.2.

Example 163

3-(4-(1-(2-cyano-1-cyclopentylethyl)-1H-pyrazol-4-yl)pyrimidin-2-ylamino)-N-(2-methoxybezyl)benzamide

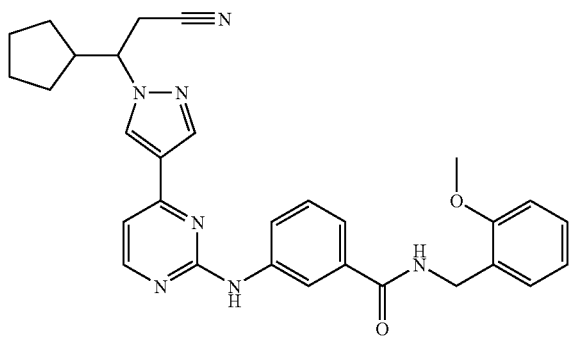

This compound was prepared as a racemic mixture according to the procedure described in example 109, using 2-methoxybenzenemethanamine instead of methylammonium chloride. LCMS (M+H) 522.4.

Example 164

3-cyclopentyl-3-(4-(2-(3-(4-phenoxypiperidine-1-carbonyl)phenylamino)pyrimidin-4-yl)-1H-pyrazol-1-yl)propanenitrile

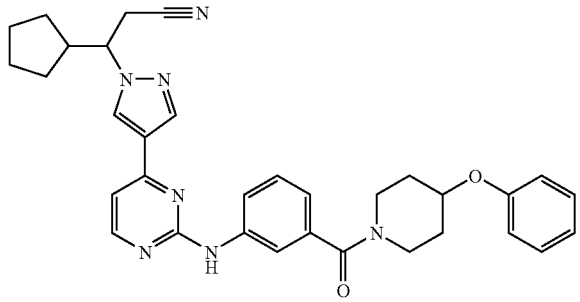

This compound was prepared as a racemic mixture according to the procedure described in example 109, using 4-phenoxypiperidine instead of methylammonium chloride. LCMS (M+H) 562.5.

Example 165

3-(4-(1-(2-cyano-1-cyclopentylethyl)-1H-pyrazol-4-yl)pyrimidin-2-ylamino)-N-(1-(hydroxymethyl)cyclopentyl)benzamide

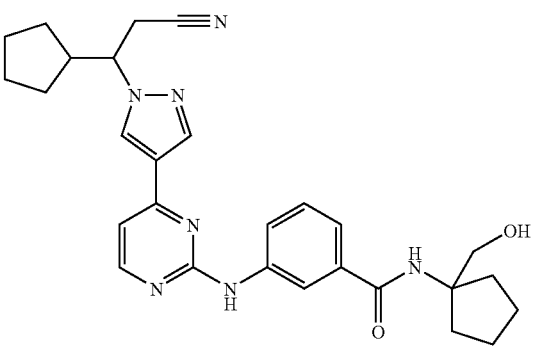

This compound was prepared as a racemic mixture according to the procedure described in example 109, using 1-aminocyclopentanemethanol instead of methylammonium chloride. LCMS (M+H) 500.2.

Example 166

4-(4-(3-(4-(1-(2-cyano-1-cyclopentylethyl)-1H-pyrazol-4-yl)pyrimidin-2-ylamino)benzoyl)piperazin-1-yl)benzonitrile

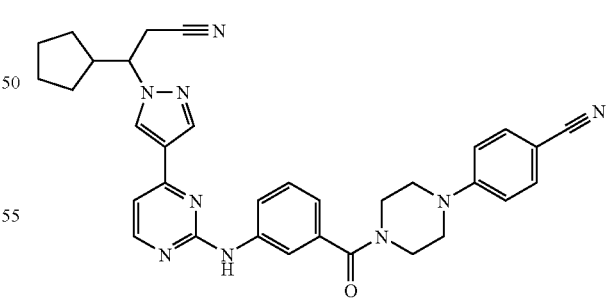

This compound was prepared as a racemic mixture according to the procedure described in example 109, using 4-(1-piperazinyl)-benzonitrile instead of methylammonium chloride. LCMS (M+H) 572.2.

Example 167

N—((S)-1-benzylpyrrolidin-3-yl)-3-(4-(1-(2-cyano-1-cyclopentylethyl)-1H-pyrazol-4-yl)pyrimidin-2-ylamino)benzamide

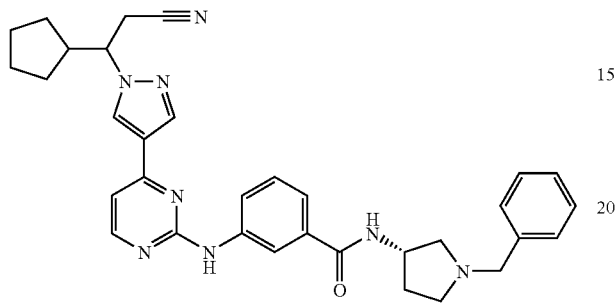

This compound was prepared as a diastereoisomeric mixture according to the procedure described in example 109, using (3S)-1-(phenylmethyl)-3-pyrrolidinamine instead of methylammonium chloride. LCMS (M+H) 561.3.

Example 168

3-cyclopentyl-3-(4-(2-(3-(4-phenylpiperazine-1-carbonyl)phenylamino)pyrimidin-4-yl)-1H-pyrazol-1-yl)propanenitrile

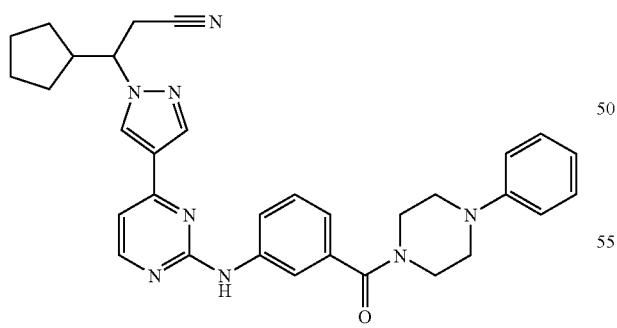

This compound was prepared as a racemic mixture according to the procedure described in example 109, using 1-phenylpiperazine instead of methylammonium chloride. LCMS (M+H) 547.2.

Example 169

3-cyclopentyl-3-(4-(2-(3-nitrophenylamino)pyrimidin-4-yl)-1H-pyrazol-1-yl)propanenitrile

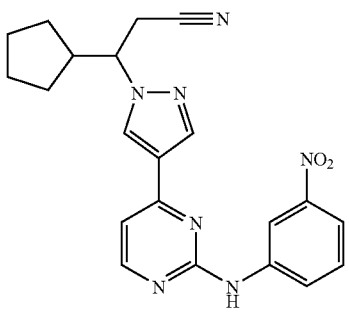

This compound was prepared as a racemic mixture according to the procedure described in example 33, using 3-nitroaniline instead of 4-aminobenzamide in step 3. LCMS (M+H) 404.4.

Example 170

3-cyclopentyl-3-(4-(2-(4-nitrophenylamino)pyrimidin-4-yl)-1H-pyrazol-1-yl)propanenitrile

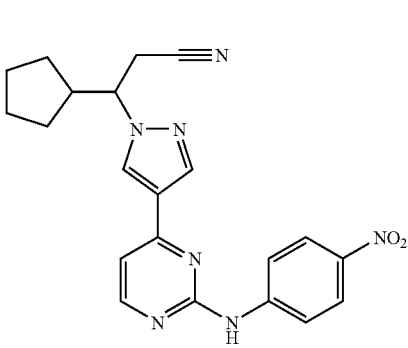

This compound was prepared as a racemic mixture according to the procedure described in example 33, using 4-nitroaniline instead of 4-aminobenzamide in step 3. LCMS (M+H) 404.4.

Example 171

3-cyclobutyl-3-(4-(2-(4-morpholinophenylamino)pyrimidin-4-yl)-1H-pyrazol-1-yl)propanenitrile

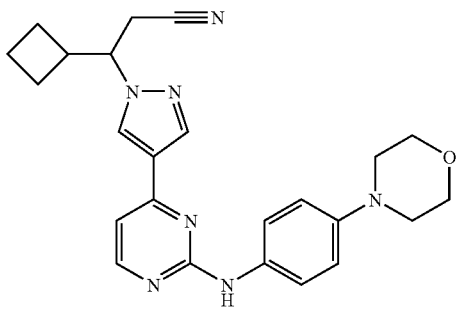

Step 1: 3-cyclobutyl-3-(4-(4,4,5,5-tetramethyl-1,3,2-dioxaborolan-2-yl)-1H-pyrazol-1-yl)propanenitrile To a solution of 4-(4,4,5,5-tetramethyl-1,3,2-dioxaborolan-2-yl)-1H-pyrazole (9.63 g, 0.0496 mol) in acetonitrile (124 mL, 2.37 mol) was added (E)-3-cyclobutylacrylonitrile (5.30 g, 0.0495 mol), followed by 1,8-diazabicyclo[5.4.0]undec-7-ene (3.70 mL, 0.0248 mol). The resulting mixture was stirred at room temperature overnight, then evaporated to dryness. The mixture was purified on silica gel, eluting with 0 to 80% EtOAc in hexanes, to give the desired product as a racemic mixture (11.2 g, 75.2%). LCMS (M+H) 302.4.

Step 2: 3-(4-(2-chloropyrimidin-4-yl)-1H-pyrazol-1-yl)-3-cyclobutylpropanenitrile A mixture of 2,4-dichloropyrimidine (4.8 g, 0.032 mol), 3-cyclobutyl-3-(4-(4,4,5,5-tetramethyl-1,3,2-dioxaborolan-2-yl)-1H-pyrazol-1-yl)propanenitrile (8.10 g, 0.0269 mol), tetrakis(triphenylphosphine)palladium (2.0 g, 0.002 mol), and potassium phosphate (17 g, 0.081 mol) in 1,4-dioxane (80 mL) and water (8 mL) was heated at 100° C. overnight. After cooling to room temperature, the mixture was diluted with EtOAc, washed with water, brine, dried over MgSO$_4$, and concentrated. The residue was purified on silica gel, eluting with 0 to 80%, to give the desired product (5.51 g, 71.2%). LCMS (M+H) 288.3.

Step 3: 3-cyclobutyl-3-(4-(2-(4-morpholinophenylamino)pyrimidin-4-yl)-1H-pyrazol-1-yl)propanenitrile A mixture of 3-(4-(2-chloropyrimidin-4-yl)-1H-pyrazol-1-yl)-3-cyclobutylpropanenitrile (30 mg, 0.1 mmol), 4-morpholin-4-ylaniline (26.6 mg, 0.149 mmol), and p-toluenesulfonic acid (14 mg, 0.084 mmol) in dry 1,4-dioxane (0.8 mL) was refluxed overnight. The mixture was diluted with acetonitrile and water, purified on RP-HPLC at pH 1 to give the desired product as a racemic mixture (TFA salt) (33 mg, 61%). LCMS (M+H) 430.4.

Example 172

3-(4-(2-(4-aminophenylamino)pyrimidin-4-yl)-1H-pyrazol-1-yl)-3-cyclopentylpropanenitrile

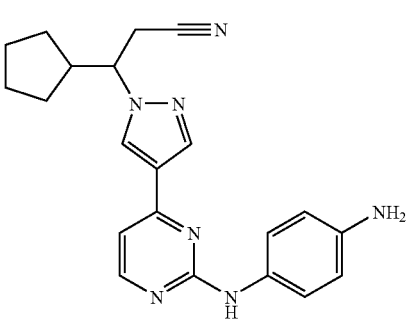

A mixture of 3-cyclopentyl-3-(4-(2-(4-nitrophenylamino)pyrimidin-4-yl)-1H-pyrazol-1-yl)propanenitrile (1.00 g, 0.00248 mol) in 20 mL of methanol was hydrogenated in the presence of catalytic amount of 10% Pd/C, under balloon pressure, overnight. The catalyst was filtered off and the filtrate was evaporated to dryness. The crude product was used directly in next step (900 mg, 97.2%). An analytically pure sample was obtained by RP-HPLC as a racemic mixture. LCMS (M+H) 374.4.

Example 173

3-(4-(2-(4-(1H-pyrazol-1-yl)phenylamino)pyrimidin-4-yl)-1H-pyrazol-1-yl)-3-cyclobutylpropanenitrile

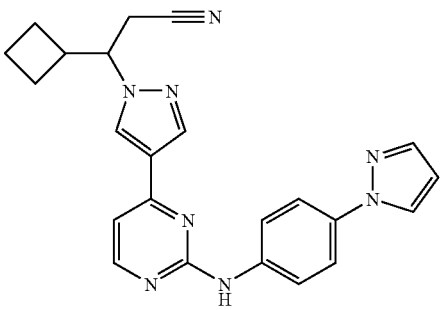

This compound was prepared as a racemic mixture according to the procedure described in example 171, replacing 4-morpholin-4-ylaniline with 4-(1H-pyrazol-1-yl)aniline in step 3. LCMS (M+H) 411.1.

Example 174

3-cyclobutyl-3-(4-(2-(4-(2-oxopiperidin-1-yl)phenylamino)pyrimidin-4-yl)-1H-pyrazl-1-yl)propanenitrile

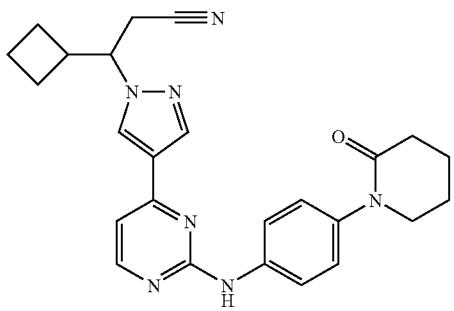

This compound was prepared as a racemic mixture according to the procedure described in example 171, replacing 4-morpholin-4-ylaniline with 1-(4-aminophenyl)-2-piperidinone in step 3. LCMS (M+H) 442.4.

Example 175

3-cyclobutyl-3-(4-(2-(4-(3-oxomorpholino)phenylamino)pyrimidin-4-yl)-1H-pyrazol-1-yl)propanenitrile

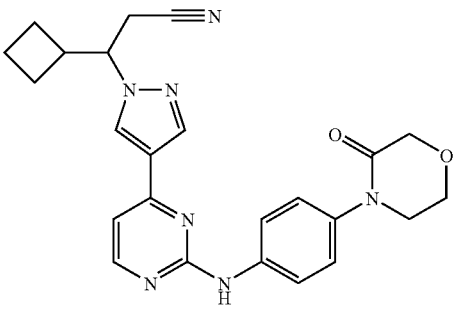

This compound was prepared as a racemic mixture according to the procedure described in example 171, replacing 4-morpholin-4-ylaniline with 4-(4-aminophenyl)-3-morpholinone in step 3. LCMS (M+H) 444.4.

Example 176

3-cyclobutyl-3-(4-(2-(3-(oxazol-5-yl)phenylamino)pyrimidin-4-yl)-1H-pyrazol-1-yl)propanenitrile

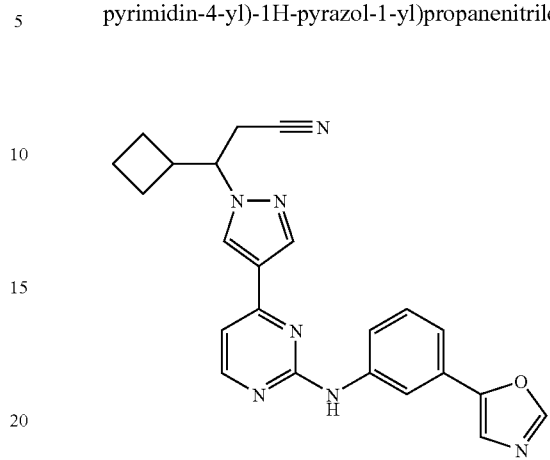

This compound was prepared as a racemic mixture according to the procedure described in example 171, replacing 4-morpholin-4-ylaniline with 3-(5-oxazolyl)-benzenamine in step 3. LCMS (M+H) 412.4.

Example 177

3-cyclopropyl-3-(4-(2-(4-morpholinophenylamino)pyrimidin-4-yl)-1H-pyrazol-1-yl)propanenitrile

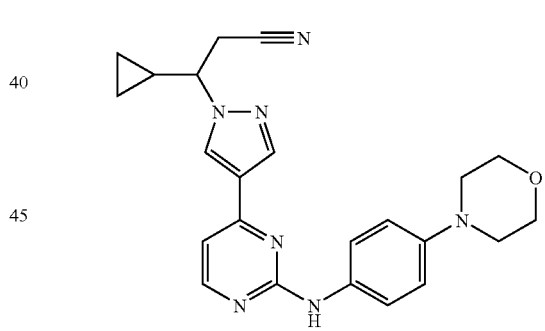

Step 1: 3-cyclopropyl-3-(4-(4,4,5,5-tetramethyl-1,3,2-dioxaborolan-2-yl)-1H-pyrazol-1-yl)propanenitrile To a solution of 4-(4,4,5,5-tetramethyl-1,3,2-dioxaborolan-2-yl)-1H-pyrazole (10.0 g, 0.0515 mol) in acetonitrile (129 mL, 2.46 mol) was added (E)-3-cyclopropylacrylonitrile (5.75 g, 0.0617 mol), followed by 1,8-diazabicyclo[5.4.0]undec-7-ene (3.85 mL, 0.0258 mol). The resulting mixture was stirred at room temperature overnight, and evaporated to dryness. The mixture was purified on silica gel, eluting with 0 to 80% EtOAc in hexanes, to give the desired product as racemic mixture (10.8 g, 73.0%). LCMS (M+H) 288.4.

Step 2. 3-(4-(2-chloropyrimidin-4-yl)-1H-pyrazol-1-yl)-3-cyclopropylpropanenitrile A mixture of 2,4-dichloropyrimidine (2.8 g, 0.019 mol), 3-cyclopropyl-3-(4-(4,4,5,5-tetramethyl-1,3,2-dioxaborolan-2-yl)-1H-pyrazol-1-yl)propanenitrile (4.50 g, 0.0157 mol), tetrakis(triphenylphosphine)palladium (1.0 g, 0.9 mmol), and potassium phosphate (0.1 g, 0.047 mol) in 1,4-dioxane (50 mL) and water (5 mL) was heated at 100° C. overnight. After cooling to room temperature, the mixture was diluted with EtOAc, washed with water, brine, dried over MgSO$_4$, and concentrated. The residue was purified on silica gel, eluting with 0 to 100% EtOAc in hexanes, to give the desired product as racemic mixture (3.08 g, 71.81%). LCMS (M+H) 274.3.

Step 3. 3-cyclopropyl-3-(4-(2-(4-morpholinophenylamino)pyrimidin-4-yl)-1H-pyrazol-1-yl)propanenitrile A mixture of 3-(4-(2-chloropyrimidin-4-yl)-1H-pyrazol-1-yl)-3-cyclopropylpropanenitrile (30 mg, 0.1 mmol), 4-morpholin-4-ylaniline (26.6 mg, 0.149 mmol), and p-toluenesulfonic acid (14 mg, 0.084 mmol) in dry 1,4-dioxane (0.8 mL) was refluxed overnight. The mixture was diluted with acetonitrile and water, purified on RP-HPLC at pH 1.0 to give the desired product as a racemic mixture (TFA salt). LCMS (M+H) 416.2.

Example 178

3-(4-(2-(4-(1H-pyrazol-1-yl)phenylmino)pyrimidin-4-yl)-1H-pyrazol-1-yl)-3-cyclopropylpropanenitrile

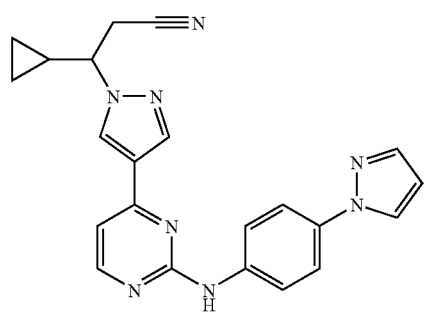

This compound was prepared as a racemic mixture according to the procedure described in example 177, replacing 4-morpholin-4-ylaniline with 4-(1H-pyrazol-1-yl)aniline in step 3. LCMS (M+H) 397.1.

Example 179

3-cyclopropyl-3-(4-(2-(4-(2-oxopiperidin-1-yl)phenylamino)pyrimidin-4-yl)-1H-pyrazol-1-yl)propanenitrile

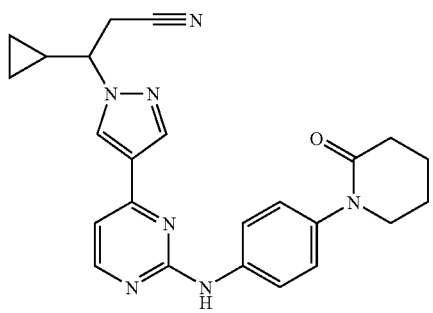

This compound was prepared as a racemic mixture according to the procedure described in example 177, replacing 4-morpholin-4-ylaniline with 1-(4-aminophenyl)-2-piperidinone in step 3. LCMS (M+H) 428.4.

Example 180

3-cyclopropyl-3-(4-(2-(4-(3-oxomorpholino)phenylamino)pyrimidin-4-yl)-1H-pyrazol-1-yl)propanenitrile

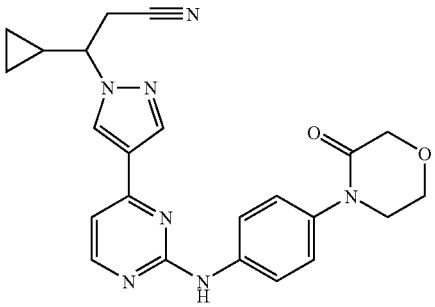

This compound was prepared as a racemic mixture according to the procedure described in example 177, replacing 4-morpholin-4-ylaniline with 4-(4-aminophenyl)-3-morpholinone in step 3. LCMS (M+H) 430.1.

Example 181

3-cyclopropyl-3-(4-(2-(3-(oxazol-5-yl)phenylamino)pyrimidin-4-yl)-1H-pyrazol-1-yl)propanenitrile

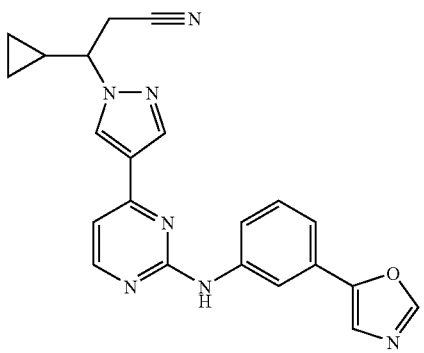

This compound was prepared as a racemic mixture according to the procedure described in example 177, replacing 4-morpholin-4-ylaniline with 3-(5-oxazolyl)-benzenamine in step 3. LCMS (M+H) 398.4

Example 182

N-(4-(4-(1-(2-cyano-1-cyclopentylethyl)-1H-pyrazol-4-yl)pyrimidin-2-ylamino)phenyl)-(cis)-2,6-dimethylmorpholine-4-sulfonamide

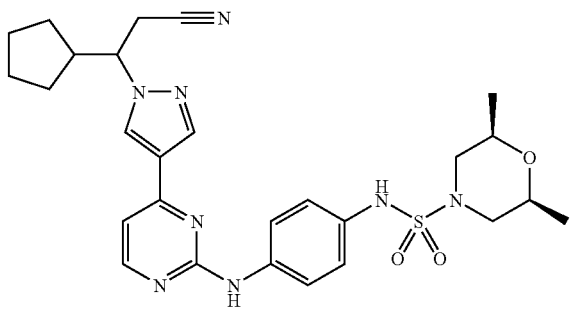

Step 1. (cis)-2,6-dimethylmorpholine-4-sulfonyl chloride

To a stirred solution of sulfuryl chloride (0.773 mL, 0.00955 mol) in methylene chloride (2.39 mL, 0.0372 mol) at 0° C. was added a mixture of triethylamine (0.666 mL, 0.00478 mol) and cis-2,6-dimethylmorpholine (0.55 g, 0.0048 mol) at such a rate as to keep the temperature below 20° C. The reaction mixture was stirred at room temperature for 2 h, then poured into iced water (5 g, 0.3 mol) and extracted with dichloromethane. The combined organic layers were washed with 10% HCl, cold water, brine, dried over calcium chloride, evaporated to dryness. The crude sulfamoyl chloride was used directly in next step.

Step 2. N-(4-(4-(6-(2-cyano-1-cyclopentylethyl)-1H-pyrazol-4-yl)pyrimidin-2-ylamino)phenyl)-(cis)-2,6-dimethylmorpholine-4-sulfonamide To a mixture of 3-(4-(2-(4-aminophenylamino)pyrimidin-4-yl)-1H-pyrazol-1-yl)-3-cyclopentylpropanenitrile (Example 172, 30 mg, 0.08 mmol) in 1,4-dioxane (0.5 mL) was added 1.0 M sodium carbonate in water (0.5 mL), followed by cis-2,6-dimethylmorpholine-4-sulfonyl chloride (26 mg, 0.12 mmol). The reaction mixture was stirred at room temperature for 1 h, then purified on RP-HPLC to give the desired product as a racemic mixture (TFA salt, 30 mg, 57%). LCMS (M+H) 551.2.

Example 183

N-(4-(4-(1-(2-cyano-1-cyclopentylethyl)-1H-pyrazol-4-yl)pyrimidin-2-ylamino)phenyl)benzamide

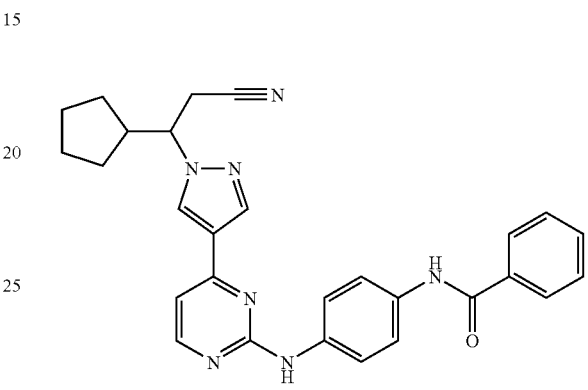

This compound was prepared as a racemic mixture according to the procedure described in example 182, using benzoyl chloride instead of cis-2,6-dimethylmorpholine-4-sulfonyl chloride in step 2. LCMS (M+H) 478.5.

Example 184

N-(4-(4-(1-(2-cyano-1-cyclopentylethyl)-1H-pyrazol-4-yl)pyrimidin-2-ylamino)phenyl)-1-(methylsulfonyl)methanesulfonamide

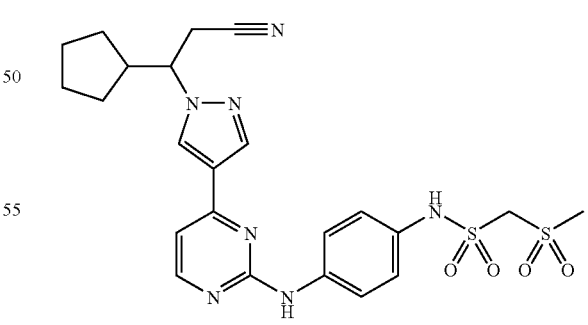

This compound was prepared as a racemic mixture according to the procedure described in example 182, using 1-(methylsulfonyl)-methanesulfonyl chloride instead of cis-2,6-dimethylmorpholine-4-sulfonyl chloride in step 2. LCMS (M+H) 530.1.

Example 185

N-(4-(4-(1-(2-cyano-1-cyclopentylethyl)-1H-pyrazol-4-yl)pyrimidin-2-ylamino)phenyl)-3,5-difluorobenzamide

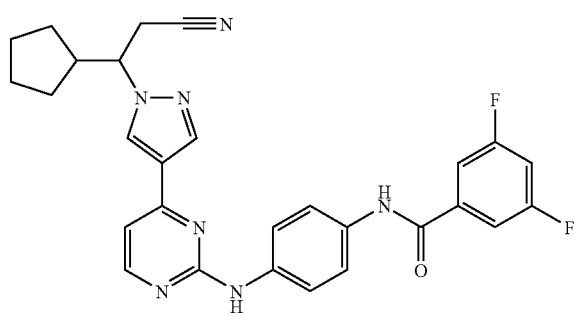

This compound was prepared as a racemic mixture according to the procedure described in example 182, using 3,5-difluorobenzoyl chloride instead of cis-2,6-dimethylmorpholine-4-sulfonyl chloride in step 2. LCMS (M+H) 514.4.

Example 186

NA-(4-(4-(1-(2-cyano-1-cyclopentylethyl)-1H-pyrazol-4-yl)pyrimidin-2-ylamino)phenyl)-N,N-dimethylsulfamide

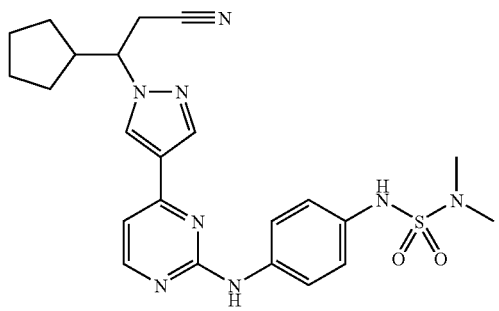

This compound was prepared as a racemic mixture according to the procedure described in example 182, using N,N-dimethyl-sulfamoyl chloride instead of cis-2,6-dimethylmorpholine-4-sulfonyl chloride in step 2. LCMS (M+H) 481.2.

Example 187

N-(4-(4-(1-(2-cyano-1-cyclopentylethyl)-1H-pyrazol-4-yl)pyrimidin-2-ylamino)phenyl)-5-methylisoxazole-3-carboxamide

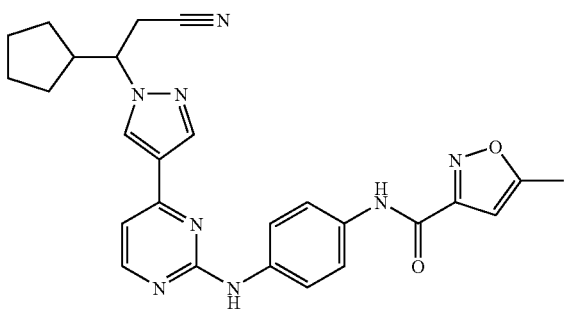

This compound was prepared as a racemic mixture according to the procedure described in example 182, using 5-methyl-3-isoxazolecarbonyl chloride instead of cis-2,6-dimethylmorpholine-4-sulfonyl chloride in step 2. LCMS (M+H) 483.2.

Example 188

N-(4-(4-(1-(2-cyano-1-cyclopentylethyl)-1H-pyrazol-4-yl)pyrimidin-2-ylamino)phenyl)isoxazole-5-carboxamide

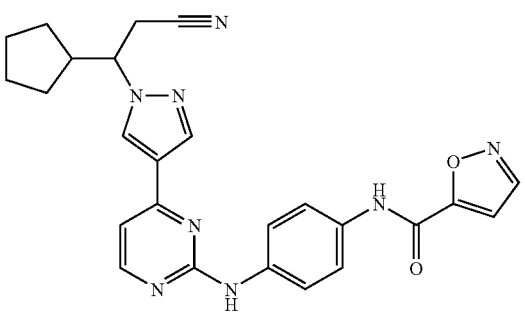

This compound was prepared as a racemic mixture according to the procedure described in example 182, using 5-isoxazolecarbonyl chloride instead of cis-2,6-dimethylmorpholine-4-sulfonyl chloride in step 2. LCMS (M+H) 469.1.

Example 189

N-(4-(4-(1-(2-cyano-1-cyclopentylethyl)-1H-pyrazol-4-yl)pyrimidin-2-ylamino)phenyl)-3,5-dimethyl-isoxazole-4-carboxamide

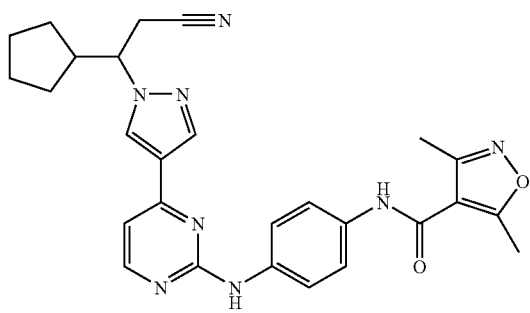

This compound was prepared as a racemic mixture according to the procedure described in example 182, using 3,5-dimethyl-4-isoxazolecarbonyl chloride instead of cis-2,6-dimethylmorpholine-4-sulfonyl chloride in step 2. LCMS (M+H) 497.2.

Example 190

N-(4-(4-(1-(2-cyano-1-cyclopentylethyl)-1H-pyrazol-4-yl)pyrimidin-2-ylamino)phenyl)-1-methyl-1H-pyrazole-3-sulfonamide

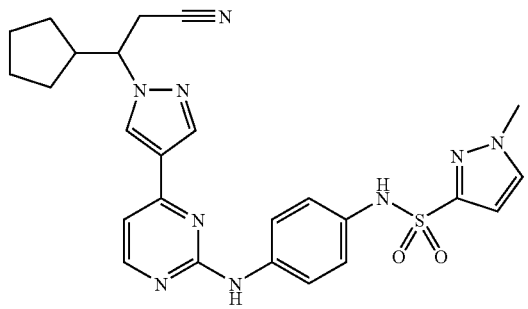

This compound was prepared as a racemic mixture according to the procedure described in example 182, using 1-methyl-1H-pyrazole-3-sulfonyl chloride instead of cis-2,6-dimethylmorpholine-4-sulfonyl chloride in step 2. LCMS (M+H) 518.1.

Example 191

N-(4-(4-(1-(2-cyano-1-cyclopentylethyl)-1H-pyrazol-4-yl)pyrimidin-2-ylamino)phenyl)-2,5-difluorobenzamide

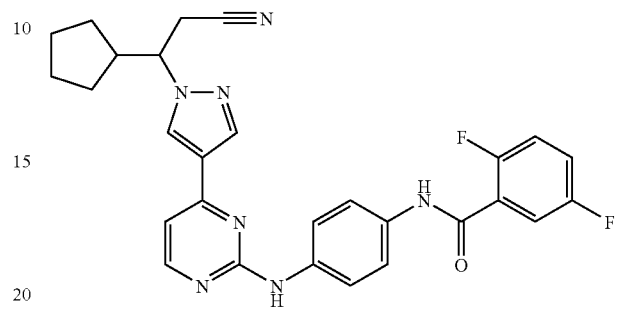

This compound was prepared as a racemic mixture according to the procedure described in example 182, using 2,4-difluorobenzoyl chloride instead of cis-2,6-dimethylmorpholine-4-sulfonyl chloride in step 2. LCMS (M+H) 514.3.

Example 192

3-cyclopentyl-3-(4-(2-(4-(1,1-dioxidoisothiazolidin-2-yl)phenyl)aminopyrimidin-4-yl)-1H-pyrazol-1-yl)propanenitrile

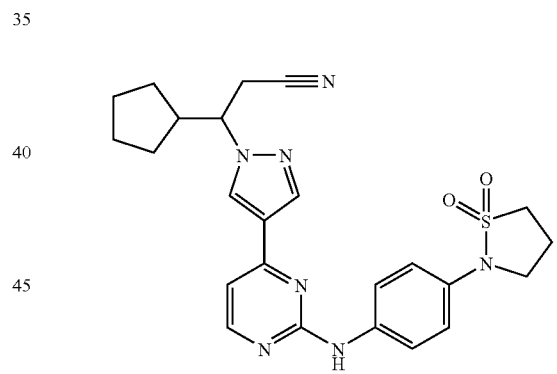

To a mixture of 3-(4-(2-(4-aminophenylamino)pyrimidin-4-yl)-1H-pyrazol-1-yl)-3-cyclopentylpropanenitrile (90.0 mg, 0.241 mmol) in 1,4-dioxane (2 mL) was added triethylamine (0.2 mL, 1 mmol), followed by 3-chloropropane-1-sulfonyl chloride (0.044 mL, 0.36 mmol). The reaction was stirred at room temperature for 1 h, quenched with 1N HCl. The mixture was extracted with EtOAc. The organic layers were separated, washed with brine, dried over MgSO$_4$, and evaporated to dryness to give the sulfonylated intermediate. LCMS (M+H) 514.

The crude intermediate made above was dissolved in N,N-dimethylformamide (0.75 mL) and triethylamine (0.3 mL, 0.002 mol). The reaction mixture was heated at 80° C. overnight. After being cooled to room temperature, the mixture was evaporated to dryness. The residue was purified on RP-HPLC to give the desired product as a racemic mixture (TFA salt, 41 mg, 35.62%). LCMS (M+H) 478.1.

Example 193

N-(4-(4-(1-(2-cyano-1-cyclopentylethyl)-1H-pyrazol-4-yl)pyrimidin-2-ylamino)phenyl)-5-(2-methylthiazol-4-yl)thiophene-2-sulfonamide

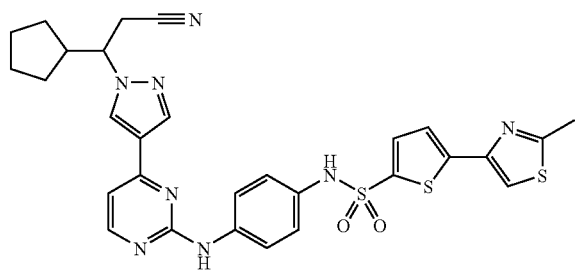

This compound was prepared as a racemic mixture according to the procedure described in example 182, using 5-(2-methyl-4-thiazolyl)-2-thiophenesulfonyl chloride instead of cis-2,6-dimethylmorpholine-4-sulfonyl chloride in step 2. LCMS (M+H) 617.1.

Example 194

N-(4-(4-(1-(2-cyano-1-cyclopentylethyl)-1H-pyrazol-4-yl)pyrimidin-2-ylamino)phenyl)-6-methylpyridine-2-sulfonamide

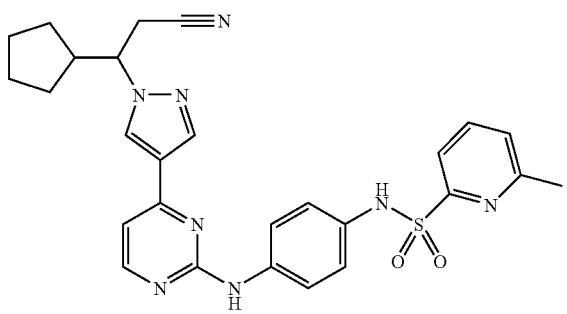

This compound was prepared as a racemic mixture according to the procedure described in example 182, using 6-methyl-2-pyridinesulfonyl chloride instead of cis-2,6-dimethylmorpholine-4-sulfonyl chloride in step 2. LCMS (M+H) 529.1.

Example 195

N-(4-(4-(1-(2-cyano-1-cyclopentylethyl)-1H-pyrazol-4-yl)pyrimidin-2-ylamino)phenyl)-5-(pyridin-2-yl)thiophene-2-sulfonamide

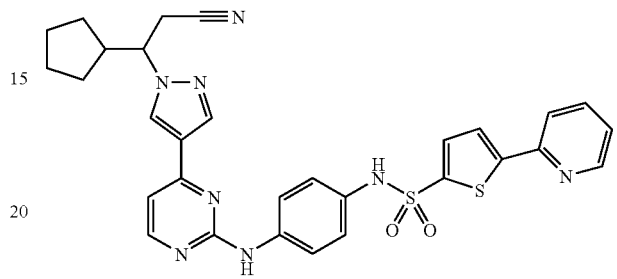

This compound was prepared as a racemic mixture according to the procedure described in example 182, using 5-(2-pyridinyl)-2-thiophenesulfonyl chloride instead of cis-2,6-dimethylmorpholine-4-sulfonyl chloride in step 2. LCMS (M+H) 597.1.

Example 196

5-chloro-N-(4-(4-(1-(2-cyano-1-cyclopentylethyl)-1H-pyrazol-4-yl)pyrimidin-2-ylamino)phenyl)thiophene-2-sulfonamide

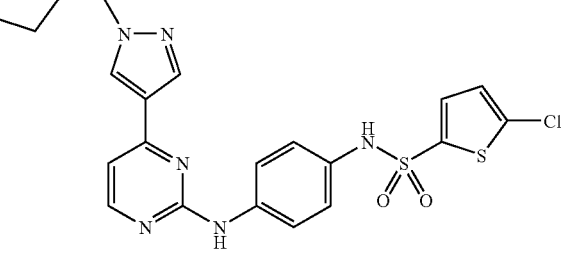

This compound was prepared as a racemic mixture according to the procedure described in example 182, using 5-chloro-2-thiophenesulfonyl chloride instead of cis-2,6-dimethylmorpholine-4-sulfonyl chloride in step 2. LCMS (M+H) 554.1.

Example 197

N-(4-(4-(1-(2-cyano-1-cyclopentylethyl)-1H-pyrazol-4-yl)pyrimidin-2-ylamino)phenyl)-6-morpholinopyridine-3-sulfonmide

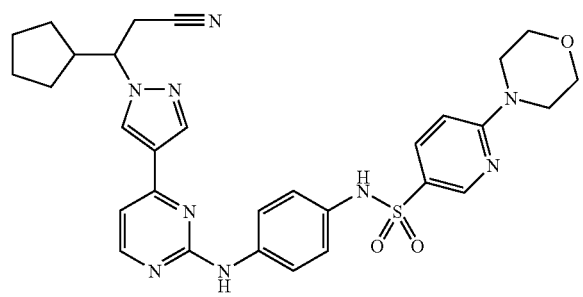

This compound was prepared as a racemic mixture according to the procedure described in example 182, using 6-(4-morpholinyl)-3-pyridinesulfonyl chloride instead of cis-2,6-dimethylmorpholine-4-sulfonyl chloride in step 2. LCMS (M+H) 600.2.

Example 199

(R)-tetrahydrofuran-3-yl 4-(4-(1-(2-cyano-1-cyclopentylethyl)-1H-pyrazol-4-yl)pyrimidin-2-ylamino)phenylcarbamate

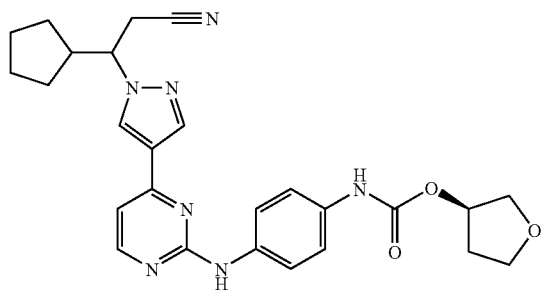

To a mixture of 3-(4-(2-(4-aminophenylamino)pyrimidin-4-yl)-1H-pyrazol-1-yl)-3-cyclopentylpropanenitrile (30 mg, 0.08 mmol) in 1,4-dioxane (0.5 mL) was added triethylamine (0.03 mL, 0.2 mmol), followed by (R)-4-nitrophenyl tetrahydrofuran-3-yl carbonate (30 mg, 0.12 mmol). The reaction was stirred at room temperature for 1 h, then purified on RP-HPLC to give the desired product as a diastereoisomer mixture (TFA salt, 27 mg, 56%). LCMS (M+H) 488.2.

Example 200

(R)-tetrahydrofuran-3-yl 3-(4-(1-(2-cyano-1-cyclopentylethyl)-1H-pyrazol-4-yl)pyrimidin-2-ylamino)phenylcarbamate

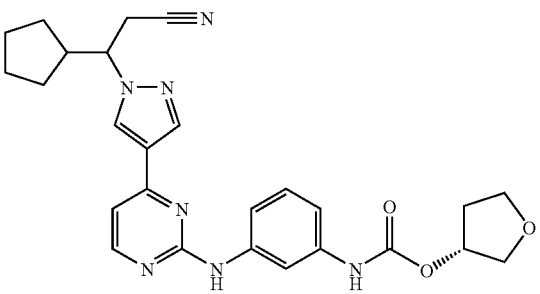

This compound was prepared as a diastereoisomer mixture according to the procedure described in example 199, using 3-(4-(2-(3-aminophenylamino)pyrimidin-4-yl)-1H-pyrazol-1-yl)-3-cyclopentylpropanenitrile instead of 3-(4-(2-(4-aminophenylamino)pyrimidin-4-yl)-1H-pyrazol-1-yl)-3-cyclopentylpropanenitrile. LCMS (M+H) 488.2.

Example 201

N-(3-(4-(1-(2-cyano-1-cyclopentylethyl)-1H-pyrazol-4-yl)pyrimidin-2-ylamino)phenyl)-1-methyl-1H-pyrazole-3-sulfonamide

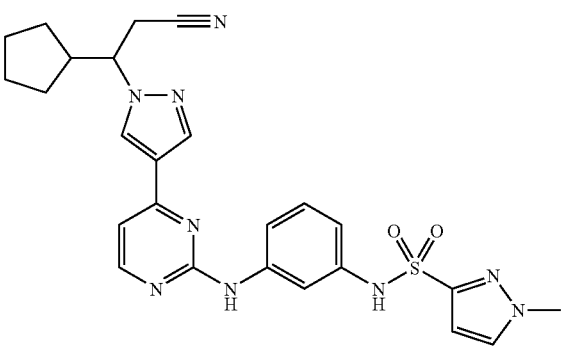

This compound was prepared as a racemic mixture according to the procedure described in example 114, using 1-methyl-1H-pyrazole-3-sulfonyl chloride instead of ethanesulfonyl chloride. LCMS (M+H) 518.2.

Example 202

NA-(3-(4-(1-(2-cyano-1-cyclopentylethyl)-1H-pyrazol-4-yl)pyrimidin-2-ylamino)phenyl)-N,N-dimethylsulfamide

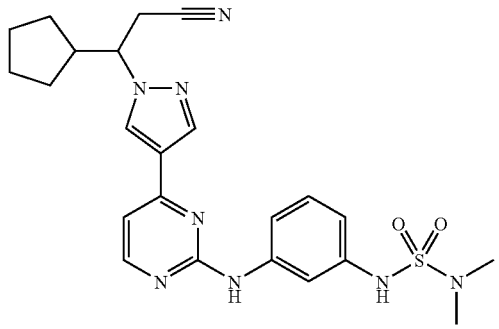

This compound was prepared as a racemic mixture according to the procedure described in example 114, using N,N-dimethyl-sulfamoyl chloride instead of ethanesulfonyl chloride. LCMS (M+H) 481.2.

Example 203

N-(4-(4-(1-(2-cyano-1-cyclopentylethyl)-1H-pyrazol-4-yl)pyrimidin-2-ylamino)phenyl)-2-(pyrrolidin-1-yl)acetamide

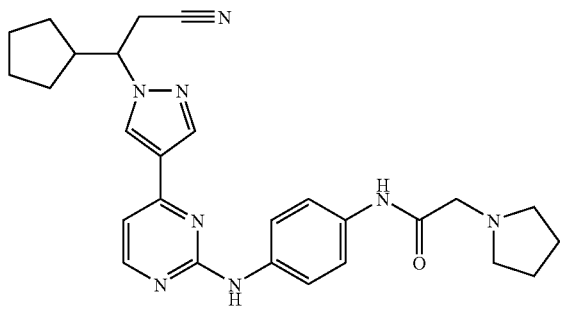

This compound was prepared as a racemic mixture according to the procedure described in example 118, using 3-(4-(2-(4-aminophenyl)amino)pyrimidin-4-yl-1H-pyrazol-1-yl)-3-cyclopentylpropanenitrile instead of 3-(4-(2-(3-aminophenyl)aminopyrimidin-4-yl-1H-pyrazol-1-yl)-3-cyclopentylpropanenitrile. LCMS (M+H) 485.2.

Example 204

N-(4-(4-(1-(2-cyano-1-cyclopentylethyl)-1H-pyrazol-4-yl)pyrimidin-2-ylamino)phenyl)-2-((R)-3-hydroxypyrrolidin-1-yl)acetamide

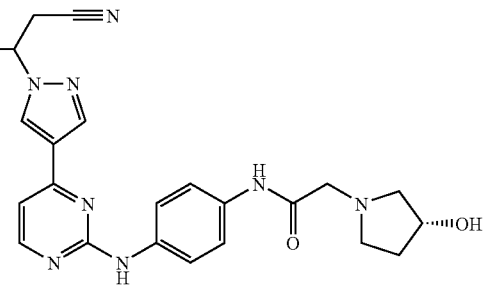

This compound was prepared as a diastereoisomer mixture according to the procedure described in example 118, using 3-(4-(2-(4-aminophenyl)amino)pyrimidin-4-yl-1H-pyrazol-1-yl)-3-cyclopentylpropanenitrile instead of 3-(4-(2-(3-aminophenyl)aminopyrimidin-4-yl-1H-pyrazol-1-yl)-3-cyclopentylpropanenitrile and using (R)-3-pyrrolidinol instead of pyrrolidine. LCMS (M+H) 501.2.

Example 205

N-(4-(4-(1-(2-cyano-1-cyclopentylethyl)-1H-pyrazol-4-yl)pyrimidin-2-ylamino)phenyl)-2-(4-hydroxypiperidin-1-yl)acetamide

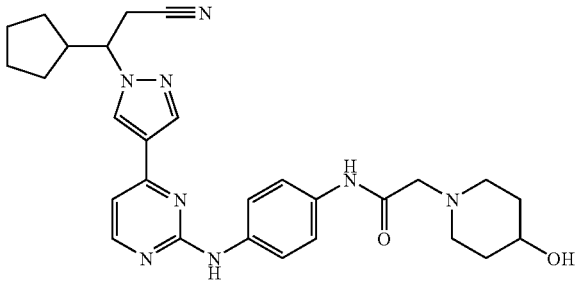

This compound was prepared as a racemic mixture according to the procedure described in example 118, using 3-(4-(2-(4-aminophenyl)amino)pyrimidin-4-yl-1H-pyrazol-1-yl)-3-cyclopentylpropanenitrile instead of 3-(4-(2-(3-aminophenyl)aminopyrimidin-4-yl-1H-pyrazol-1-yl)-3-cyclopentylpropanenitrile and using 4-hydroxypiperidine instead of pyrrolidine. LCMS (M+H) 515.2.

Example 206

N-(4-(4-(1-(2-cyano-1-cyclopentylethyl)-1H-pyrazol-4-yl)pyrimidin-2-ylamino)phenyl)-2-(3-oxopiperazin-1-yl)acetamide

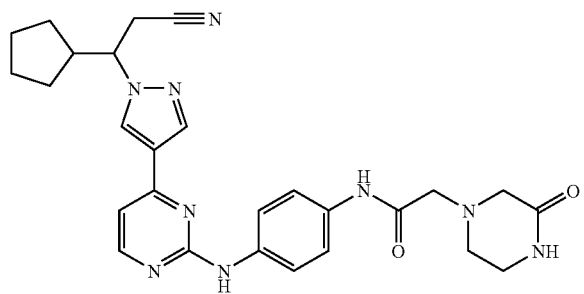

This compound was prepared as a racemic mixture according to the procedure described in example 118, using 3-(4-(2-(4-aminophenyl)amino)pyrimidin-4-yl-1H-pyrazol-1-yl)-3-cyclopentylpropanenitrile instead of 3-(4-(2-(3-aminophenyl)aminopyrimidin-4-yl-1H-pyrazol-1-yl)-3-cyclopentylpropanenitrile and using 2-piperazinone instead of pyrrolidine. LCMS (M+H) 514.2.

Example 207

N-(4-(4-(1-(2-cyano-1-cyclopentylethyl)-1H-pyrazol-4-yl)pyrimidin-2-ylamino)phenyl)-2-morpholinoacetamide

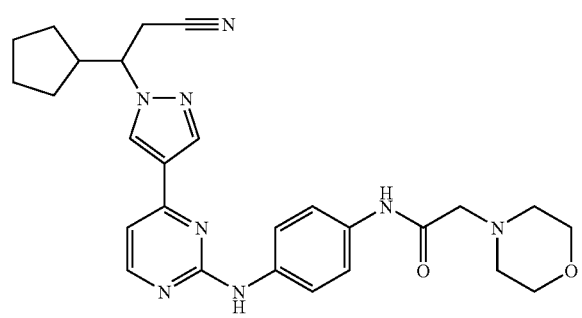

This compound was prepared as a racemic mixture according to the procedure described in example 118, using 3-(4-(2-(4-aminophenyl)amino)pyrimidin-4-yl-1H-pyrazol-1-yl)-3-cyclopentylpropanenitrile instead of 3-(4-(2-(3-aminophenyl)aminopyrimidin-4-yl-1H-pyrazol-1-yl)-3-cyclopentylpropanenitrile and using morpholine instead of pyrrolidine. LCMS (M+H) 501.5.

Example 208

N-(4-(4-(1-(2-cyano-1-cyclopentylethyl)-1H-pyrazol-4-yl)pyrimidin-2-ylamino)phenyl)-2-((tetrahydro-2H-pyran-4-yl)methylamino)acetamide

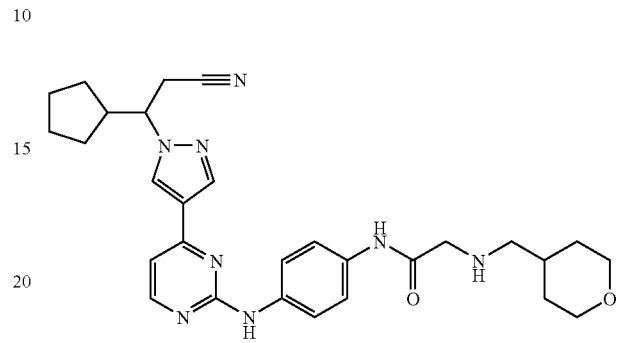

This compound was prepared as a racemic mixture according to the procedure described in example 118, using 3-(4-(2-(4-aminophenyl)amino)pyrimidin-4-yl-1H-pyrazol-1-yl)-3-cyclopentylpropanenitrile instead of 3-(4-(2-(3-aminophenyl)aminopyrimidin-4-yl-1H-pyrazol-1-yl)-3-cyclopentylpropanenitrile and using 4-aminomethyl-tetrahydropyran instead of pyrrolidine. LCMS (M+H) 529.5.

Example 209

N-(4-(4-(1-(2-cyano-1-cyclopentylethyl)-1H-pyrazol-4-yl)pyrimidin-2-ylamino)phenyl)-2-((R)-2-(methoxymethyl)pyrrolidin-1-yl)acetamide

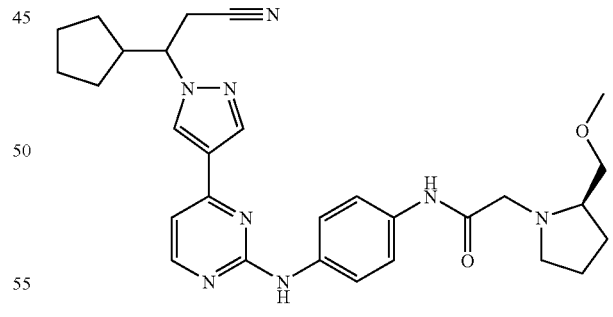

This compound was prepared as a diastereoisomeric mixture according to the procedure described in example 118, using 3-(4-(2-(4-aminophenyl)amino)pyrimidin-4-yl-1H-pyrazol-1-yl)-3-cyclopentylpropanenitrile instead of 3-(4-(2-(3-aminophenyl)aminopyrimidin-4-yl-1H-pyrazol-1-yl)-3-cyclopentylpropanenitrile and using (R)-2-methoxymethyl-pyrrolidine instead of pyrrolidine. LCMS (M+H) 529.5.

Example 210

N-(4-(4-(1-(2-cyano-1-cyclopentylethyl)-1H-pyrazol-4-yl)pyrimidin-2-ylamino)phenyl)-2-(cyclopropylmethylamino)acetamide

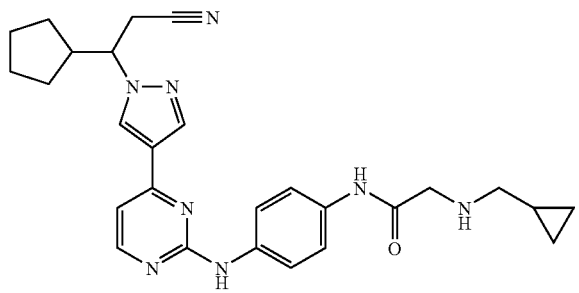

This compound was prepared as a racemic mixture according to the procedure described in example 118, using 3-(4-(2-(4-aminophenyl)amino)pyrimidin-4-yl-1H-pyrazol-1-yl)-3-cyclopentylpropanenitrile instead of 3-(4-(2-(3-aminophenyl)aminopyrimidin-4-yl-1H-pyrazol-1-yl)-3-cyclopentylpropanenitrile and using cyclopropanemethylamine instead of pyrrolidine. LCMS (M+H) 485.5.

Example 211

N-(4-(4-(1-(2-cyano-1-cyclopentylethyl)-1H-pyrazol-4-yl)pyrimidin-2-ylamino)phenyl)-2-(1-methoxypropan-2-ylamino)acetamide

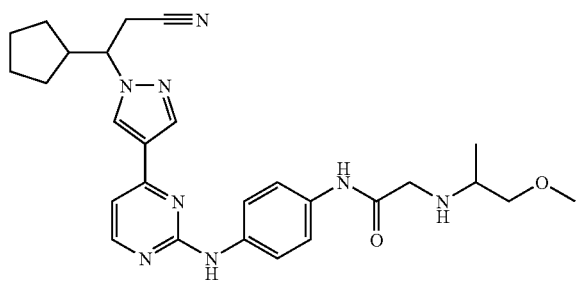

This compound was prepared as a diastereoisomeric mixture according to the procedure described in example 118, using 3-(4-(2-(4-aminophenyl)amino)pyrimidin-4-yl-1H-pyrazol-1-yl)-3-cyclopentylpropanenitrile instead of 3-(4-(2-(3-aminophenyl)aminopyrimidin-4-yl-1H-pyrazol-1-yl)-3-cyclopentylpropanenitrile and using 1-methoxy-2-propylamine instead of pyrrolidine. LCMS (M+H) 503.2.

Example 212

2-(4-(5-methylisoxazol-3-yloxy)-1-(4-(2-(4-morpholinophenylamino)pyrimidin-4-yl)-1H-pyrazol-1-yl)cyclohexyl)acetonitrile

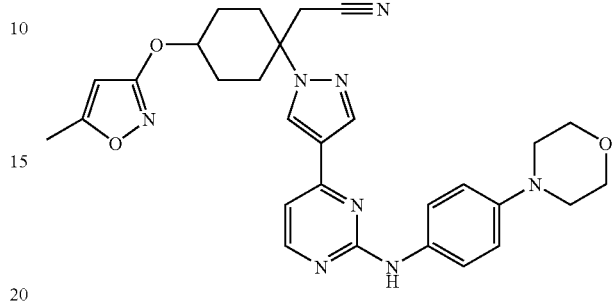

Step 1. (4-(tert-butyl(dimethyl)silyl)oxycyclohexylidene)acetonitrile

To a solution of 1.0 M of potassium tert-butoxide in tetrahydrofuran (46.0 mL) at 0° C. was added drop wise a solution of diethyl cyanomethylphosphonate (7.80 mL, 0.0482 mol) in tetrahydrofuran (80 mL). The reaction was warmed to room temperature and then cooled at 0° C. again. To the reaction mixture was a solution of 4-(tert-butyl(dimethyl)silyl)oxycyclohexanone (10.0 g, 0.04378 mol) in tetrahydrofuran (40 mL). The reaction was allowed to warm up to room temperature and stirred overnight. After being quenched with water, the mixture was extracted with ether. The combined organic layers were washed with water, brine, dried over MgSO$_4$ and evaporated to dryness. The crude mixture was purified on silica gel, eluting with 0 to 20% EtOAc in hexanes, to give the desired product (8.54 g, 77.58%). LCMS (M+H) 252.4.

Step 2. 4-(tert-butyl(dimethyl)silyl)oxy-1-(4-(4,4,5,5-tetramethyl-1,3,2-dioxaborolan-2-yl)-1H-pyrazol-1-yl)cyclohexylacetonitrile To a solution of 4-(4,4,5,5-tetramethyl-1,3,2-dioxaborolan-2-yl)-1H-pyrazole (3.09 g, 0.0159 mol) in acetonitrile (39.8 mL) was added (4-(tert-butyl(dimethyl)silyl)oxycyclohexylidene)acetonitrile (4.80 g, 0.0191 mol), followed by 1,8-diazabicyclo[5.4.0]undec-7-ene (1.19 mL, 0.00797 mol). The resulting mixture was stirred at room temperature overnight, then evaporated to dryness. The mixture was purified on silica gel, eluting with 0 to 20% EtOAc in hexanes, to give the desired product as cis- and trans-mixture (2.33 g, 33%). LCMS (M+H) 446.3.

Step 3. 1-(4-(2-chloropyrimidin-4-yl)-1H-pyrazol-1-yl)-4-hydroxycyclohexylacetonitrile To a mixture of 4-(tert-butyl(dimethyl)silyl)oxy-1-(4-(2-chloropyrimidin-4-yl)-1H-pyrazol-1-yl)cyclohexylacetonitrile (1.8 g, 0.0042 mol) in acetonitrile (69.74 mL) was added fluorosilicic acid (2.0 M in water, 4.17 mL). The mixture was stirred at room temperature overnight. After evaporation of most of the solvent, the mixture was neutralized with aqueous sodium bicarbonate, extracted with ether. The organic layers were combined, washed with brine, dried over MgSO₄, and concentrated to dryness. The residue (a 1:3.5 mixture of cis- and trans-isomers) was used directly in next step (1.20 g, 90.6%). LCMS (M+H) 318.3.

Step 4. 1-(4-(2-chloropyrimidin-4-yl)-1H-pyrazol-1-yl)-4-((5-methylisoxazol-3-yl)oxy)cyclohexylacetonitrile To a solution of 1-(4-(2-chloropyrimidin-4-yl)-1H-pyrazol-1-yl)-4-hydroxycyclohexylacetonitrile (0.6 g, 0.00189 mol) in tetrahydrofuran (9 mL) was added 5-methylisoxazol-3-ol (0.22 g, 0.0023 mol), triphenylphosphine (0.594 g, 0.00226 mol), followed by diisopropyl azodicarboxylate (0.446 mL, 0.00226 mol). The mixture was heated at 70° C. overnight. After evaporating to dryness, the residue was purified on silica gel, eluting with 0 to 80% EtOAc in hexanes, to give the desired product. LCMS (M+H) 399.1.

Step 5. (4-((5-methylisoxazol-3-yl)oxy)-1-(4-2-((4-morpholin-4-ylphenyl)amino)pyrimidin-4-yl-1H-pyrazol-1-yl)cyclohexyl)acetonitrile A mixture of 1-(4-(2-chloropyrimidin-4-yl)-1H-pyrazol-1-yl)-4-((5-methylisoxazol-3-yl)oxy)cyclohexylacetonitrile (30 mg, 0.08 mmol), 4-morpholin-4-ylaniline (20.1 mg, 0.113 mmol), and p-toluenesulfonic acid (11 mg, 0.064 mmol) in dry 1,4-dioxane (0.6 mL) was refluxed overnight. The mixture was diluted with acetonitrile and water, purified on RP-HPLC at pH 1.0 to give two desired products as TFA salt. First peak retention time 1.618 min, LCMS (M+H) 541.5; Second peak retention time 1.641 min, LCMS (M+H) 541.5.

Example 213

3-cyclopentyl-3-(4-(2-(4-(morpholine-4-carbonyl)phenylamino)pyrimidin-4-yl)-1H-pyrazol-1-yl)propanenitrile

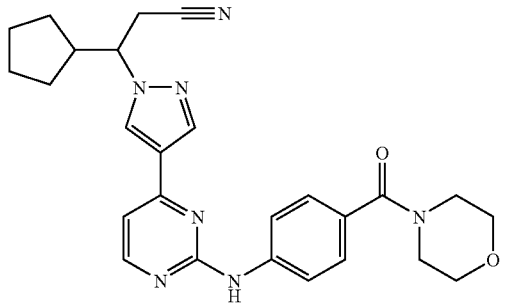

This compound was prepared as a racemic mixture according to the procedure described in example 120, using morpholine instead of 1-methylpiperazine. LCMS (M+H) 472.2.

Example 214

4-(4-(1-(2-cyano-1-cyclopentylethyl)-1H-pyrazol-4-yl)pyrimidin-2-ylamino)-N-((tetrahydro-2H-pyran-4-yl)methyl)benzamide

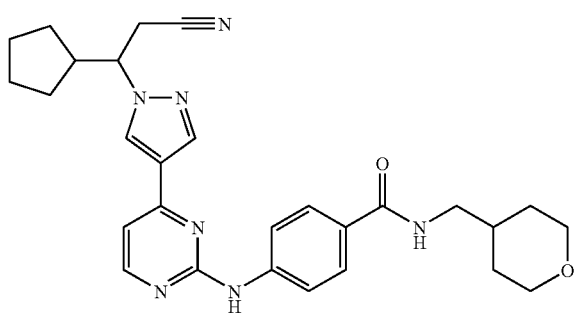

This compound was prepared as a racemic mixture according to the procedure described in example 120, using 4-aminomethyltetrahydropyran instead of 1-methylpiperazine. LCMS (M+H) 500.2.

Example 215

3-cyclopentyl-3-(4-(2-(4-((3-endo)-3-hydroxy-8-azabicyclo[3.2.1]octane-8-carbonyl)phenylamino)pyrimidin-4-yl)-1H-pyrazol-1-yl)propanenitrile

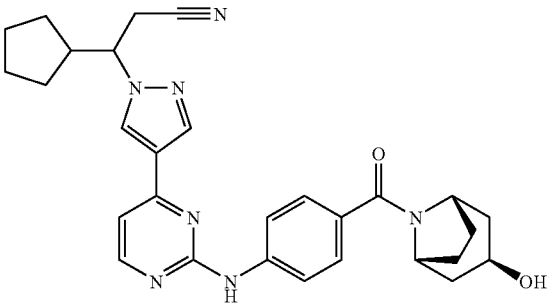

This compound was prepared as a racemic mixture according to the procedure described in example 120, using (3-endo)-8-azabicyclo[3.2.1]octan-3-ol hydrochloride instead of 1-methylpiperazine. LCMS (M+H) 512.2.

Example 216

3-cyclopentyl-3-(4-(2-(4-(2-oxa-6-azatricyclo[3.3.1.1(3,7)]dec-6-ylcarbonyl)phenyl)aminopyrimidin-4-yl)-1H-pyrazol-1-yl)propanenitrile

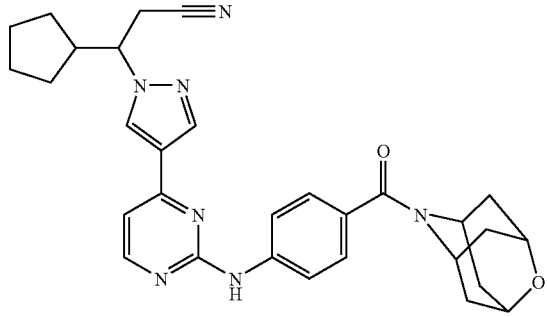

This compound was prepared as a racemic mixture according to the procedure described in example 120, using 2-oxa-6-azatricyclo[3.3.1.13,7]decane hydrochloride instead of 1-methylpiperazine. LCMS (M+H) 524.2.

Example 217

4-(4-(1-(2-cyano-1-cyclopentylethyl)-1H-pyrazol-4-yl)pyrimidin-2-ylamino)-N-(cis-4-hydroxycyclohexyl)-N-methylbenzamide

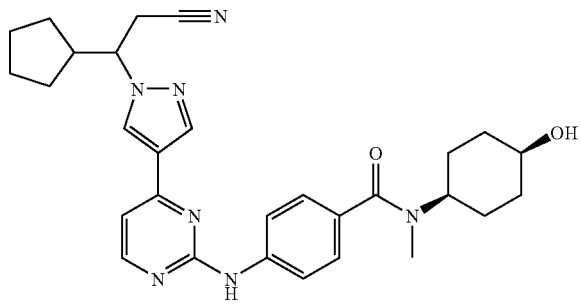

This compound was prepared as a racemic mixture according to the procedure described in example 120, using cis-4-(methylamino)-cyclohexanol hydrochloride instead of 1-methylpiperazine. LCMS (M+H) 514.2.

Example 218

4-(4-(1-(2-cyano-1-cyclopentylethyl)-1H-pyrazol-4-yl)pyrimidin-2-ylamino)-N-methyl-N-(tetrahydro-2H-pyran-4-yl)benzamide

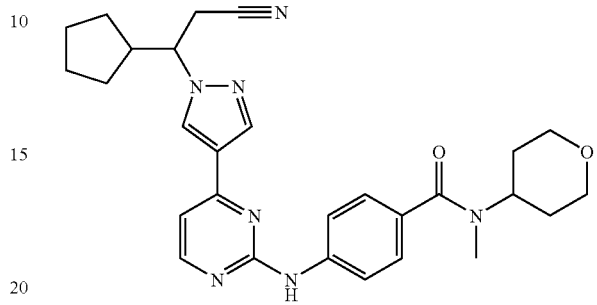

This compound was prepared as a racemic mixture according to the procedure described in example 120, using tetrahydro-N-methyl-2H-pyran-4-amine instead of 1-methylpiperazine. LCMS (M+H) 500.2.

Example 219

3-cyclopentyl-3-(4-(2-(4-((S*)-4,4-dimethyl-2-oxo-1-oxa-3,7-diazaspiro[4.4]nonane-7-carbonyl)phenylamino)pyrimidin-4-yl)-1H-pyrazol-1-yl)propanenitrile

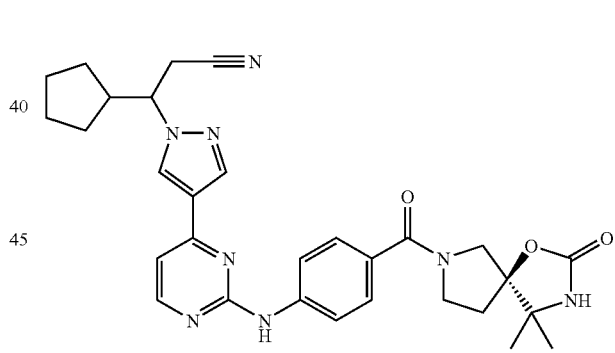

Step 1. Benzyl 3-(1,1-dimethylprop-2-en-1-yl)-3-hydroxypyrrolidine-1-carboxylate To a suspension of benzyl 3-oxopyrrolidine-1-carboxylate (4.50 g, 0.0205 mol), 4-bromo-2-methyl-2-butene (4.75 mL, 0.0412 mol) in 25.0 mL saturated ammonium chloride and tetrahydrofuran (4.75 mL, 0.0586 mol), at room temperature, was added zinc (2.70 g, 0.0412 mol). As soon as stirring was started, gas and heat were evolved. After 30 to 45 min, the resulting light grey mixture was filtered through celite. The filtrate was extracted with EtOAc. The organic layers were combined, washed with brine, dried and evaporated to dryness. The residue was purified on silica gel, eluting with 0 to 40% EtOAc in hexanes, to provide the desired product (5.22 g, 87.89%). LCMS (M+H) 290.2.

Step 2. Benzyl 3-(1,1-dimethyl-2-oxoethyl)-3-hydroxypyrrolidine-1-carboxylate A solution of benzyl 3-(1,1-dimethylprop-2-en-1-yl)-3-hydroxypyrrolidine-1-carboxylate (20.00 g, 0.06912 mol) in methylene chloride (500.0 mL, 7.8 mol) was ozonized at −78° C. until the solution turned blue. The mixture was purged with oxygen for 1 min, quenched with dimethyl sulfide (15.2 mL, 0.207 mol) and allowed to warm up to room temperature gradually. LCMS shown the peroxide intermediate, (M+H) 338.2. To the mixture was added another 10 mL of dimethyl sulfide and the mixture was stirred at room temperature overnight. After being evaporated to dryness, the residue was directly applied on silica gel (eluting with 0 to 80% EtOAc in hexanes) to provide the aldehyde product (14.1 g, 70.07%). LCMS (M+H) 292.2.

Step 3. 2-{1-[(benzyloxy)carbonyl]-3-hydroxypyrrolidin-3-yl}-2-methylpropanoic Acid Benzyl 3-(1,1-dimethyl-2-oxoethyl)-3-hydroxypyrrolidine-1-carboxylate (12.70 g, 0.04359 mol) was dissolved in acetone (179.5 mL, 2.444 mol) and cooled to 15° C. and 1.0 M of hydrogen chloride in water (65.39 mL, 0.06539 mol) was added dropwise. After addition of the HCl was complete, a solution of potassium permanganate (11.0 g, 0.0697 mol) in acetone (493.6 mL, 6.722 mol) was added dropwise. The reaction mixture was stirred at room temperature for 6 h, filtered and the filter cake was washed with acetone. The filtrate was evaporated, in vacuo, diluted with methylene chloride, dried, filtered and the solvent was evaporated, in vacuo, to provide a crude product which was used directly in next step. LCMS (M+H) 308.2.

Step 4. Benzyl 4,4-dimethyl-2-oxo-1-oxa-3,7-diazaspiro[4.4]nonane-7-carboxylate To a stirred solution of 2-{1-[(benzyloxy)carbonyl]-3-hydroxypyrrolidin-3-yl}-2-methylpropanoic acid (13.40 g, 0.04360 mol) in tetrahydrofuran (170.2 mL, 2.099 mol) was added diphenylphosphonic azide (9.40 mL, 0.0436 mol) and triethylamine (6.08 mL, 0.0436 mol) and the mixture was refluxed for 4 h under nitrogen. The reaction mixture was then concentrated under reduced pressure, diluted with EtOAc, washed with aqueous sodium bicarbonate. The organic layers were combined, washed with brine, dried, and evaporated to dryness. Purification on silica gel, eluting with 0 to 100% EtOAc in hexanes, yielded the cyclic carbamate (2.53 g, 19.07%). LCMS (M+H) 305.2. The racemic carbamates were separated using chiral HPLC to provide the two enantiomers.

Step 5. 4,4-dimethyl-1-oxa-3,7-diazaspiro[4.4]nonan-2-one

A mixture of benzyl 4,4-dimethyl-2-oxo-1-oxa-3,7-diazaspiro[4.4]nonane-7-carboxylate (0.50 g, 0.0016 mol) (2nd peak from chiral separation) in 20 mL of MeOH was hydrogenated in the presence of 10% Pd/C, under a balloon pressure of hydrogen, for 2 h. After filtering off the catalyst, the filtrate was concentrated to dryness and the resultant residue was used directly in next step. LCMS (M+H) 171.2.

Step 6. 3-cyclopentyl-3-(4-(2-(4-((S*)-4,4-dimethyl-2-oxo-1-oxa-3,7-diazaspiro[4.4]nonane-7-carbonyl)phenylamino)pyrimidin-4-yl)-1H-pyrazol-1-yl)propanenitrile This compound was prepared as a diastereoisomeric mixture according to the procedure described in example 120, using 4,4-dimethyl-1-oxa-3,7-diazaspiro[4.4]nonan-2-one instead of 1-methylpiperazine. LCMS (M+H) 555.2.

Example 220

3-cyclopentyl-3-(4-(2-(4-(4,4-dimethyl-1-oxa-7-azaspiro[4.4]nonane-7-carbonyl)phenylamino)pyrimidin-4-yl)-1H-pyrazol-1-yl)propanenitrile

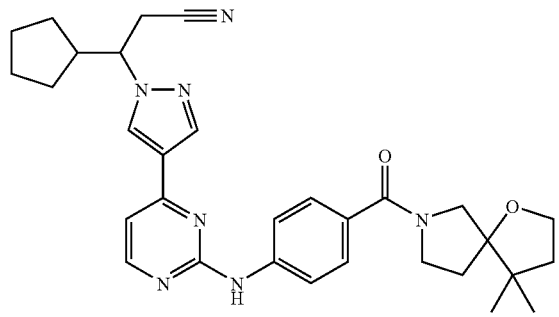

This compound was prepared as a diastereoisomeric mixture according to the procedure described in example 120, using 4,4-dimethyl-1-oxa-7-azaspiro[4.4]nonane TFA salt instead of 1-methylpiperazine. LCMS (M+H) 540.5.

Example 221

3-cyclopentyl-3-(4-(2-(4-(4-methoxypiperidine-1-carbonyl)phenylamino)pyrimidin-4-yl)-1H-pyrazol-1-yl)propanenitrile

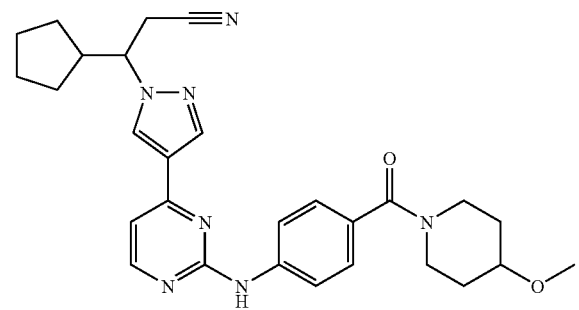

This compound was prepared as a racemic mixture according to the procedure described in example 120, using 4-methoxypiperidine hydrochloride instead of 1-methylpiperazine. LCMS (M+H) 500.2.

Example 222

N-((3S)-1-(4-(4-(1-(2-cyano-1-cyclopentylethyl)-1H-pyrazol-4-yl)pyrimidin-2-ylamino)benzoyl)pyrrolidin-3-yl)acetamide

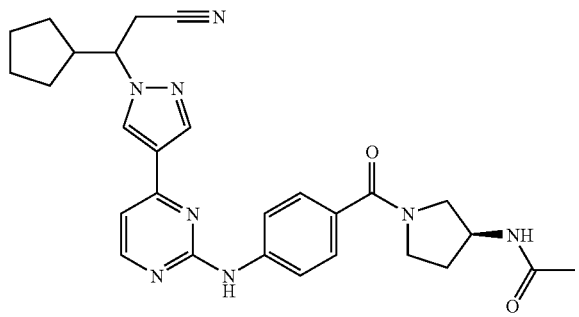

This compound was prepared as a diastereoisomeric mixture according to the procedure described in example 120, using N-(3R)-3-pyrrolidinyl-acetamide instead of 1-methylpiperazine. LCMS (M+H) 513.2.

Example 223

4-(4-(1-(2-cyano-1-cyclopentylethyl)-1H-pyrazol-4-yl)pyrimidin-2-ylamino)-N-(cis-4-hydroxycyclohexyl)benzamide

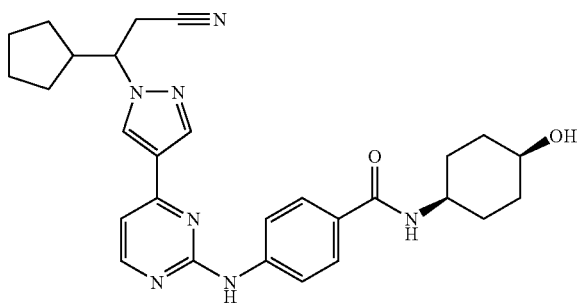

This compound was prepared as a racemic mixture according to the procedure described in example 120, using cis-4-amino-cyclohexanol hydrochloride instead of 1-methylpiperazine. LCMS (M+H) 500.2.

Example 224

3-(4-(2-(4-(4-acetylpiperazine-1-carbonyl)phenylamino)pyrimidin-4-yl)-1H-pyrazol-1-yl)-3-cyclopentylpropanenitrile

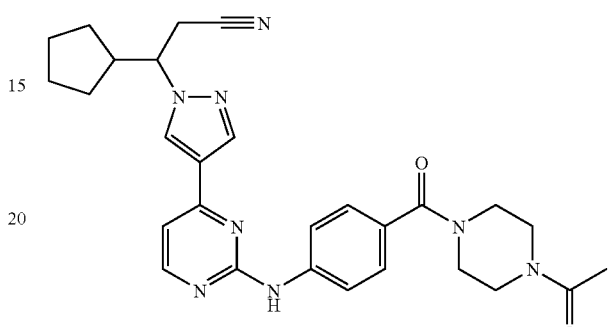

This compound was prepared as a racemic mixture according to the procedure described in example 120, using 1-acetylpiperazine instead of 1-methylpiperazine. LCMS (M+H) 513.2.

Example 225

(3S)-1-(4-(4-(1-(2-cyano-1-cyclopentylethyl)-1H-pyrazol-4-yl)pyrimidin-2-ylamino)benzoyl)pyrrolidine-3-carbonitrile

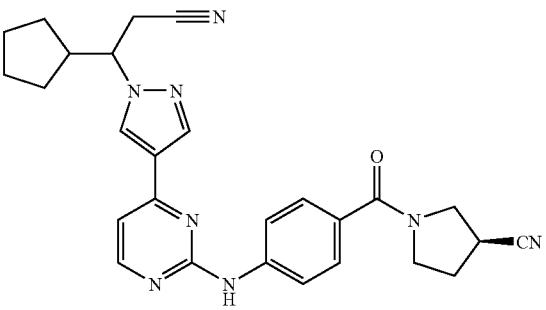

This compound was prepared as a diastereoisomeric mixture according to the procedure described in example 120, using (S)-3-pyrrolidinecarbonitrile hydrochloride instead of 1-methylpiperazine. LCMS (M+H) 481.4.

Example 226

3-cyclopentyl-3-(4-(2-(4-((S)-3-methoxypyrrolidine-1-carbonyl)phenylamino)pyrimidin-4-yl)-1H-pyrazol-1-yl)propanentrile

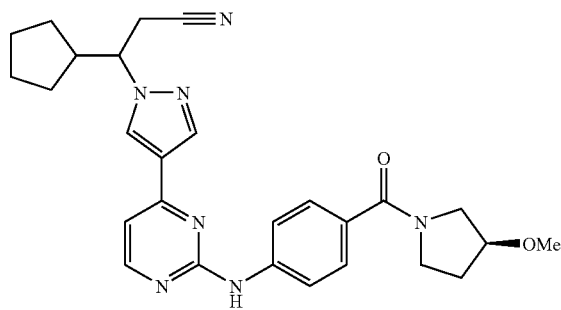

This compound was prepared as a diastereoisomeric mixture according to the procedure described in example 120, using (3S)-3-methoxy-pyrrolidine hydrochloride instead of 1-methylpiperazine. LCMS (M+H) 486.2.

Example 227

4-(4-(1-(2-cyano-1-cyclopentylethyl)-1H-pyrazol-4-yl)pyrimidin-2-ylamino)-N-(1-methylpiperidin-4-yl)benzamide

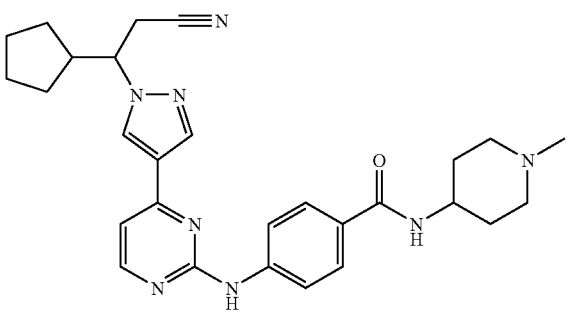

This compound was prepared as a racemic mixture according to the procedure described in example 120, using 1-methyl-4-piperidinamine instead of 1-methylpiperazine. LCMS (M+H) 499.3.

Example 228

3-cyclopentyl-3-(4-(2-(4-(3-oxo-2,8-diazaspiro[4.5]decane-8-carbonyl)phenylamino)pyrimidin-4-yl)-1H-pyrazol-1-yl)propanenitile

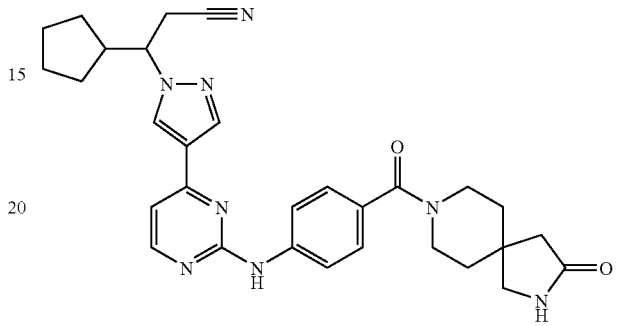

This compound was prepared as a racemic mixture according to the procedure described in example 120, using 2,8-diazaspiro[4.5]decan-3-one instead of 1-methylpiperazine. LCMS (M+H) 539.2.

Example 229

3-cyclopentyl-3-(4-(2-(4-((S)-3-fluoropyrrolidine-1-carbonyl)phenylamino)pyrimidin-4-yl)-1H-pyrazol-1-yl)propanenitrile

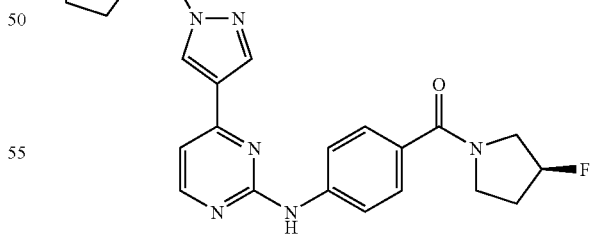

This compound was prepared as a diastereoisomeric mixture according to the procedure described in example 120, using (3S)-3-fluoro-pyrrolidine hydrochloride instead of 1-methylpiperazine. LCMS (M+H) 474.4.

Example 230

3-cyclopentyl-3-(4-(2-(4-(3-(dimethylamino)pyrrolidine-1-carbonyl)phenylamino)pyrimidin-4-yl)-1H-pyrazol-1-yl)propanenitrile

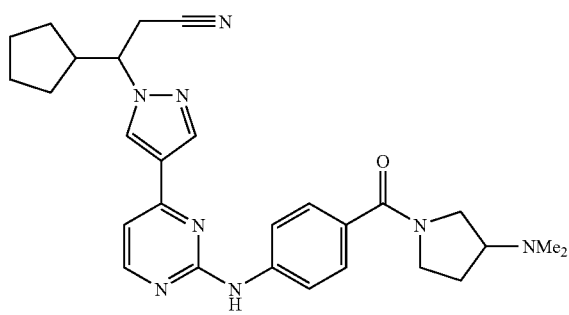

This compound was prepared as a diastereoisomeric mixture according to the procedure described in example 120, using N,N-dimethyl-3-pyrrolidinamine instead of 1-methylpiperazine. LCMS (M+H) 499.5.

Example 231

Ethyl 4-(4-(4-(1-(2-cyano-1-cyclopentylethyl)-1H-pyrazol-4-yl)pyrimidin-2-ylamino)benzamido)piperidine-1-carboxylate

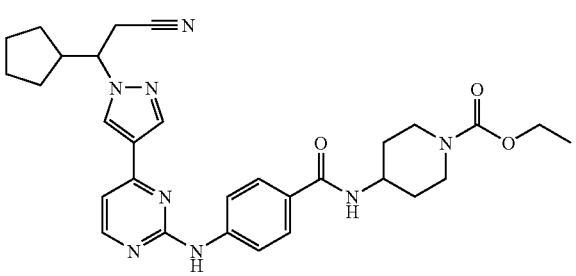

This compound was prepared as a racemic mixture according to the procedure described in example 120, using 4-amino-1-piperidinecarboxylic acid ethyl ester instead of 1-methylpiperazine. LCMS (M+H) 557.5.

Example 232

4-(4-(1-(2-cyano-1-cyclopentylethyl)-1H-pyrazol-4-yl)pyrimidin-2-ylamino)-N-(1-(pyridin-2-yl)pyrrolidin-3-yl)benzamide

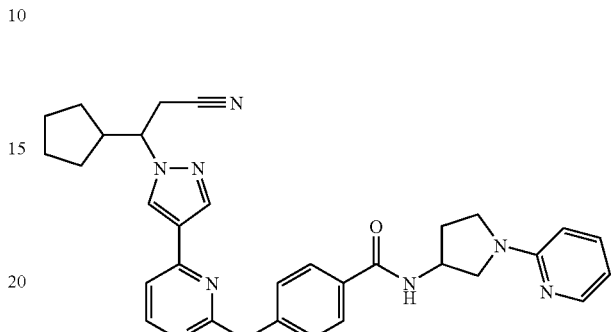

This compound was prepared as a diastereoisomeric mixture according to the procedure described in example 120, using 1-(2-pyridinyl)-3-pyrrolidinamine instead of 1-methylpiperazine. LCMS (M+H) 548.4.

Example 233

3-cyclopentyl-3-(4-(2-(4-(3-(pyridin-2-yloxy)pyrrolidine-1-carbonyl)phenylamino)pyrimidin-4-yl)-1H-pyrazol-1-yl)propanenitrile

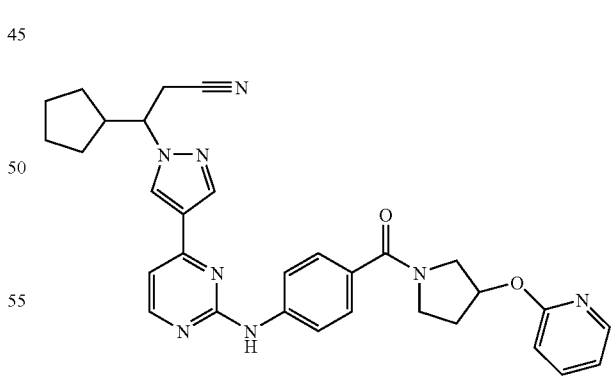

This compound was prepared as a diastereoisomeric mixture according to the procedure described in example 120, using 2-(3-pyrrolidinyloxy)-pyridine instead of 1-methylpiperazine. LCMS (M+H) 549.2.

Example 234

1-(4-(4-(1-(2-cyano-1-cyclopentylethyl)-1H-pyrazol-4-yl)pyrimidin-2-ylamino)benzoyl)-N,N-dimethylpiperidine-4-carboxamide

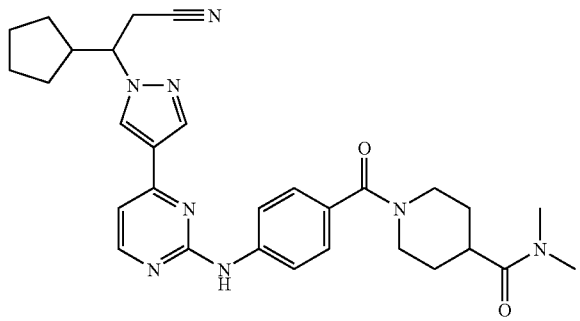

This compound was prepared as a racemic mixture according to the procedure described in example 120, using N,N-dimethyl-4-piperidinecarboxamide instead of 1-methylpiperazine. LCMS (M+H) 541.2.

Example 235

4-(4-(1-(2-cyano-1-cyclopentylethyl)-1H-pyrazol-4-yl)pyrimidin-2-ylamino)-N—((S)-1-(dimethylamino)-1-oxobutan-2-yl)benzamide

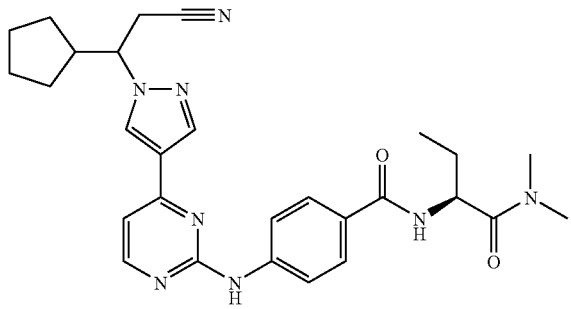

This compound was prepared as a diastereoisomeric mixture according to the procedure described in example 120, using (2S)-2-amino-N,N-dimethyl-butanamide hydrochloride instead of 1-methylpiperazine. LCMS (M+H) 515.2.

Example 236

N-(3-(4-(1-(2-cyano-1-cyclopentylethyl)-1H-pyrazol-4-yl)pyrimidin-2-ylamino)phenyl)-2-(4-methylpiperazin-1-yl)acetamide

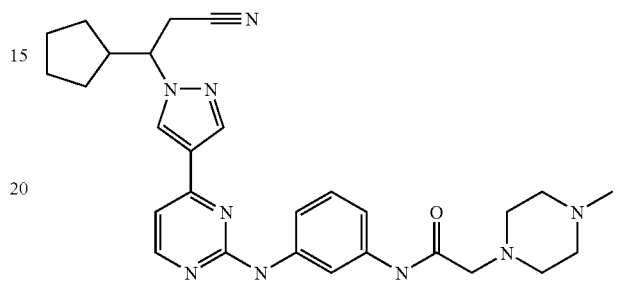

This compound was prepared as a racemic mixture according to the procedure described in example 118, using 1-methylpiperazine instead of pyrrolidine. LCMS (M+H) 514.2.

Example 237

N-(3-(4-(1-(2-cyano-1-cyclopentylethyl)-1H-pyrazol-4-yl)pyrimidin-2-ylamino)phenyl)-2-((R)-3-hydroxypyrrolidin-1-yl)acetamide

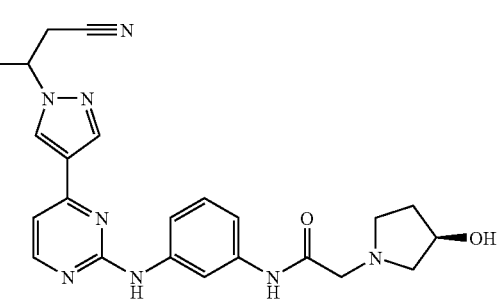

This compound was prepared as a diastereoisomeric mixture according to the procedure described in example 118, using (3R)-3-pyrrolidinol instead of pyrrolidine. LCMS (M+H) 501.2.

Example 238

N-(3-(4-(1-(2-cyano-1-cyclopentylethyl)-1H-pyrazol-4-yl)pyrimidin-2-ylamino)phenyl)-2-(3-oxopiperazin-1-yl)acetamide

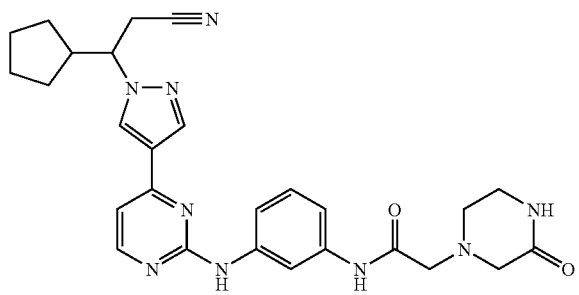

This compound was prepared as a racemic mixture according to the procedure described in example 118, using 2-piperazinone instead of pyrrolidine. LCMS (M+H) 514.2.

Example 239

N-(3-(4-(1-(2-cyano-1-cyclopentylethyl)-1H-pyrazol-4-yl)pyrimidin-2-ylamino)phenyl)-2-(4-hydroxypiperidin-1-yl)acetamide

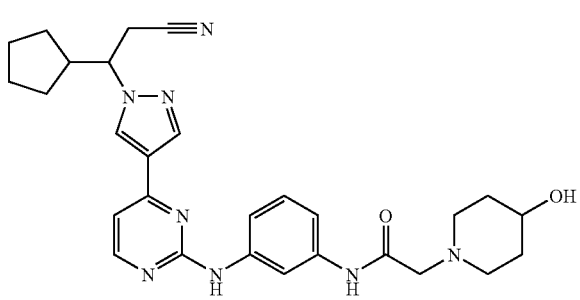

This compound was prepared as a racemic mixture according to the procedure described in example 118, using 4-hydroxypiperidine instead of pyrrolidine. LCMS (M+H) 515.5.

Example 240

N-(3-(4-(1-(2-cyano-1-cyclopentylethyl)-1H-pyrazol-4-yl)pyrimidin-2-ylamino)phenyl)-2-(4-(2-hydroxyethyl)piperazin-1-yl)acetamide

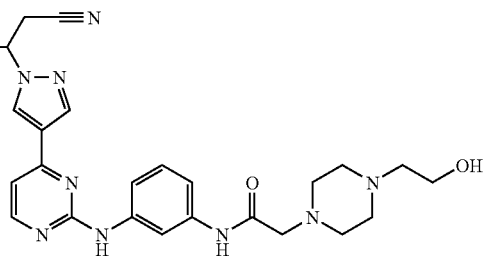

This compound was prepared as a racemic mixture according to the procedure described in example 118, using 1-piperazineethanol instead of pyrrolidine. LCMS (M+H) 544.2.

Example 241

N-(3-(4-(1-(2-cyano-1-cyclopentylethyl)-1H-pyrazol-4-yl)pyrimidin-2-ylamino)phenyl)-2-(cyclopropylmethylamino)acetamide

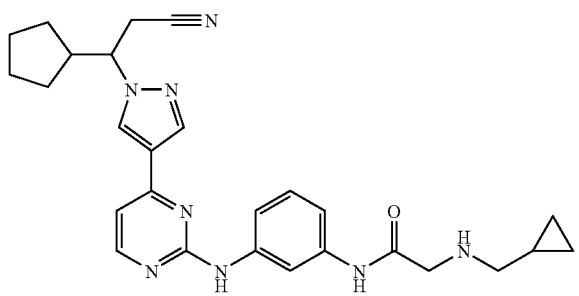

This compound was prepared as a racemic mixture according to the procedure described in example 118, using cyclopropanemethylamine instead of pyrrolidine. LCMS (M+H) 485.5.

Example 242

N-(3-(4-(1-(2-cyano-1-cyclopentylethyl)-1H-pyrazol-4-yl)pyrimidin-2-ylamino)phenyl)-2-morpholinoacetamide

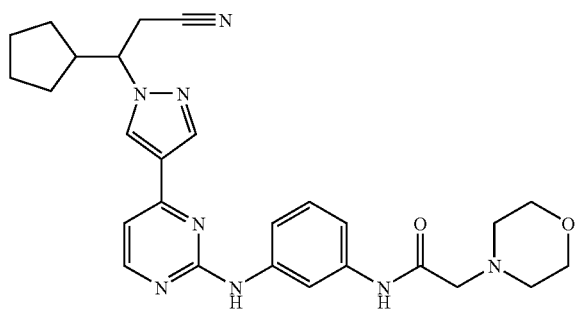

This compound was prepared as a racemic mixture according to the procedure described in example 118, using morpholine instead of pyrrolidine. LCMS (M+H) 501.2.

Example 243

N-(3-(4-(1-(2-cyano-1-cyclopentylethyl)-1H-pyrazol-4-yl)pyrimidin-2-ylamino)phenyl)-2-(ethylamino)acetamide

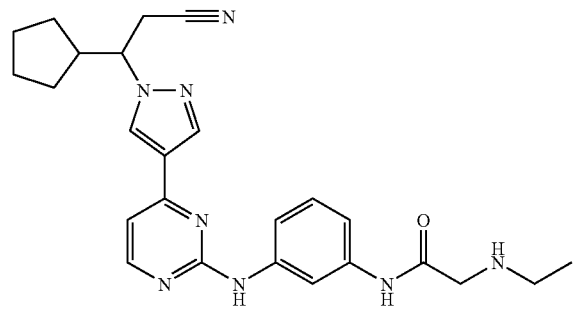

This compound was prepared as a racemic mixture according to the procedure described in example 118, using ethylamine instead of pyrrolidine. LCMS (M+H) 459.4.

Example 244

2-(4-(5-methylisoxazol-3-yloxy)-1-(4-(2-(4-(3-oxomorpholino)phenylamino)pyrimidin-4-yl)-1H-pyrazol-1-yl)cyclohexyl)acetonitrile

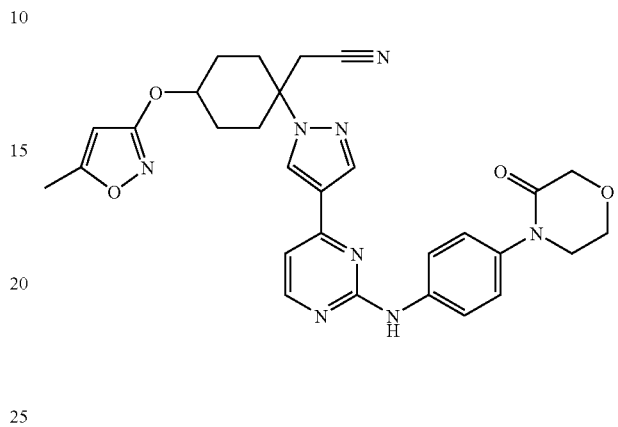

The cis- and trans-isomers of the titled compound were prepared according to the procedure described in example 212, replacing 4-morpholin-4-ylaniline with 4-(4-aminophenyl)-3-morpholinone in step 5. First peak retention time 1.663 min, LCMS (M+H) 555.5; Second peak retention time 1.694 min, LCMS (M+H) 555.5.

Example 245

2-(4-(5-methylisoxazol-3-yloxy)-1-(4-(2-(4-(2-oxopiperidin-1-yl)phenylamino)pyrimidin-4-yl)-1H-pyrazol-1-yl)cyclohexyl)acetonitrile

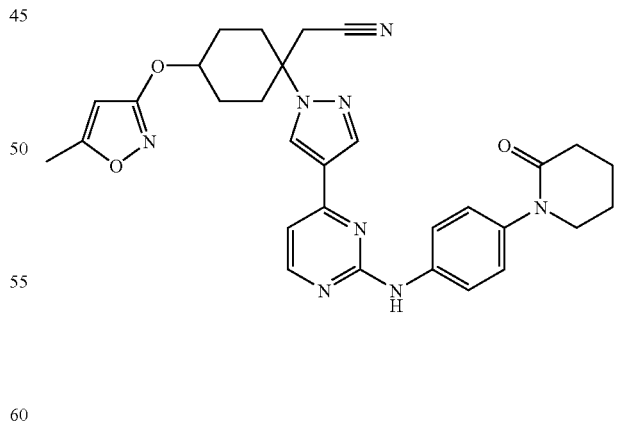

The cis- and trans-isomers of the titled compound were prepared according to the procedure described in example 212, replacing 4-morpholin-4-ylaniline with 1-(4-aminophenyl)-2-piperidinone in step 5. One isomer retention time 1.762 min, LCMS (M+H) 553.5; another isomer retention time 1.737 min, LCMS (M+H) 553.2.

Example 246

2-(1-(4-(2-(4-(1H-pyrazol-1-yl)phenylamino)pyrimidin-4-yl)-1H-pyrazol-1-yl)-4-(5-methylisoxazol-3-yloxy)cyclohexyl)acetonitrile

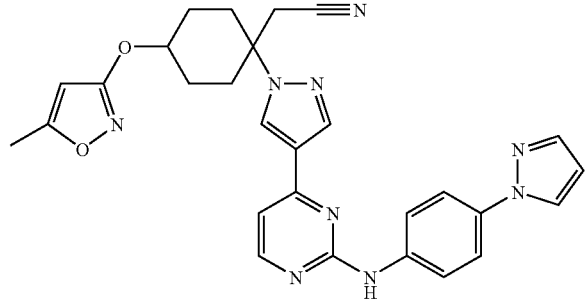

The cis- and trans-isomers of the titled compound were prepared according to the procedure described in example 212, replacing 4-morpholin-4-ylaniline with 4-(1H-pyrazol-1-yl)aniline in step 5. First peak retention time 1.954 min, LCMS (M+H) 522.2; Second peak retention time 1.964 min, LCMS (M+H) 522.2.

Example 247

2-(4-(5-methylisoxazol-3-yloxy)-1-(4-(2-(3-(oxazol-5-yl)phenylamino)pyrimidin-4-yl)-1H-pyrazol-1-yl)cyclohexyl)acetonitrile

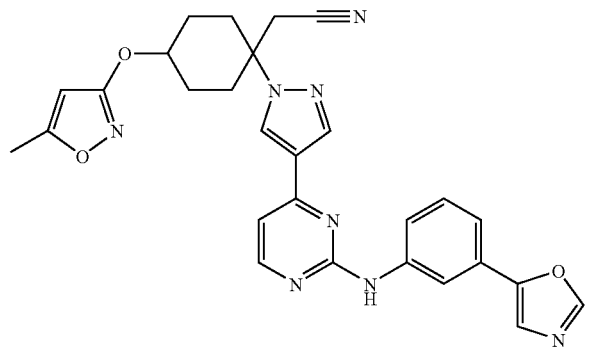

The cis- and trans-isomers of the titled compound were prepared according to the procedure described in example 212, replacing 4-morpholin-4-ylaniline with 3-(5-oxazolyl)-benzenamine in step 5. First peak retention time 1.999 min, LCMS (M+H) 523.4; Second peak retention time 2.022 min, LCMS (M+H) 523.4.

Example 248

3-(cyanomethyl)-3-(4-(2-(4-morpholinophenylamino)pyrimidin-4-yl)-1H-pyrazol-1-yl)cyclobutanecarbonitrile

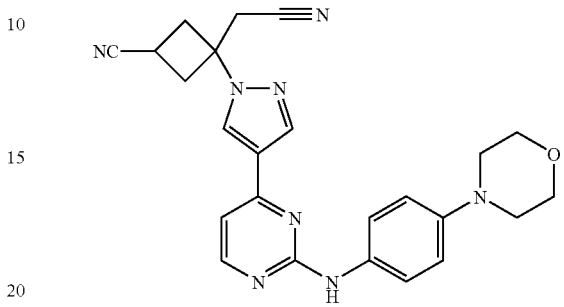

Step 1. 3-oxocyclobutanecarbonitrile

A mixture of 3-methylenecyclobutanecarbonitrile (10.0 g, 0.1074 mol), and 0.2 M of osmium tetroxide in water (2 mL) in water (100 mL) and 1,4-dioxane (300 mL), was stirred for 5 min, during which time the mixture became brown. While the temperature was maintained at room temperature, sodium periodate (48.2 g, 0.225 mol) was added in portions over a period of 30 min. The mixture was stirred for an additional 1.5 h. The mixture was extracted with EtOAc and combined organic layers were dried over $MgSO_4$. After removal of the solvents, the crude product was used directly in next step (7.10 g, 69.5%).

Step 2. 3-(cyanomethylene)cyclobutanecarbonitrile

To a solution of 1.0 M of potassium tert-butoxide in tetrahydrofuran (78.4 mL) at 0° C. was added drop wise a solution of diethyl cyanomethylphosphonate (13.3 mL, 0.0822 mol) in tetrahydrofuran (100 mL, 2 mol). The reaction was warmed to room temperature and then cooled at 0° C. again. To the reaction mixture was a solution of 3-oxocyclobutanecarbonitrile (7.10 g, 0.0746 mol) in tetrahydrofuran (70 mL). The reaction was allowed to warm up to room temperature and stirred overnight. After being quenched with water, the mixture was extracted with ether. The combined organic layers were washed with water, brine, dried over $MgSO_4$, and evaporated to dryness. The crude mixture was purified on silica gel, eluting with 0 to 40% EtOAc in hexanes, to give the desired product (2.05 g, 23.2%).

Step 3. 3-(cyanomethyl)-3-(4-(4,4,5,5-tetramethyl-1,3,2-dioxaborolan-2-yl)-1H-pyrazol-1-yl)cyclobutanecarbonitrile To a solution of 4-(4,4,5,5-tetramethyl-1,3,2-dioxaborolan-2-yl)-1H-pyrazole (1.73 g, 0.00890 mol) in acetonitrile (22.2 mL) was added 3-(cyanomethylene)cyclobutanecarbonitrile (1.05 g, 0.00889 mol), followed by 1,8-diazabicyclo[5.4.0]undec-7-ene (0.666 mL, 0.00445 mol). The resulting mixture was stirred at room temperature overnight, then evaporated to dryness. The mixture was purified on silica gel, eluting with 0 to 80% EtOAc in hexanes, to give the desired product as racemic mixture (320 mg, 11.5%). LCMS (M+H) 313.4.

Step 4. 3-(4-(2-chloropyrimidin-4-yl)-1H-pyrazol-1-yl)-3-(cyanomethyl)cyclobutanecarbonitrile A mixture of 2,4-dichloropyrimidine (0.916 g, 0.00615 mol), 3-(cyanomethyl)-3-(4-(4,4,5,5-tetramethyl-1,3,2-dioxaborolan-2-yl)-1H-pyrazol-1-yl)cyclobutanecarbonitrile (1.60 g, 0.00512 mol), tetrakis(triphenylphosphine)palladium (400 mg, 0.3 mmol), and potassium phosphate (3.3 g, 0.015 mol) in 1,4-dioxane (20 mL) and water (2 mL) was heated at 100° C. overnight. After cooling to room temperature, the mixture was diluted with EtOAc, washed with water, brine, dried over MgSO₄, and concentrated. The residue was purified on silica gel, eluting with 0 to 100%, to give the desired product (1.15 g, 75.1%). LCMS (M+H) 299.3.

Step 5. 3-(cyanomethyl)-3-(4-2-((4-morpholin-4-ylphenyl)amino)pyrimidin-4-yl-1H-pyrazol-1-yl)cyclobutanecarbonitrile A mixture of 3-(4-(2-chloropyrimidin-4-yl)-1H-pyrazol-1-yl)-3-(cyanomethyl)cyclobutanecarbonitrile (30 mg, 0.1 mmol), 4-morpholin-4-ylaniline (26.8 mg, 0.151 mmol), and p-toluenesulfonic Acid (15 mg, 0.085 mmol) in dry 1,4-dioxane (0.8 mL) was refluxed overnight. The mixture was diluted with acetonitrile and water, purified on RP-HPLC at pH 1.0 to give two desired cis- and trans-products as TFA salts. First peak retention time 1.267 min, LCMS (M+H) 441.4; Second peak retention time 1.296 min, LCMS (M+H) 441.4.

Example 249

4-(4-(1-(3-(cyanomethyl)-1-(ethylsulfonyl)azetidin-3-yl)-1H-pyrazol-4-yl)pyrimidin-2-ylamino)benzoic Acid

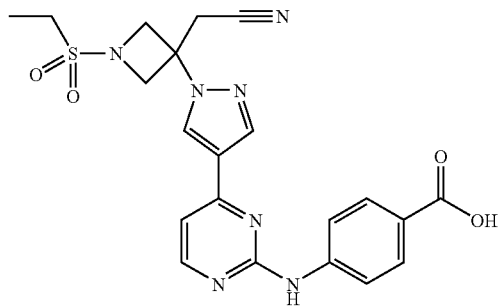

Step 1. (3-(4-(2-chloropyrimidin-4-yl)-1H-pyrazol-1-yl)-1-(ethylsulfonyl)azetidin-3-yl)acetonitrile To a mixture of 3-(4-(2-chloropyrimidin-4-yl)-1H-pyrazol-1-yl)azetidin-3-ylacetonitrile hydrochloride (1.42 g, 0.00456 mol) in dichloromethane (30 mL) was added triethylamine (1.59 mL, 0.0114 mol) followed by ethanesulfonyl chloride (0.497 mL, 0.00525 mol) at 0° C. The reaction was stirred at room temperature for 1 h, quenched with 1N HCl. The organic layer was separated, washed with aqueous sodium bicarbonate, dried over sodium sulfate, and evaporated to dryness. The crude product was used directly in next step (1.26 g, 75.3%). LCMS (M+H) 367.3.

Step 2. 4-((4-1-(3-(cyanomethyl)-1-(ethylsulfonyl)azetidin-3-yl-1H-pyrazol-4-ylpyrimidin-2-yl)amino)benzoic Acid A mixture of (3-(4-(2-chloropyrimidin-4-yl)-1H-pyrazol-1-yl)-1-(ethylsulfonyl)azetidin-3-yl)acetonitrile (0.926 g, 0.00252 mol), p-aminobenzoic acid (0.519 g, 0.00379 mol), and p-toluenesulfonic acid (0.37 g, 0.0021 mol) in dry 1,4-dioxane (20 mL) was refluxed overnight. The mixture was cooled to room temperature, filtered. The solid was washed with dioxane, air dried to provide the desired product (812 mg, 68.8%). LCMS (M+H) 468.4.

Example 250

4-(4-(1-(2-cyano-1-cyclopropylethyl)-1H-pyrazol-4-yl)pyrimidin-2-ylamino)benzoic Acid

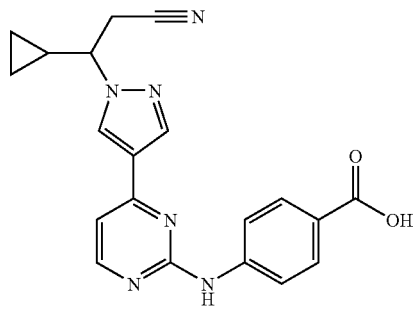

A mixture of 3-(4-(2-chloropyrimidin-4-yl)-1H-pyrazol-1-yl)-3-cyclopropylpropanenitrile (2.74 g, 0.0100 mol), p-aminobenzoic acid (2.06 g, 0.0150 mol), and p-toluenesulfonic acid (1.5 g, 0.0085 mol) in dry 1,4-dioxane (80 mL) was refluxed overnight. The mixture was cooled to room temperature, filtered. The solid was washed with dioxane, air dried to yield the desired product as a racemic mixture (3.02 g, 80.58%). LCMS (M+H) 375.3.

Example 251

3-cyclopropyl-3-(4-(2-(4-(4-hydroxypiperidine-1-carbonyl)phenylamino)pyrimidin-4-yl)-1H-pyrazol-1-yl)propanenitrile

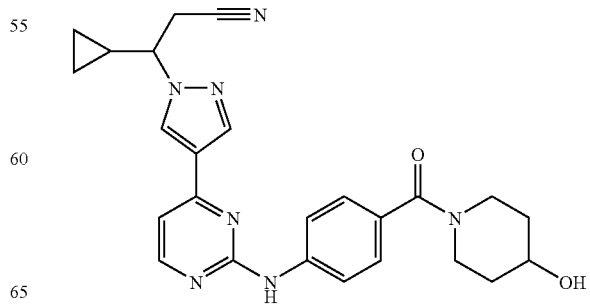

To a mixture of 4-(4-(1-(2-cyano-1-cyclopropylethyl)-1H-pyrazol-4-yl)pyrimidin-2-ylamino)benzoic acid (30 mg, 0.07 mmol), 4-hydroxypiperidine (7.5 mg, 0.074 mmol) and benzotriazol-1-yloxytris(dimethylamino)phosphonium hexafluorophosphate (40 mg, 0.089 mmol) in N,N-dimethylformamide (0.5 mL) was added N,N-diisopropylethylamine (31 µL, 0.18 mmol). The reaction was stirred at room temperature for 1 h, quenched with water, purified on HPLC to give the desired product as a racemic mixture (TFA salt). LCMS (M+H) 458.2.

Example 252

3-cyclopropyl-3-(4-(2-(4-((3-endo)-3-hydroxy-8-azabicyclo[3.2.1]octane-8-carbonyl)phenylamino)pyrimidin-4-yl)-1H-pyrazol-1l)propanenitrile

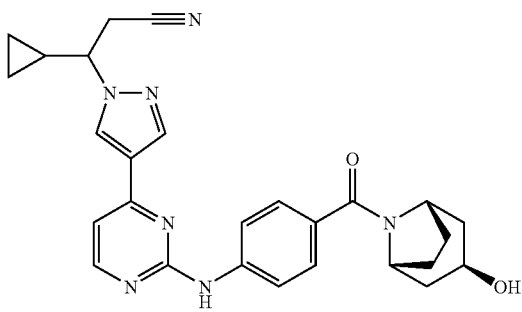

This compound was prepared as a racemic mixture according to the procedure described in example 251, using (3-endo)-8-azabicyclo[3.2.1]octan-3-ol hydrochloride instead of 4-hydroxypiperidine. LCMS (M+H) 484.2.

Example 253

3-cyclopropyl-3-(4-(2-(4-(pyrrolidine-1-carbonyl)phenylamino)pyrimidin-4-yl)-1H-pyrazol-1-yl)propanenitrile

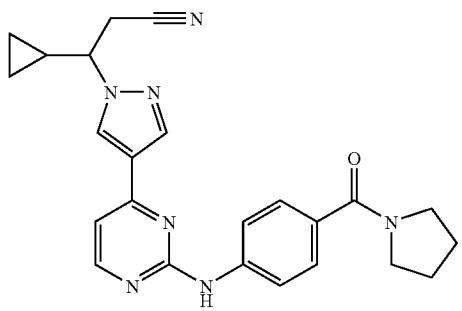

This compound was prepared as a racemic mixture according to the procedure described in example 251, using pyrrolidine instead of 4-hydroxypiperidine. LCMS (M+H) 428.2.

Example 254

4-(4-(1-(2-cyano-1-cyclopropylethyl)-1H-pyrazol-4-yl)pyrimidin-2-ylamino)-N-(tetrahydro-2H-pyran-4-yl)benzamide

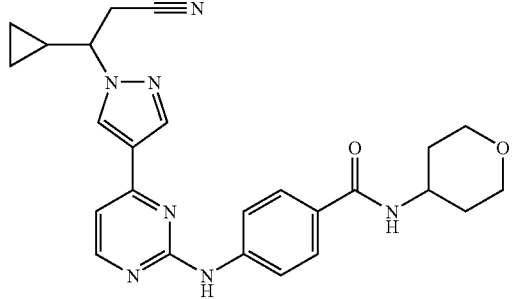

This compound was prepared as a racemic mixture according to the procedure described in example 251, using tetrahydro-2H-pyran-4-amine instead of 4-hydroxypiperidine. LCMS (M+H) 458.4.

Example 255

2-(1-(ethylsulfonyl)-3-(4-(2-(4-(morpholine-4-carbonyl)phenylamino)pyrimidin-4-yl)-1H-pyrazol-1-yl)azetidin-3-yl)acetonitrile

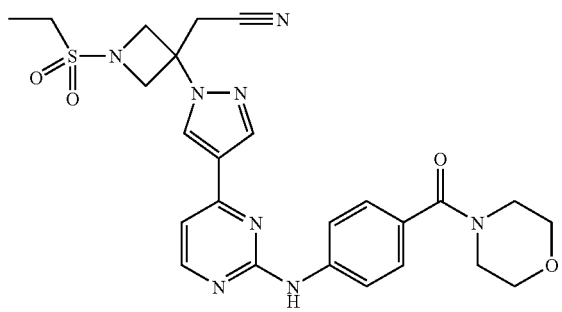

To a mixture of 4-((4-1-(3-(cyanomethyl)-1-(ethylsulfonyl)azetidin-3-yl)-1H-pyrazol-4-ylpyrimidin-2-yl)amino)benzoic acid (30 mg, 0.07 mmol), morpholine (0.0065 g, 0.074 mmol) and benzotriazol-1-yloxytris(dimethylamino)phosphonium hexafluorophosphate (40 mg, 0.089 mmol) in N,N-dimethylformamide (0.5 mL) was added N,N-diisopropylethylamine (31 µL, 0.18 mmol). The reaction was stirred at room temperature for 1 h, quenched with water, purified on HPLC to give the desired product as TFA salt. LCMS (M+H) 537.5.

Example 256

2-(1-(ethylsulfonyl)-3-(4-(2-(4-(4-hydroxypiperidine-1-carbonyl)phenylamino)pyrimidin-4-yl)-1H-pyrazol-1-yl)azetidin-3-yl)acetonitrile

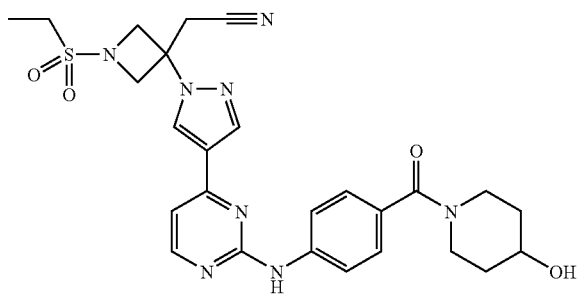

This compound was prepared according to the procedure described in example 255, using 4-hydroxypiperidine instead of morpholine. LCMS (M+H) 551.2.

Example 257

2-(1-(ethylsulfonyl)-3-(4-(2-(4-((3-endo)-3-hydroxy-8-azabicyclo[3.2.1]octane-8-carbonyl)phenylamino)pyrimidin-4-yl)-1H-pyrazol-1-yl)azetidin-3-yl)acetonitrile

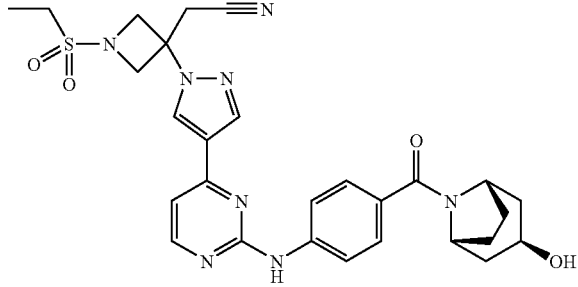

This compound was prepared according to the procedure described in example 255, using (3-endo)-8-azabicyclo[3.2.1]octan-3-ol hydrochloride instead of morpholine. LCMS (M+H) 577.2.

Example 258

2-(1-(ethylsulfonyl)-3-(4-(2-(4-(pyrrolidine-1-carbonyl)phenylamino)pyrimidin-4-yl)-1H-pyrazol-1-yl)azetidin-3-yl)acetonitrile

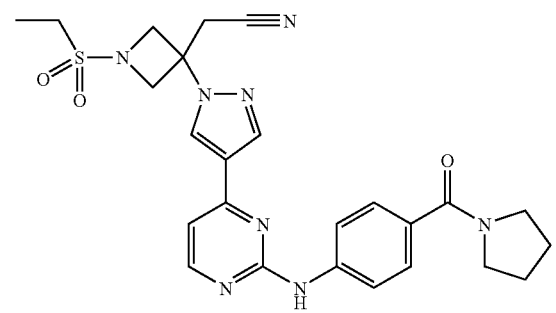

This compound was prepared according to the procedure described in example 255, using pyrrolidine instead of morpholine. LCMS (M+H) 521.1.

Example 259

4-(4-(1-(3-(cyanomethyl)-1-(ethylsulfonyl)azetidin-3-yl)-1H-pyrazol-4-yl)pyrimidin-2-ylamino)-N-(tetrahydro-2H-pyran-4-yl)benzamide

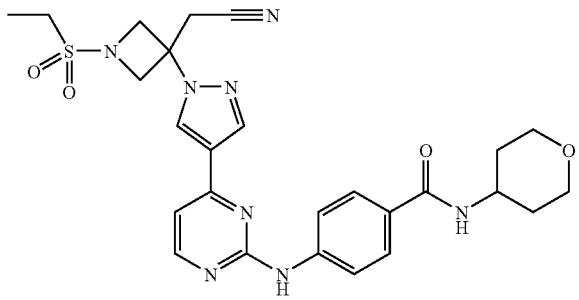

This compound was prepared according to the procedure described in example 255, using tetrahydro-2H-pyran-4-amine instead of morpholine. LCMS (M+H) 551.1.

Example 260

3-cyclopropyl-3-(4-(2-(4-(morpholine-4-carbonyl)phenylamino)pyrimidin-4-yl)-1H-pyrazo-1-yl)propanenitrile

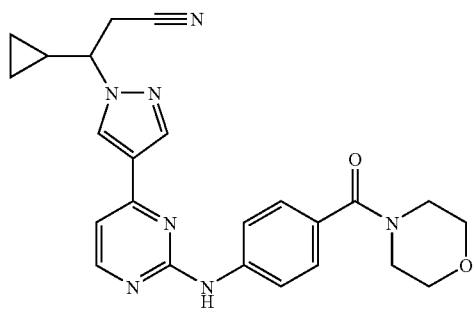

This compound was prepared as a racemic mixture according to the procedure described in example 251, using morpholine instead of 4-hydroxypiperidine. LCMS (M+H) 444.1

Example 261

3-(4-(2-(4-(azetidine-1-carbonyl)phenylamino)pyrimidin-4-yl)-1H-pyrazol-1-yl)-3-cyclopropylpropanenitrile

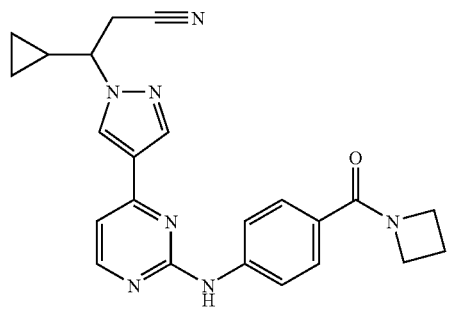

This compound was prepared as a racemic mixture according to the procedure described in example 251, using azetidine hydrochloride instead of 4-hydroxypiperidine. LCMS (M+H) 414.2.

Example 262

3-cyclopropyl-3-(4-(2-(4-(2-oxa-6-azatricyclo[3.3.1.1(3,7)]dec-6-ylcarbonyl)phenyl)aminopyrimidin-4-yl)-1H-pyrazol-1-yl)propanenitrile

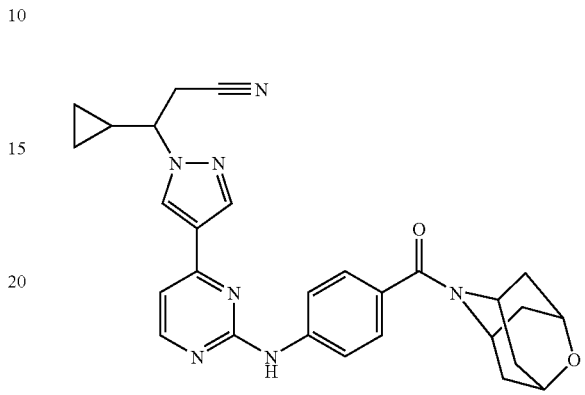

This compound was prepared as a racemic mixture according to the procedure described in example 251, using 2-oxa-6-azatricyclo[3.3.1.13,7]decane hydrochloride instead of 4-hydroxypiperidine. LCMS (M+H) 496.2.

Example 263

3-cyclopropyl-3-(4-(2-(4-(4-methoxypiperidine-1-carbonyl)phenylamino)pyrimidin-4-yl)-1H-pyrazol-1-yl)propanenitrile

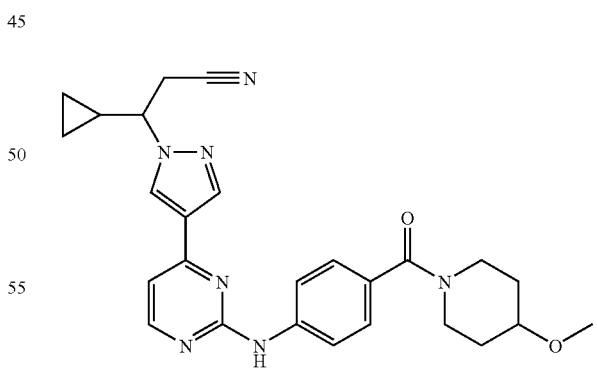

This compound was prepared as a racemic mixture according to the procedure described in example 251, using 4-methoxypiperidine hydrochloride instead of 4-hydroxypiperidine. LCMS (M+H) 472.2.

Example 264

(3R)-1-(4-(4-(1-(2-cyano-1-cyclopropylethyl)-1H-pyrazol-4-yl)pyrimidin-2-ylamino)benzoyl)pyrrolidine-3-carbonitrile

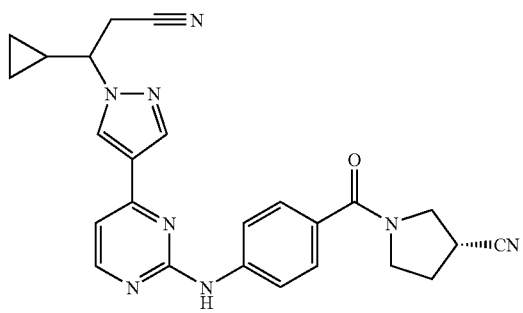

This compound was prepared as a diastereoisomeric mixture according to the procedure described in example 251, using (3R)-3-pyrrolidinecarbonitrile hydrochloride instead of 4-hydroxypiperidine. LCMS (M+H) 453.2.

Example 265

3-cyclopropyl-3-(4-(2-(4-((S)-3-methoxypyrrolidine-1-carbonyl)phenylamino)pyrimidin-4-yl)-1H-pyrazol-1-yl)propanenitrile

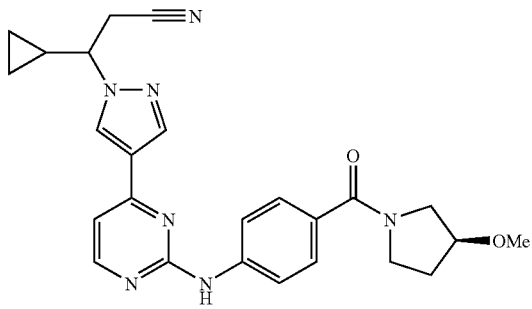

This compound was prepared as a diastereoisomeric mixture according to the procedure described in example 251, using (3S)-3-methoxy-pyrrolidine hydrochloride instead of 4-hydroxypiperidine. LCMS (M+H) 458.1.

Example 266

3-cyclopropyl-3-(4-(2-(4-((R)-3-hydroxypyrrolidine-1-carbonyl)phenylamino)pyrimidin-4-yl)-1H-pyrazol-1-yl)propanenitrile

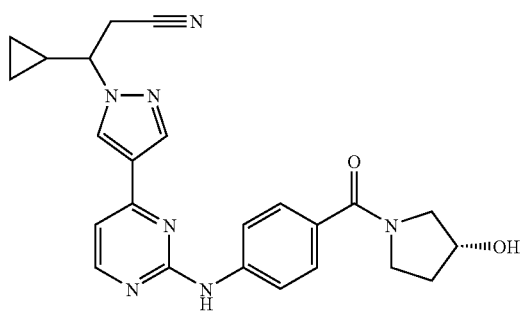

This compound was prepared as a diastereoisomeric mixture according to the procedure described in example 251, using (3R)-3-pyrrolidinol instead of 4-hydroxypiperidine. LCMS (M+H) 444.2.

Example 267

3-cyclopropyl-3-(4-(2-(4-(4-methylpiperazine-1-carbonyl)phenylamino)pyrimidin-4-yl)-1H-pyrazol-1-yl)propanenitrile

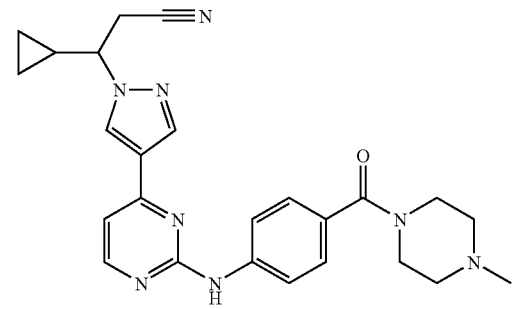

This compound was prepared as a racemic mixture according to the procedure described in example 251, using 1-methylpiperazine instead of 4-hydroxypiperidine. LCMS (M+H) 457.2.

Example 268

N-((3R)-1-(4-(4-(1-(2-cyano-1-cyclopropylethyl)-1H-pyrazol-4-yl)pyrimidin-2-ylamino)benzoyl)pyrrolidin-3-yl)acetamide

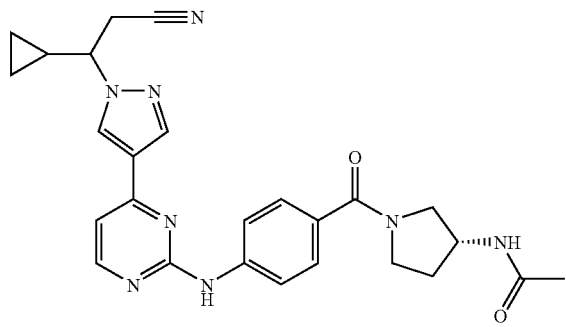

This compound was prepared as a diastereoisomeric mixture according to the procedure described in example 251, using N-(3R)-3-pyrrolidinyl-acetamide instead of 4-hydroxypiperidine. LCMS (M+H) 485.2.

Example 269

3-(4-(2-(4-(4-acetylpiperazine-1-carbonyl)phenylamino)pyrimidin-4-yl)-1H-pyrazol-1-yl)-3-cyclopropylpropanenitrile

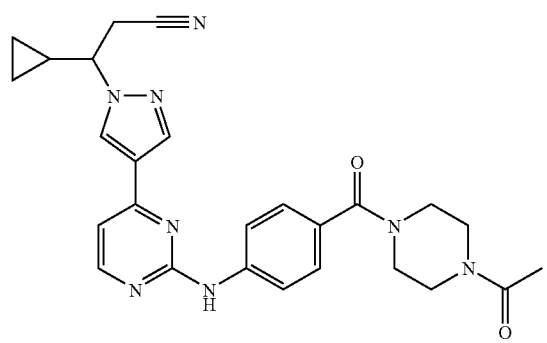

This compound was prepared as a racemic mixture according to the procedure described in example 251, using 1-acetylpiperazine instead of 4-hydroxypiperidine. LCMS (M+H) 485.4.

Example 270

3-cyclopropyl-3-(4-(2-(4-(3-(dimethylamino)pyrrolidine-1-carbonyl)phenylamino)pyrimidin-4-yl)-1H-pyrazol-1-yl)propanenirile

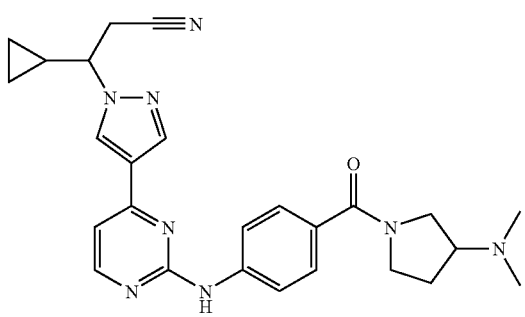

This compound was prepared as a diastereoisomeric mixture according to the procedure described in example 251, using N,N-dimethyl-3-pyrrolidinamine instead of 4-hydroxypiperidine. LCMS (M+H) 471.5.

Example 271

3-cyclopropyl-3-(4-(2-(4-((S)-3-fluoropyrrolidine-1-carbonyl)phenylamino)pyrimidin-4-yl)-1H-pyrazol-1-yl)propanenitrile

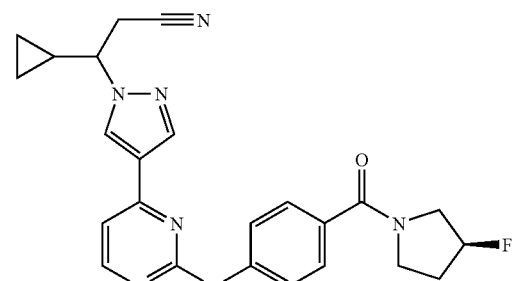

This compound was prepared as a diastereoisomeric mixture according to the procedure described in example 251, using (3S)-3-fluoro-pyrrolidine hydrochloride instead of 4-hydroxypiperidine. LCMS (M+H) 446.1.

Example 272

Ethyl 4-(4-(4-(1-(2-cyano-1-cyclopropylethyl)-1H-pyrazol-4-yl)pyrimidin-2-ylamino)benzoyl)aminopiperidine-1-carboxylate

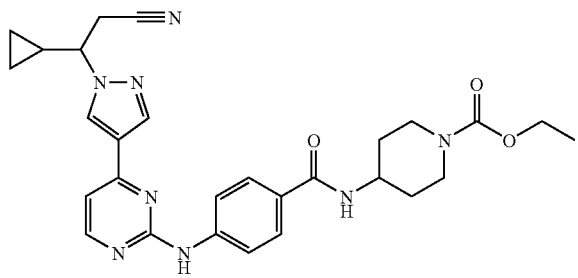

This compound was prepared as a racemic mixture according to the procedure described in example 251, using 4-amino-1-piperidinecarboxylic acid ethyl ester instead of 4-hydroxypiperidine. LCMS (M+H) 529.2.

Example 273

2-(3-(4-(2-(4-(azetidine-1-carbonyl)phenylamino)pyrimidin-4-yl)-1H-pyrazol-1-yl)-1-(ethylsulfonyl)azetidin-3-yl)acetonitrile

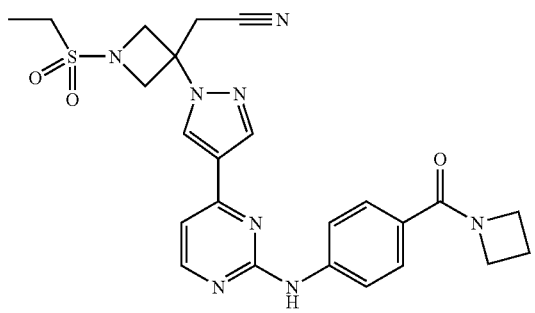

This compound was prepared according to the procedure described in example 255, using azetidine hydrochloride instead of morpholine. LCMS (M+H) 507.1.

Example 274

1-(ethylsulfonyl)-3-(4-(2-(4-(2-oxa-6-azatricyclo[3.3.1.1(3,7)]dec-6-ylcarbonyl)phenyl)aminopyrimidin-4-yl)-1H-pyrazol-1-yl)azetidin-3-ylacetonitrile This compound was prepared according to the procedure described in example 255, using 2-oxa-6-azatricyclo[3.3.1.13,7]decane hydrochloride instead of morpholine. LCMS (M+H) 589.4.

Example 275

(1-(ethylsulfonyl)-3-4-(2-(4-((4-methoxypiperidin-1-yl)carbonyl)phenylamino)pyrimidin-4-yl)-1H-pyrazol-1-ylazetidin-3-yl)acetonitrile

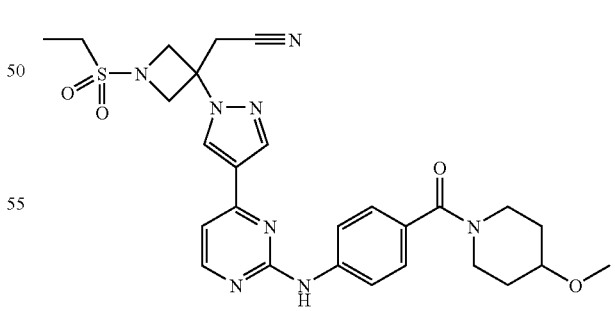

This compound was prepared according to the procedure described in example 255, using 4-methoxypiperidine hydrochloride instead of morpholine. LCMS (M+H) 565.4.

Example 276

(R)-1-(4-(4-(1-(3-(cyanomethyl)-1-(ethylsulfonyl)
azetidin-3-yl)-1H-pyrazol-4-yl)pyrimidin-2-ylamino)
benzoyl)pyrrolidine-3-carbonitrile

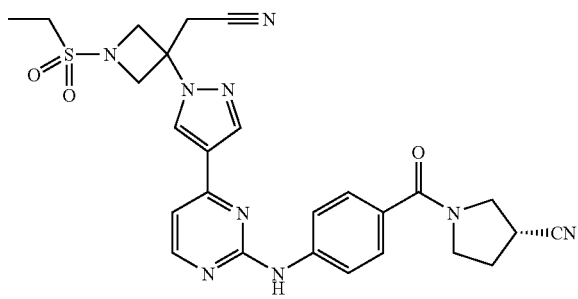

This compound was prepared according to the procedure described in example 255, using (3R)-3-pyrrolidinecarbonitrile hydrochloride instead of morpholine. LCMS (M+H) 546.4.

Example 277

(S)-2-(1-(ethylsulfonyl)-3-(4-(2-(4-(3-methoxypyrrolidine-1-carbonyl)phenylamino)pyrimidin-4-yl)-1H-pyrazol-1-yl)azetidin-3-yl)acetonitrile

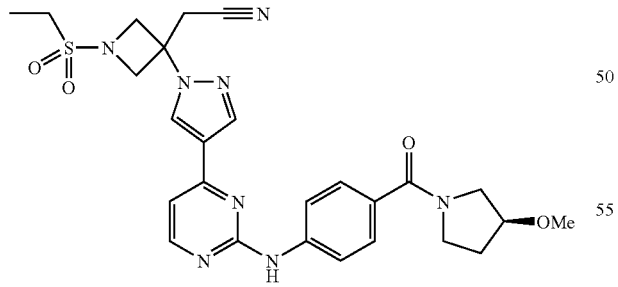

This compound was prepared according to the procedure described in example 255, using (3S)-3-methoxy-pyrrolidine hydrochloride instead of morpholine. LCMS (M+H) 551.2.

Example 278

(R)-2-(1-(ethylsulfonyl)-3-(4-(2-(4-(3-hydroxypyrrolidine-1-carbonyl)phenylamino)pyrimidin-4-yl)-1H-pyrazol-1-yl)azetidin-3-yl)acetonitrile

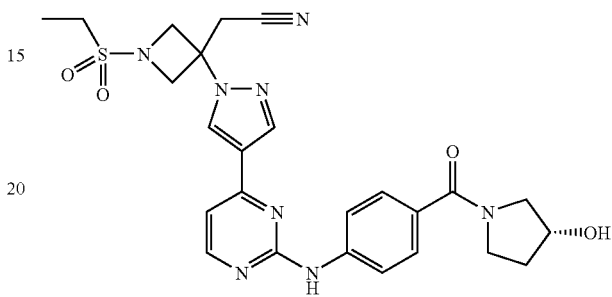

This compound was prepared according to the procedure described in example 255, using (3R)-3-pyrrolidinol instead of morpholine. LCMS (M+H) 537.3.

Example 279

2-(1-(ethylsulfonyl)-3-(4-(2-(4-(4-methylpiperazine-1-carbonyl)phenylamino)pyrimidin-4-yl)-1H-pyrazol-1-yl)azetidin-3-yl)acetonitrile

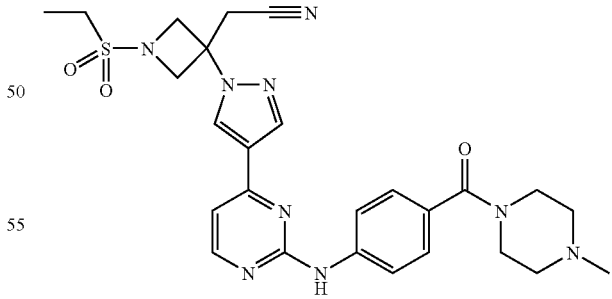

This compound was prepared according to the procedure described in example 255, using 1-methylpiperazine instead of morpholine. LCMS (M+H) 550.2.

Example 280

(R)—N-(1-(4-(4-(1-(3-(cyanomethyl)-1-(ethylsulfonyl)azetidin-3-yl)-1H-pyrazol-4-yl)pyrimidin-2-ylamino)benzoyl)pyrrolidin-3-yl)acetamide

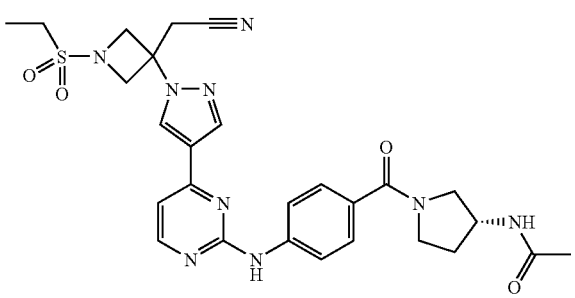

This compound was prepared according to the procedure described in example 255, using N-(3R)-3-pyrrolidinyl-acetamide instead of morpholine. LCMS (M+H) 578.2.

Example 281

2-(3-(4-(2-(4-(4-acetylpiperazine-1-carbonyl)phenylamino)pyrimidin-4-yl)-1H-pyrazol-1-yl)-1-(ethylsulfonyl)azetidin-3-yl)acetonitrile

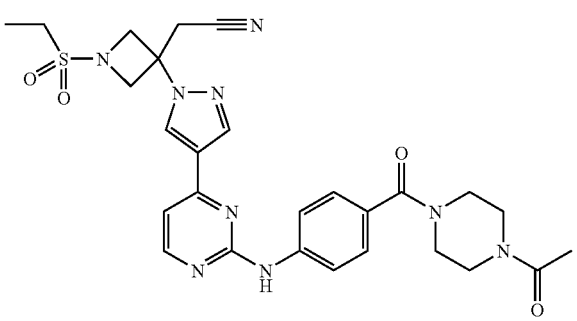

This compound was prepared according to the procedure described in example 255, using 1-acetylpiperazine instead of morpholine. LCMS (M+H) 578.2.

Example 282

2-(3-(4-(2-(4-(3-(dimethylamino)pyrrolidine-1-carbonyl)phenylamino)pyrimidin-4-yl)-1H-pyrazol-1-yl)-1-(ethylsulfonyl)azetidin-3-yl)acetonitrile This compound was prepared as a racemic mixture according to the procedure described in example 255, using N,N-dimethyl-3-pyrrolidinamine instead of morpholine. LCMS (M+H) 564.4.

Example 283

(S)-2-(1-(ethylsulfonyl)-3-(4-(2-(4-(3-fluoropyrrolidine-1-carbonyl)phenylamino)pyrimidin-4-yl)-1H-pyrazol-1-yl)azetidin-3-yl)acetonitrile

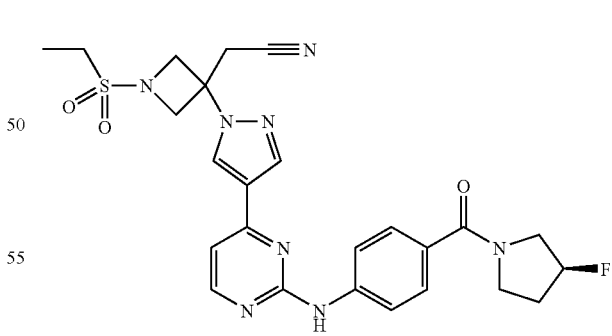

This compound was prepared according to the procedure described in example 255, using (3S)-3-fluoro-pyrrolidine hydrochloride instead of morpholine. LCMS (M+H) 539.1.

Example 284

Ethyl 4-(4-(4-(1-(3-(cyanomethyl)-1-(ethylsulfonyl)azetidin-3-yl)-1H-pyrazol-4-yl)pyrimidin-2-ylamino)benzamido)piperidine-1-carboxylate

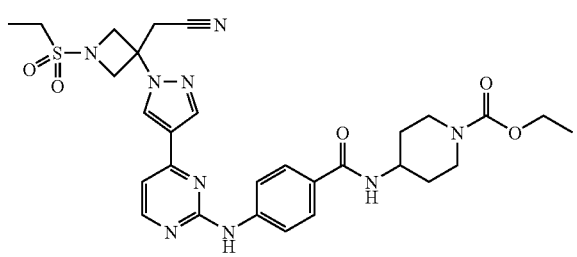

This compound was prepared according to the procedure described in example 255, using 4-amino-1-piperidinecarboxylic acid ethyl ester instead of morpholine. LCMS (M+H) 622.2.

Example 285

4-(4-(1-(3-cyano-1-(cyanomethyl)cyclobutyl)-1H-pyrazol-4-yl)pyrimidin-2-ylamino)benzoic Acid

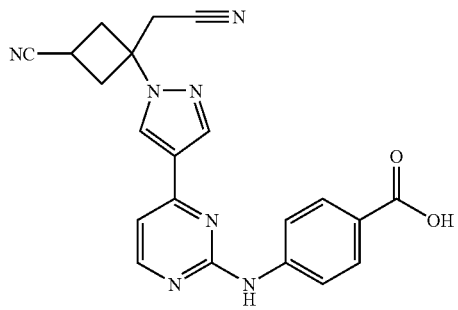

A mixture of 3-(4-(2-chloropyrimidin-4-yl)-1H-pyrazol-1-yl)-3-(cyanomethyl)-cyclobutanecarbonitrile (300 mg, 0.00100 mol), p-aminobenzoic acid (206 mg, 0.00151 mol), and p-toluenesulfonic acid (150 mg, 0.00085 mol) in dry 1,4-dioxane (8 mL) was refluxed overnight, cooled to room temperature. The solid was filtered and collected to give the titled compound as a cis- and trans-isomer mixture, which was used directly in next step (310 mg, 77.3%). LCMS (M+H) 400.4.

Example 286

4-(4-(1-(2-cyano-1-cyclopentylethyl)-1H-pyrazol-4-yl)-5-methoxypyrimidin-2-ylamino)benzoic Acid

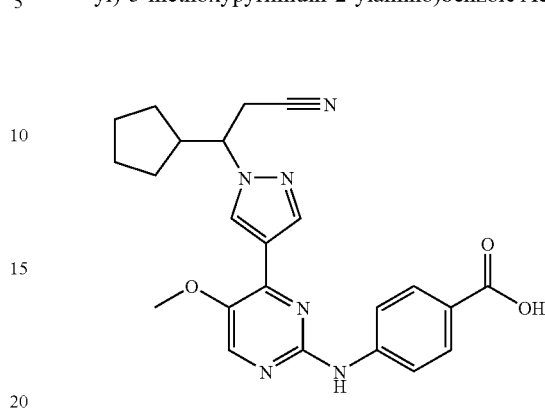

A mixture of 3-(4-(2-chloro-5-methoxypyrimidin-4-yl)-1H-pyrazol-1-yl)-3-cyclopentylpropanenitrile (120 mg, 0.36 mmol), p-aminobenzoic acid (74.4 mg, 0.542 mmol), and p-toluenesulfonic acid (53 mg, 0.31 mmol) in dry 1,4-dioxane (3 mL) was refluxed overnight. The mixture was cooled to room temperature. The resulting solid was filtered and washed with dioxane to give the desired product as a racemic mixture (120 mg, 76.7%). LCMS (M+H) 433.3.

Example 287

3-(cyanomethyl)-3-(4-(2-(4-(morpholine-4-carbonyl)phenylamino)pyrimidin-4-yl)-1H-pyrazol-1-yl)cyclobutanecarbonitrile

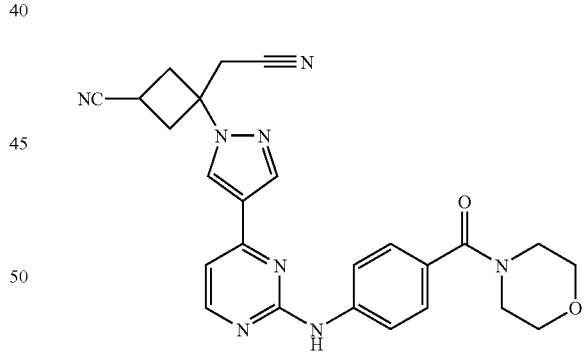

To a mixture of 4-((4-1-(3-cyano-1-(cyanomethyl)cyclobutyl)-1H-pyrazol-4-ylpyrimidin-2-yl)amino)benzoic acid (30 mg, 0.07 mmol), morpholine (6.5 µL, 0.074 mmol) and benzotriazol-1-yloxytris(dimethylamino)phosphonium hexafluorophosphate (40 mg, 0.089 mol) in N,N-dimethylformamide (0.5 mL) was added N,N-diisopropylethylamine (31 µL, 0.18 mol). The reaction was stirred at room temperature for 1 h, quenched with water, purified on HPLC to give the desired cis- and trans-product as free base. First peak retention time 1.421 min, LCMS (M+H) 469.4; Second peak retention time 1.452 min, LCMS (M+H) 469.4.

Example 288

3-(cyanomethyl)-3-(4-(2-(4-(pyrrolidine-1-carbonyl)phenylamino)pyrimidin-4-yl)-1H-pyrazol-1-yl)cyclobutanecarbonitrile

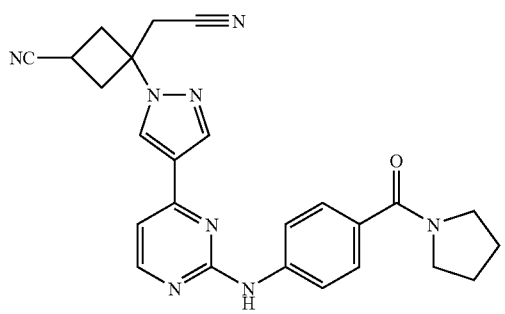

The cis- and trans-isomers of the titled compound were prepared according to the procedure described in example 287, using pyrrolidine instead of morpholine. First peak retention time 1.566 min, LCMS (M+H) 453.4; Second peak retention time 1.599 min, LCMS (M+H) 453.4.

Example 289

4-(4-(1-(3-cyano-1-(cyanomethyl)cyclobutyl)-1H-pyrazol-4-yl)pyrimidin-2-ylamino)-N-(tetrahydro-2H-pyran-4-yl)benzamide

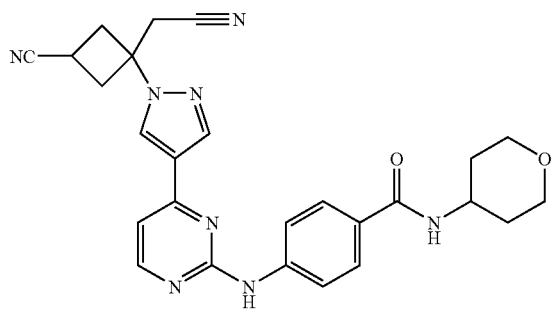

The cis- and trans-isomers of the titled compound were prepared according to the procedure described in example 287, using tetrahydro-2H-pyran-4-amine instead of morpholine. First peak retention time 1.468 min, LCMS (M+H) 483.4; Second peak retention time 1.490 min, LCMS (M+H) 483.4.

Example 290

(R)-3-(cyanomethyl)-3-(4-(2-(4-(3-hydroxypyrrolidine-1-carbonyl)phenylamino)pyrimidin-4-yl)-1H-pyrazol-1-yl)cyclobutanecarbonitrile

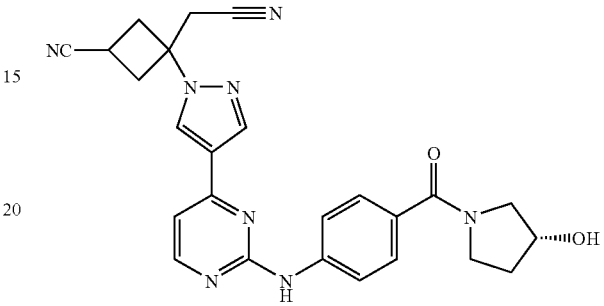

The cis- and trans-isomers of the titled compound were prepared according to the procedure described in example 287, using (3R)-3-pyrrolidinol instead of morpholine. First peak retention time 1.205 min, LCMS (M+H) 469.1; Second peak retention time 1.228 min, LCMS (M+H) 469.1.

Example 291

4-(4-(1-(3-cyano-1-(cyanomethyl)cyclobutyl)-1H-pyrazol-4-yl)pyrimidin-2-ylamino)-N-((5-methyl-isoxazol-3-yl)methyl)benzamide

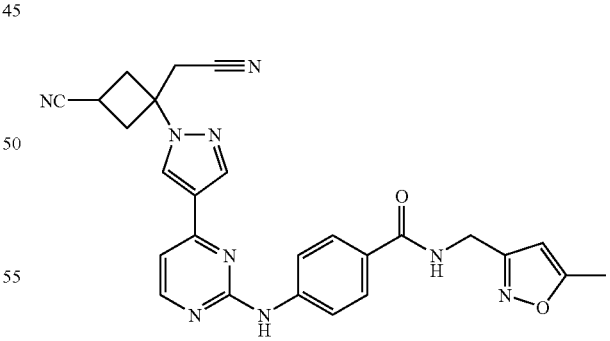

The cis- and trans-isomers of the titled compound were prepared according to the procedure described in example 287, using 5-methyl-3-isoxazolemethanamine instead of morpholine. First peak retention time 494.4; Second retention time 1.637 min, LCMS (M+H) 494.4.

Example 292

3-(4-(2-(4-(azetidine-1-carbonyl)phenylamino)pyrimidin-4-yl)-1H-pyrazol-1-yl)-3-(cyanomethyl)cyclobutanecarbonitrile

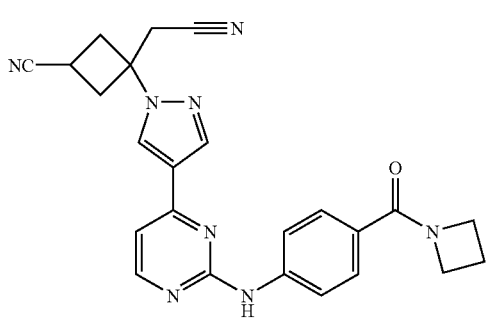

The cis- and trans-isomers of the titled compound were prepared according to the procedure described in example 287, using azetidine hydrochloride instead of morpholine. First peak retention time 1.498 min, LCMS (M+H) 439.4; Second peak retention time 1.525 min, LCMS (M+H) 439.4.

Example 293

3-(cyanomethyl)-3-(4-(2-(4-(4-methylpiperazine-1-carbonyl)phenylamino)pyrimidin-4-yl)-1H-pyrazol-1-yl)cyclobutanecarbonitrile

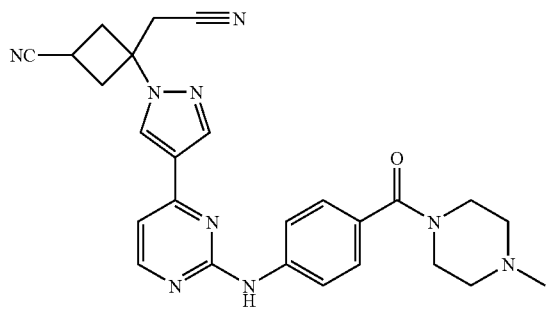

The cis- and trans-isomers of the titled compound were prepared according to the procedure described in example 287, using 1-methylpiperazine instead of morpholine. First peak retention time 1.032 min, LCMS (M+H) 482.4; Second peak retention time 1.041 min, LCMS (M+H) 482.4

Example 294

(S)-3-(cyanomethyl)-3-(4-(2-(4-(3-fluoropyrrolidine-1-carbonyl)phenylamino)pyrimidin-4-yl)-1H-pyrazol-1-yl)cyclobutanecarbonitrile

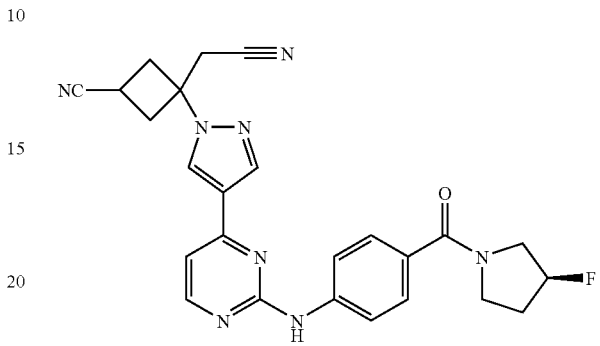

The cis- and trans-isomers of the titled compound were prepared according to the procedure described in example 287, using (3S)-3-fluoro-pyrrolidine hydrochloride instead of morpholine. First peak retention time 1.529 min, LCMS (M+H) 471.4; Second peak retention time 1.561 min, LCMS (M+H) 471.4.

Example 295

3-(cyanomethyl)-3-(4-(2-(4-(4-methoxypiperidine-1-carbonyl)phenylamino)pyrimidin-4-yl)-1H-pyrazol-1-yl)cyclobutanecarbonitrile

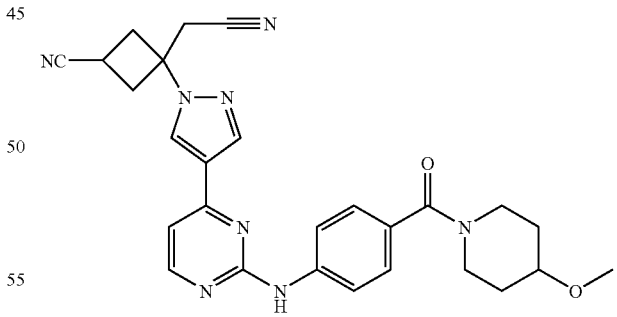

The cis- and trans-isomers of the titled compound were prepared according to the procedure described in example 287, using 4-methoxypiperidine hydrochloride instead of morpholine. First peak retention time 1.550 min, LCMS (M+H) 497.4; Second peak retention time 1.583 min, LCMS (M+H) 497.4.

Example 296

(S)-3-(cyanomethyl)-3-(4-(2-(4-(3-methoxypyrrolidine-1-carbonyl)phenylamino)pyrimidin-4-yl)-1H-pyrazol-1-yl)cyclobutanecarbonitrile

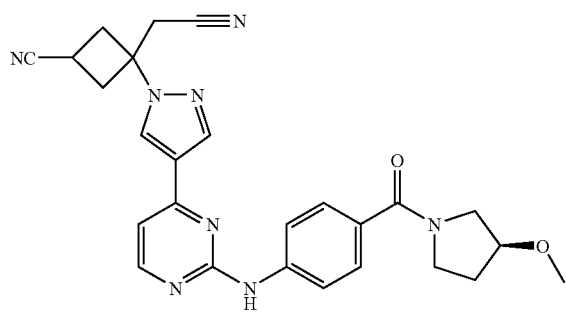

The cis- and trans-isomers of the titled compound were prepared according to the procedure described in example 287, using (3S)-3-methoxy-pyrrolidine hydrochloride instead of morpholine. First peak retention time 1.480 min, LCMS (M+H) 483.5; Second peak retention time 1.511 min, LCMS (M+H) 483.4.

Example 297

(R)-1-(4-(4-(1-(3-cyano-1-(cyanomethyl)cyclobutyl)-1H-pyrazol-4-yl)pyrimidin-2-ylamino)benzoyl)pyrrolidine-3-carbonitrile

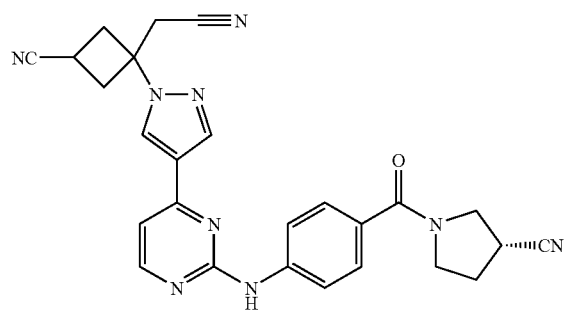

The cis- and trans-isomers of the titled compound were prepared according to the procedure described in example 287, using (3R)-3-pyrrolidinecarbonitrile hydrochloride instead of morpholine. First isomer retention time 1.474 min, LCMS (M+H) 478.4; Second isomer retention time 1.505 min, LCMS (M+H) 478.4.

Example 298

3-(4-(2-(4-(4-acetylpiperazine-1-carbonyl)phenylamino)pyrimidin-4-yl)-1H-pyrazol-1-yl)-3-(cyanomethyl)cyclobutanecarbonitrile

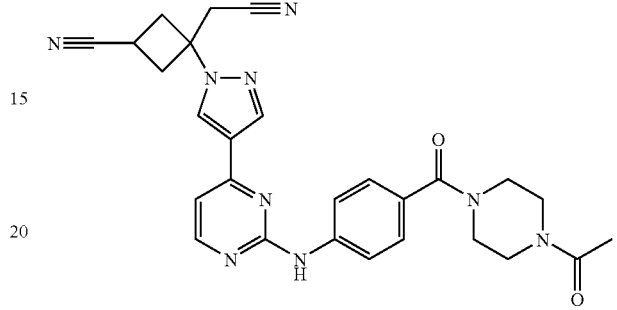

The cis- and trans-isomers of the titled compound were prepared according to the procedure described in example 287, using 1-acetylpiperazine instead of morpholine. First isomer has retention time 1.331 min, LCMS (M+H) 510.4; Second isomer retention time 1.355 min, LCMS (M+H) 510.4.

Example 299

(R)—N-(1-(4-(4-(1-(3-cyano-1-(cyanomethyl)cyclobutyl)-1H-pyrazol-4-yl)pyrimidin-2-ylamino)benzoyl)pyrrolidin-3-yl)acetamide

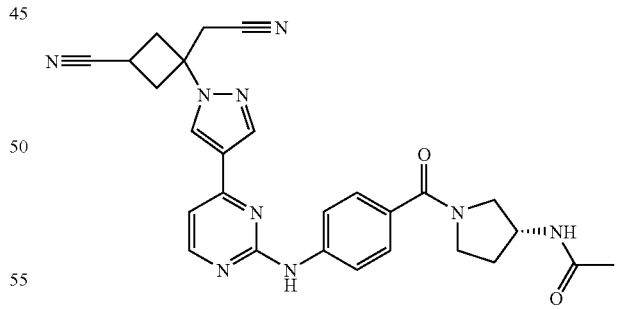

The cis- and trans-isomers of the titled compound were prepared according to the procedure described in example 287, using N-(3R)-3-pyrrolidinyl-acetamide instead of morpholine. First isomer retention time 1.226 min, LCMS (M+H) 510.1; Second isomer retention time 1.252 min, LCMS (M+H) 510.1.

Example 300

3-(cyanomethyl)-3-(4-(2-(4-((3-endo)-3-hydroxy-8-azabicyclo[3.2.1]octane-8-carbonyl)phenylamino)pyrimidin-4-yl)-1H-pyrazol-1-yl)cyclobutanecarbonitrile

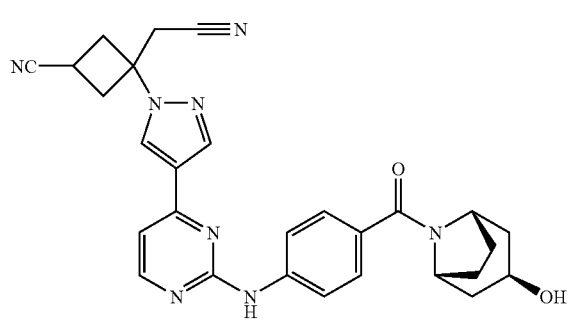

The cis- and trans-isomers of the titled compound were prepared according to the procedure described in example 287, using (3-endo)-8-azabicyclo[3.2.1]octan-3-ol hydrochloride instead of morpholine. First isomer retention time 1.411 min, LCMS (M+H) 509.4; Second isomer retention time 1.440 min, LCMS (M+H) 509.4.

Example 301

3-(cyanomethyl)-3-(4-(2-(4-(4-hydroxypiperidine-1-carbonyl)phenylamino)pyrimidin-4-yl)-1H-pyrazol-1-yl)cyclobutanecarbonitrile

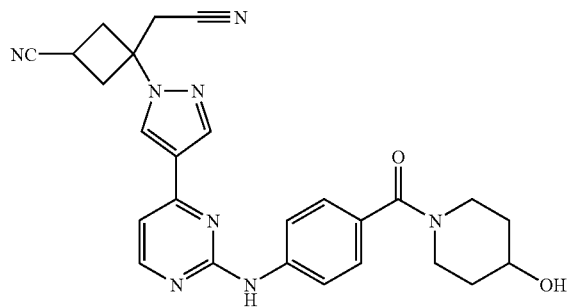

The cis- and trans-isomers of the titled compound were prepared according to the procedure described in example 287, using 4-hydroxypiperidine instead of morpholine. First isomer retention time 1.195 min, LCMS (M+H) 483.1; Second isomer retention time 1.220 min, LCMS (M+H) 483.1.

Example 302

3-cyclopentyl-3-(4-(5-methoxy-2-(4-(morpholine-4-carbonyl)phenylamino)pyrimidin-4-yl)-1H-pyrazol-1-yl)propanenitrile

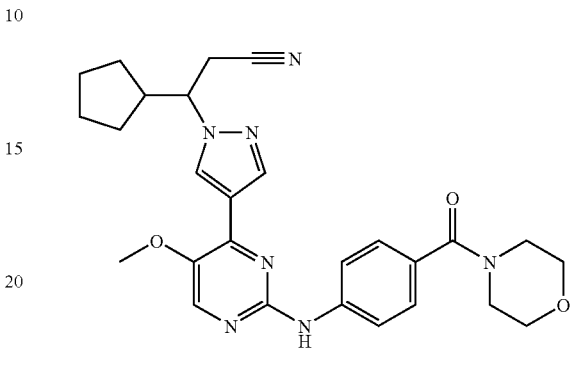

To a mixture of 4-(4-(1-(2-cyano-1-cyclopentylethyl)-1H-pyrazol-4-yl)-5-methoxypyrimidin-2-ylamino)benzoic acid (25 mg, 0.058 mmol), morpholine (5.0 µL, 0.058 mmol) and benzotriazol-1-yloxytris(dimethylamino)phosphonium hexafluorophosphate (31 mg, 0.069 mmol) in N,N-dimethylformamide (0.4 mL) was added N,N-diisopropylethylamine (24 µL, 0.14 mmol). The reaction was stirred at room temperature for 1 h, quenched with water, purified on HPLC to give the desired product as a racemic mixture. LCMS (M+H) 502.5.

Example 303

3-cyclopentyl-3-(4-(5-methoxy-2-(4-(pyrrolidine-1-carbonyl)phenylamino)pyrimidin-4-yl)-1H-pyrazol-1-yl)propanenitrile

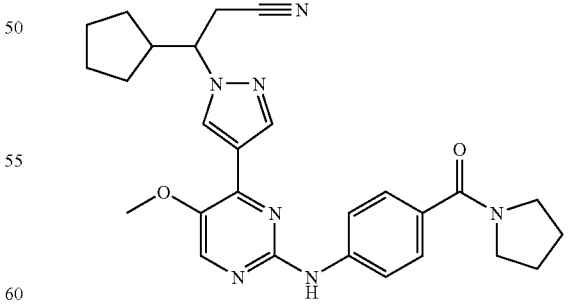

This compound was prepared as a racemic mixture according to the procedure described in example 302, using pyrrolidine instead of morpholine. LCMS (M+H) 486.5.

Example 304

3-cyclopentyl-3-(4-(5-methoxy-2-(4-(4-methylpiperazine-1-carbonyl)phenylamino)pyrimidin-4-yl)-1H-pyrazol-1-yl)propanenitrile

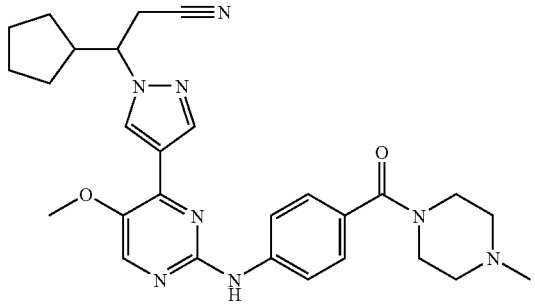

This compound was prepared as a racemic mixture according to the procedure described in example 302, using 1-methylpiperazine instead of morpholine. LCMS (M+H) 515.5.

Example 305

4-(4-(1-(2-cyano-1-cyclopentylethyl)-1H-pyrazol-4-yl)-5-methoxypyrimidin-2-ylamino)-N-(tetrahydro-2H-pyran-4-yl)benzamide

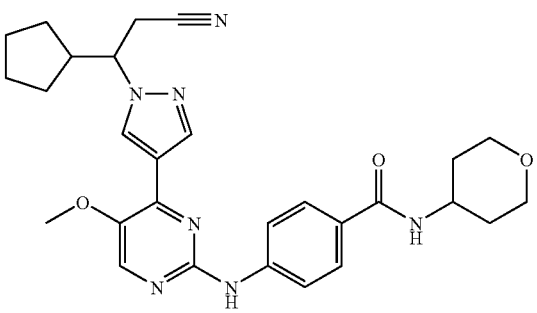

This compound was prepared as a racemic mixture according to the procedure described in example 302, using tetrahydro-2H-pyran-4-amine instead of morpholine. LCMS (M+H) 516.4.

Example 306

3-cyclopentyl-3-[4-(2-{[4-(2-pyrrolidin-1-ylethoxy)phenyl]amino}pyrimidin-4-yl)-1H-pyrazol-1-yl]propanenitrile

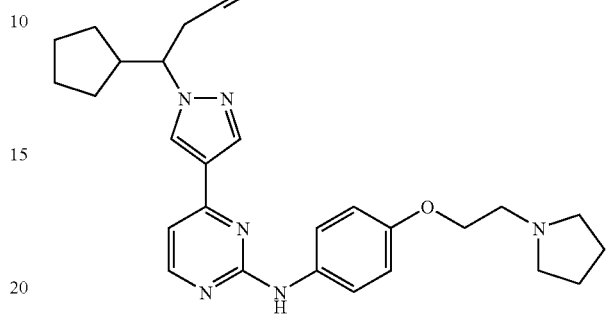

Step 1. 4-(2-pyrrolidin-1-ylethoxy)aniline

A mixture of 1-[2-(4-nitrophenoxy)ethyl]pyrrolidine (from Combi-Blocks, LLC, 5.00 g, 0.0212 mol) in 100 mL of MeOH was hydrogenated in the presence of 0.5 g 10% Pd/C, under balloon pressure of hydrogen, overnight. After filtering off the catalyst, the filtrate was evaporated to dryness and used directly in next step (4.36 g, 99.88%). LCMS (M+H) 207.4.

Step 2. 3-cyclopentyl-3-[4-(2-{[4-(2-pyrrolidin-1-ylethoxy)phenyl]amino}pyrimidin-4-yl)-1H-pyrazol-1-yl]propanenitrile A mixture of 3-[4-(2-chloropyrimidin-4-yl)-1H-pyrazol-1-yl]-3-cyclopentylpropanenitrile (prepared according to the procedure described in Example 33, Step 2; 0.030 g, 0.000099 mol) and 4-(2-pyrrolidin-1-ylethoxy)aniline (0.0308 g, 0.000149 mol) in acetic acid (0.7 mL, 0.01 mol) was refluxed overnight. After being evaporated to dryness, the residue was diluted with EtOAc, washed with aqueous sodium bicarbonate, brine, dried, and concentrated. The residue was applied on RP-HPLC to obtain the desired product as a racemic mixture (free base). LCMS (M+H) 472.4.

Example 307

3-(cyanomethyl)-3-[4-(2-{[4-(2-pyrrolidin-1-ylethoxy)phenyl]amino}pyrimidin-4-yl)-1H-pyrazol-1-yl]cyclobutanecarbonitrile

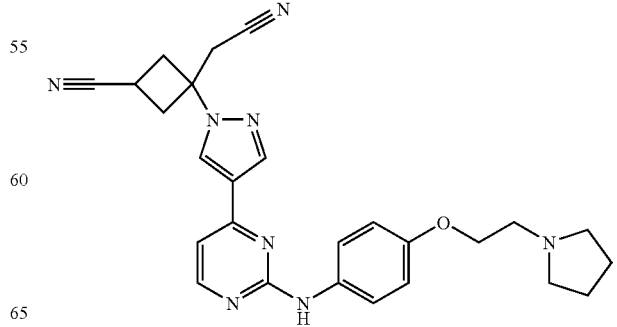

The cis- and trans-isomers of the titled compound were prepared as a racemic mixture according to the procedure described in example 306, using 3-(4-(2-chloropyrimidin-4-yl)-1H-pyrazol-1-yl)-3-(cyanomethyl)-cyclobutanecarbonitrile and 1-[2-(4-nitrophenoxy)ethyl]pyrrolidine as starting materials. First isomer retention time 1.055 min, LCMS (M+H) 469.4. Second peak retention time 1.072 min, LCMS (M+H) 469.4.

Example 308

3-(4-{2-[(4-morpholin-4-ylphenyl)amino]pyrimidin-4-yl}-1H-pyrazol-1-yl)-3-(tetrahydro-2H-pyran-4-yl)propanenitrile

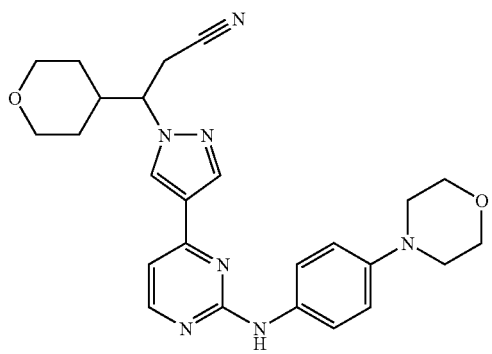

Step 1.
(2E)-3-(tetrahydro-2H-pyran-4-yl)acrylonitrile

To a solution of 1.0 M of potassium tert-butoxide in tetrahydrofuran (9.20 mL, 0.00920 mol) at 0° C. was added dropwise a solution of diethyl cyanomethylphosphonate (1.56 mL, 0.00965 mol) in tetrahydrofuran (11.73 mL, 0.1447 mol). The reaction was warmed to room temperature and then cooled at 0° C. again. To the reaction mixture was added a solution of tetrahydro-2H-pyran-4-carbaldehyde (1.0 g, 0.0088 mol) in tetrahydrofuran (2.35 mL, 0.0289 mol). The reaction was allowed to warm up to room temperature and stirred overnight. After being quenched with water, the mixture was extracted with EtOAc. The combined organic layers were washed with brine, dried and evaporated to dryness. The crude mixture was used directly in next step. LCMS (M+H) 138.0.

Step 2. 3-(tetrahydro-2H-pyran-4-yl)-3-[4-(4,4,5,5-tetramethyl-1,3,2-dioxaborolan-2-yl)-1H-pyrazol-1-yl]propanenitrile To a solution of 4-(4,4,5,5-tetramethyl-1,3,2-dioxaborolan-2-yl)-1H-pyrazole (1.25 g, 0.00644 mol) in acetonitrile (20 mL, 0.4 mol) was added (2E)-3-(tetrahydro-2H-pyran-4-yl)acrylonitrile (1.00 g, 0.00729 mol), followed by 1,8-diazabicyclo[5.4.0]undec-7-ene (1.09 mL, 0.00729 mol). The resulting mixture was stirred at room temperature overnight. After being evaporated to dryness, the residue was purified on silica gel, eluting with 0-100% EtOAc in hexanes, to provide the desired product (1.30 g, 60.93%). LCMS (M+H) 332.4.

Step 3. 3-[4-(2-chloropyrimidin-4-yl)-1H-pyrazol-1-yl]-3-(tetrahydro-2H-pyran-4-yl)propanenitrile A mixture of 2,4-dichloropyrimidine (0.589 g, 0.00395 mol), 3-(tetrahydro-2H-pyran-4-yl)-3-[4-(4,4,5,5-tetramethyl-1,3,2-dioxaborolan-2-yl)-1H-pyrazol-1-yl]propanenitrile (1.30 g, 0.00392 mol), tetrakis(triphenylphosphine)palladium(0) (0.3 g, 0.0002 mol), and potassium phosphate (2.5 g, 0.012 mol) in 1,4-dioxane (10 mL, 0.1 mol) and water (1 mL, 0.06 mol) was heated at 100° C. overnight. After cooling to room temperature, the mixture was diluted with EtOAc, washed with water, brine, dried over MgSO₄, filtered and concentrated. The residue was purified on silica gel, eluting with 0 to 100% EtOAc in hexanes, to provide the desired product (890 mg, 71.36%). LCMS (M+H) 318.3

Step 4. 3-(4-{2-[(4-morpholin-4-ylphenyl)amino]pyrimidin-4-yl}-1H-pyrazol-1-yl)-3-(tetrahydro-2H-pyran-4-yl)propanenitrile A mixture of 3-[4-(2-chloropyrimidin-4-yl)-1H-pyrazol-1-yl]-3-(tetrahydro-2H-pyran-4-yl)propanenitrile (20 mg, 0.00008 mol), 4-morpholin-4-ylaniline (20.1 mg, 0.000113 mol), and p-toluenesulfonic acid (11 mg, 0.000064 mol) in dry 1,4-dioxane (0.5 mL, 0.006 mol) was refluxed overnight. The mixture was diluted with acetonitrile and water, purified on RP-HPLC at pH 10 to provide the desired product as a racemic mixture (free base). LCMS (M+H) 460.4.

Example 309

4-[(4-{1-[2-cyano-1-(tetrahydro-2H-pyran-4-yl)ethyl]-1H-pyrazol-4-yl}pyrimidin-2-yl)amino]-N-(tetrahydro-2H-pyran-4-yl)benzamide

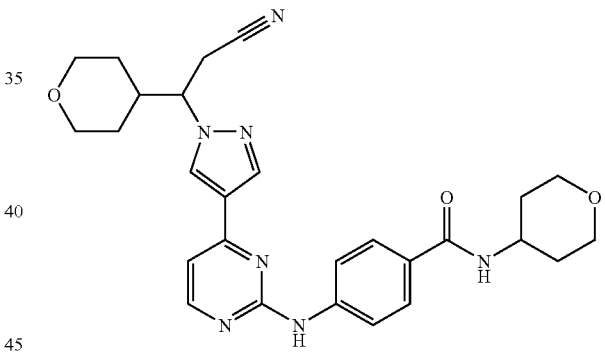

Step 1. 4-[(4-{1-[2-cyano-1-(tetrahydro-2H-pyran-4-yl)ethyl]-1H-pyrazol-4-yl}pyrimidin-2-yl)amino]benzoic Acid A mixture of 3-[4-(2-chloropyrimidin-4-yl)-1H-pyrazol-1-yl]-3-(tetrahydro-2H-pyran-4-yl)propanenitrile (from example 308 step 3, 140 mg, 0.00044 mol), p-aminobenzoic acid (90.6 mg, 0.000661 mol), and p-toluenesulfonic acid (64 mg, 0.00037 mol) in dry 1,4-dioxane (3 mL, 0.04 mol) was refluxed overnight, cooled to room temperature. The desired product crashed out and was collected by filtration (180 mg, 97.64%). LCMS (M+H) 419.3.

Step 2. 4-[(4-{1-[2-cyano-1-(tetrahydro-2H-pyran-4-yl)ethyl]-1H-pyrazol-4-yl}pyrimidin-2-yl)amino]-N-(tetrahydro-2H-pyran-4-yl)benzamide To a mixture of 4-[(4-{1-[2-cyano-1-(tetrahydro-2H-pyran-4-yl)ethyl]-1H-pyrazol-4-yl}pyrimidin-2-yl)amino]benzoic acid (20 mg, 0.00005 mol), tetrahydro-2H-pyran-4- amine (4.8 mg, 0.000048 mol) and benzotriazol-1-yloxytris(dimethylamino)phosphonium hexafluorophosphate (25 mg, 0.000057 mol) in N,N-dimethylformamide (0.3 mL, 0.004 mol) was added N,N-diisopropylethylamine (20 μL, 0.00011 mol). The reaction was stirred at room temperature for 1 h, quenched with water, purified on HPLC to obtain the desired product as a racemic mixture (free base). LCMS (M+H) 502.4.

Example 310

3-[4-(2-{[4-(pyrrolidin-1-ylcarbonyl)phenyl]amino}pyrimidin-4-yl)-1H-pyrazol-1-yl]-3-(tetrahydro-2H-pyran-4-yl)propanenitrile

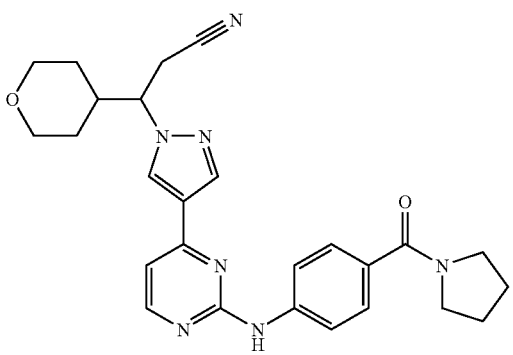

This compound was prepared as a racemic mixture according to the procedure described in example 309, using pyrrolidine instead of tetrahydro-2H-pyran-4-amine in step 2. LCMS (M+H) 472.4.

Example 311

3-[4-(2-{[4-(morpholin-4-ylcarbonyl)phenyl]amino}pyrimidin-4-yl)-1H-pyrazol-1-yl]-3-(tetrahydro-2H-pyran-4-yl)propanenitrile

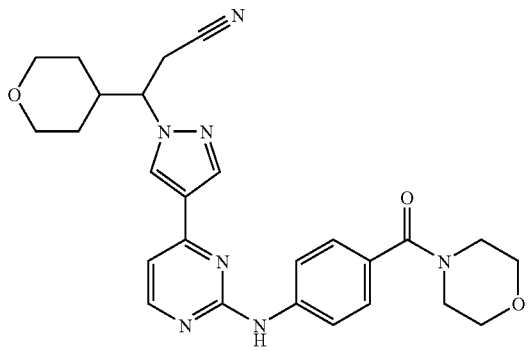

This compound was prepared as a racemic mixture according to the procedure described in example 309, using morpholine instead of tetrahydro-2H-pyran-4-amine in step 2. LCMS (M+H) 488.4.

Example 312

3-{4-[2-({4-[(4-hydroxypiperidin-1-yl)carbonyl]phenyl}amino)pyrimidin-4-yl]-1H-pyrazol-1-yl}-3-(tetrahydro-2H-pyran-4-yl)propanenitrile

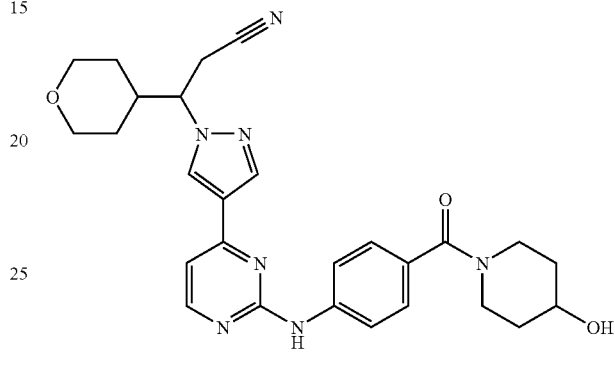

This compound was prepared as a racemic mixture according to the procedure described in example 309, using 4-hydroxypiperidine instead of tetrahydro-2H-pyran-4-amine in step 2. LCMS (M+H) 502.4.

Example 313

3-{4-[2-({4-[(4-methoxypiperidin-1-yl)carbonyl]phenyl}amino)pyrimidin-4-yl]-1H-pyrazol-1-yl}-3-(tetrahydro-2H-pyran-4-yl)propanenitrile

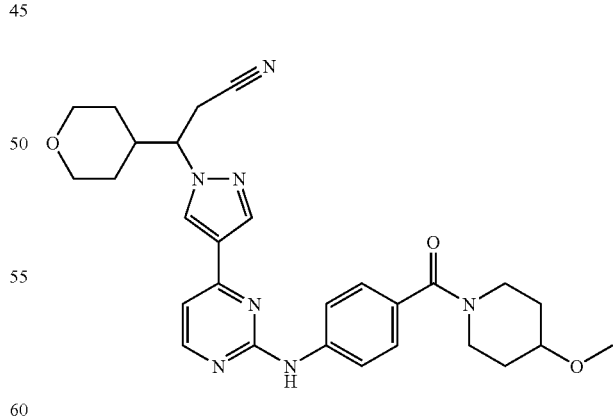

This compound was prepared as a racemic mixture according to the procedure described in example 309, using 4-methoxypiperidine hydrochloride instead of tetrahydro-2H-pyran-4-amine in step 2. LCMS (M+H) 516.4.

Example 314

1-{4-[(4-{1-[2-cyano-1-(tetrahydro-2H-pyran-4-yl)ethyl]-1H-pyrazol-4-yl}pyrimidin-2-yl)amino]benzoyl}piperidine-4-carbonitrile

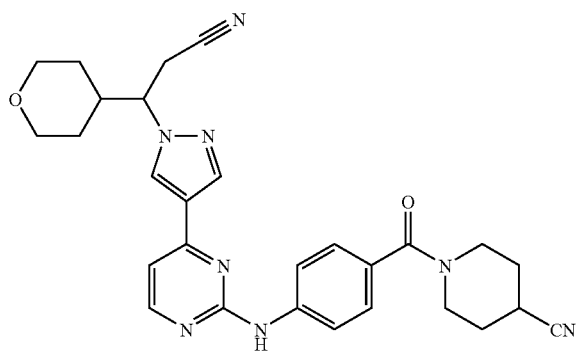

This compound was prepared as a racemic mixture according to the procedure described in example 309, using 4-cyanopiperidine hydrochloride instead of tetrahydro-2H-pyran-4-amine in step 2. LCMS (M+H) 511.4.

Example 315

3-(4-{2-[(4-{[(3R)-3-hydroxypyrrolidin-1-yl]carbonyl}phenyl)amino]pyrimidin-4-yl}-1H-pyrazol-1-yl)-3-(tetrahydro-2H-pyran-4-yl)propanenitrile

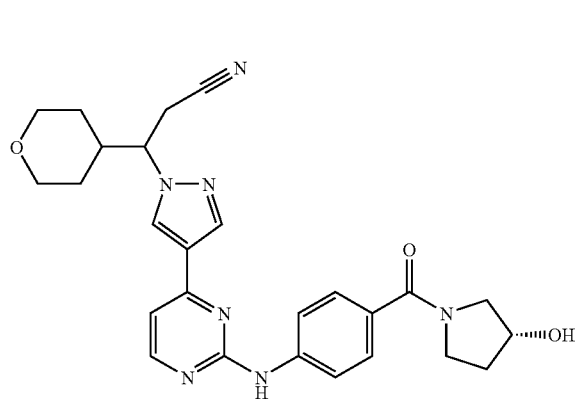

This compound was prepared as a diastereoisomeric mixture according to the procedure described in example 309, using (3R)-3-pyrrolidinol instead of tetrahydro-2H-pyran-4-amine in step 2. LCMS (M+H) 488.4.

Example 316

3-(4-{2-[(4-{[(3S)-3-methoxypyrrolidin-1-yl]carbonyl}phenyl)amino]pyrimidin-4-yl}-1H-pyrazol-1-yl)-3-(tetrahydro-2H-pyran-4-yl)propanenitrile

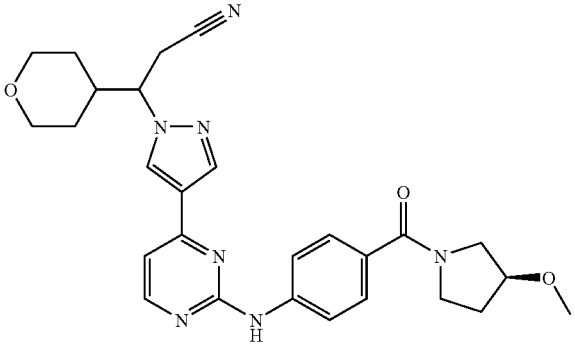

This compound was prepared as a diastereoisomeric mixture according to the procedure described in example 309, using (3S)-3-methoxypyrrolidine instead of tetrahydro-2H-pyran-4-amine in step 2. LCMS (M+H) 502.4.

Example 317

(3S)-1-{4-[(4-{1-[2-cyano-1-(tetrahydro-2H-pyran-4-yl)ethyl]-1H-pyrazol-4-yl}pyrimidin-2-yl)amino]benzoyl}pyrrolidine-3-carbonitrile

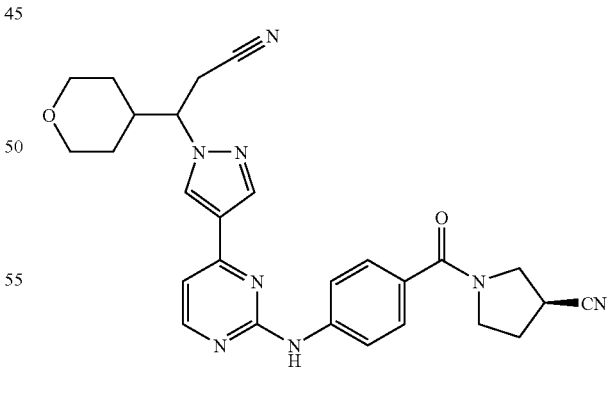

This compound was prepared as a diastereoisomeric mixture according to the procedure described in example 309, using (3S)-3-cyanopyrrolidine instead of tetrahydro-2H-pyran-4-amine in step 2. LCMS (M+H) 497.4.

Example 318

1-[4-({4-[1-(2-cyano-1-cyclopropylethyl)-1H-pyrazol-4-yl]pyrimidin-2-yl}amino)benzoyl]piperidine-4-carbonitrile

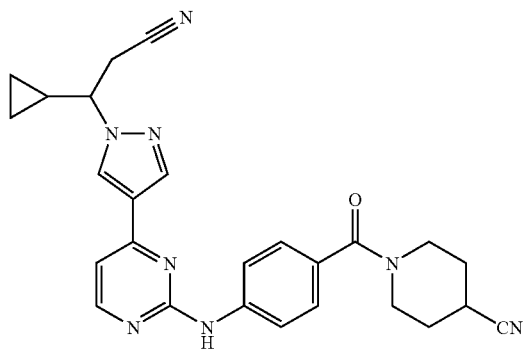

This compound was prepared as a racemic mixture according to the procedure described in example 251, using 4-cyanopiperidine hydrochloride instead of 4-hydroxypiperidine. LCMS (M+H) 467.4.

Example 319

1-{4-[(4-{1-[3-(cyanomethyl)-1-(ethylsulfonyl)azetidin-3-yl]-1H-pyrazol-4-yl}pyrimidin-2-yl)amino]benzoyl}piperidine-4-carbonitrile

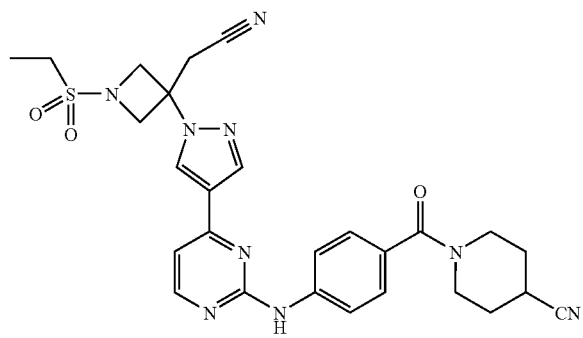

This compound was prepared as a racemic mixture according to the procedure described in example 255, using 4-cyanopiperidine hydrochloride instead of morpholine. LCMS (M+H) 560.4.

Example 320

3-cyclopropyl-3-[4-(5-methoxy-2-{[3-(1,3-oxazol-5-yl)phenyl]amino}pyrimidin-4-yl)-1H-pyrazol-1-yl]propanenitrile

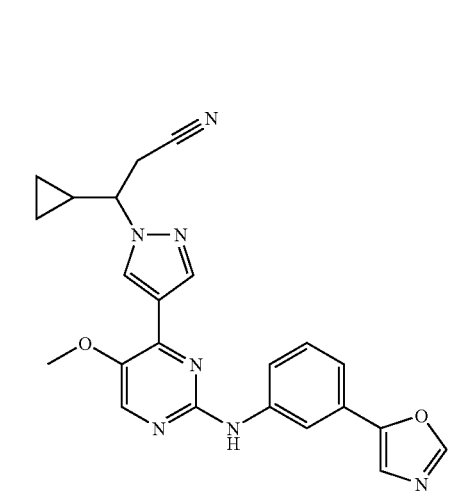

Step 1. 3-[4-(2-chloro-5-methoxypyrimidin-4-yl)-1H-pyrazol-1-yl]-3-cyclopropylpropanenitrile A mixture of 2,4-dichloro-5-methoxypyrimidine (from Aldrich Chemicals, 1.47 g, 0.00821 mol), 3-cyclopropyl-3-[4-(4,4,5,5-tetramethyl-1,3,2-dioxaborolan-2-yl)-1H-pyrazol-1-yl]propanenitrile (from example 177 step 1, 2.34 g, 0.00815 mol), tetrakis(triphenylphosphine)palladium(0) (0.6 g, 0.0005 mol), and potassium phosphate (5.2 g, 0.025 mol) in 1,4-dioxane (20 mL, 0.3 mol) and water (2 mL, 0.1 mol) was heated at 100° C. overnight. After cooling to room temperature, the mixture was dilute with AcOEt, washed with water, brine, dried over MgSO₄, concentrated. The residue was purified on silica gel, eluting with 0 to 60%, to give the desired product (580 mg, 23.43%). LCMS (M+H) 304.3

Step 2. 3-cyclopropyl-3-[4-(5-methoxy-2-{[3-(1,3-oxazol-5-yl)phenyl]amino}pyrimidin-4-yl)-1H-pyrazol-1-yl]propanenitrile A mixture of 3-[4-(2-chloro-5-methoxypyrimidin-4-yl)-1H-pyrazol-1-yl]-3-cyclopropylpropanenitrile (20 mg, 0.00008 mol), 3-(1,3-oxazol-5-yl)aniline (18.1 mg, 0.000113 mol), and p-toluenesulfonic acid (11 mg, 0.000064 mol) in dry 1,4-dioxane (0.5 mL, 0.006 mol) was refluxed overnight. The mixture was diluted with acetonitrile and water, purified on RP-HPLC at pH 10 to give the desired product as a racemic mixture (free base). LCMS (M+H) 428.1.

Example 321

3-cyclopropyl-3-(4-{5-methoxy-2-[(3-nitrophenyl)amino]pyrimidin-4-yl}-1H-pyrazol-1-yl)propanenitrile

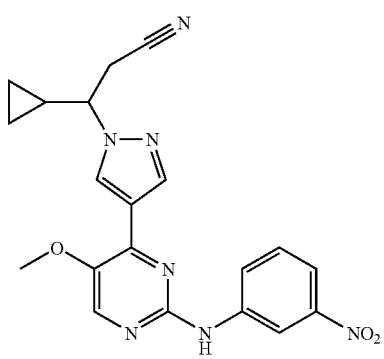

A solution of a mixture of 3-[4-(2-chloro-5-methoxypyrimidin-4-yl)-1H-pyrazol-1-yl]-3-cyclopropylpropanenitrile (from example 320 step 1, 60 mg, 0.0002 mol), m-nitroaniline (40.9 mg, 0.000296 mol), and p-toluenesulfonic acid (29 mg, 0.00017 mol) in dry 1,4-dioxane (1 mL, 0.02 mol) was refluxed overnight. The mixture was diluted with acetonitrile and water, purified on RP-HPLC at pH 10 to give the desired product as a racemic mixture (free base). LCMS (M+H) 406.2.

Example 323

3-({4-[1-(2-cyano-1-cyclopropylethyl)-1H-pyrazol-4-yl]-5-methoxypyrimidin-2-yl}amino)-N-(tetrahydro-2H-pyran-4-yl)benzamide

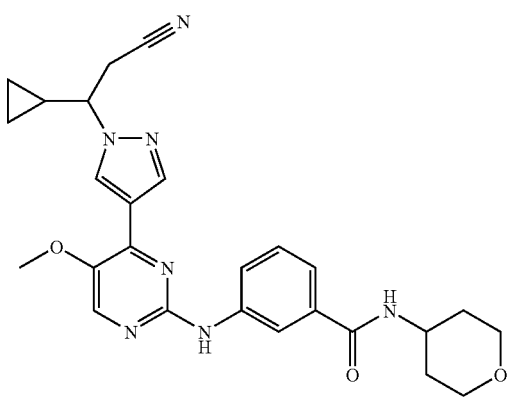

Step 1. 3-({4-[1-(2-cyano-1-cyclopropylethyl)-1H-pyrazol-4-yl]-5-methoxypyrimidin-2-yl}amino)benzoic Acid A mixture of 3-[4-(2-chloro-5-methoxypyrimidin-4-yl)-1H-pyrazol-1-yl]-3-cyclopropylpropanenitrile (from example 320 step 1, 250 mg, 0.00082 mol), 3-aminobenzoic acid (169 mg, 0.00123 mol), and p-toluenesulfonic acid (120 mg, 0.00070 mol) in dry 1,4-dioxane (5 mL, 0.07 mol) was refluxed overnight, then cooled to room temperature. The insoluble material was filtered off. The filtration was evaporated to dryness to give the crude product (330 mg, 99.14%). LCMS (M+H) 405.3.

Step 2. 3-({4-[1-(2-cyano-1-cyclopropylethyl)-1H-pyrazol-4-yl]-5-methoxypyrimidin-2-yl}amino)-N-(tetrahydro-2H-pyran-4-yl)benzamide To a mixture of 3-({4-[1-(2-cyano-1-cyclopropylethyl)-1H-pyrazol-4-yl]-5-methoxypyrimidin-2-yl}amino)benzoic acid (30 mg, 0.00007 mol), tetrahydro-2H-pyran-4-amine (7.5 mg, 0.000074 mol) and benzotriazol-1-yloxytris(dimethylamino)phosphonium hexafluorophosphate (39 mg, 0.000089 mol) in N,N-dimethylformamide (0.5 mL, 0.006 mol) was added N,N-diisopropylethylamine (31 μL, 0.00018 mol). The reaction was stirred at room temperature for 1 h, quenched with water, purified on HPLC to give the desired product as a diastereomeric mixture (free base). LCMS (M+H) 488.2.

Example 324

3-cyclopropyl-3-[4-(5-methoxy-2-{[3-(pyrrolidin-1-ylcarbonyl)phenyl]amino}pyrimidin-4-yl)-1H-pyrazol-1-yl]propanenitrile

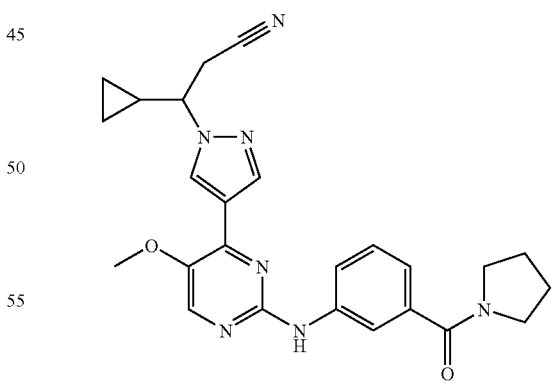

This compound was prepared as a racemic mixture according to the procedure described in example 323, using pyrrolidine instead of tetrahydro-2H-pyran-4-amine. LCMS (M+H) 458.3.

Example 325

3-cyclopropyl-3-(4-{2-[(3-{[(3R)-3-hydroxypyrrolidin-1-yl]carbonyl}phenyl)amino]-5-methoxypyrimidin-4-yl}-1H-pyrazol-1-yl)propanenitrile

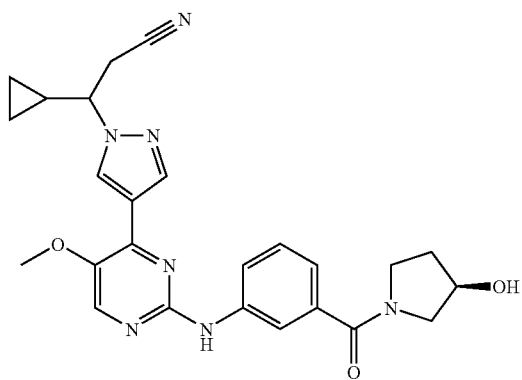

This compound was prepared as a diastereoisomeric mixture according to the procedure described in example 323, using (3R)-3-pyrrolidinol instead of tetrahydro-2H-pyran-4-amine. LCMS (M+H) 474.3.

Example 326

3-cyclopropyl-3-(4-{5-methoxy-2-[(3-{[(3S)-3-methoxypyrrolidin-1-yl]carbonyl}phenyl)amino]pyrimidin-4-yl}-1H-pyrazol-1-yl)propanenitrile

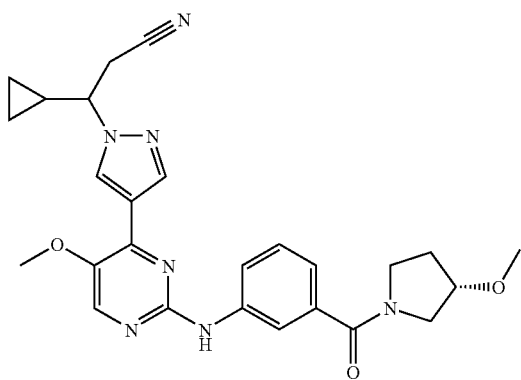

This compound was prepared as a diastereoisomeric mixture according to the procedure described in example 323, using (3S)-3-methoxypyrrolidine hydrochloride instead of tetrahydro-2H-pyran-4-amine. LCMS (M+H) 488.3.

Example 327

(3S)-1-[3-({4-[1-(2-cyano-1-cyclopropylethyl)-1H-pyrazol-4-yl]-5-methoxypyrimidin-2-yl}amino)benzoyl]pyrrolidine-3-carbonitrile

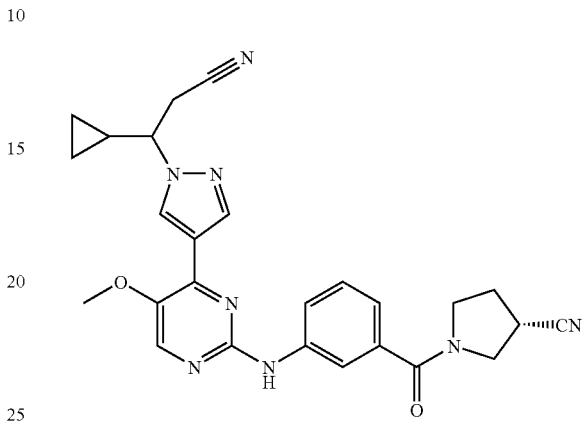

This compound was prepared as a diastereoisomeric mixture according to the procedure described in example 323, using (3S)-3-cyanopyrrolidine instead of tetrahydro-2H-pyran-4-amine. LCMS (M+H) 483.2.

Example 328

3-cyclopropyl-3-[4-(5-methoxy-2-{[3-(morpholin-4-ylcarbonyl)phenyl]amino}pyrimidin-4-yl)-1H-pyrazol-1-yl]propanenitrile

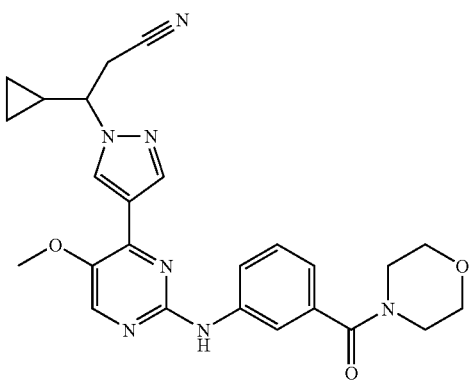

This compound was prepared as a racemic mixture according to the procedure described in example 323, using morpholine instead of tetrahydro-2H-pyran-4-amine. LCMS (M+H) 474.3.

Example 329

3-cyclopropyl-3-{4-[2-({3-[(4-hydroxypiperidin-1-yl)carbonyl]phenyl}amino)-5-methoxypyrimidin-4-yl]-1H-pyrazol-1-yl}propanenitrile

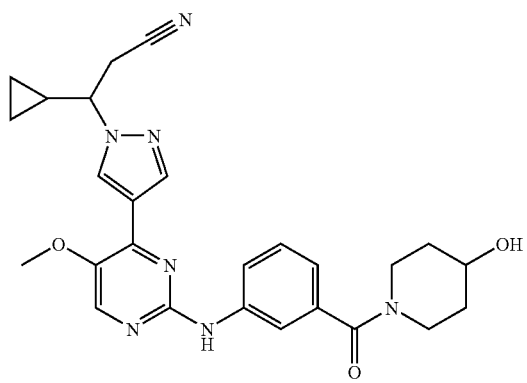

This compound was prepared as a racemic mixture according to the procedure described in example 323, using 4-hydroxypiperidine instead of tetrahydro-2H-pyran-4-amine. LCMS (M+H) 488.3.

Example 330

3-cyclopropyl-3-{4-[5-methoxy-2-({3-[(4-methoxypiperidin-1-yl)carbonyl]phenyl}amino)pyrimidin-4-yl]-1H-pyrazol-1-yl}propanenitrile

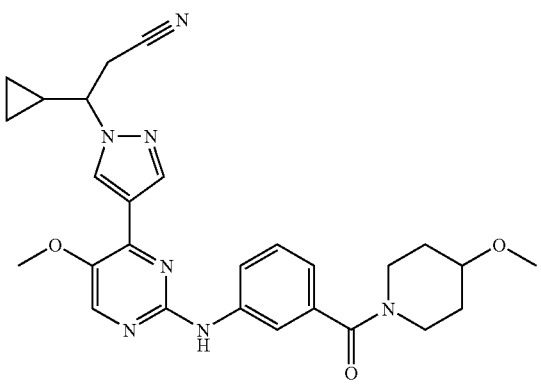

This compound was prepared as a racemic mixture according to the procedure described in example 323, using 4-methoxypiperidine hydrochloride instead of tetrahydro-2H-pyran-4-amine. LCMS (M+H) 502.3.

Example 331

1-[3-({4-[1-(2-cyano-1-cyclopropylethyl)-1H-pyrazol-4-yl]-5-methoxypyrimidin-2-yl}amino)benzoyl]piperidine-4-carbonitrile

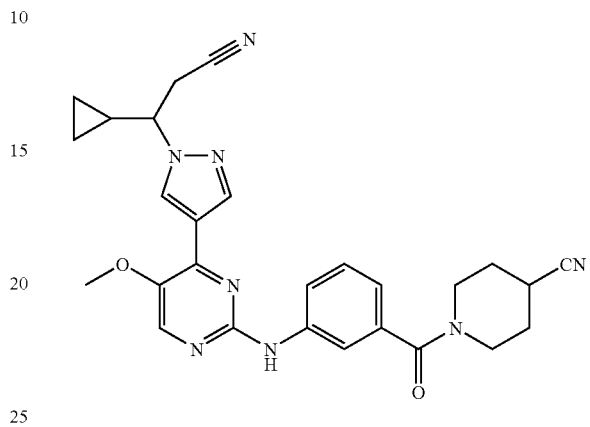

This compound was prepared as a racemic mixture according to the procedure described in example 323, using 4-cyanopiperidine hydrochloride instead of tetrahydro-2H-pyran-4-amine. LCMS (M+H) 497.2.

Example 332

3-cyclopropyl-3-(4-{2-[(3-{[(3-endo)-3-hydroxy-8-azabicyclo[3.2.1]oct-8-yl]carbonyl}phenyl)amino]-5-methoxypyrimidin-4-yl}-1H-pyrazol-1-yl)propanenitrile

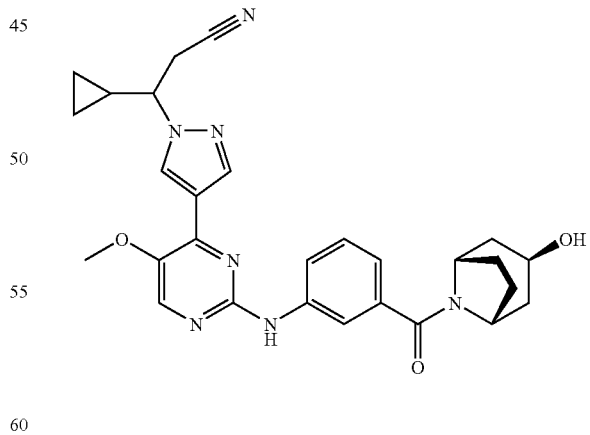

This compound was prepared as a racemic mixture according to the procedure described in example 323, using (3-endo)-8-azabicyclo[3.2.1]octan-3-ol hydrochloride instead of tetrahydro-2H-pyran-4-amine. LCMS (M+H) 514.1.

Example 333

3-({4-[1-(2-cyano-1-cyclopropylethyl)-1H-pyrazol-4-yl]-5-methoxypyrimidin-2-yl}amino)-N-[(5-methylisoxazol-3-yl)methyl]benzamide

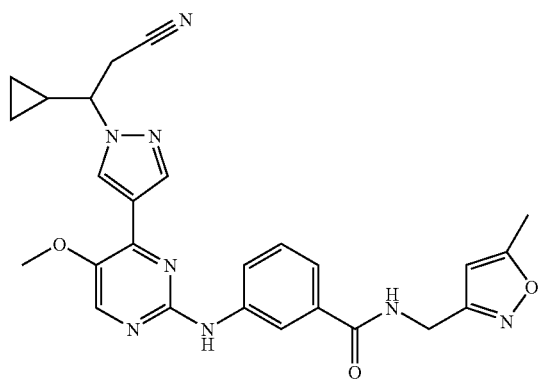

This compound was prepared as a racemic mixture according to the procedure described in example 323, using 5-methyl-3-isoxazolemethanamine instead of tetrahydro-2H-pyran-4-amine. LCMS (M+H) 499.1.

Example 334

3-[4-(2-{[3-(azetidin-1-ylcarbonyl)phenyl]amino}-5-methoxypyrimidin-4-yl)-1H-pyrazol-1-yl]-3-cyclopropylpropanenitrile

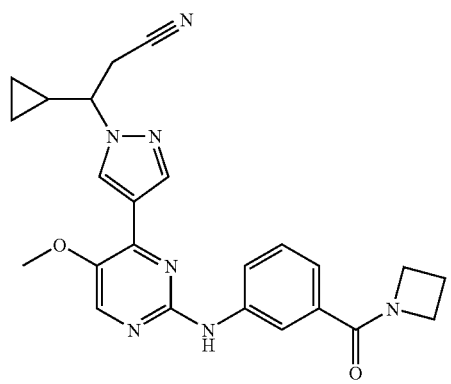

This compound was prepared as a racemic mixture according to the procedure described in example 323, using azetidine hydrochloride instead of tetrahydro-2H-pyran-4-amine. LCMS (M+H) 444.1.

Example 336

3-(cyanomethyl)-3-[4-(2-{[4-(2-oxopiperidin-1-yl)phenyl]amino}pyrimidin-4-yl)-1H-pyrazol-1-yl]cyclobutanecarbonitrile

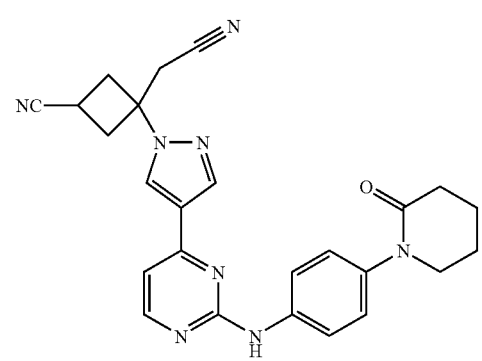

The cis- and trans-isomers of the titled compound were prepared according to the procedure described in example 248, using 1-(4-aminophenyl)-2-piperidinone instead of 4-morpholin-4-ylaniline in step 5. First peak retention time 1.315 min, LCMS (M+H) 453.3. Second peak retention time 1.340, LCMS (M+H) 453.3.

Example 337

3-(cyanomethyl)-3-[4-(2-{[4-(2-oxo-1,3-oxazinan-3-yl)phenyl]amino}pyrimidin-4-yl)-1H-pyrazol-1-yl]cyclobutanecarbonitrile

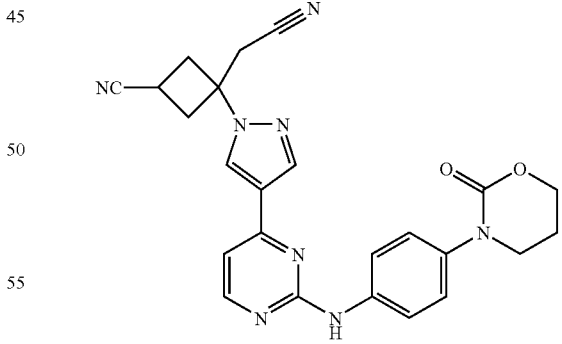

The cis- and trans-isomers of the titled compound were prepared according to the procedure described in example 248, using 3-(4-aminophenyl)-1,3-oxazinan-2-one instead of 4-morpholin-4-ylaniline in step 5. First peak retention time 1.196 min, LCMS (M+H) 455.2. Second peak retention time 1.231, LCMS (M+H) 455.2.

Example 338

3-(cyanomethyl)-3-[4-(2-{[4-(3-oxomorpholin-4-yl)
phenyl]amino}pyrimidin-4-yl)-1H-pyrazol-1-yl]
cyclobutancarbonitrile

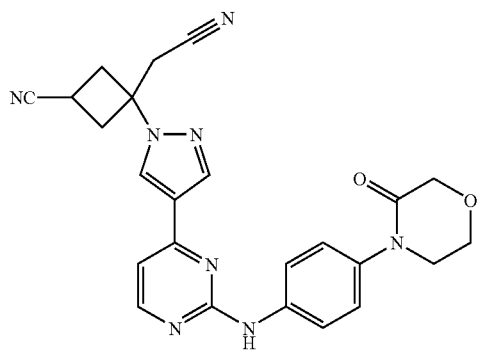

The cis- and trans-isomers of the titled compound were prepared according to the procedure described in example 248, using 4-(4-aminophenyl)-3-morpholinone instead of 4-morpholin-4-ylaniline in step 5. First peak retention time 1.205 min, LCMS (M+H) 455.3. Second peak retention time 1.238, LCMS (M+H) 455.3.

Example 339

3-(cyanomethyl)-3-[4-(2-{[4-(2-oxo-1,3-oxazolidin-3-yl)phenyl]amino}pyrimidin-4-yl)-1H-pyrazol-1-yl]
cyclobutanecarbonitrile

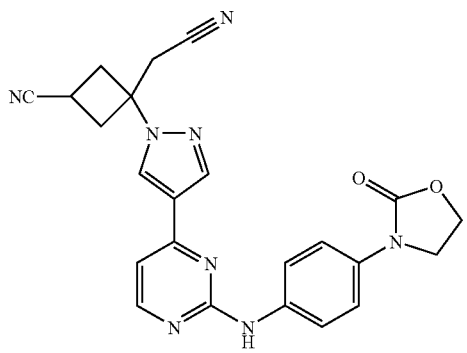

The cis- and trans-isomers of the titled compound were prepared according to the procedure described in example 248, using 3-(4-aminophenyl)-2-oxazolidinone instead of 4-morpholin-4-ylaniline in step 5. First peak retention time 1.271 min, LCMS (M+H) 441.1. Second peak retention time 1.294 min, LCMS (M+H) 441.1.

Example 340

3-(cyanomethyl)-3-[4-(2-{[4-(2-oxopyrrolidin-1-yl)
phenyl]amino}pyrimidin-4-yl)-1H-pyrazol-1-yl]
cyclobutanecarboitrile

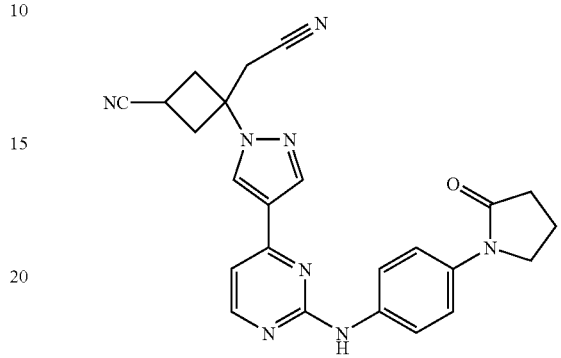

The cis- and trans-isomers of the titled compound were prepared according to the procedure described in example 248, using 1-(4-aminophenyl)-2-pyrrolidinone instead of 4-morpholin-4-ylaniline in step 5. First peak retention time 1.434 min, LCMS (M+H) 439.4. Second peak retention time 1.467, LCMS (M+H) 439.4.

Example 341

3-(cyanomethyl)-3-[4-(2-{[4-(1H-pyrazol-1-yl)phenyl]amino}pyrimidin-4-yl)-1H-pyrazol-1-yl]cyclobutanecarbonitrile

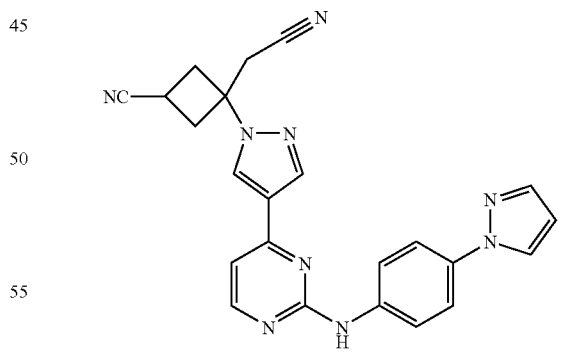

The cis- and trans-isomers of the titled compound were prepared according to the procedure described in example 248, using 4-(1H-pyrazol-1-yl)aniline instead of 4-morpholin-4-ylaniline in step 5. First peak retention time 1.683 min, LCMS (M+H) 422.4. Second peak retention time 1.718 min, LCMS (M+H) 422.4.

Example 342

3-(cyanomethyl)-3-[4-(2-{[4-(1,3-oxazol-5-yl)phenyl]amino}pyrimidin-4-yl)-1H-pyrazol-1-yl]cyclobutanecarbonitrile

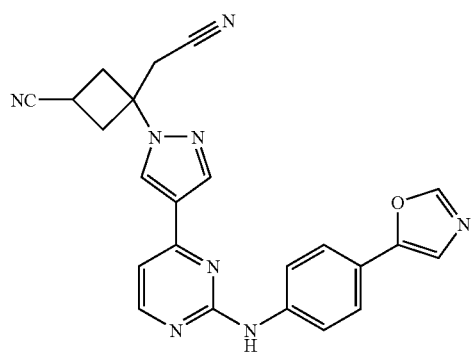

The cis- and trans-isomers of the titled compound were prepared according to the procedure described in example 248, using 4-(5-oxazolyl)-benzenamine instead of 4-morpholin-4-ylaniline in step 5. First peak retention time 1.592 min, LCMS (M+H) 423.4. Second peak retention time 1.720 min, LCMS (M+H) 423.3.

Example 343

3-(cyanomethyl)-3-[4-(2-{[3-(1,3-oxazol-5-yl)phenyl]amino}pyrimidin-4-yl)-1H-pyrazol-1-yl]cyclobutanecarbonitrile

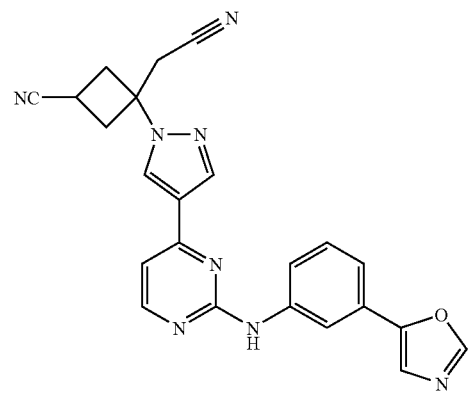

The cis- and trans-isomers of the titled compound were prepared according to the procedure described in example 248, using 3-(5-oxazolyl)-benzenamine instead of 4-morpholin-4-ylaniline in step 5. First peak retention time 1.670 min, LCMS (M+H) 423.4. Second peak retention time 1.703 min, LCMS (M+H) 423.3.

Example 344

3-(cyanomethyl)-3-[4-(2-{[4-(morpholin-4-ylsulfonyl)phenyl]amino}pyrimidin-4-yl)-1H-pyrazol-1-yl]cyclobutanecarbonitrile

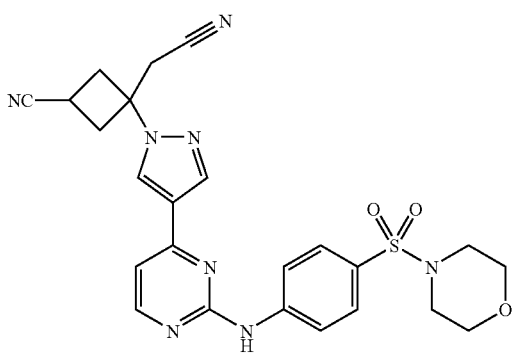

The cis- and trans-isomers of the titled compound were prepared according to the procedure described in example 248, using 4-(4-morpholinylsulfonyl)-benzenamine instead of 4-morpholin-4-ylaniline in step 5. First peak retention time 1.747 min, LCMS (M+H) 505.3. Second peak retention time 1.782 min, LCMS (M+H) 505.3.

Example 345

3-(4-{2-[(3-aminophenyl)amino]-5-methoxypyrimidin-4-yl}-1H-pyrazol-1-yl)-3-cyclopropylpropanenitrile

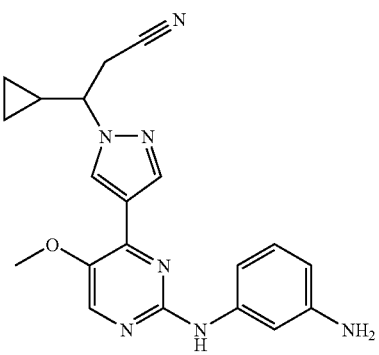

A mixture of 3-cyclopropyl-3-(4-{5-methoxy-2-[(3-nitrophenyl)amino]pyrimidin-4-yl}-1H-pyrazol-1-yl)propanenitrile (from example 321, 0.010 g, 0.000025 mol) in 2 mL of MeOH was hydrogenated in the presence of 10% Pd/C, under balloon pressure of hydrogen, for 2 h. After filtering off the catalyst, the filtrate was evaporated to dryness to provide the desired product as a racemic mixture (8 mg, 86.39%). LCMS (M+H) 376.1.

Example 346

3-cyclopropyl-3-[4-(2-{[3-(1,1-dioxidoisothiazolidin-2-yl)phenyl]amino}-5-methoxypyrimidin-4-yl)-1H-pyrazol-1-yl]proanenitrile

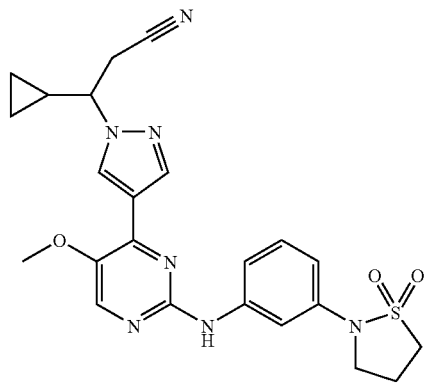

Step 1. 3-chloro-N-(3-(4-(1-(2-cyano-1-cyclopropylethyl)-1H-pyrazol-4-yl)-5-methoxypyrimidin-2-ylamino)phenyl)propane-1-sulfonamide To a mixture of 3-(4-{2-[(3-aminophenyl)amino]-5-methoxypyrimidin-4-yl}-1H-pyrazol-1-yl)-3-cyclopropylpropanenitrile (prepared according to Example 345, 8.0 mg, 0.000021 mol) in 1,4-dioxane (0.1 mL, 0.002 mol) was added triethylamine (0.02 mL, 0.0001 mol), followed by 3-chloropropane-1-sulfonyl chloride (0.0039 mL, 0.000032 mol). The reaction was stirred at room temperature for 1 h, quenched with 1 N HCl. The mixture was extracted with EtOAc and the organic layer was separated. The combined organic layers were washed with brine, dried over MgSO₄, and evaporated to dryness to provide the desired sulfonylated intermediate.

Step 2. 3-cyclopropyl-3-[4-(2-{[3-(1,1-dioxidoisothiazolidin-2-yl)phenyl]amino}-5-methoxypyrimidin-4-yl)-1H-pyrazol-1-yl]propanenitrile The crude product made above was dissolved in N,N-dimethylformamide (0.066 mL, 0.00086 mol) and triethylamine (0.03 mL, 0.0002 mol). The reaction mixture was heated at 80° C. overnight. After being cooled to room temperature, the mixture was evaporated to dryness. The residue was purified on RP-HPLC at pH 10 to provide the desired product as a racemic mixture (free base). LCMS (M+H) 480.3.

Example 347

4-[1-(2,4-difluorobenzoyl)piperidin-4-yl]-3-{4-[5-methoxy-2-(pyridin-3-ylamino)pyrimidin-4-yl]-1H-pyrazol-1-yl}butanenitrile

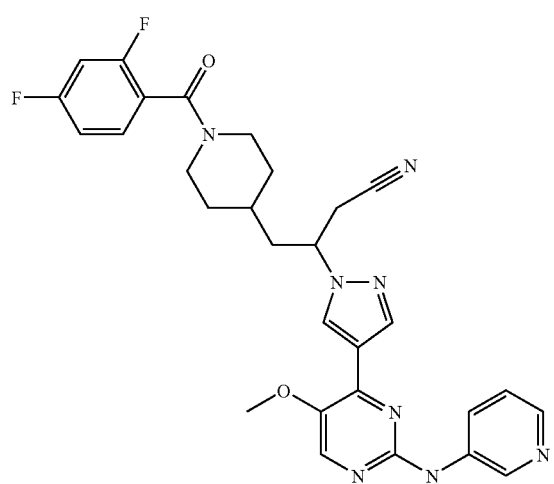

Step 1. tert-butyl 4-{2-[4-(2-chloro-5-methoxypyrimidin-4-yl)-1H-pyrazol-1-yl]-3-cyanopropyl}piperidine-1-carboxylate To a mixture of 2,4-dichloro-5-methoxypyrimidine (0.967 g, 0.00540 mol), and tert-butyl 4-{3-cyano-2-[4-(4,4,5,5-tetramethyl-1,3,2-dioxaborolan-2-yl)-1H-pyrazol-1-yl]propyl}piperidine-1-carboxylate (from example 1 step 3, 2.00 g, 0.00450 mol) in 1,4-dioxane (40 mL, 0.5 mol) was added a 1 M solution of sodium carbonate (0.954 g, 0.00900 mol) in water (8.99 mL, 0.499 mol) and tetrakis(triphenylphosphine)palladium(0) (0.4 g, 0.0003 mol). The reaction mixture was heated at 100° C. overnight. After cooling to room temperature, the mixture was diluted with EtOAc, washed with water, brine, dried over MgSO₄, and concentrated. The residue was purified on silica gel, eluting with 0 to 80% EtOAc in hexanes, to provide the desired product (1.59 g, 76.64%). LCMS (M+Na) 483.4.

Step 2. 3-(4-(2-chloro-5-methoxypyrimidin-4-yl)-1H-pyrazol-1-yl)-4-(piperidin-4-yl)butanenitrile A mixture of tert-butyl 4-{2-[4-(2-chloro-5-methoxypyrimidin-4-yl)-1H-pyrazol-1-yl]-3-cyanopropyl}piperidine-1-carboxylate (0.030 g, 0.000065 mol) and 0.5 mL of TFA was stirred at room temperature for 1 h. After being evaporated to dryness, the residue was used directly in next step.

Step 3. 3-(4-(2-chloro-5-methoxypyrimidin-4-yl)-1H-pyrazol-1-yl)-4-(1-(2,4-difluorobenzoyl)piperidin-4-yl)butanenitrile To a mixture of the TFA salt made above and methylene chloride (0.5 mL, 0.008 mol) was added 2,4-difluorobenzoyl chloride (9.99 µL, 0.0000814 mol), followed by triethylamine (0.027 mL, 0.00020 mol). The reaction mixture was stirred at room temperature for 1 h, quenched with aqueous sodium bicarbonate, and extracted with EtOAc. The combined organic layers were washed with water, brine, dried over MgSO$_4$, and evaporated to dryness. The residue was used in next step without further purification. LCMS (M+H) 501.3.

Step 4. 4-[1-(2,4-difluorobenzoyl)piperidin-4-yl]-3-{4-[5-ethoxy-2-(pyridin-3-ylamino)pyrimidin-4-yl]-1H-pyrazol-1-yl}butanenitrile The crude amide (from step 3), p-toluenesulfonic acid monohydrate (0.0105 g, 0.0000553 mol), and 2-pyridinamine (0.00919 g, 0.0000976 mol) were dissolved in 0.5 mL of dioxane and heated at 100° C. for 5 h. The reaction mixture was applied on RP-HPLC at pH 2 to obtain the racemic mixture of desired product as TFA salt. LCMS (M+H) 559.4.

Example 348

3-(cyanomethyl)-3-[4-(2-{[3-(2-oxopyrrolidin-1-yl)phenyl]amino}pyrimidin-4-yl)-1H-pyrazol-1-yl]cyclobutanecarbonitrile

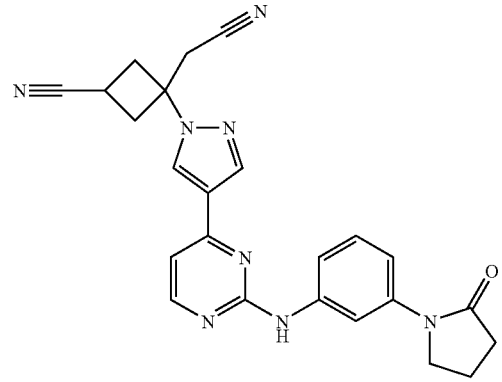

The cis- and trans-isomers of the titled compound were prepared according to the procedure described in Example 248, using 1-(3-aminophenyl)-2-pyrrolidinone (from Matrix Scientific) instead of 4-morpholin-4-ylaniline in step 5. First peak retention time 1.526 min, LCMS (M+H) 439.3. Second peak retention time 1.575 min, LCMS (M+H) 439.3.

Table of NMR Data for Selected Examples:

| Example | $^1$H NMR (400 MHz) δ (ppm) |
|---|---|
| 5 (CD$_3$OD) | 8.63 (1H, d, J = 9.6 Hz), 8.28 (1H, s), 8.20 (1H, d, J = 6.4 Hz), 7.59 (2H, d, J = 8.8 Hz), 7.40 (1H, m), 7.23 (3H, m), 7.06 (2H, m), 4.85 (1H, m), 4.58 (1H, m), 3.92 (4H, m), 3.48 (1H, m), 3.45 (4H, m), 3.08 (3H, m), 2.77 (1H, m), 2.17 (1H, m), 1.81 (2H, m), 1.34~1.20 (4H, m). |
| 24 (CD$_3$OD) | 8.58 (1H, s), 8.31 (1H, s), 8.20 (1H, d, J = 6.4 Hz), 7.60 (2H, m), 7.25 (3H, m), 4.54 (1H, m), 3.92 (4H, m), 3.79 (1H, m), 3.66 (1H, m), 3.37 (4H, m), 3.22 (2H, m), 2.80 (3H, s), 2.76 (1H, dt, J = 2.4 and 12.0 Hz), 2.63 (1H, dt, J = 2.4 and 12.0 Hz), 2.13 (1H, m), 1.98 (1H, d, J = 12.8), 1.42~1.33 (2H, m), 1.27 (1H, m). |
| 25 (CD$_3$OD) | 8.54 (1H, s), 8.26 (1H, s), 8.19 (1H, d, J = 6.0 Hz), 7.74 (2H, m), 7.65 (1H, m), 7.59 (4H, m), 7.22 (3H, m), 4.48 (1H, m), 3.92 (4H, m), 3.84 (1H, m), 3.73 (1H, m), 3.36 (4H, m), 3.15 (2H, m), 2.29 (1H, m), 2.16 (1H, m), 1.90 (2H, m), 1.35 (2H, m), 1.22 (1H, m). |
| 29 (CD$_3$OD) | 8.61 (1H, s), 8.28 (1H, d, J = 5.6 Hz), 8.21 (1H, s), 7.57 (2H, m), 7.02 (1H, d, J = 5.6 Hz), 6.98 (2H, m), 3.84 (2H, m), 3.67 (2H, m), 3.31 (2H, s), 3.10 (6H, m), 3.01 (2H, t, J = 11.2 Hz), 2.85 (2H, d, J = 14.8 Hz), 2.39 (1H, m), 2.19 (2H, m), 1.00 (2H, m), 0.93 (2H, m). |
| 35 (CD$_3$OD) | 8.59 (1H, s), 8.27 (1H, s), 8.18 (1H, d, J = 6.4 Hz), 7.58 (2H, d, J = 8.8 Hz), 7.23 (3H, m), 4.46 (1H, dt, J = 4.0 and 10.0 Hz), 3.91 (4H, m), 3.33 (4H, m), 3.22~3.08 (2H, m), 2.51 (1H, m), 1.94 (1H, m), 1.74~1.53 (4H, m), 1.38 (2H, m), 1.21 (1H, m). |
| 42 (CD$_3$OD) | 8.63 (1H, s), 8.28 (1H, s), 8.21 (1H, d, J = 6.4 Hz), 7.60 (2H, d, J = 8.8 Hz), 7.22 (3H, m), 4.84 (1H, m), 3.92 (4H, m), 3.70 (1H, m), 3.64 (1H, m), 3.35 (4H, m), 3.08 (2H, m), 2.95 (2H, q, J = 7.2 Hz), 2.69 (1H, dt, J = 2.4 and 12.0 Hz), 2.16 (1H, m), 1.93 (1H, m), 1.80 (1H, m), 1.58 (1H, m), 1.26 (3H, t, J = 7.2 Hz), 1.72~1.17 (4H, m). |
| 55 (CD$_3$OD) | 8.59 (1H, s), 8.25 (1H, s), 8.19 (1H, d, J = 6.0 Hz), 7.69 (1H, d, J = 2.4 Hz), 7.59 (2H, d, J = 8.8 Hz), 7.24 (2H, d, J = 8.8 Hz), 7.20 (1H, d, J = 6.0 Hz), 6.59 (1H, d, J = 2.4 Hz), 4.83 (1H, m), 3.92 (4H, m), 3.91 (3H, s), 3.73 (1H, m), 3.66 (1H, m), 3.53 (4H, m), 3.06 (2H, m), 2.33 (2H, t, J = 12.4 Hz), 2.11 (1H, m), 1.91 (1H, m), 1.76 (1H, m), 1.55 (1H, m), 1.30 (2H, m), 1.00 (1H, m). |
| 93 (CD$_3$OD) | 8.81 (1H, s), 8.31 (1H, s), 8.25 (1H, d, J = 6.0 Hz), 7.64 (2H, d, J = 8.8 Hz), 7.27 (2H, d, J = 8.8 Hz), 7.23 (1H, d, J = 6.0 Hz), 4.60 (2H, d, J = 9.2 Hz), 4.32 (2H, d, J = 9.2 Hz), 3.93 (4H, m), 3.58 (2H, s), 3.38 (4H, m), 2.65 (1H, m), 1.10 (4H, m). |
| 94 (CD$_3$OD) | 8.85 (1H, s), 8.53 (1H, d, J = 2.0 Hz), 8.33 (1H, s), 8.21 (1H, d, J = 6.4 Hz), 7.60 (2H, d, J = 8.8 Hz), 7.27 (3H, m), 6.85 (1H, d, J = 2.0 Hz), 4.38 (1H, d, J = 15.6 Hz), 4.00 (1H, d, J = 15.6 Hz), 3.92 (4H, m), 3.41 (1H, m), 3.36 (4H, m), 3.21 (1H, m), 3.16 (2H, s), 2.84 (2H, m), 2.23 (2H, m). |
| 101 (CD$_3$OD) | 8.60 (1H, s), 8.35 (1H, s), 8.06 (1H, s), 7.68 (2H, m), 7.31 (2H, m), 4.47 (1H, dt, J = 3.2 and 9.6 Hz), 4.02 (3H, s), 3.95 (4H, m), 3.41 (4H, m), 3.22~3.07 (2H, m), 2.51 (1H, m), 1.93 (1H, m), 1.73~1.54 (4H, m), 1.39 (2H, m), 1.22 (1H, m). |

| Example | $^1$H NMR (400 MHz) δ (ppm) |
| --- | --- |
| 122 (CD$_3$OD) | 8.46 (1H, s), 8.38 (1H, d, J = 5.2 Hz), 8.20 (1H, s), 7.87 (2H, d, J = 8.8 Hz), 7.54 (2H, d, J = 8.8 Hz), 7.10 (1H, d, J = 5.2 Hz), 4.43 (1H, dt, J = 4.4 and 10.4 Hz), 3.59 (4H, m), 3.14 (2H, m), 2.51 (1H, m), 1.99 (2H, m), 1.92 (2H, m), 1.55 (4H, m), 1.45~1.23 (4H, m). |
| 124 (CD$_3$OD) | 8.45 (1H, s), 8.38 (1H, d, J = 5.2 Hz), 8.20 (1 H, s), 7.87 (2H, dd, J = 2.0 and 7.2 Hz), 7.41 (2H, dd, J = 2.0 and 7.2 Hz), 7.09 (1H, d, J = 5.2 Hz), 4.43 (1H, dt, J = 10.0 and 1.1 Hz), 4.17 (1 H, m), 3.89 (1H, m), 3.80 (1 H, m), 3.32 (2 H, m), 3.13 (2H, m), 2.50 (1H, m), 1.93 (3H, m), 1.74~1.23 (9H, m). |
| 132 (CD$_3$OD) | 8.58 (1H, s), 8.41 (1H, s), 8.30 (2H, m), 8.21 (1H, s), 7.57 (1H, m), 7.52 (1H, s), 7.42 (1H, m), 7.39 (1H, m), 4.47 (1H, m), 4.03 (3H, s), 3.16 (2H, m), 2.51 (1H, m), 1.92~1.22 (8H, m). |
| 171 (CD$_3$OD) | 8.57 (1H, s), 8.26 (1H, s), 8.17 (1H, d, J = 6.0 Hz), 7.58 (2H, d, J = 9.2 Hz), 7.23 (3H, m), 4.65 (1H, m), 3.92 (4H, m), 3.34 (4H, m), 3.03 (2H, m), 2.97 (1H, m), 2.20 (1H, m), 1.94~1.81 (5H, m). |
| 177 (CD$_3$OD) | 8.63 (1H, s), 8.28 (1H, s), 8.17 (1H, d, J = 6.4 Hz), 7.57 (2H, d, J = 9.2 Hz), 7.24 (2H, d, J = 9.2 Hz), 7.23 (1H, d, J = 6.4 Hz), 3.96 (1H, m), 3.91 (4H, t, J = 5.2 Hz), 3.34 (4H, t, J = 5.2 Hz), 3.27 (2H, m), 1.50 (1H, m), 0.84 (1H, m), 0.66 (1H, m), 0.57 (1H, m), 0.48 (1H, m). |
| 212 1$^{st}$ isomer (CD$_3$OD) | 8.81 (1H, s), 8.31 (1H, s), 8.18 (1H, d, J = 6.4 Hz), 7.59 (2H, d, J = 9.2 Hz), 7.29 (1H, d, J = 6.4 Hz), 7.23 (2H, d, J = 9.2 Hz), 5.73 (1H, s), 4.67 (1H, m), 3.91 (4H, t, J = 4.8 Hz), 3.33 (4H, t, J = 4.8 Hz), 3.10 (2H, s), 2.79 (2H, m), 2.30 (3H, s), 2.18~2.06 (4H, m), 1.61 (2H, m). |
| 212 2$^{nd}$ isomer (CD$_3$OD) | 8.77 (1H, s), 8.29 (1H, s), 8.19 (1H, d, J = 6.2 Hz), 7.57 (2H, m), 7.27 (1H, d, J = 6.2 Hz), 7.21 (2H, m), 5.82 (1H, s), 4.73 (1H, m), 3.90 (4H, br s), 3.21 (4H, br s), 3.09 (2H, s), 2.59 (2H, m), 2.33 (3H, s), 2.08 (4H, m), 1.74 (2H, m). |
| 213 (CD$_3$OD) | 8.56 (1H, s), 8.33 (1H, d, J = 6.0 Hz), 8.26 (1H, s), 7.81 (2H, d, J = 8.8 Hz), 7.50 (2H, d, J = 8.8 Hz), 7.24 (1H, d, J = 6.0 Hz), 4.46 (1H, dt, J = 3.6 and 9.6 Hz), 3.71 (8H, m), 3.22~3.07 (2H, m), 3.51 (1H, m), 1.93 (1H, m), 1.74~1.54 (4H, m), 1.39 (2H, m), 1.23 (1H, m). |
| 221 (CD$_3$OD) | 8.57 (1H, s), 8.32 (1H, d, J = 6.0 Hz), 8.26 (1H, s), 7.80 (2H, d, J = 8.8 Hz), 7.48 (2H, d, J = 8.4 Hz), 7.25 (1H, d, J = 6.0 Hz), 4.46 (1H, dt, J = 4.4 and 10.0 Hz), 4.01 (1H, m), 3.61 (1H, m), 3.54 (1H, m), 3.44 (1H, m), 3.37 (3H, s), 3.22~3.07 (3H, m), 2.51 (1H, m), 1.93 (3H, m), 1.74~1.54 (6H, m), 1.38 (2H, m), 1.23 (1H, m). |
| 225 (CD$_3$OD) | 8.57 (1H, s), 8.33 (1H, d, J = 6.0 Hz), 8.27 (1H, s), 7.81 (2H, d, J = 8.8 Hz), 7.63 (2H, d, J = 8.8 Hz), 7.26 (1H, d, J = 6.0 Hz), 4.66 (1H, dt, J = 4.0 and 10.0 Hz), 3.91 (1H, m), 3.82 (2H, m), 3.71 (1H, m), 3.22~3.08 (3H, m), 2.51 (1H, m), 2.32 (2H, m), 1.93 (1H, m), 1.73~1.54 (4H, m), 1.39 (2H, m), 1.22 (1H, m). |
| 226 (CD$_3$OD) | 8.56 (1H, s), 8.33 (1H, d, J = 5.6 Hz), 8.26 (1H, s), 7.81 (2H, dd, J = 1.6 and 8.8 Hz), 7.59 (2H, dd, J = 1.6 and 8.8 Hz), 7.23 (1H, d, J = 5.6 Hz), 4.46 (1H, dt, J = 4.4 and 10.0 Hz), 3.68 (3H, m), 3.68 (1H, m), 3.57 (1H, m), 3.14 (2H, m), 2.51 (1H, m), 2.12 (2H, m), 1.94 (2H, m), 1.74~1.54 (6H, m), 1.39 (2H, m), 1.23 (1H, m). |
| 227 (CD$_3$OD) | 8.53 (1H, s), 8.36 (1H, d, J = 6.0 Hz), 8.25 (1H, s), 7.86 (4H, m), 7.23 (1H, d, J = 6.0 Hz), 4.46 (1H, dt, J = 10.0 and 4.0 Hz), 4.15 (1H, m), 3.59 (1H, br d, J = 12.8 Hz), 3.40 (1H, m), 3.14 (4H, m), 2.89 (3 H, m), 2.51 (1H, m), 2.25 (2H, br d, J = 12.8 Hz), 1.92 (3H, m), 1.74~1.54 (4 H, m), 1.40 (2H, m), 1.23 (1H, m). |
| 248 1$^{st}$ isomer (CD$_3$OD) | 8.74 (1H, s), 8.31 (1H, s), 8.20 (1H, d, J = 6.4 Hz), 7.61 (2H, d, J = 8.8 Hz), 7.25 (3H, m), 3.92 (4H, m), 3.40 (2H, s), 3.36 (4H, m), 3.17 (3H, m), 3.00 (2H, m). |
| 248 2$^{nd}$ isomer (CD$_3$OD) | 8.77 (1H, s), 8.30 (1H, s), 8.22 (1H, d, J = 6.4 Hz), 7.61 (1H, d, J = 6.4 Hz), 7.25 (3H, m), 3.92 (4H, m), 3.47 (1H, m), 3.40 (2H, s), 3.36 (4H, m), 3.18 (2H, m), 2.96 (2H, m). |
| 251 (CD$_3$OD) | 8.48 (1H, s), 8.38 (1H, d, J = 5.2 Hz), 8.20 (1H, s), 7.87 (2H, m), 7.40 (2H, m), 7.10 (1H, d, J = 5.2 Hz), 4.18 (1H, m), 3.90 (2H, m), 3.80 (1H, m), 3.26 (4H, m), 1.91 (2H, m), 1.51 (3H, m), 0.83 (1H, m), 0.66 (1H, m), 0.57 (1H, m), 0.50 (1H, m). |
| 253 (CD$_3$OD) | 8.60 (1H, s), 8.32 (1H, d, J = 6.0 Hz), 8.26 (1H, s), 7.78 (2H, d, J = 8.8 Hz), 7.60 (2H, d, J = 8.8 Hz), 7.26 (1H, d, J = 6.0 Hz), 3.95 (1H, m), 3.58 (4H, td, J = 6.8 and 18.8 Hz), 3.27 (2H, m), 1.96 (4H, m), 1.50 (1H, m), 0.84 (1H, m), 0.66 (1H, m), 0.58 (1H, m), 0.49 (1H, m). |
| 254 (CD$_3$OD) | 8.60 (1H, s), 8.34 (1H, d, J = 5.6 Hz), 8.27 (1H, s), 7.99 (2H, d, J = 8.4 Hz), 7.79 (2H, d, J = 8.4 Hz), 7.28 (1H, d, J = 5.6 Hz), 4.85 (1H, m), 4.12 (1H, m), 3.98 (3H, m), 3.53 (2H, m), 3.26 (1H, m), 1.91 (2H, m), 1.69 (2H, m), 1.51 (1H, m), 0.85 (1H, m), 0.66 (1H, m), 0.58 (1H, m), 0.49 (1H, m). |
| 255 (CD$_3$OD) | 8.67 (1H, s), 8.40 (1H, d, J = 5.2 Hz), 8.27 (1H, s), 7.88 (2H, m), 7.44 (2H, m), 7.13 (1H, d, J = 5.2 Hz), 4.60 (2H, d, J = 9.2 Hz ), 4.26 (2H, d, J = 9.2 Hz), 3.70 (8H, m), 3.57 (2H, s), 3.03 (2H, q, J = 7.2 Hz), 1.36 (3H, t, J = 7.4 Hz). |
| 258 (CD$_3$OD) | 8.67 (1H, s), 8.41 (1H, d, J = 5.2 Hz), 8.27 (1H, s), 7.86 (2H, d, J = 8.8 Hz), 7.54 (2H, d, J = 8.8 Hz), 7.13 (1H ,d , J = 5.2 Hz), 4.60 (2H, d, J = 9.6 Hz), 4.26 (2H, d, J = 9.6 Hz), 3.58 (4H, m), 3.57 (2H, s), 3.16 (2H, q, J = 7.6 Hz), 1.98 (2H, m), 1.92 (2H, m), 1.36 (3H, t, J = 7.6 Hz). |
| 259 (CD$_3$OD) | 8.67 (1H, s), 8.42 (1H, d, J = 5.6 Hz), 8.27 (1H, s), 7.85 (4H, m), 7.15 (1H, d, J = 5.6 Hz), 4.59 (2H, d, J = 9.6 Hz), 4.27 (2H, d, J = 9.6 Hz), 4.00 (1H, m), 3.57 (2H, s), 3.34~3.13 (6H, m), 1.90 (1H, m), 1.65 (1H, m), 1.36 (3H, t, J = 7.2 Hz), 1.29 (2H, m). |
| 260 (CD$_3$OD) | 8.49 (1H, s), 8.38 (1H, d, J = 4.8 Hz), 8.20 (1H, s), 7.88 (2H, m), 7.43 (2H, m), 7.10 (1H, d, J = 5.2 Hz), 3.94 (1H, m), 3.70 (8H, m), 3.26 (2H, m), 1.50 (1H, m), 0.84 (1H, m), 0.66 (1H, m), 0.57 (1H, m), 0.49 (1H, m). |
| 263 (CD$_3$OD) | 8.48 (1H, s), 8.38 (1H, d, J = 5.2 Hz), 8.20 (1H, s), 7.87 (2H, d, J = 8.4 Hz), 7.40 (2H, d, J = 8.4 Hz), 7.10 (1H, d, J = 5.2 Hz), 4.0 (1H, br s), 3.94 (1H, m), 3.75 (1H, br s), 3.53 (1H, m), 3.42 (1H, br s), 3.37 (3H, s), 3.26 (2H, m), 1.92 (2H, br s), 1.59 (2H, br s), 1.49 (1H, m), 1.29 (2H, d, J = 6.8 Hz), 0.83 (1H, m), 0.65 (1H, m), 0.56 (1H, m), 0.49 (1H, m). |

-continued

| Example | $^1$H NMR (400 MHz) δ (ppm) |
|---|---|
| 265 (CD$_3$OD) | 8.63 (1H, s), 8.30 (1H, d, J = 6.0 Hz), 8.29 (1H, s), 7.60 (2H, m), 7.63 (2H, m), 7.32 (1H, d, J = 6.0 Hz), 3.97 (1H, m), 3.68 (4H, m), 3.55 (1H, m), 3.29 (3H, s), 3.27 (2H, m), 2.18~1.98 (2H, m), 1.50 (1H, m), 0.85 (1H, m), 0.65 (1H, m), 0.58 (1H, m), 0.49 (1H, m). |
| 266 (DMSO-d$_6$) | 9.80 (1H, s), 8.56 (1H, s), 8.45 (1H, d, J = 5.2 Hz), 8.23 (1H, s), 7.88 (2H, d, J = 8.8 Hz), 7.50 (2H, m), 7.16 (2H, d, J = 8.8 Hz), 4.96 (1H, dd, J = 30.4 and 3.2 Hz), 4.26 (1H, br d, J = 30.6 Hz), 4.03 (1H, m), 3.63 (1H, m), 3.55 (1H, m), 3.48 (1H, m), 3.28 (2H, t, J = 8.0 Hz), 1.90 (1H, m), 1.79 (1H, m), 1.39 (1H, m), 0.70 (1H, m), 0.52 (2H, m), 0.43 (1H, m) |
| 276 (CD$_3$OD) | 8.71 (1H, s), 8.40 (2H, d, J = 5.6 Hz), 8.29 (1H, s), 7.87 (2H, d, J = 8.4 Hz), 7.59 (2H, d, J = 8.4 Hz), 7.19 (2H, d, J = 5.6 Hz), 4.60 (2H, d, J = 9.2 Hz), 4.26 (2H, d, J = 9.2 Hz), 3.94~3.70 (5H, m), 3.58 (2H, s), 3.16 (2H, q, J = 7.2 Hz), 1.36 (3H, t, J = 7.2 Hz). |
| 277 (CD$_3$OD) | 8.74 (1H, s), 8.37 (1H, d, J = 5.6 Hz), 8.30 (1H, s), 7.82 (2H, m), 7.58 (2H, m), 7.22 (1H, d, J = 5.6 Hz), 4.59 (2H, d, J = 9.6 Hz), 4.26 (2H, d, J = 9.6 Hz), 3.69 (4H, m), 3.59 (1H, m), 3.58 (3H, s), 3.38 (2H, s), 3.16 (2H, q, J = 7.5 Hz), 2.10 (1H, m), 1.36 (3H, t, J = 7.6 Hz). |
| 290 1$^{st}$ isomer (CD$_3$OD) | 8.59 (1H, s), 8.40 (1H, d, J = 5.2 Hz), 8.25 (1H, s), 7.87 (2H, m), 7.55 (2H, m), 7.13 (1H, d, J = 5.2 Hz), 3.78~3.52 (3H, m), 3.48 (2H, m), 3.38 (2H, s), 3.35 (1H, m), 3.18 (2H, m), 2.97 (2H, m), 2.02 (1H, m), 1.30 (1H, m). |
| 290 2$^{nd}$ isomer (CD$_3$OD) | 8.63 (1H, s), 8.40 (1H, d, J = 5.2 Hz), 8.25 (1H, s), 7.86 (2H, m), 7.55 (2H, dd, J = 6.8 and 8.4 Hz), 7.12 (1H, d, J = 5.2 Hz), 3.80~3.43 (6H, m), 3.94 (2H, m), 3.38 (2H, s), 3.34 (1H, m), 2.01 (2H, m), 1.26 (1H, m). |
| 293 1$^{st}$ isomer (CD$_3$OD) | 8.59 (1H, s), 8.39 (1H, d, J = 5.6 Hz), 8.25 (1H, s), 7.89 (2H, d, J = 8.8 Hz), 7.45 (2H, d, J = 8.8 Hz), 7.14 (1H, d, J = 5.6 Hz), 3.77 (4H, m), 3.48 (1H, t, J = 8.8 Hz), 3.39 (2H, s), 3.19 (2H, m), 2.97 (2H, m), 2.83 (4H, m), 2.58 (3H, s). |
| 293 2$^{nd}$ isomer (CD$_3$OD) | 8.63 (1H, s), 8.40 (2H, d, J = 5.2 Hz), 8.25 (1H, s), 7.88 (2H, d, J = 8.4 Hz), 7.44 (2H, d, J = 8.4 Hz), 7.13 (1H, d, J = 5.2 Hz), 3.73 (4H, m), 3.47 (1H, m), 3.38 (2H, s), 3.34 (2H, m), 2.95 (2H, m), 2.70 (4H, m), 2.49 (3H, s). |
| 295 1$^{st}$ isomer (CD$_3$OD) | 8.58 (1H, s), 8.39 (1H, d, J = 5.2 Hz), 8.25 (1H, s), 7.87 (2H, d, J = 8.8 Hz), 7.41 (2H, d, J = 8.8 Hz), 7.13 (1H, d, J = 5.2 Hz), 3.54~3.35 (6H, m), 3.38 (3H, s), 3.37 (2H, s), 3.18 (2H, m), 2.97 (2H, m), 1.93 (1H, m), 1.61 (1H, m), 1.25 (2H, m). |
| 295 2$^{nd}$ isomer (CD$_3$OD) | 8.63 (1H, s), 8.39 (1H, d, J = 5.2 Hz), 8.25 (1H, s), 7.87 (2H, m), 7.40 (2H, m), 7.12 (1H, d, J = 5.2 Hz), 3.51 (1H, m), 3.45 (2H, m), 3.40 (1H, m), 3.38 (3H, s), 3.33 (2H, s), 3.32 (2H, m), 3.25 (2H, m), 2.95 (1H, m), 1.92 (1H, m), 1.60 (1H, m), 1.26 (2H, m). |
| 296 1$^{st}$ isomer (CD$_3$OD) | 8.59 (1H, s), 8.40 (1H, d, J = 5.2 Hz), 8.25 (1H, s), 7.87 (2H, d, J = 8.4 Hz), 7.54 (2H, d, J = 8.4 Hz), 7.13 (1H, d, J = 5.2 Hz), 3.75~3.56 (3H, m), 3.47 (1H, m), 3.38 (3H, s), 3.22 (2H, s), 3.18 (2H, m), 2.98 (2H, m), 2.10 (1H, m), 1.22 (2H, m). |
| 296 2$^{nd}$ isomer (CD$_3$OD) | 8.63 (1H, s), 8.40 (1H, d, J = 5.2 Hz), 8.25 (1H, s), 7.87 (2H, d, J = 8.4 Hz), 7.54 (2H, d, J = 8.4 Hz), 7.13 (1H, d, J = 5.2 Hz), 3.72~3.45 (6H, m), 3.38 (3H, s), 3.34 (1H, m), 3.27 (2H, m), 2.95 (2H, m), 2.10 (2H, m), 1.25 (1H, m). |
| 297 1$^{st}$ isomer (CD$_3$OD) | 8.59 (1H, s), 8.40 (1H, d, J = 5.2 Hz), 8.25 (1H, s), 7.89 (2H, d, J = 8.0 Hz), 7.57 (2H, d, J = 8.8 Hz), 7.14 (1H, d, J = 5.2 Hz), 3.93~3.73 (4H, m), 3.50~3.43 (2H, m), 3.38 (2H, s), 3.19 (2H, m), 2.97 (2H, m), 1.25 (2H, m). |
| 297 2$^{nd}$ isomer (CD$_3$OD) | 8.63 (1H, s), 8.40 (1H, d, J = 5.2 Hz), 8.25 (1H, s), 7.88 (2H, d, J = 8.4 Hz), 7.56 (2H, d, J = 8.4 Hz), 7.13 (1H, d, J = 5.2 Hz), 3.81 (3H, m), 3.47 (2H, m), 3.38 (2H, s), 3.36 (1H, m), 3.26 (2H, m), 2.95 (2H, m), 1.27 (2H, m). |
| 308 (DMSO-d$_6$) | 9.24 (1H, s), 8.44 (1H, s), 8.29 (1H, d, J = 5.2 Hz), 8.14 (1H, s), 7.61 (2H, d, J = 8.8 Hz), 6.96 (1H, d, J = 5.2 Hz), 6.85 (2H, d, J = 8.8 Hz), 4.47 (1H, m), 3.81 (1H, dd, J = 11.6 and 3.2 Hz), 3.70 (1H, dd, J = 11.6 and 3.2 Hz), 3.67 (4H, m), 3.28 (1H, m), 3.23~3.06 (4H, m), 2.97 (4H, m), 2.01 (1H, m), 1.62 (1H, m), 1.17 (2H, m), 0.82 (1H, br d, J = 12.4 Hz). |
| 309 (DMSO-d$_6$) | 9.78 (1H, s), 8.50 (1H, s), 8.41 (2H, d, J = 5.2 Hz), 8.20 (1H, s), 8.06 (1H, d, J = 7.6 Hz), 7.85 (2H, d, J = 8.8 Hz), 7.76 (2H, d, J = 8.8 Hz), 7.12 (1H, d, 7.6 Hz), 4.50 (1H, m), 3.93 (1H, m), 3.82 (3H, m), 3.71 (1H, dd, J = 11.6 and 5.8 Hz), 3.31 (2H, m), 3.24~3.07 (5H, m), 2.03 (1H, m), 1.67 (3H, m), 1.51 (2H, qd, J = 13.2 and 4.8 Hz), 1.18 (2H, m), 0.83 (1H, br d, J = 12.4 Hz). |
| 310 (DMSO-d$_6$) | 9.75 (1H, s), 8.50 (1H, s), 8.40 (1H, d, J = 4.8 Hz), 8.20 (1H, s), 7.83 (2H, d, J = 8.8 Hz), 7.46 (2H, d, J = 8.8 Hz), 7.10 (1H, d, J = 4.8 Hz), 4.49 (1H, m), 3.82 (1H, dd, J = 16.2 and 2.8 Hz), 3.71 (1H, dd, J = 11.6 and 2.8 Hz), 3.40 (4H, m), 3.24~3.07 (4H, m), 2.03 (1H, m), 1.77(4H, m), 1.63 (1H, br d, J = 12.0 Hz), 1.18 (2H, m), 0.88~0.82 (2H, m). |
| 312 (DMSO-d$_6$) | 9.74 (1H, s), 8.50 (1H, s), 8.40 (1H, d, J = 5.2 Hz), 8.20 (1H, s), 7.83 (2H, d, J = 8.4 Hz), 7.29 (2H, d, J = 8.4 Hz), 7.10 (1H, d, J = 5.2 Hz), 4.74 (1H, d, J = 3.6 Hz), 4.49 (1H, m), 3.82 (1H, dd, J = 11.2 and 2.4 Hz), 3.71 (1H, dd, J = 11.2 and 2.4 Hz), 3.67 (2H, m), 3.23~3.07 (7H, m), 2.03 (1H, m), 1.64 (3H, m), 1.27 (2H, m), 1.18 (2H, m), 0.83 (1H, br d, J = 12.0 Hz). |
| 336 1$^{st}$ isomer (DMSO-d$_6$) | 9.62 (1H, s), 8.72 (1H, s), 8.44 (1H, d, J = 5.2 Hz), 8.24 (1H, s), 7.79 (2H, d, J = 8.4 Hz), 7.15 (3H, m), 3.55 (3H, m), 3.33 (2H, s), 3.08 (2H, m), 2.82 (2H, m), 2.36 (2H, t, J = 6.8 Hz), 1.82 (4H, m). |
| 336 2$^{nd}$ isomer (DMSO-d$_6$) | 9.56 (1H, s), 8.71 (1H, s), 8.39 (1H, d, J = 5.2 Hz), 8.20 (1H, s), 7.74 (2H, d, J = 9.2 Hz), 7.10 (3H, m), 3.49 (3H, m), 3.40 (2H, s), 3.10 (2H, m), 2.84 (2H, m), 2.30 (2H, t, J = 6.4 Hz), 1.78 (4H, m). |
| 347 (DMSO-d$_6$) | 9.31 (1H, t, J = 2.0 Hz), 9.24 (1H, dd, J = 6.0 and 1.2 Hz), 8.92 (1H, d, J = 14.4 Hz), 8.81 (1H, s), 8.55 (1H, d, J = 2.8 Hz), 7.89 (1H, m), 7.82 (1H, m), 7.41 (1H, m), 7.34 (1H, m), 7.15 (1H, m), 6.88 (1H, br s), 4.92 (1H, m), 4.42 (1H, m), 4.34 (1H, m), 4.18 (3H, s), 3.28 (1H, m), 3.16 (2H, m), 2.89 (1H, m), 2.65 (1H, m), 2.02 (1H, m), 1.92 (1H, m), 1.74 (2H, m), 1.23 (1H, m), 1.06 (2H, m). |

-continued

| Example | $^1$H NMR (400 MHz) δ (ppm) |
|---|---|
| 348 1$^{st}$ isomer (DMSO-d$_6$) | 9.61 (1H, s), 8.94 (1H, s), 8.80 (1H, m), 8.44 (1H, d, J = 5.2 Hz), 8.34 (1H, s), 7.24 (2H, m), 7.18 (1H, d, J = 5.2 Hz), 7.01 (1H, d, J = 7.2 Hz), 3.85 (2H, t, J = 7.2 Hz), 3.57 (1H, dd, J = 8.8 and 8.8 Hz), 3.33 (2H, s), 3.14 (2H, m), 2.83 (2H, m), 2.54 (2H, t, J = 7.6 Hz), 2.07 (2H, m). |
| 348 2$^{nd}$ isomer (DMSO-d$_6$) | 9.56 (1H, s), 8.93 (1H, s), 8.77 (1H, m), 8.38 (1H, d, J = 5.2 Hz), 8.30 (1H, s), 7.19 (2H, m), 7.12 (1H, d, J = 5.2 Hz), 6.95 (1H, d, J = 7.6 Hz), 3.80 (2H, t, J = 7.2 Hz), 3.49 (1H, m), 3.27 (2H, s), 3.16 (2H, m), 2.85 (2H, m), 2.48 (2H, t, J = 7.6 Hz), 2.02 (2H, m). |

Example A

In Vitro JAK Kinase Assay

Compounds herein were tested for inhibitory activity of JAK targets according to the following in vitro assay described in Park et al, *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). IC$_{50}$s of compounds were measured for each kinase in the reactions that contain the enzyme, ATP and 500 nM peptide in 50 mM Tris (pH 7.8) buffer with 100 mM NaCl, 5 mM DTT, and 0.1 mg/mL (0.01%) BSA. The ATP concentration in the reactions was 90 μM for JAK1, 30 μM for Jak2 and 3 μM for JAK3. Reactions were carried out at room temperature for 1 hr and then stopped with 20 μL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). Certain of the above compounds were tested according to this assay. Compounds having an IC$_{50}$ of 100 μM or less for any of the above-mentioned JAK targets were considered active.

Table of IC$_{50}$ data for JAK kinase assay

| Example | JAK-2 IC$_{50}$ (nM) |
|---|---|
| 1 | <100 |
| 2 | <100 |
| 3 | <100 |
| 4 | <100 |
| 5 | <100 |
| 6 | <100 |
| 7 | <100 |
| 8 | <100 |
| 11 | <100 |
| 12 | <100 |
| 13 | <100 |
| 14 | <100 |
| 15 | <100 |
| 16 | <100 |
| 17 | <100 |
| 18 | <100 |
| 19 | <100 |
| 20 | <100 |
| 21 | <100 |
| 22 | <100 |
| 23 | <100 |
| 24 | <100 |
| 25 | <100 |
| 26 | <100 |
| 27 | <100 |
| 28 | <100 |
| 29 | <100 |
| 30 | <100 |
| 31 | <100 |
| 32 | <100 |
| 33 | <100 |
| 34 | <100 |
| 35 | <100 |
| 36 | <100 |
| 37 | <100 |
| 38 | <100 |
| 39 | <100 |
| 40 | <100 |
| 41 | <100 |
| 42 | <100 |
| 43 | <100 |
| 44 | <100 |
| 45 | <100 |
| 46 | <100 |
| 47 | <100 |
| 48 | <100 |
| 49 | <100 |
| 50 | <100 |
| 51 | <100 |
| 52 | <100 |
| 53 | <100 |
| 54 | <100 |
| 55 | <100 |
| 56 | <100 |
| 57 | <100 |
| 58 | <100 |
| 59 | <100 |
| 60 | <100 |
| 61 | <100 |
| 62 | <100 |
| 63 | <100 |
| 64 | <100 |
| 65 | <100 |
| 66 | <100 |
| 67 | <100 |
| 68 | <100 |
| 69 | <100 |
| 70 | <100 |
| 71 | <100 |
| 72 | <100 |
| 73 | <100 |
| 74 | <100 |
| 75 | <100 |
| 76 | <100 |
| 77 | <100 |
| 78 | <100 |
| 79 | <100 |
| 80 | <100 |
| 81 | <100 |
| 82 | <100 |
| 83 | <100 |
| 84 | <100 |
| 85 | <100 |
| 86 | <100 |

Table of IC$_{50}$ data for JAK kinase assay

| Example | JAK-2 IC$_{50}$ (nM) |
|---|---|
| 87 | <100 |
| 88 | <100 |
| 89 | <100 |
| 90 | <100 |
| 91 | <100 |
| 92 | >100 |
| 93 | <100 |
| 94 | <100 |
| 95 | <100 |
| 96 | <100 |
| 97 | <100 |
| 98 | <100 |
| 99 | <100 |
| 100 | — |
| 101 | <100 |
| 102 | <100 |
| 103 | <100 |
| 104 | <100 |
| 105 | <100 |
| 106 | <100 |
| 107 | <100 |
| 108 | <100 |
| 109 | <100 |
| 110 | <100 |
| 111 | <100 |
| 112 | <100 |
| 113 | <100 |
| 114 | <100 |
| 115 | <100 |
| 116 | <100 |
| 117 | <100 |
| 118 | <100 |
| 119 | — |
| 120 | <100 |
| 121 | <100 |
| 122 | <100 |
| 123 | <100 |
| 124 | <100 |
| 125 | <100 |
| 126 | <100 |
| 127 | <100 |
| 128 | <100 |
| 129 | <100 |
| 130 | <100 |
| 131 | <100 |
| 132 | <100 |
| 133 | <100 |
| 134 | <100 |
| 135 | <100 |
| 136 | <100 |
| 137 | <100 |
| 138 | <100 |
| 139 | <100 |
| 140 | <100 |
| 141 | <100 |
| 142 | <100 |
| 143 | <100 |
| 144 | <100 |
| 145 | <100 |
| 146 | <100 |
| 147 | <100 |
| 148 | <100 |
| 149 | <100 |
| 150 | <100 |
| 151 | <100 |
| 152 | <100 |
| 153 | <100 |
| 154 | <100 |
| 155 | <100 |
| 156 | <100 |
| 157 | <100 |
| 158 | <100 |
| 159 | <100 |
| 160 | <100 |
| 161 | <100 |
| 162 | <100 |
| 163 | <100 |
| 164 | <100 |
| 165 | <100 |
| 166 | <100 |
| 167 | <100 |
| 168 | <100 |
| 169 | — |
| 170 | — |
| 171 | <100 |
| 172 | — |
| 173 | <100 |
| 174 | <100 |
| 175 | <100 |
| 176 | <100 |
| 177 | <100 |
| 178 | <100 |
| 179 | <100 |
| 180 | <100 |
| 181 | <100 |
| 182 | <100 |
| 183 | <100 |
| 184 | <100 |
| 185 | <100 |
| 186 | <100 |
| 187 | <100 |
| 188 | <100 |
| 189 | <100 |
| 190 | <100 |
| 191 | — |
| 192 | <100 |
| 193 | <100 |
| 194 | <100 |
| 195 | <100 |
| 196 | <100 |
| 197 | <100 |
| 199 | <100 |
| 200 | <100 |
| 201 | <100 |
| 202 | <100 |
| 203 | <100 |
| 204 | <100 |
| 205 | <100 |
| 206 | <100 |
| 207 | <100 |
| 208 | <100 |
| 209 | <100 |
| 210 | <100 |
| 211 | <100 |
| 212 | <100 |
| 213 | <100 |
| 214 | <100 |
| 215 | <100 |
| 216 | <100 |
| 217 | <100 |
| 218 | <100 |
| 219 | <100 |
| 220 | <100 |
| 221 | <100 |
| 222 | <100 |
| 223 | <100 |
| 224 | <100 |
| 225 | <100 |
| 226 | <100 |
| 227 | <100 |
| 228 | <100 |
| 229 | <100 |
| 230 | <100 |
| 231 | <100 |
| 232 | <100 |
| 233 | <100 |
| 234 | <100 |
| 235 | <100 |
| 236 | <100 |
| 237 | <100 |

Table of IC$_{50}$ data for JAK kinase assay

| Example | JAK-2 IC$_{50}$ (nM) |
|---|---|
| 238 | <100 |
| 239 | <100 |
| 240 | <100 |
| 241 | <100 |
| 242 | <100 |
| 243 | <100 |
| 244 | <100 |
| 245 | <100 |
| 246 | <100 |
| 247 | <100 |
| 248 | <100 |
| 249 | — |
| 250 | — |
| 251 | <100 |
| 252 | <100 |
| 253 | <100 |
| 254 | <100 |
| 255 | <100 |
| 256 | <100 |
| 257 | <100 |
| 258 | <100 |
| 259 | <100 |
| 260 | <100 |
| 261 | <100 |
| 262 | <100 |
| 263 | <100 |
| 264 | <100 |
| 265 | <100 |
| 266 | <100 |
| 267 | <100 |
| 268 | <100 |
| 269 | <100 |
| 270 | <100 |
| 271 | <100 |
| 272 | <100 |
| 273 | <100 |
| 274 | <100 |
| 275 | <100 |
| 276 | <100 |
| 277 | <100 |
| 278 | <100 |
| 279 | <100 |
| 280 | <100 |
| 281 | <100 |
| 282 | <100 |
| 283 | <100 |
| 284 | <100 |
| 285 | — |
| 286 | — |
| 287 | <100 |
| 288 | <100 |
| 289 | <100 |
| 290 | <100 |
| 291 | <100 |
| 292 | <100 |
| 293 | <100 |
| 294 | <100 |
| 295 | <100 |
| 296 | <100 |
| 297 | <100 |
| 298 | <100 |
| 299 | <100 |
| 300 | <100 |
| 301 | <100 |
| 302 | <100 |
| 303 | <100 |
| 304 | <100 |
| 305 | <100 |
| 306 | <100 |
| 307 | <100 |
| 308 | <100 |
| 309 | <100 |
| 310 | <100 |
| 311 | <100 |
| 312 | <100 |
| 313 | <100 |
| 314 | <100 |
| 315 | <100 |
| 316 | <100 |
| 317 | <100 |
| 318 | <100 |
| 319 | <100 |
| 320 | <100 |
| 321 | <100 |
| 323 | <100 |
| 324 | <100 |
| 325 | <100 |
| 326 | <100 |
| 327 | <100 |
| 328 | <100 |
| 329 | <100 |
| 330 | <100 |
| 331 | <100 |
| 332 | <100 |
| 333 | <100 |
| 334 | <100 |
| 336 | <100 |
| 337 | <100 |
| 338 | <100 |
| 339 | <100 |
| 340 | <100 |
| 341 | <100 |
| 342 | <100 |
| 343 | <100 |
| 344 | <100 |
| 345 | — |
| 346 | <100 |
| 347 | <100 |
| 348 | <100 |

Example B

Cellular Assays

One or more compounds herein were tested for inhibitory activity of JAK targets according to at least one of the following cellular assays.

Cancer cell lines dependent on cytokines and hence JAK/STAT signal transduction, for growth, were plated at 6000 cells per well (96 well plate format) in RPMI 1640, 10% FBS, and 1 nG/mL of appropriate cytokine. Compounds were added to the cells in DMSO/media (final concentration 0.2% DMSO) and incubated for 72 hours at 37° C., 5% CO$_2$. The effect of compound on cell viability was assessed using the CellTiter-Glo Luminescent Cell Viability Assay (Promega) followed by TopCount (Perkin Elmer, Boston, Mass.) quantitation. Potential off-target effects of compounds were measured in parallel using a non-JAK driven cell line with the same assay readout. Compounds having an IC$_{50}$ of 10 μM or less with selectivity for JAK driven proliferation were considered active. All experiments were performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-112, IL-23, or IFN can be used to stimulate JAK activation resulting in phosphorylation of STAT protein (s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al *Nature* 434:1144-1148; Staerk, J., et al. *J. Biol. Chem.* 280:41893-41899). Endpoints include the effects of compounds on cell survival, proliferation, and phosphorylated JAK, STAT, Akt, or Erk proteins.

Certain compounds herein have been or can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 µg/ml streptomycin) at a density of $2 \times 10^6$ cells/ml at 37° C. for up to 2 days. For IL-2 stimulated cell proliferation analysis, T-cells are first treated with Phytohemagglutinin (PHA) at a final concentration of 10 µg/mL for 72 h. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. *Hematol J.* 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound (s) can be assessed using xenograft tumor models that are driven by other know kinases (e.g. BCR-ABL1) such as the K562 tumor model.

Example D

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today.* 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 µL (10 µL on the internal pinna and 10 µL on the external pinna) at a concentration of 0.2%. Twenty-four to seventy-two hours after the challenge, ears are measured again. Treatment with the test compounds was given throughout the sensitization and challenge phases (day −1 to day 7) or prior to and throughout the challenge phase (usually afternoon of day 4 to day 7). Treatment of the test compounds (in different concentration) was administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In Vivo Anti-Inflammatory Activity

Compounds herein can be or have been evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroiditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3, Coligan, J. E. et al, Wiley Press; Methods in Molecular Biology: Vol. 225, Inflammation Protocols, Winyard, P. G. and Willoughby, D. A., Humana Press, 2003).

Example F

ABL1 and T315I Cell Based Assays

Cancer cell lines dependent on ABL1 kinase activity for proliferation and/or survival can be plated at 3000 cells per well (96 well plate format) in RPMI 1640, and 10% FBS. Compounds can be added to the cells in DMSO/media (final concentration 0.2% DMSO) and incubated for 72 hours at 37° C., 5% $CO_2$. The effect of compound on cell viability is assessed using the CellTiter-Glo Luminescent Cell Viability Assay (Promega) followed by TopCount (Perkin Elmer, Boston, Mass.) quantitation. ABL1-dependent cell lines can include those naturally dependent on ABL1 activity or those engineered to be dependent on ABL1 activity or those engineered to be dependent on ABL1 activity (e.g. BaF/3 cells). The latter can be generated using wild-type ABL I or mutant ABL I (such as T315I ABL1) so that the activity of compounds can be assessed against different variants of the ABL1 kinase. Potential off-target effects of compounds were measured in parallel using a non-ABL1 driven cell line with the same assay readout. Compounds having an $IC_{50}$ of 10 µM or less with selectivity for JAK driven proliferation are considered active. All experiments were performed in duplicate or greater.

The above cell lines can also be used to examine the effects of compounds on phosphorylation of ABL1 and/or ABL1 substrates, such as STAT proteins, Akt, Erk, or Crk1. These experiments can be performed following incubation of cells with compound(s) for varying period of time (usually 10 minutes to 4 hours), depending on a number of factors (e.g. the half-life of the phosphor-proteins of interest). Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on both cancerous and normal cells.

These same cell lines can be used to examine the effects of inhibiting both ABL and JAK kinases with unique or the same compound. For instance, BaF/3 cells expressing BCR-ABL1 (mutant or wild-type) can be used to evaluate the impact of compounds on the growth, survival, and signaling of cells driven by the ABL 1-kinase. However, if these same cells are grown in the presence of specific cytokines (e.g. IL-3) that activate JAK kinases, the impact of compounds can be assessed in cells in which both ABL and JAK kinases contribute to the tumor cell viability and proliferation.

Example G

ABL1 and T315I ABL1 HTRF Assay

Compounds herein described can be tested for inhibitory activity of ABL1 kinase (wild-type and T315I mutant) as described below. The catalytic domains of ABL1 kinases (residues 27 to the C-termini) can be N-terminal His tagged and expressed by baculovirus in insect cells and purified. These can be purchased in purified form from Upstate Cell Signaling Solutions. ABL1 and T315I ABL1 catalyze the phosphorylation of p28. The phosphorylated p28 can be detected by Homogeneous Time Resolved Fluorescence (HTRF). $IC_{50}$s of compounds can be measured for each kinase in the reactions that contain: 1-2 nM ABL1 or T315I ABL1, 500 nM peptide, 35 µM ATP for ABL1 and 10 µM ATP for T315I ABL1, 2.0% DMSO in assay buffer containing 50 mM Tris, pH 7.8, 100 mM NaCl, 10 mM $MgCl_2$, 5 mM DTT, 0.6 mg/mL BSA. Reactions usually proceed at room temperature for one and half hour and can be stopped by adding 20 µL additional 50 mM NaCl, 0.4 mg/mL BSA, 45 mM EDTA, 200 nM SA-APC, 4 nM Eu-Py20 in assay buffer. The plates can be incubated at room temperature for 40 min and HTRF can then be measured on a plate reader.

Other kinase assays may be run in similar fashion using commercially available kinases and substrates and/or through contract service providers such as Invitrogen, Cerep, or Upstate Biosciences.

Example H

In Vivo Anti-Tumor Efficacy

Compounds herein can be evaluated in human tumor xenograft models in immune competent or compromised mice. For example, a tumorigenic variant of the BaF/3 cell line that has been transformed with BCR-ABL1 (wild-type or mutant) can be used to inoculate Balb/c or Balb/c nu/nu mice subcutaneously or intravenously. Tumor cell bearing animals can then be randomized into drug or vehicle treatment groups and different doses of compounds can be administered by any number of the usual routes including oral, i.p. or continuous infusion using implantable pumps. Tumor cell growth is followed over time using calipers (for subcutaneous inoculations) and the survival of animals can also be tracked (for intravenous inoculations). Further, tumor cell samples can be harvested at any time after the initiation of treatment for analysis as described above to evaluate compound effects on kinase activity (JAK, ABL, or other) and downstream signaling pathways. In addition, selectivity of the compound(s) can be assessed using xenograft tumor models that are driven by other 'off-target' kinases.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula IIa, IIb, IIc, IId, IIe, IIf, or IIg:

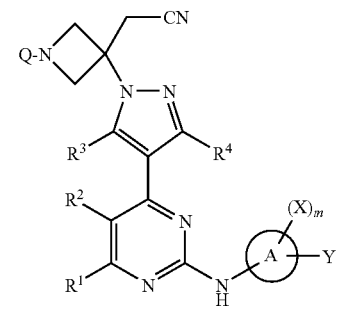
IIa

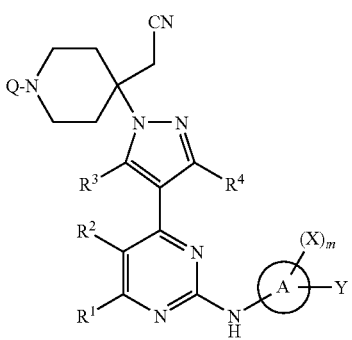
IIb

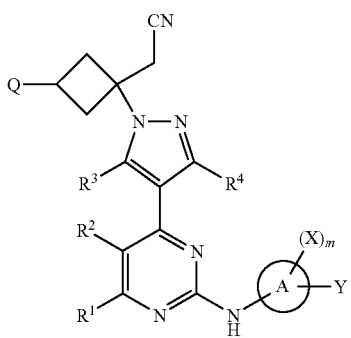
IIc

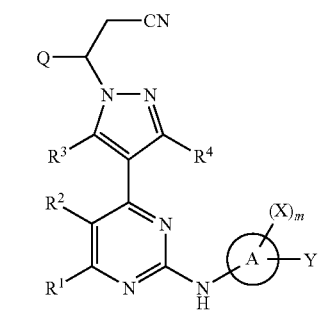
IId

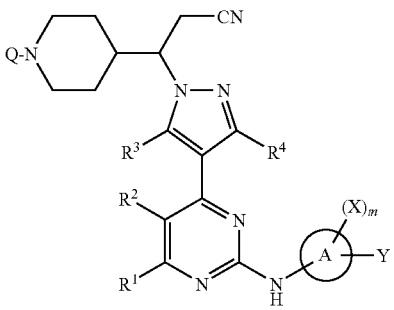
IIe

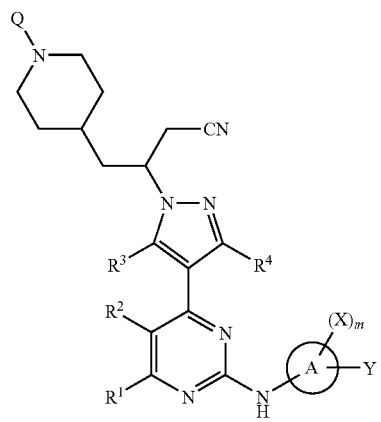
IIf

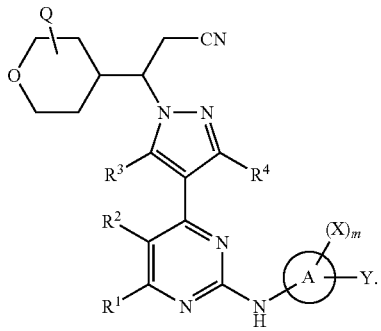
IIg or a pharmaceutically acceptable salt thereof, wherein:

Ring A is aryl or heteroaryl;

Q is H, $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein said $C_{1-6}$ alkyl, $C_{2-6}$ alkenyl, or $C_{2-6}$ alkynyl, are optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

X is H, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^{c1}C(O)R^b$, $NR^{c1}C(O)NR^cR^d$, $NR^{c1}C(O)OR^a$, $C(=NR^g)NR^cR^d$, $NR^{c1}C(=NR^g)NR^cR^d$, $S(O)R^b$, $S(O)NR^cR^d$, $S(O)_2R^b$, $NR^{c1}S(O)_2R^b$, or $S(O)_2NR^cR^d$;

Y is H, $Cy^2$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein said $C_{1-6}$ alkyl, $C_{2-6}$ alkenyl, $C_{2-6}$ alkynyl, or $C_{1-6}$ haloalkyl, is optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^1$, $R^2$, $R^3$, and $R^4$ are independently selected from H, halo, $C_{1-6}$ alkyl, $C_{2-6}$ alkenyl, $C_{2-6}$ alkynyl, $C_{1-6}$ haloalkyl, CN, $(CH_2)_m CN$, $NO_2$, $OR^a$, $(CH_2)_m OR^a$, $SR^a$, $C(O)R^b$, $C(O)NR^cR^d$, $C(O)OR^a$, $NR^cR^d$, $(CH_2)_m NR^cR^d$, $NR^cC(O)R^b$, $NR^cS(O)_2R^b$, and $S(O)_2NR^cR^d$;

$Cy^1$ and $Cy^2$ are independently selected from aryl, cycloalkyl, heteroaryl, and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, aryl, cycloalkyl, heteroaryl, heterocycloalkyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, $C_{2-6}$ alkynyl, aryl, cycloalkyl, heteroaryl, or heterocycloalkyl that is substituted on $Cy^1$ or $Cy^2$ is further optionally substituted by 1, 2, or 3 substituents independently selected from halo, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^a$, $R^b$, $R^c$, and $R^d$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^c$ and $R^d$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{a1}$, $R^{b1}$, $R^{c1}$, and $R^{d1}$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^g)NR^{c2}R^{d2}$, $S(O)_2R^{b2}$, $NR^{c2}S(O)_2R^{b2}$, and $S(O)_2NR^{c2}R^{d2}$;

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from $C_{1-6}$ alkyl, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^2C(O)OR^{a2}$, $C(=NR^g)NR^{c2}R^{d2}$, $NR^{c2}C(=NR^g)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^{a2}$, $R^{b2}$, $R^{c2}$, and $R^{d2}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c2}$ and $R^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^g$ is H, CN, or $NO_2$; and m is 0, 1, 2, or 3.

2. A compound of claim 1, or pharmaceutically acceptable salt thereof, wherein A is aryl.

3. A compound of claim 1, or pharmaceutically acceptable salt thereof, wherein A is phenyl.

4. A compound of claim 1, or pharmaceutically acceptable salt thereof, wherein A is heteroaryl.

5. A compound of claim 1, or pharmaceutically acceptable salt thereof, wherein A is pyrazolyl.

6. A compound of claim 1, or pharmaceutically acceptable salt thereof, wherein A is pyridyl.

7. A compound of claim 1, or pharmaceutically acceptable salt thereof, wherein Q is H, $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, or $SR^{a1}$, wherein said $C_{1-6}$ alkyl, $C_{2-6}$ alkenyl, or $C_{2-6}$ alkynyl, are optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

8. A compound of claim 1, or pharmaceutically acceptable salt thereof, wherein Q is $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$.

9. A compound of claim 1, or pharmaceutically acceptable salt thereof, wherein Q is $Cy^1$, $C(O)R^{b1}$, $S(O)_2R^{b1}$, or $OR^{a1}$.

10. A compound of claim 1, or pharmaceutically acceptable salt thereof, wherein $Cy^1$ is aryl or cycloalkyl, each optionally substituted by 1, 2, 3, 4, or 5 substituents independently selected from halo, $C_{1-6}$ alkyl, $C_{2-6}$ alkenyl, $C_{2-6}$ alkynyl, aryl, cycloalkyl, heteroaryl, heterocycloalkyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

11. A compound of claim 1, or pharmaceutically acceptable salt thereof, wherein $Cy^1$ is heteroaryl or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, aryl, cycloalkyl, heteroaryl, heterocycloalkyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

12. A compound of claim 1, or pharmaceutically acceptable salt thereof, wherein $R^1$ is H.

13. A compound of claim 1, or pharmaceutically acceptable salt thereof, wherein $R^2$ is H.

14. A compound of claim 1, or pharmaceutically acceptable salt thereof, wherein $R^2$ is $C_{1-6}$ alkyl.

15. A compound of claim 1, or pharmaceutically acceptable salt thereof, wherein $R^2$ is methyl.

16. A compound of claim 1, or pharmaceutically acceptable salt thereof, wherein $R^2$ is $C_{1-6}$ alkoxy.

17. A compound of claim 1, or pharmaceutically acceptable salt thereof, wherein $R^2$ is methoxy.

18. A compound of claim 1, or pharmaceutically acceptable salt thereof, wherein $R^3$ is H.

19. A compound of claim 1, or pharmaceutically acceptable salt thereof, wherein $R^4$ is H.

20. A compound of claim 1, or pharmaceutically acceptable salt thereof, wherein X is H, halo, $C_{1-6}$ alkyl, $C_{2-6}$ alkenyl, $C_{2-6}$ alkynyl, haloalkyl, CN, $SR^a$, $C(O)R^b$, $C(O)OR^a$, $OC(O)R^b$, $OC(O)NR^cR^d$, $NR^{c1}C(O)NR^cR^d$, $C(=NR^g)NR^cR^d$, $NR^{c1}C(=NR^g)NR^cR^d$, $S(O)R^b$, $S(O)NR^cR^d$, or $S(O)_2R^b$.

21. A compound of claim 1, or pharmaceutically acceptable salt thereof, wherein X is $NO_2$, $OR^a$, $C(O)NR^cR^d$, $NR^cR^d$, $NR^{c1}C(O)R^b$, $NR^{c1}C(O)OR^a$, $NR^{c1}S(O)_2R^b$, or $S(O)_2NR^cR^d$.

22. A compound of claim 1, or pharmaceutically acceptable salt thereof, wherein X is $OCH_3$, $OC_6H_5$, $NO_2$, $NH_2$, or $N(CH_2CH_3)_2$.

23. A compound of claim 1, or pharmaceutically acceptable salt thereof, wherein X is H.

24. A compound of claim 1, or pharmaceutically acceptable salt thereof, wherein Y is $C_{1-6}$ alkyl, $C_{2-6}$ alkenyl, $C_{2-6}$ alkynyl, or $C_{1-6}$ haloalkyl, wherein said $C_{1-6}$ alkyl, $C_{2-6}$ alkenyl, or $C_{2-6}$ alkynyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)NR^{b1}$, $S(O)NR^{c1}R^{d1}$, $S(O)_2R^b$, $NR^{c1}S(O)_2R^{b1}$, and $S(O)_2NR^{c1}R^{d1}$.

25. A compound of claim 1, or pharmaceutically acceptable salt thereof, wherein Y is H, $Cy^2$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$.

26. A compound of claim 1, or pharmaceutically acceptable salt thereof, wherein Y is H.

27. A compound of claim 1, or pharmaceutically acceptable salt thereof, wherein $Cy^2$ is aryl or cycloalkyl, each optionally substituted by 1, 2, 3, 4, or 5 substituents independently selected from halo, $C_{1-6}$ alkyl, $C_{2-6}$ alkenyl, $C_{2-6}$ alkynyl, aryl, cycloalkyl, heteroaryl, heterocycloalkyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

28. A compound of claim 1, or pharmaceutically acceptable salt thereof, wherein $Cy^2$ is heteroaryl or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, aryl, cycloalkyl, heteroaryl, heterocycloalkyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

29. A compound of claim 1 selected from:
- 3-(4-(2-(4-(1H-imidazol-1-yl)phenylamino)pyrimidin-4-yl)-1H-pyrazol-1-yl)-4-(1-(2,4-difluorobenzoyl)piperidin-4-yl)butanenitrile;
- 4-(1-(2,4-difluorobenzoyl)piperidin-4-yl)-3-(4-(2-(4-(piperazin-1-yl)phenylamino)pyrimidin-4-yl)-1H-pyrazol-1-yl)butanenitrile;
- 4-(1-(2,4-difluorobenzoyl)piperidin-4-yl)-3-(4-(2-(4-methoxyphenylamino)pyrimidin-4-yl)-1H-pyrazol-1-yl)butanenitrile;
- 4-(1-(2,4-difluorobenzoyl)piperidin-4-yl)-3-(4-(2-(phenylamino)pyrimidin-4-yl)-1H-pyrazol-1-yl)butanenitrile;
- 4-(1-(2,4-difluorobenzoyl)piperidin-4-yl)-3-(4-(2-(4-morpholinophenylamino)pyrimidin-4-yl)-1H-pyrazol-1-yl)butanenitrile;
- 3-(4-(2-(4-(1H-pyrazol-1-yl)phenylamino)pyrimidin-4-yl)-1H-pyrazol-1-yl)-4-(1-(2,4-difluorobenzoyl)piperidin-4-yl)butanenitrile;
- 4-(1-(2,4-difluorobenzoyl)piperidin-4-yl)-3-(4-(2-(3-(oxazol-5-yl)phenylamino)pyrimidin-4-yl)-1H-pyrazol-1-yl)butanenitrile;
- 4-(1-(2,4-difluorobenzoyl)piperidin-4-yl)-3-(4-(2-(1-methyl-1H-pyrazol-3-ylamino)pyrimidin-4-yl)-1H-pyrazol-1-yl)butanenitrile;
- 4-(1-(2,4-difluorobenzoyl)piperidin-4-yl)-3-(4-(2-(4-phenoxyphenylamino)pyrimidin-4-yl)-1H-pyrazol-1-yl)butanenitrile;
- 2-(4-(4-(2-(4-(1H-pyrazol-1-yl)phenylamino)pyrimidin-4-yl)-1H-pyrazol-1-yl)-1-(isoxazole-5-carbonyl)piperidin-4-yl)acetonitrile;
- 2-(1-(isoxazole-5-carbonyl)-4-(4-(2-(3-(oxazol-5-yl)phenylamino)pyrimidin-4-yl)-1H-pyrazol-1-yl)piperidin-4-yl)acetonitrile;
- 2-(4-(4-(2-(3-(1H-tetrazol-5-yl)phenylamino)pyrimidin-4-yl)-1H-pyrazol-1-yl)-1-(isoxazole-5-carbonyl)piperidin-4-yl)acetonitrile;
- 2-(1-(isoxazole-5-carbonyl)-4-(4-(2-(4-(morpholino sulfonyl)phenylamino)pyrimidin-4-yl)-1H-pyrazol-1-yl)piperidin-4-yl)acetonitrile;

2-(1-(isoxazole-5-carbonyl)-4-(4-(2-(6-methoxypyridin-3-ylamino)pyrimidin-4-yl)-1H-pyrazol-1-yl)piperidin-4-yl)acetonitrile;
2-(3-(4-(2-(4-(1H-pyrazol-1-yl)phenylamino)pyrimidin-4-yl)-1H-pyrazol-1-yl)-1-(cyclopropylsulfonyl)azetidin-3-yl)acetonitrile;
2-(1-(cyclopropylsulfonyl)-3-(4-(2-(3-(oxazol-5-yl)phenylamino)pyrimidin-4-yl)-1H-pyrazol-1-yl)azetidin-3-yl)acetonitrile;
N-(4-(4-(1-(3-(cyanomethyl)-1-(cyclopropylsulfonyl)azetidin-3-yl)-1H-pyrazol-4-yl)pyrimidin-2-ylamino)phenyl)acetamide;
2-(1-(cyclopropylsulfonyl)-3-(4-(2-(3-(2-methylpyrimidin-4-yl)phenylamino)pyrimidin-4-yl)-1H-pyrazol-1-yl)azetidin-3-yl)acetonitrile;
2-(1-(cyclopropylsulfonyl)-3-(4-(2-(4-(oxazol-5-yl)phenylamino)pyrimidin-4-yl)-1H-pyrazol-1-yl)azetidin-3-yl)acetonitrile;
3-(4-(2-(4-morpholinophenylamino)pyrimidin-4-yl)-1H-pyrazol-1-yl)-3-(piperidin-4-yl)propanenitrile;
3-(1-(5-fluoropyrimidin-2-yl)piperidin-4-yl)-3-(4-(2-(4-morpholinophenylamino)pyrimidin-4-yl)-1H-pyrazol-1-yl)propanenitrile;
3-(1-(methylsulfonyl)piperidin-4-yl)-3-(4-(2-(4-morpholinophenylamino)pyrimidin-4-yl)-1H-pyrazol-1-yl)propanenitrile;
3-(4-(2-(4-morpholinophenylamino)pyrimidin-4-yl)-1H-pyrazol-1-yl)-3-(1-(phenylsulfonyl)piperidin-4-yl)propanenitrile;
3-(1-acetylpiperidin-4-yl)-3-(4-(2-(4-morpholinophenylamino)pyrimidin-4-yl)-1H-pyrazol-1-yl)propanenitrile;
3-(1-benzoylpiperidin-4-yl)-3-(4-(2-(4-morpholinophenylamino)pyrimidin-4-yl)-1H-pyrazol-1-yl)propanenitrile;
2-(4-(4-(2-(4-(1H-pyrazol-1-yl)phenylamino)pyrimidin-4-yl)-1H-pyrazol-1-yl)-1-(cyclopropylsulfonyl)piperidin-4-yl)acetonitrile;
2-(1-(cyclopropylsulfonyl)-4-(4-(2-(4-morpholinophenylamino)pyrimidin-4-yl)-1H-pyrazol-1-yl)piperidin-4-yl)acetonitrile;
4-(4-(1-(4-(cyanomethyl)-1-(cyclopropylsulfonyl)piperidin-4-yl)-1H-pyrazol-4-yl)pyrimidin-2-ylamino)benzamide;
4-(4-(1-(4-(cyanomethyl)-1-(cyclopropylsulfonyl)piperidin-4-yl)-1H-pyrazol-4-yl)pyrimidin-2-ylamino)-N-(2-hydroxyethyl)benzamide;
4-(4-(1-(4-(cyanomethyl)-1-(cyclopropylsulfonyl)piperidin-4-yl)-1H-pyrazol-4-yl)pyrimidin-2-ylamino)-N,N-dimethylbenzamide;
4-(4-(1-(2-cyano-1-cyclopentylethyl)-1H-pyrazol-4-yl)pyrimidin-2-ylamino)benzamide;
3-(4-(2-(4-(1H-pyrazol-1-yl)phenylamino)pyrimidin-4-yl)-1H-pyrazol-1-yl)-3-cyclopentylpropanenitrile;
3-cyclopentyl-3-(4-(2-(4-morpholinophenylamino)pyrimidin-4-yl)-1H-pyrazol-1-yl)propanenitrile;
3-cyclopentyl-3-(4-(2-(phenylamino)pyrimidin-4-yl)-1H-pyrazol-1-yl)propanenitrile;
3-cyclopentyl-3-(4-(2-(3-(oxazol-5-yl)phenylamino)pyrimidin-4-yl)-1H-pyrazol-1-yl)propanenitrile;
3-cyclopentyl-3-(4-(2-(4-methoxyphenylamino)pyrimidin-4-yl)-1H-pyrazol-1-yl)propanenitrile;
N-(4-(4-(1-(2-cyano-1-cyclopentylethyl)-1H-pyrazol-4-yl)pyrimidin-2-ylamino)phenyl)acetamide;
4-(4-(1-(2-cyano-1-cyclopentylethyl)-1H-pyrazol-4-yl)pyrimidin-2-ylamino)-N,N-dimethylbenzamide;
3-cyclopentyl-3-(4-(2-(4-(piperazin-1-yl)phenylamino)pyrimidin-4-yl)-1H-pyrazol-1-yl)propanenitrile;
4-(1-(ethylsulfonyl)piperidin-4-yl)-3-(4-(2-(4-morpholinophenylamino)pyrimidin-4-yl)-1H-pyrazol-1-yl)butanenitrile;
3-(4-(2-(4-(1H-pyrazol-1-yl)phenylamino)pyrimidin-4-yl)-1H-pyrazol-1-yl)-4-(1-(ethylsulfonyl)piperidin-4-yl)butanenitrile;
4-(1-(ethylsulfonyl)piperidin-4-yl)-3-(4-(2-(phenylamino)pyrimidin-4-yl)-1H-pyrazol-1-yl)butanenitrile;
N-(4-(4-(1-(1-cyano-3-(1-(1-methyl-1H-pyrazol-3-ylsulfonyl)piperidin-4-yl)propan-2-yl)-1H-pyrazol-4-yl)pyrimidin-2-ylamino)phenyl)acetamide;
4-(4-(1-(1-cyano-3-(1-(ethylsulfonyl)piperidin-4-yl)propan-2-yl)-1H-pyrazol-4-yl)pyrimidin-2-ylamino)-N,N-dimethylbenzamide;
4-(4-(1-(1-cyano-3-(1-(1-methyl-1H-pyrazol-3-ylsulfonyl)piperidin-4-yl)propan-2-yl)-1H-pyrazol-4-yl)pyrimidin-2-ylamino)benzamide;
4-(1-(ethylsulfonyl)piperidin-4-yl)-3-(4-(5-methyl-2-(4-morpholinophenylamino)pyrimidin-4-yl)-1H-pyrazol-1-yl)butanenitrile;
3-(4-(2-(4-(1H-pyrazol-1-yl)phenylamino)-5-methylpyrimidin-4-yl)-1H-pyrazol-1-yl)-4-(1-(ethylsulfonyl)piperidin-4-yl)butanenitrile;
4-(1-(ethylsulfonyl)piperidin-4-yl)-3-(4-(5-methyl-2-(phenylamino)pyrimidin-4-yl)-1H-pyrazol-1-yl)butanenitrile;
N-(4-(4-(1-(1-cyano-3-(1-(1-methyl-1H-pyrazol-3-ylsulfonyl)piperidin-4-yl)propan-2-yl)-1H-pyrazol-4-yl)-5-methylpyrimidin-2-ylamino)phenyl)acetamide;
4-(4-(1-(1-cyano-3-(1-(ethylsulfonyl)piperidin-4-yl)propan-2-yl)-1H-pyrazol-4-yl)-5-methylpyrimidin-2-ylamino)-N,N-dimethylbenzamide;
4-(4-(1-(1-cyano-3-(1-(1-methyl-1H-pyrazol-3-ylsulfonyl)piperidin-4-yl)propan-2-yl)-1H-pyrazol-4-yl)-5-methylpyrimidin-2-ylamino)benzamide;
3-cyclopentyl-3-(4-(2-(4-(4-(methylsulfonyl)piperazin-1-yl)phenylamino)pyrimidin-4-yl)-1H-pyrazol-1-yl)propanenitrile;
4-(1-(1-methyl-1H-pyrazol-3-ylsulfonyl)piperidin-4-yl)-3-(4-(2-(4-morpholinophenylamino)pyrimidin-4-yl)-1H-pyrazol-1-yl)butanenitrile;
3-(4-(2-(4-(1H-pyrazol-1-yl)phenylamino)pyrimidin-4-yl)-1H-pyrazol-1-yl)-4-(1-(1-methyl-1H-pyrazol-3-ylsulfonyl)piperidin-4-yl)butanenitrile;
4-(1-(1-methyl-1H-pyrazol-3-ylsulfonyl)piperidin-4-yl)-3-(4-(2-(phenylamino)pyrimidin-4-yl)-1H-pyrazol-1-yl)butanenitrile;
4-(4-(1-(1-cyano-3-(1-(1-methyl-1H-pyrazol-3-ylsulfonyl)piperidin-4-yl)propan-2-yl)-1H-pyrazol-4-yl)pyrimidin-2-ylamino)-N,N-dimethylbenzamide;
4-(4-(1-(1-cyano-3-(1-(2,4-difluorobenzoyl)piperidin-4-yl)propan-2-yl)-1H-pyrazol-4-yl)pyrimidin-2-ylamino)-N,N-dimethylbenzamide;
N-(4-(4-(1-(1-cyano-3-(1-(2,4-difluorobenzoyl)piperidin-4-yl)propan-2-yl)-1H-pyrazol-4-yl)pyrimidin-2-ylamino)phenyl)acetamide;
4-(1-(1-methyl-1H-pyrazol-3-ylsulfonyl)piperidin-4-yl)-3-(4-(5-methyl-2-(4-morpholinophenylamino)pyrimidin-4-yl)-1H-pyrazol-1-yl)butanenitrile;
4-(1-(2,4-difluorobenzoyl)piperidin-4-yl)-3-(4-(5-methyl-2-(4-morpholinophenylamino)pyrimidin-4-yl)-1H-pyrazol-1-yl)butanenitrile;
3-(4-(2-(4-(1H-pyrazol-1-yl)phenylamino)-5-methylpyrimidin-4-yl)-1H-pyrazol-1-yl)-4-(1-(1-methyl-1H-pyrazol-3-ylsulfonyl)piperidin-4-yl)butanenitrile;

3-(4-(2-(4-(1H-pyrazol-1-yl)phenylamino)-5-methylpyrimidin-4-yl)-1H-pyrazol-1-yl)-4-(1-(2,4-difluorobenzoyl)piperidin-4-yl)butanenitrile;
4-(1-(1-methyl-1H-pyrazol-3-ylsulfonyl)piperidin-4-yl)-3-(4-(5-methyl-2-(phenylamino)pyrimidin-4-yl)-1H-pyrazol-1-yl)butanenitrile;
4-(1-(2,4-difluorobenzoyl)piperidin-4-yl)-3-(4-(5-methyl-2-(phenylamino)pyrimidin-4-yl)-1H-pyrazol-1-yl)butanenitrile;
4-(4-(1-(1-cyano-3-(1-(1-methyl-1H-pyrazol-3-ylsulfonyl)piperidin-4-yl)propan-2-yl)-1H-pyrazol-4-yl)-5-methylpyrimidin-2-ylamino)-N,N-dimethylbenzamide;
4-(4-(1-(1-cyano-3-(1-(2,4-difluorobenzoyl)piperidin-4-yl)propan-2-yl)-1H-pyrazol-4-yl)-5-methylpyrimidin-2-ylamino)-N,N-dimethylbenzamide;
N-(4-(4-(1-(1-cyano-3-(1-(2,4-difluorobenzoyl)piperidin-4-yl)propan-2-yl)-1H-pyrazol-4-yl)-5-methylpyrimidin-2-ylamino)phenyl)acetamide;
4-(4-(1-(2-cyano-1-cyclopentylethyl)-1H-pyrazol-4-yl)-5-methylpyrimidin-2-ylamino)benzamide;
3-(4-(2-(4-(1H-pyrazol-1-yl)phenylamino)-5-methylpyrimidin-4-yl)-1H-pyrazol-1-yl)-3-cyclopentylpropanenitrile;
3-cyclopentyl-3-(4-(5-methyl-2-(4-morpholinophenylamino)pyrimidin-4-yl)-1H-pyrazol-1-yl)propanenitrile;
3-cyclopentyl-3-(4-(5-methyl-2-(phenylamino)pyrimidin-4-yl)-1H-pyrazol-1-yl)propanenitrile;
3-cyclopentyl-3-(4-(5-methyl-2-(4-(oxazol-5-yl)phenylamino)pyrimidin-4-yl)-1H-pyrazol-1-yl)propanenitrile;
3-cyclopentyl-3-(4-(2-(4-methoxyphenylamino)-5-methylpyrimidin-4-yl)-1H-pyrazol-1-yl)propanenitrile;
3-cyclopentyl-3-(4-(5-methyl-2-(4-(piperazin-1-yl)phenylamino)pyrimidin-4-yl)-1H-pyrazol-1-yl)propanenitrile;
3-cyclopentyl-3-(4-(2-(4-(diethylamino)phenylamino)-5-methylpyrimidin-4-yl)-1H-pyrazol-1-yl)propanenitrile;
3-cyclopentyl-3-(4-(2-(4-(ethyl(3-hydroxypropyl)amino)phenylamino)-5-methylpyrimidin-4-yl)-1H-pyrazol-1-yl)propanenitrile;
4-(4-(1-(2-cyano-1-cyclopentylethyl)-1H-pyrazol-4-yl)-5-methylpyrimidin-2-ylamino)benzoic acid;
3-cyclopentyl-3-(4-(5-methyl-2-(4-nitrophenylamino)pyrimidin-4-yl)-1H-pyrazol-1-yl)propanenitrile;
4-(4-(1-(2-cyano-1-cyclopentylethyl)-1H-pyrazol-4-yl)-5-methylpyrimidin-2-ylamino)-N-(2-hydroxyethyl)benzamide;
3-cyclopentyl-3-(4-(5-methyl-2-(3-(oxazol-5-yl)phenylamino)pyrimidin-4-yl)-1H-pyrazol-1-yl)propanenitrile;
3-(4-(2-(4-aminophenylamino)-5-methylpyrimidin-4-yl)-1H-pyrazol-1-yl)-3-cyclopentylpropanenitrile;
4-(4-(1-(2-cyano-1-cyclopentylethyl)-1H-pyrazol-4-yl)-5-methylpyrimidin-2-ylamino)-N-methylbenzamide;
4-(4-(1-(2-cyano-1-cyclopentylethyl)-1H-pyrazol-4-yl)-5-methylpyrimidin-2-ylamino)-N-(1-methoxypropan-2-yl)benzamide;
3-cyclopentyl-3-(4-(2-(4-(4-hydroxypiperidine-1-carbonyl)phenylamino)-5-methylpyrimidin-4-yl)-1H-pyrazol-1-yl)propanenitrile;
N-(4-(4-(1-(2-cyano-1-cyclopentylethyl)-1H-pyrazol-4-yl)-5-methylpyrimidin-2-ylamino)phenyl)methane sulfonamide;
Methyl 4-(4-(1-(2-cyano-1-cyclopentylethyl)-1H-pyrazol-4-yl)-5-methylpyrimidin-2-ylamino)phenylcarbamate;
N-(4-(4-(1-(2-cyano-1-cyclopentylethyl)-1H-pyrazol-4-yl)-5-methylpyrimidin-2-ylamino)phenyl)-2-(pyrrolidin-1-yl)acetamide;
3-(4-(2-(4-(3-oxomorpholino)phenylamino)pyrimidin-4-yl)-1H-pyrazol-1-yl)-4-(piperidin-4-yl)butanenitrile;
2-(1-(cyclopropylsulfonyl)-3-(4-(2-(4-morpholinophenylamino)pyrimidin-4-yl)-1H-pyrazol-1-yl)azetidin-3-yl)acetonitrile;
2-(1-(isoxazole-5-carbonyl)-4-(4-(2-(4-morpholinophenylamino)pyrimidin-4-yl)-1H-pyrazol-1-yl)piperidin-4-yl)acetonitrile;
4-(1-(methylsulfonyl)piperidin-4-yl)-3-(4-(2-(4-(3-oxomorpholino)phenylamino)pyrimidin-4-yl)-1H-pyrazol-1-yl)butanenitrile;
4-(1-(ethylsulfonyl)piperidin-4-yl)-3-(4-(2-(4-(3-oxomorpholino)phenylamino)pyrimidin-4-yl)-1H-pyrazol-1-yl)butanenitrile;
4-(1-(cyclopropylsulfonyl)piperidin-4-yl)-3-(4-(2-(4-(3-oxomorpholino)phenylamino)pyrimidin-4-yl)-1H-pyrazol-1-yl)butanenitrile;
3-cyclopentyl-3-(4-(2-(4-(3-oxomorpholino)phenylamino)pyrimidin-4-yl)-1H-pyrazol-1-yl)propanenitrile;
3-cyclopentyl-3-(4-(2-(3-(2-methylpyrimidin-4-yl)phenylamino)pyrimidin-4-yl)-1H-pyrazol-1-yl)propanenitrile;
3-(4-(1-(2-cyano-1-cyclopentylethyl)-1H-pyrazol-4-yl)pyrimidin-2-ylamino)benzoic acid;
3-cyclopentyl-3-(4-(5-methoxy-2-(4-morpholinophenylamino)pyrimidin-4-yl)-1H-pyrazol-1-yl)propanenitrile;
3-(4-(2-(4-(1H-pyrazol-1-yl)phenylamino)-5-methoxypyrimidin-4-yl)-1H-pyrazol-1-yl)-3-cyclopentylpropanenitrile;
N-(4-(4-(1-(2-cyano-1-cyclopentylethyl)-1H-pyrazol-4-yl)-5-methoxypyrimidin-2-ylamino)phenyl)acetamide;
4-(4-(1-(2-cyano-1-cyclopentylethyl)-1H-pyrazol-4-yl)-5-methoxypyrimidin-2-ylamino)-N,N-dimethylbenzamide;
3-cyclopentyl-3-(4-(2-(4-(2-oxopiperidin-1-yl)phenylamino)pyrimidin-4-yl)-1H-pyrazol-1-yl)propanenitrile;
3-cyclopentyl-3-(4-(2-(4-(2-oxo-1,3-oxazinan-3-yl)phenylamino)pyrimidin-4-yl)-1H-pyrazol-1-yl)propanenitrile;
3-cyclopentyl-3-(4-(2-(4-(2-oxooxazolidin-3-yl)phenylamino)pyrimidin-4-yl)-1H-pyrazol-1-yl)propanenitrile;
3-(4-(2-(3-aminophenylamino)pyrimidin-4-yl)-1H-pyrazol-1-yl)-3-cyclopentylpropanenitrile;
3-(4-(1-(2-cyano-1-cyclopentylethyl)-1H-pyrazol-4-yl)pyrimidin-2-ylamino)-N-methylbenzamide;
3-(4-(1-(2-cyano-1-cyclopentylethyl)-1H-pyrazol-4-yl)pyrimidin-2-ylamino)-N,N-dimethylbenzamide;
3-cyclopentyl-3-(4-(2-(3-(4-hydroxypiperidine-1-carbonyl)phenylamino)pyrimidin-4-yl)-1H-pyrazol-1-yl)propanenitrile;
3-(4-(1-(2-cyano-1-cyclopentylethyl)-1H-pyrazol-4-yl)pyrimidin-2-ylamino)-N-(2-hydroxyethyl)benzamide;
3-(4-(1-(2-cyano-1-cyclopentylethyl)-1H-pyrazol-4-yl)pyrimidin-2-ylamino)-N-(1-methoxypropan-2-yl)benzamide;
N-(3-(4-(1-(2-cyano-1-cyclopentylethyl)-1H-pyrazol-4-yl)pyrimidin-2-ylamino)phenyl)ethane sulfonamide;

N-(3-(4-(1-(2-cyano-1-cyclopentylethyl)-1H-pyrazol-4-yl)pyrimidin-2-ylamino)phenyl)methane sulfonamide;
methyl 3-(4-(1-(2-cyano-1-cyclopentylethyl)-1H-pyrazol-4-yl)pyrimidin-2-ylamino)phenylcarbamate;
N-(3-(4-(1-(2-cyano-1-cyclopentylethyl)-1H-pyrazol-4-yl)pyrimidin-2-ylamino)phenyl)acetamide;
N-(3-(4-(1-(2-cyano-1-cyclopentylethyl)-1H-pyrazol-4-yl)pyrimidin-2-ylamino)phenyl)-2-(pyrrolidin-1-yl)acetamide;
4-(4-(1-(2-cyano-1-cyclopentylethyl)-1H-pyrazol-4-yl)pyrimidin-2-ylamino)benzoic acid;
3-cyclopentyl-3-(4-(2-(4-(4-methylpiperazine-1-carbonyl)phenylamino)pyrimidin-4-yl)-1H-pyrazol-1-yl)propanenitrile;
3-cyclopentyl-3-(4-(2-(4-(4-(2-hydroxyethyl)piperazine-1-carbonyl)phenylamino)pyrimidin-4-yl)-1H-pyrazol-1-yl)propanenitrile;
3-cyclopentyl-3-(4-(2-(4-(pyrrolidine-1-carbonyl)phenylamino)pyrimidin-4-yl)-1H-pyrazol-1-yl)propanenitrile;
3-cyclopentyl-3-(4-(2-(4-(3-oxopiperazine-1-carbonyl)phenylamino)pyrimidin-4-yl)-1H-pyrazol-1-yl)propanenitrile;
3-cyclopentyl-3-(4-(2-(4-(4-hydroxypiperidine-1-carbonyl)phenylamino)pyrimidin-4-yl)-1H-pyrazol-1-yl)propanenitrile;
4-(4-(1-(2-cyano-1-cyclopentylethyl)-1H-pyrazol-4-yl)pyrimidin-2-ylamino)-N-(cyclopropylmethyl)-N-propylbenzamide;
4-(4-(1-(2-cyano-1-cyclopentylethyl)-1H-pyrazol-4-yl)pyrimidin-2-ylamino)-N-(cyclopropylmethyl)benzamide;
3-cyclopentyl-3-(4-(2-(4-(3-hydroxypyrrolidine-1-carbonyl)phenylamino)pyrimidin-4-yl)-1H-pyrazol-1-yl)propanenitrile;
3-(4-(2-(4-(azetidine-1-carbonyl)phenylamino)pyrimidin-4-yl)-1H-pyrazol-1-yl)-3-cyclopentylpropanenitrile;
3-cyclopentyl-3-(4-(2-(4-(2-oxopyrrolidin-1-yl)phenylamino)pyrimidin-4-yl)-1H-pyrazol-1-yl)propanenitrile;
3-cyclopentyl-3-(4-(5-methoxy-2-(4-(2-oxopyrrolidin-1-yl)phenylamino)pyrimidin-4-yl)-1H-pyrazol-1-yl)propanenitrile;
3-cyclopentyl-3-(4-(5-methoxy-2-(4-(oxazol-5-yl)phenylamino)pyrimidin-4-yl)-1H-pyrazol-1-yl)propanenitrile;
3-cyclopentyl-3-(4-(5-methoxy-2-(3-(oxazol-5-yl)phenylamino)pyrimidin-4-yl)-1H-pyrazol-1-yl)propanenitrile;
3-cyclopentyl-3-(4-(5-methoxy-2-(4-(3-oxomorpholino)phenylamino)pyrimidin-4-yl)-1H-pyrazol-1-yl)propanenitrile;
3-cyclopentyl-3-(4-(5-methoxy-2-(3-(2-methylpyrimidin-4-yl)phenylamino)pyrimidin-4-yl)-1H-pyrazol-1-yl)propanenitrile;
3-cyclopentyl-3-(4-(5-methoxy-2-(4-(2-oxopiperidin-1-yl)phenylamino)pyrimidin-4-yl)-1H-pyrazol-1-yl)propanenitrile;
3-cyclopentyl-3-(4-(5-methoxy-2-(4-(2-oxooxazolidin-3-yl)phenylamino)pyrimidin-4-yl)-1H-pyrazol-1-yl)propanenitrile;
3-cyclopentyl-3-(4-(2-(3-(4-methylpiperazine-1-carbonyl)phenylamino)pyrimidin-4-yl)-1H-pyrazol-1-yl)propanenitrile;
3-cyclopentyl-3-(4-(2-(3-(4-(2-hydroxyethyl)piperazine-1-carbonyl)phenylamino)pyrimidin-4-yl)-1H-pyrazol-1-yl)propanenitrile;
3-cyclopentyl-3-(4-(2-(3-(pyrrolidine-1-carbonyl)phenylamino)pyrimidin-4-yl)-1H-pyrazol-1-yl)propanenitrile;
3-cyclopentyl-3-(4-(2-(3-(3-oxopiperazine-1-carbonyl)phenylamino)pyrimidin-4-yl)-1H-pyrazol-1-yl)propanenitrile;
3-cyclopentyl-3-(4-(2-(3-(3-hydroxypyrrolidine-1-carbonyl)phenylamino)pyrimidin-4-yl)-1H-pyrazol-1-yl)propanenitrile;
3-(4-(2-(3-(azetidine-1-carbonyl)phenylamino)pyrimidin-4-yl)-1H-pyrazol-1-yl)-3-cyclopentylpropanenitrile;
3-(4-(2-(3-(4-acetylpiperazine-1-carbonyl)phenylamino)pyrimidin-4-yl)-1H-pyrazol-1-yl)-3-cyclopentylpropanenitrile;
3-cyclopentyl-3-(4-(2-(3-(4-(pyridin-3-ylmethyl)piperidine-1-carbonyl)phenylamino)pyrimidin-4-yl)-1H-pyrazol-1-yl)propanenitrile;
3-(4-(1-(2-cyano-1-cyclopentylethyl)-1H-pyrazol-4-yl)pyrimidin-2-ylamino)-N-(1-(3-methoxyphenyl)ethyl)benzamide;
3-(4-(1-(2-cyano-1-cyclopentylethyl)-1H-pyrazol-4-yl)pyrimidin-2-ylamino)-N-(pyridin-3-ylmethyl)benzamide;
3-cyclopentyl-3-(4-(2-(3-(morpholine-4-carbonyl)phenylamino)pyrimidin-4-yl)-1H-pyrazol-1-yl)propanenitrile;
3-(4-(1-(2-cyano-1-cyclopentylethyl)-1H-pyrazol-4-yl)pyrimidin-2-ylamino)-N-((5-methylisoxazol-3-yl)methyl)benzamide;
3-(4-(1-(2-cyano-1-cyclopentylethyl)-1H-pyrazol-4-yl)pyrimidin-2-ylamino)-N-(2-(1-methylpyrrolidin-2-yl)ethyl)benzamide;
3-cyclopentyl-3-(4-(2-(3-(4-hydroxy-4-phenylpiperidine-1-carbonyl)phenylamino)pyrimidin-4-yl)-1H-pyrazol-1-yl)propanenitrile;
3-(4-(2-(3-(4-benzyl-4-hydroxypiperidine-1-carbonyl)phenylamino)pyrimidin-4-yl)-1H-pyrazol-1-yl)-3-cyclopentylpropanenitrile;
3-cyclopentyl-3-(4-(2-(3-(3-(pyridin-2-yl)pyrrolidine-1-carbonyl)phenylamino)pyrimidin-4-yl)-1H-pyrazol-1-yl)propanenitrile;
3-(4-(1-(2-cyano-1-cyclopentylethyl)-1H-pyrazol-4-yl)pyrimidin-2-ylamino)-N-((tetrahydro-2H-pyran-4-yl)methyl)benzamide;
3-(4-(1-(2-cyano-1-cyclopentylethyl)-1H-pyrazol-4-yl)pyrimidin-2-ylamino)-N-(1-methylpiperidin-4-yl)benzamide;
3-cyclopentyl-3-(4-(2-(3-(4-phenylpiperidine-1-carbonyl)phenylamino)pyrimidin-4-yl)-1H-pyrazol-1-yl)propanenitrile;
3-(4-(1-(2-cyano-1-cyclopentylethyl)-1H-pyrazol-4-yl)pyrimidin-2-ylamino)-N-(1-(pyridin-2-yl)ethyl)benzamide;
3-cyclopentyl-3-(4-(2-(3-(3-(3-fluorophenyl)pyrrolidine-1-carbonyl)phenylamino)pyrimidin-4-yl)-1H-pyrazol-1-yl)propanenitrile;
N-((3R)-1-(3-(4-(1-(2-cyano-1-cyclopentylethyl)-1H-pyrazol-4-yl)pyrimidin-2-ylamino)benzoyl)pyrrolidin-3-yl)acetamide;
3-(4-(1-(2-cyano-1-cyclopentylethyl)-1H-pyrazol-4-yl)pyrimidin-2-ylamino)-N-(2-(2-oxoimidazolidin-1-yl)ethyl)benzamide;

3-cyclopentyl-3-(4-(2-(3-(4-(pyrimidin-2-yl)piperazine-1-carbonyl)phenylamino)pyrimidin-4-yl)-1H-pyrazol-1-yl)propanenitrile;
3-(4-(1-(2-cyano-1-cyclopentylethyl)-1H-pyrazol-4-yl)pyrimidin-2-ylamino)-N-(2-(pyridin-3-yl)ethyl)benzamide;
3-cyclopentyl-3-(4-(2-(3-(2-(methoxymethyl)pyrrolidine-1-carbonyl)phenylamino)pyrimidin-4-yl)-1H-pyrazol-1-yl)propanenitrile;
3-(4-(1-(2-cyano-1-cyclopentylethyl)-1H-pyrazol-4-yl)pyrimidin-2-ylamino)-N-(2-methoxybenzyl)benzamide;
3-cyclopentyl-3-(4-(2-(3-(4-phenoxypiperidine-1-carbonyl)phenylamino)pyrimidin-4-yl)-1H-pyrazol-1-yl)propanenitrile;
3-(4-(1-(2-cyano-1-cyclopentylethyl)-1H-pyrazol-4-yl)pyrimidin-2-ylamino)-N-(1-(hydroxymethyl)cyclopentyl)benzamide;
4-(4-(3-(4-(1-(2-cyano-1-cyclopentylethyl)-1H-pyrazol-4-yl)pyrimidin-2-ylamino)benzoyl)piperazin-1-yl)benzonitrile;
N-(1-benzylpyrrolidin-3-yl)-3-(4-(1-(2-cyano-1-cyclopentylethyl)-1H-pyrazol-4-yl)pyrimidin-2-ylamino)benzamide;
3-cyclopentyl-3-(4-(2-(3-(4-phenylpiperazine-1-carbonyl)phenylamino)pyrimidin-4-yl)-1H-pyrazol-1-yl)propanenitrile;
3-cyclopentyl-3-(4-(2-(3-nitrophenylamino)pyrimidin-4-yl)-1H-pyrazol-1-yl)propanenitrile;
3-cyclopentyl-3-(4-(2-(4-nitrophenylamino)pyrimidin-4-yl)-1H-pyrazol-1-yl)propanenitrile;
3-cyclobutyl-3-(4-(2-(4-morpholinophenylamino)pyrimidin-4-yl)-1H-pyrazol-1-yl)propanenitrile;
3-(4-(2-(4-aminophenylamino)pyrimidin-4-yl)-1H-pyrazol-1-yl)-3-cyclopentylpropanenitrile;
3-(4-(2-(4-(1H-pyrazol-1-yl)phenylamino)pyrimidin-4-yl)-1H-pyrazol-1-yl)-3-cyclobutylpropanenitrile;
3-cyclobutyl-3-(4-(2-(4-(2-oxopiperidin-1-yl)phenylamino)pyrimidin-4-yl)-1H-pyrazol-1-yl)propanenitrile;
3-cyclobutyl-3-(4-(2-(4-(3-oxomorpholino)phenylamino)pyrimidin-4-yl)-1H-pyrazol-1-yl)propanenitrile;
3-cyclobutyl-3-(4-(2-(3-(oxazol-5-yl)phenylamino)pyrimidin-4-yl)-1H-pyrazol-1-yl)propanenitrile;
3-cyclopropyl-3-(4-(2-(4-morpholinophenylamino)pyrimidin-4-yl)-1H-pyrazol-1-yl)propanenitrile;
3-(4-(2-(4-(1H-pyrazol-1-yl)phenylamino)pyrimidin-4-yl)-1H-pyrazol-1-yl)-3-cyclopropylpropanenitrile;
3-cyclopropyl-3-(4-(2-(4-(2-oxopiperidin-1-yl)phenylamino)pyrimidin-4-yl)-1H-pyrazol-1-yl)propanenitrile;
3-cyclopropyl-3-(4-(2-(4-(3-oxomorpholino)phenylamino)pyrimidin-4-yl)-1H-pyrazol-1-yl)propanenitrile;
3-cyclopropyl-3-(4-(2-(3-(oxazol-5-yl)phenylamino)pyrimidin-4-yl)-1H-pyrazol-1-yl)propanenitrile;
N-(4-(4-(1-(2-cyano-1-cyclopentylethyl)-1H-pyrazol-4-yl)pyrimidin-2-ylamino)phenyl)-2,6-(cis)-dimethylmorpholine-4-sulfonamide;
N-(4-(4-(1-(2-cyano-1-cyclopentylethyl)-1H-pyrazol-4-yl)pyrimidin-2-ylamino)phenyl)benzamide;
N-(4-(4-(1-(2-cyano-1-cyclopentylethyl)-1H-pyrazol-4-yl)pyrimidin-2-ylamino)phenyl)-1-(methylsulfonyl)methane sulfonamide;
N-(4-(4-(1-(2-cyano-1-cyclopentylethyl)-1H-pyrazol-4-yl)pyrimidin-2-ylamino)phenyl)-3,5-difluorobenzamide;
N'-(4-(4-(1-(2-cyano-1-cyclopentylethyl)-1H-pyrazol-4-yl)pyrimidin-2-ylamino)phenyl)-N,N-dimethylsulfamide;
N-(4-(4-(1-(2-cyano-1-cyclopentylethyl)-1H-pyrazol-4-yl)pyrimidin-2-ylamino)phenyl)-5-methylisoxazole-3-carboxamide;
N-(4-(4-(1-(2-cyano-1-cyclopentylethyl)-1H-pyrazol-4-yl)pyrimidin-2-ylamino)phenyl)isoxazole-5-carboxamide;
N-(4-(4-(1-(2-cyano-1-cyclopentylethyl)-1H-pyrazol-4-yl)pyrimidin-2-ylamino)phenyl)-3,5-dimethylisoxazole-4-carboxamide;
N-(4-(4-(1-(2-cyano-1-cyclopentylethyl)-1H-pyrazol-4-yl)pyrimidin-2-ylamino)phenyl)-1-methyl-1H-pyrazole-3-sulfonamide;
N-(4-(4-(1-(2-cyano-1-cyclopentylethyl)-1H-pyrazol-4-yl)pyrimidin-2-ylamino)phenyl)-2,5-difluorobenzamide;
3-cyclopentyl-3-(4-(2-(4-(1,1-dioxidoisothiazolidin-2-yl)phenyl)aminopyrimidin-4-yl)-1H-pyrazol-1-yl)propanenitrile;
N-(4-(4-(1-(2-cyano-1-cyclopentylethyl)-1H-pyrazol-4-yl)pyrimidin-2-ylamino)phenyl)-5-(2-methylthiazol-4-yl)thiophene-2-sulfonamide;
N-(4-(4-(1-(2-cyano-1-cyclopentylethyl)-1H-pyrazol-4-yl)pyrimidin-2-ylamino)phenyl)-6-methylpyridine-2-sulfonamide;
N-(4-(4-(1-(2-cyano-1-cyclopentylethyl)-1H-pyrazol-4-yl)pyrimidin-2-ylamino)phenyl)-5-(pyridin-2-yl)thiophene-2-sulfonamide;
5-chloro-N-(4-(4-(1-(2-cyano-1-cyclopentylethyl)-1H-pyrazol-4-yl)pyrimidin-2-ylamino)phenyl)thiophene-2-sulfonamide;
N-(4-(4-(1-(2-cyano-1-cyclopentylethyl)-1H-pyrazol-4-yl)pyrimidin-2-ylamino)phenyl)-6-morpholinopyridine-3-sulfonamide;
tetrahydrofuran-3-yl 4-(4-(1-(2-cyano-1-cyclopentylethyl)-1H-pyrazol-4-yl)pyrimidin-2-ylamino)phenylcarbamate;
tetrahydrofuran-3-yl 3-(4-(1-(2-cyano-1-cyclopentylethyl)-1H-pyrazol-4-yl)pyrimidin-2-ylamino)phenylcarbamate;
N-(3-(4-(1-(2-cyano-1-cyclopentylethyl)-1H-pyrazol-4-yl)pyrimidin-2-ylamino)phenyl)-1-methyl-1H-pyrazole-3-sulfonamide;
N'-(3-(4-(1-(2-cyano-1-cyclopentylethyl)-1H-pyrazol-4-yl)pyrimidin-2-ylamino)phenyl)-N,N-dimethylsulfamide;
N-(4-(4-(1-(2-cyano-1-cyclopentylethyl)-1H-pyrazol-4-yl)pyrimidin-2-ylamino)phenyl)-2-(pyrrolidin-1-yl)acetamide;
N-(4-(4-(1-(2-cyano-1-cyclopentylethyl)-1H-pyrazol-4-yl)pyrimidin-2-ylamino)phenyl)-2-(3-hydroxypyrrolidin-1-yl)acetamide;
N-(4-(4-(1-(2-cyano-1-cyclopentylethyl)-1H-pyrazol-4-yl)pyrimidin-2-ylamino)phenyl)-2-(4-hydroxypiperidin-1-yl)acetamide;
N-(4-(4-(1-(2-cyano-1-cyclopentylethyl)-1H-pyrazol-4-yl)pyrimidin-2-ylamino)phenyl)-2-(3-oxopiperazin-1-yl)acetamide;
N-(4-(4-(1-(2-cyano-1-cyclopentylethyl)-1H-pyrazol-4-yl)pyrimidin-2-ylamino)phenyl)-2-morpholinoacetamide;
N-(4-(4-(1-(2-cyano-1-cyclopentylethyl)-1H-pyrazol-4-yl)pyrimidin-2-ylamino)phenyl)-2-((tetrahydro-2H-pyran-4-yl)methylamino)acetamide;

N-(4-(4-(1-(2-cyano-1-cyclopentylethyl)-1H-pyrazol-4-yl)pyrimidin-2-ylamino)phenyl)-2-(2-(methoxymethyl)pyrrolidin-1-yl)acetamide;

N-(4-(4-(1-(2-cyano-1-cyclopentylethyl)-1H-pyrazol-4-yl)pyrimidin-2-ylamino)phenyl)-2-(cyclopropylmethylamino)acetamide;

N-(4-(4-(1-(2-cyano-1-cyclopentylethyl)-1H-pyrazol-4-yl)pyrimidin-2-ylamino)phenyl)-2-(1-methoxypropan-2-ylamino)acetamide;

2-(4-(5-methylisoxazol-3-yloxy)-1-(4-(2-(4-morpholinophenylamino)pyrimidin-4-yl)-1H-pyrazol-1-yl)cyclohexyl)acetonitrile;

3-cyclopentyl-3-(4-(2-(4-(morpholine-4-carbonyl)phenylamino)pyrimidin-4-yl)-1H-pyrazol-1-yl)propanenitrile;

4-(4-(1-(2-cyano-1-cyclopentylethyl)-1H-pyrazol-4-yl)pyrimidin-2-ylamino)-N-((tetrahydro-2H-pyran-4-yl)methyl)benzamide;

3-cyclopentyl-3-(4-(2-(4-(3-endo)-3-hydroxy-8-azabicyclo[3.2.1]octane-8-carbonyl)phenylamino)pyrimidin-4-yl)-1H-pyrazol-1-yl)propanenitrile;

3-cyclopentyl-3-(4-(2-(4-(2-oxa-6-azatricyclo[3.3.1.1(3,7)]dec-6-ylcarbonyl)phenyl)aminopyrimidin-4-yl)-1H-pyrazol-1-yl)propanenitrile;

4-(4-(1-(2-cyano-1-cyclopentylethyl)-1H-pyrazol-4-yl)pyrimidin-2-ylamino)-N-(cis-4-hydroxycyclohexyl)-N-methylbenzamide;

4-(4-(1-(2-cyano-1-cyclopentylethyl)-1H-pyrazol-4-yl)pyrimidin-2-ylamino)-N-methyl-N-(tetrahydro-2H-pyran-4-yl)benzamide;

3-cyclopentyl-3-(4-(2-(4-(S*)-(4,4-dimethyl-2-oxo-1-oxa-3,7-diazaspiro[4.4]nonane-7-carbonyl)phenylamino)pyrimidin-4-yl)-1H-pyrazol-1-yl)propanenitrile;

3-cyclopentyl-3-(4-(2-(4-(4,4-dimethyl-1-oxa-7-azaspiro[4.4]nonane-7-carbonyl)phenylamino)pyrimidin-4-yl)-1H-pyrazol-1-yl)propanenitrile;

3-cyclopentyl-3-(4-(2-(4-(4-methoxypiperidine-1-carbonyl)phenylamino)pyrimidin-4-yl)-1H-pyrazol-1-yl)propanenitrile;

N-((3S)-1-(4-(4-(1-(2-cyano-1-cyclopentylethyl)-1H-pyrazol-4-yl)pyrimidin-2-ylamino)benzoyl)pyrrolidin-3-yl)acetamide;

4-(4-(1-(2-cyano-1-cyclopentylethyl)-1H-pyrazol-4-yl)pyrimidin-2-ylamino)-N-(cis-4-hydroxycyclohexyl)benzamide;

3-(4-(2-(4-(4-acetylpiperazine-1-carbonyl)phenylamino)pyrimidin-4-yl)-1H-pyrazol-1-yl)-3-cyclopentylpropanenitrile;

(3S)-1-(4-(4-(1-(2-cyano-1-cyclopentylethyl)-1H-pyrazol-4-yl)pyrimidin-2-ylamino)benzoyl)pyrrolidine-3-carbonitrile;

3-cyclopentyl-3-(4-(2-(4-(3-methoxypyrrolidine-1-carbonyl)phenylamino)pyrimidin-4-yl)-1H-pyrazol-1-yl)propanenitrile;

4-(4-(1-(2-cyano-1-cyclopentylethyl)-1H-pyrazol-4-yl)pyrimidin-2-ylamino)-N-(1-methylpiperidin-4-yl)benzamide;

3-cyclopentyl-3-(4-(2-(4-(3-oxo-2,8-diazaspiro[4.5]decane-8-carbonyl)phenylamino)pyrimidin-4-yl)-1H-pyrazol-1-yl)propanenitrile;

3-cyclopentyl-3-(4-(2-(4-(3-fluoropyrrolidine-1-carbonyl)phenylamino)pyrimidin-4-yl)-1H-pyrazol-1-yl)propanenitrile;

3-cyclopentyl-3-(4-(2-(4-(3-(dimethylamino)pyrrolidine-1-carbonyl)phenylamino)pyrimidin-4-yl)-1H-pyrazol-1-yl)propanenitrile;

ethyl 4-(4-(4-(1-(2-cyano-1-cyclopentylethyl)-1H-pyrazol-4-yl)pyrimidin-2-ylamino)benzamido)piperidine-1-carboxylate;

4-(4-(1-(2-cyano-1-cyclopentylethyl)-1H-pyrazol-4-yl)pyrimidin-2-ylamino)-N-(1-(pyridin-2-yl)pyrrolidin-3-yl)benzamide;

3-cyclopentyl-3-(4-(2-(4-(3-(pyridin-2-yloxy)pyrrolidine-1-carbonyl)phenylamino)pyrimidin-4-yl)-1H-pyrazol-1-yl)propanenitrile;

1-(4-(4-(1-(2-cyano-1-cyclopentylethyl)-1H-pyrazol-4-yl)pyrimidin-2-ylamino)benzoyl)-N,N-dimethylpiperidine-4-carboxamide;

4-(4-(1-(2-cyano-1-cyclopentylethyl)-1H-pyrazol-4-yl)pyrimidin-2-ylamino)-N-(1-(dimethylamino)-1-oxobutan-2-yl)benzamide;

N-(3-(4-(1-(2-cyano-1-cyclopentylethyl)-1H-pyrazol-4-yl)pyrimidin-2-ylamino)phenyl)-2-(4-methylpiperazin-1-yl)acetamide;

N-(3-(4-(1-(2-cyano-1-cyclopentylethyl)-1H-pyrazol-4-yl)pyrimidin-2-ylamino)phenyl)-2-(3-hydroxypyrrolidin-1-yl)acetamide;

N-(3-(4-(1-(2-cyano-1-cyclopentylethyl)-1H-pyrazol-4-yl)pyrimidin-2-ylamino)phenyl)-2-(3-oxopiperazin-1-yl)acetamide;

N-(3-(4-(1-(2-cyano-1-cyclopentylethyl)-1H-pyrazol-4-yl)pyrimidin-2-ylamino)phenyl)-2-(4-hydroxypiperidin-1-yl)acetamide;

N-(3-(4-(1-(2-cyano-1-cyclopentylethyl)-1H-pyrazol-4-yl)pyrimidin-2-ylamino)phenyl)-2-(4-(2-hydroxyethyl)piperazin-1-yl)acetamide;

N-(3-(4-(1-(2-cyano-1-cyclopentylethyl)-1H-pyrazol-4-yl)pyrimidin-2-ylamino)phenyl)-2-(cyclopropylmethylamino)acetamide;

N-(3-(4-(1-(2-cyano-1-cyclopentylethyl)-1H-pyrazol-4-yl)pyrimidin-2-ylamino)phenyl)-2-morpholinoacetamide;

N-(3-(4-(1-(2-cyano-1-cyclopentylethyl)-1H-pyrazol-4-yl)pyrimidin-2-ylamino)phenyl)-2-(ethylamino)acetamide;

2-(4-(5-methylisoxazol-3-yloxy)-1-(4-(2-(4-(3-oxomorpholino)phenylamino)pyrimidin-4-yl)-1H-pyrazol-1-yl)cyclohexyl)acetonitrile;

2-(4-(5-methylisoxazol-3-yloxy)-1-(4-(2-(4-(2-oxopiperidin-1-yl)phenylamino)pyrimidin-4-yl)-1H-pyrazol-1-yl)cyclohexyl)acetonitrile;

2-(1-(4-(2-(4-(1H-pyrazol-1-yl)phenylamino)pyrimidin-4-yl)-1H-pyrazol-1-yl)-4-(5-methylisoxazol-3-yloxy)cyclohexyl)acetonitrile;

2-(4-(5-methylisoxazol-3-yloxy)-1-(4-(2-(3-(oxazol-5-yl)phenylamino)pyrimidin-4-yl)-1H-pyrazol-1-yl)cyclohexyl)acetonitrile;

3-(cyanomethyl)-3-(4-(2-(4-morpholinophenylamino)pyrimidin-4-yl)-1H-pyrazol-1-yl)cyclobutanecarbonitrile;

4-(4-(1-(3-(cyanomethyl)-1-(ethylsulfonyl)azetidin-3-yl)-1H-pyrazol-4-yl)pyrimidin-2-ylamino)benzoic acid;

4-(4-(1-(2-cyano-1-cyclopropylethyl)-1H-pyrazol-4-yl)pyrimidin-2-ylamino)benzoic acid;

3-cyclopropyl-3-(4-(2-(4-(4-hydroxypiperidine-1-carbonyl)phenylamino)pyrimidin-4-yl)-1H-pyrazol-1-yl)propanenitrile;

3-cyclopropyl-3-(4-(2-(4-(4-3-endo)-3-hydroxy-8-azabicyclo[3.2.1]octane-8-carbonyl)phenylamino)pyrimidin-4-yl)-1H-pyrazol-1-yl)propanenitrile;

3-cyclopropyl-3-(4-(2-(4-(pyrrolidine-1-carbonyl)phenylamino)pyrimidin-4-yl)-1H-pyrazol-1-yl)propanenitrile;

4-(4-(1-(2-cyano-1-cyclopropylethyl)-1H-pyrazol-4-yl)pyrimidin-2-ylamino)-N-(tetrahydro-2H-pyran-4-yl)benzamide;

2-(1-(ethylsulfonyl)-3-(4-(2-(4-(morpholine-4-carbonyl)phenylamino)pyrimidin-4-yl)-1H-pyrazol-1-yl)azetidin-3-yl)acetonitrile;

2-(1-(ethylsulfonyl)-3-(4-(2-(4-(4-hydroxypiperidine-1-carbonyl)phenylamino)pyrimidin-4-yl)-1H-pyrazol-1-yl)azetidin-3-yl)acetonitrile;

2-(1-(ethylsulfonyl)-3-(4-(2-(4-(3-endo)-3-hydroxy-8-azabicyclo[3.2.1]octane-8-carbonyl)phenylamino)pyrimidin-4-yl)-1H-pyrazol-1-yl)azetidin-3-yl)acetonitrile;

2-(1-(ethylsulfonyl)-3-(4-(2-(4-(pyrrolidine-1-carbonyl)phenylamino)pyrimidin-4-yl)-1H-pyrazol-1-yl)azetidin-3-yl)acetonitrile;

4-(4-(1-(3-(cyanomethyl)-1-(ethylsulfonyl)azetidin-3-yl)-1H-pyrazol-4-yl)pyrimidin-2-ylamino)-N-(tetrahydro-2H-pyran-4-yl)benzamide;

3-cyclopropyl-3-(4-(2-(4-(morpholine-4-carbonyl)phenylamino)pyrimidin-4-yl)-1H-pyrazol-1-yl)propanenitrile;

3-(4-(2-(4-(azetidine-1-carbonyl)phenylamino)pyrimidin-4-yl)-1H-pyrazol-1-yl)-3-cyclopropylpropanenitrile;

3-cyclopropyl-3-(4-(2-(4-(2-oxa-6-azatricyclo[3.3.1.1(3,7)]dec-6-ylcarbonyl)phenyl)aminopyrimidin-4-yl)-1H-pyrazol-1-yl)propanenitrile;

3-cyclopropyl-3-(4-(2-(4-(4-methoxypiperidine-1-carbonyl)phenylamino)pyrimidin-4-yl)-1H-pyrazol-1-yl)propanenitrile;

(3R)-1-(4-(4-(1-(2-cyano-1-cyclopropylethyl)-1H-pyrazol-4-yl)pyrimidin-2-ylamino)benzoyl)pyrrolidine-3-carbonitrile;

3-cyclopropyl-3-(4-(2-(4-(3-methoxypyrrolidine-1-carbonyl)phenylamino)pyrimidin-4-yl)-1H-pyrazol-1-yl)propanenitrile;

3-cyclopropyl-3-(4-(2-(4-(3-hydroxypyrrolidine-1-carbonyl)phenylamino)pyrimidin-4-yl)-1H-pyrazol-1-yl)propanenitrile;

3-cyclopropyl-3-(4-(2-(4-(4-methylpiperazine-1-carbonyl)phenylamino)pyrimidin-4-yl)-1H-pyrazol-1-yl)propanenitrile;

N-((3R)-1-(4-(4-(1-(2-cyano-1-cyclopropylethyl)-1H-pyrazol-4-yl)pyrimidin-2-ylamino)benzoyl)pyrrolidin-3-yl)acetamide;

3-(4-(2-(4-(4-acetylpiperazine-1-carbonyl)phenylamino)pyrimidin-4-yl)-1H-pyrazol-1-yl)-3-cyclopropylpropanenitrile;

3-cyclopropyl-3-(4-(2-(4-(3-(dimethylamino)pyrrolidine-1-carbonyl)phenylamino)pyrimidin-4-yl)-1H-pyrazol-1-yl)propanenitrile;

3-cyclopropyl-3-(4-(2-(4-(3-fluoropyrrolidine-1-carbonyl)phenylamino)pyrimidin-4-yl)-1H-pyrazol-1-yl)propanenitrile;

ethyl 4-(4-(4-(1-(2-cyano-1-cyclopropylethyl)-1H-pyrazol-4-yl)pyrimidin-2-ylamino)benzoyl)aminopiperidine-1-carboxylate;

2-(3-(4-(2-(4-(azetidine-1-carbonyl)phenylamino)pyrimidin-4-yl)-1H-pyrazol-1-yl)-1-(ethylsulfonyl)azetidin-3-yl)acetonitrile;

1-(ethylsulfonyl)-3-(4-(2-(4-(2-oxa-6-azatricyclo[3.3.1.1(3,7)]dec-6-ylcarbonyl)phenyl)aminopyrimidin-4-yl)-1H-pyrazol-1-yl)azetidin-3-ylacetonitrile;

(1-(ethylsulfonyl)-3-4-(2-(4-((4-methoxypiperidin-1-yl)carbonyl)phenylamino)pyrimidin-4-yl)-1H-pyrazol-1-ylazetidin-3-yl)acetonitrile;

1-(4-(4-(1-(3-(cyanomethyl)-1-(ethylsulfonyl)azetidin-3-yl)-1H-pyrazol-4-yl)pyrimidin-2-ylamino)benzoyl)pyrrolidine-3-carbonitrile;

2-(1-(ethylsulfonyl)-3-(4-(2-(4-(3-methoxypyrrolidine-1-carbonyl)phenylamino)pyrimidin-4-yl)-1H-pyrazol-1-yl)azetidin-3-yl)acetonitrile;

2-(1-(ethylsulfonyl)-3-(4-(2-(4-(3-hydroxypyrrolidine-1-carbonyl)phenylamino)pyrimidin-4-yl)-1H-pyrazol-1-yl)azetidin-3-yl)acetonitrile;

2-(1-(ethylsulfonyl)-3-(4-(2-(4-(4-methylpiperazine-1-carbonyl)phenylamino)pyrimidin-4-yl)-1H-pyrazol-1-yl)azetidin-3-yl)acetonitrile;

N-(1-(4-(4-(1-(3-(cyanomethyl)-1-(ethylsulfonyl)azetidin-3-yl)-1H-pyrazol-4-yl)pyrimidin-2-ylamino)benzoyl)pyrrolidin-3-yl)acetamide;

2-(3-(4-(2-(4-(4-acetylpiperazine-1-carbonyl)phenylamino)pyrimidin-4-yl)-1H-pyrazol-1-yl)-1-(ethylsulfonyl)azetidin-3-yl)acetonitrile;

2-(3-(4-(2-(4-(3-(dimethylamino)pyrrolidine-1-carbonyl)phenylamino)pyrimidin-4-yl)-1H-pyrazol-1-yl)-1-(ethylsulfonyl)azetidin-3-yl)acetonitrile;

2-(1-(ethylsulfonyl)-3-(4-(2-(4-(3-fluoropyrrolidine-1-carbonyl)phenylamino)pyrimidin-4-yl)-1H-pyrazol-1-yl)azetidin-3-yl)acetonitrile;

ethyl 4-(4-(4-(1-(3-(cyanomethyl)-1-(ethylsulfonyl)azetidin-3-yl)-1H-pyrazol-4-yl)pyrimidin-2-ylamino)benzamido)piperidine-1-carboxylate;

4-(4-(1-(3-cyano-1-(cyanomethyl)cyclobutyl)-1H-pyrazol-4-yl)pyrimidin-2-ylamino)benzoic acid;

4-(4-(1-(2-cyano-1-cyclopentylethyl)-1H-pyrazol-4-yl)-5-methoxypyrimidin-2-ylamino)benzoic acid;

3-(cyanomethyl)-3-(4-(2-(4-(morpholine-4-carbonyl)phenylamino)pyrimidin-4-yl)-1H-pyrazol-1-yl)cyclobutanecarbonitrile;

3-(cyanomethyl)-3-(4-(2-(4-(pyrrolidine-1-carbonyl)phenylamino)pyrimidin-4-yl)-1H-pyrazol-1-yl)cyclobutanecarbonitrile;

4-(4-(1-(3-cyano-1-(cyanomethyl)cyclobutyl)-1H-pyrazol-4-yl)pyrimidin-2-ylamino)-N-(tetrahydro-2H-pyran-4-yl)benzamide;

3-(cyanomethyl)-3-(4-(2-(4-(3-hydroxypyrrolidine-1-carbonyl)phenylamino)pyrimidin-4-yl)-1H-pyrazol-1-yl)cyclobutanecarbonitrile;

4-(4-(1-(3-cyano-1-(cyanomethyl)cyclobutyl)-1H-pyrazol-4-yl)pyrimidin-2-ylamino)-N-((5-methylisoxazol-3-yl)methyl)benzamide;

3-(4-(2-(4-(azetidine-1-carbonyl)phenylamino)pyrimidin-4-yl)-1H-pyrazol-1-yl)-3-(cyanomethyl)cyclobutanecarbonitrile;

3-(cyanomethyl)-3-(4-(2-(4-(4-methylpiperazine-1-carbonyl)phenylamino)pyrimidin-4-yl)-1H-pyrazol-1-yl)cyclobutanecarbonitrile;

3-(cyanomethyl)-3-(4-(2-(4-(3-fluoropyrrolidine-1-carbonyl)phenylamino)pyrimidin-4-yl)-1H-pyrazol-1-yl)cyclobutanecarbonitrile;

3-(cyanomethyl)-3-(4-(2-(4-(4-methoxypiperidine-1-carbonyl)phenylamino)pyrimidin-4-yl)-1H-pyrazol-1-yl)cyclobutanecarbonitrile;

3-(cyanomethyl)-3-(4-(2-(4-(3-methoxypyrrolidine-1-carbonyl)phenylamino)pyrimidin-4-yl)-1H-pyrazol-1-yl)cyclobutanecarbonitrile;

1-(4-(4-(1-(3-cyano-1-(cyanomethyl)cyclobutyl)-1H-pyrazol-4-yl)pyrimidin-2-ylamino)benzoyl)pyrrolidine-3-carbonitrile;

3-(4-(2-(4-(4-acetylpiperazine-1-carbonyl)phenylamino) pyrimidin-4-yl)-1H-pyrazol-1-yl)-3-(cyanomethyl)cyclobutanecarbonitrile;

N-(1-(4-(4-(1-(3-cyano-1-(cyanomethyl)cyclobutyl)-1H-pyrazol-4-yl)pyrimidin-2-ylamino)benzoyl)pyrrolidin-3-yl)acetamide;

3-(cyanomethyl)-3-(4-(2-(4-((3-endo)-3-hydroxy-8-azabicyclo[3.2.1]octane-8-carbonyl)phenylamino)pyrimidin-4-yl)-1H-pyrazol-1-yl)cyclobutanecarbonitrile;

3-(cyanomethyl)-3-(4-(2-(4-(4-hydroxypiperidine-1-carbonyl)phenylamino)pyrimidin-4-yl)-1H-pyrazol-1-yl)cyclobutanecarbonitrile;

3-cyclopentyl-3-(4-(5-methoxy-2-(4-(morpholine-4-carbonyl)phenylamino)pyrimidin-4-yl)-1H-pyrazol-1-yl)propanenitrile;

3-cyclopentyl-3-(4-(5-methoxy-2-(4-(pyrrolidine-1-carbonyl)phenylamino)pyrimidin-4-yl)-1H-pyrazol-1-yl)propanenitrile;

3-cyclopentyl-3-(4-(5-methoxy-2-(4-(4-methylpiperazine-1-carbonyl)phenylamino)pyrimidin-4-yl)-1H-pyrazol-1-yl)propanenitrile;

4-(4-(1-(2-cyano-1-cyclopentylethyl)-1H-pyrazol-4-yl)-5-methoxypyrimidin-2-ylamino)-N-(tetrahydro-2H-pyran-4-yl)benzamide;

3-cyclopentyl-3-[4-(2-{[4-(2-pyrrolidin-1-ylethoxy)phenyl]amino}pyrimidin-4-yl)-1H-pyrazol-1-yl]propanenitrile;

3-(cyanomethyl)-3-[4-(2-{[4-(2-pyrrolidin-1-ylethoxy)phenyl]amino}pyrimidin-4-yl)-1H-pyrazol-1-yl]cyclobutanecarbonitrile;

3-(4-{2-[(4-morpholin-4-ylphenyl)amino]pyrimidin-4-yl}-1H-pyrazol-1-yl)-3-(tetrahydro-2H-pyran-4-yl)propanenitrile;

4-[(4-{1-[2-cyano-1-(tetrahydro-2H-pyran-4-yl)ethyl]-1H-pyrazol-4-yl}pyrimidin-2-yl)amino]-N-(tetrahydro-2H-pyran-4-yl)benzamide;

3-[4-(2-{[4-(pyrrolidin-1-ylcarbonyl)phenyl]amino}pyrimidin-4-yl)-1H-pyrazol-1-yl]-3-(tetrahydro-2H-pyran-4-yl)propanenitrile;

3-[4-(2-{[4-(morpholin-4-ylcarbonyl)phenyl]amino}pyrimidin-4-yl)-1H-pyrazol-1-yl]-3-(tetrahydro-2H-pyran-4-yl)propanenitrile;

3-{4-[2-({4-[(4-hydroxypiperidin-1-yl)carbonyl]phenyl}amino)pyrimidin-4-yl]-1H-pyrazol-1-yl}-3-(tetrahydro-2H-pyran-4-yl)propanenitrile;

3-{4-[2-({4-[(4-methoxypiperidin-1-yl)carbonyl]phenyl}amino)pyrimidin-4-yl]-1H-pyrazol-1-yl}-3-(tetrahydro-2H-pyran-4-yl)propanenitrile;

1-{4-[(4-{1-[2-cyano-1-(tetrahydro-2H-pyran-4-yl)ethyl]-1H-pyrazol-4-yl}pyrimidin-2-yl)amino]benzoyl}piperidine-4-carbonitrile;

3-(4-{2-[(4-{[(3R)-3-hydroxypyrrolidin-1-yl]carbonyl}phenyl)amino]pyrimidin-4-yl}-1H-pyrazol-1-yl)-3-(tetrahydro-2H-pyran-4-yl)propanenitrile;

3-(4-{2-[(4-{[(3S)-3-methoxypyrrolidin-1-yl]carbonyl}phenyl)amino]pyrimidin-4-yl}-1H-pyrazol-1-yl)-3-(tetrahydro-2H-pyran-4-yl)propanenitrile;

(3S)-1-{4-[(4-{1-[2-cyano-1-(tetrahydro-2H-pyran-4-yl)ethyl]1H-pyrazol-4-yl}pyrimidin-2-yl)amino]benzoyl}pyrrolidine-3-carbonitrile;

1-[4-({4-[1-(2-cyano-1-cyclopropylethyl)-1H-pyrazol-4-yl]pyrimidin-2-yl}amino)benzoyl]piperidine-4-carbonitrile;

1-{4-[(4-{1-[3-(cyanomethyl)-1-(ethylsulfonyl)azetidin-3-yl]-1H-pyrazol-4-yl}pyrimidin-2-yl)amino]benzoyl}piperidine-4-carbonitrile;

3-cyclopropyl-3-[4-(5-methoxy-2-{[3-(1,3-oxazol-5-yl)phenyl]amino}pyrimidin-4-yl)-1H-pyrazol-1-yl]propanenitrile;

3-cyclopropyl-3-(4-{5-methoxy-2-[(3-nitrophenyl)amino]pyrimidin-4-yl}-1H-pyrazol-1-yl)propanenitrile;

3-({4-[1-(2-cyano-1-cyclopropylethyl)-1H-pyrazol-4-yl]-5-methoxypyrimidin-2-yl}amino)-N-(tetrahydro-2H-pyran-4-yl)benzamide;

3-cyclopropyl-3-[4-(5-methoxy-2-{[3-(pyrrolidin-1-ylcarbonyl)phenyl]amino}pyrimidin-4-yl)-1H-pyrazol-1-yl]propanenitrile;

3-cyclopropyl-3-(4-{2-[(3-{[(3R)-3-hydroxypyrrolidin-1-yl]carbonyl}phenyl)amino]-5-methoxypyrimidin-4-yl}-1H-pyrazol-1-yl)propanenitrile;

3-cyclopropyl-3-(4-{5-methoxy-2-[(3-{[(3S)-3-methoxypyrrolidin-1-yl]carbonyl}phenyl)amino]pyrimidin-4-yl}-1H-pyrazol-1-yl)propanenitrile;

(3S)-1-[3-({4-[1-(2-cyano-1-cyclopropylethyl)-1H-pyrazol-4-yl]-5-methoxypyrimidin-2-yl}amino)benzoyl]pyrrolidine-3-carbonitrile;

3-cyclopropyl-3-[4-(5-methoxy-2-{[3-(morpholin-4-ylcarbonyl)phenyl]amino}pyrimidin-4-yl)-1H-pyrazol-1-yl]propanenitrile;

3-cyclopropyl-3-{4-[2-({3-[(4-hydroxypiperidin-1-yl)carbonyl]phenyl}amino)-5-methoxypyrimidin-4-yl]-1H-pyrazol-1-yl}propanenitrile;

3-cyclopropyl-3-{4-[5-methoxy-2-({3-[(4-methoxypiperidin-1-yl)carbonyl]phenyl}amino)pyrimidin-4-yl]-1H-pyrazol-1-yl}propanenitrile;

1-[3-({4-[1-(2-cyano-1-cyclopropylethyl)-1H-pyrazol-4-yl]-5-methoxypyrimidin-2-yl}amino)benzoyl]piperidine-4-carbonitrile;

3-cyclopropyl-3-(4-{2-[(3-{[(3-endo)-3-hydroxy-8-azabicyclo[3.2.1]oct-8-yl]carbonyl}phenyl)amino]-5-methoxypyrimidin-4-yl}-1H-pyrazol-1-yl)propanenitrile;

3-({4-[1-(2-cyano-1-cyclopropylethyl)-1H-pyrazol-4-yl]-5-methoxypyrimidin-2-yl}amino)-N-[(5-methylisoxazol-3-yl)methyl]benzamide;

3-[4-(2-{[3-(azetidin-1-ylcarbonyl)phenyl]amino}-5-methoxypyrimidin-4-yl)-1H-pyrazol-1-yl]-3-cyclopropylpropanenitrile;

3-(cyanomethyl)-3-[4-(2-{[4-(2-oxopiperidin-1-yl)phenyl]amino}pyrimidin-4-yl)-1H-pyrazol-1-yl]cyclobutanecarbonitrile;

3-(cyanomethyl)-3-[4-(2-{[4-(2-oxo-1,3-oxazinan-3-yl)phenyl]amino}pyrimidin-4-yl)-1H-pyrazol-1-yl]cyclobutanecarbonitrile;

3-(cyanomethyl)-3-[4-(2-{[4-(3-oxomorpholin-4-yl)phenyl]amino}pyrimidin-4-yl)-1H-pyrazol-1-yl]cyclobutanecarbonitrile;

3-(cyanomethyl)-3-[4-(2-{[4-(2-oxo-1,3-oxazolidin-3-yl)phenyl]amino}pyrimidin-4-yl)-1H-pyrazol-1-yl]cyclobutanecarbonitrile;

3-(cyanomethyl)-3-[4-(2-{[4-(2-oxopyrrolidin-1-yl)phenyl]amino}pyrimidin-4-yl)-1H-pyrazol-1-yl]cyclobutanecarbonitrile;

3-(cyanomethyl)-3-[4-(2-{[4-(1H-pyrazol-1-yl)phenyl]amino}pyrimidin-4-yl)-1H-pyrazol-1-yl]cyclobutanecarbonitrile;

3-(cyanomethyl)-3-[4-(2-{[4-(1,3-oxazol-5-yl)phenyl]amino}pyrimidin-4-yl)-1H-pyrazol-1-yl]cyclobutanecarbonitrile;

3-(cyanomethyl)-3-[4-(2-{[3-(1,3-oxazol-5-yl)phenyl]amino}pyrimidin-4-yl)-1H-pyrazol-1-yl]cyclobutanecarbonitrile;

3-(cyanomethyl)-3-[4-(2-{[4-(morpholin-4-ylsulfonyl) phenyl]amino}pyrimidin-4-yl)-1H-pyrazol-1-yl]cyclobutanecarbonitrile;

3-(4-{2-[(3-aminophenyl)amino]-5-methoxypyrimidin-4-yl}-1H-pyrazol-1-yl)-3-cyclopropylpropanenitrile;

3-cyclopropyl-3-[4-(2-{[3-(1,1-dioxidoisothiazolidin-2-yl)phenyl]amino}-5-methoxypyrimidin-4-yl)-1H-pyrazol-1-yl]propanenitrile;

4-[1-(2,4-difluorobenzoyl)piperidin-4-yl]-3-{4-[5-methoxy-2-(pyridin-3-ylamino)pyrimidin-4-yl]-1H-pyrazol-1-yl}butanenitrile; and 3-(cyanomethyl)-3-[4-(2-{[3-(2-oxopyrrolidin-1-yl)phenyl]amino}pyrimidin-4-yl)-1H-pyrazol-1-yl]cyclobutanecarbonitrile, or pharmaceutically acceptable salt thereof.

30. A composition comprising a compound according to claim 1, or pharmaceutically acceptable salt thereof, and at least one pharmaceutically acceptable carrier.

31. The composition of claim 30 which is suitable for topical administration.

32. A method of treating rheumatoid arthritis in a patient comprising administering to said patient a therapeutically effective amount of a compound of claim 1 or pharmaceutically acceptable salt thereof.

33. A method of treating psoriasis in a patient comprising administering to said patient a therapeutically effective amount of a compound of claim 1 or pharmaceutically acceptable salt thereof.

34. A method of treating a myeloproliferative disorder in a patient comprising administering to said patient a therapeutically effective amount of a compound of claim 1 or pharmaceutically acceptable salt thereof.

35. The method of claim 34 wherein said myeloproliferative disorder (MPD) is polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), idiopathic myelofibrosis (IMF), or systemic mast cell disease (SMCD).

* * * * *

UNITED STATES PATENT AND TRADEMARK OFFICE
CERTIFICATE OF CORRECTION

PATENT NO. : 8,309,718 B2
APPLICATION NO. : 12/270135
DATED : November 13, 2012
INVENTOR(S) : Yun-Long Li, Wenqing Yao and James D. Rodgers It is certified that error appears in the above-identified patent and that said Letters Patent is hereby corrected as shown below:

In the Claims:

Column 231
Line 2, delete the first occurrence of "IIe," and insert -- IIc, --.

Column 235
Line 40, delete "haloalkyl" and insert -- $C_{1-6}$ haloalkyl, --.

Column 235
Line 41, delete "$NR^{c1}C(O)NR^cR^d$," and insert -- $NR^cC(O)NR^cR^d$, --.

Column 235
Line 42, delete "$NR^{c1}C(=NR^g)NR^cR^d$," and insert -- $NR^cC(=NR^g)NR^cR^d$, --.

Column 235
Line 46, delete "$NR^{c1}C(O)R^b$," and insert -- $NR^cC(O)R^b$, --.

Column 235
Line 46, delete "$NR^{c1}C(O)R^a$," and insert -- $NR^cC(O)R^a$, --.

Column 235
Line 46, delete "$NR^{c1}S(O_2)R^b$," and insert -- $NR^cS(O_2)R^b$, --.

Column 235
Lines 62-63, delete "$S(O)_2R^b$," and insert -- $S(O)_2R^{b1}$, --.

Signed and Sealed this
Thirtieth Day of April, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,309,718 B2 | Page 1 of 1 |
| APPLICATION NO. | : 12/270135 | |
| DATED | : November 13, 2012 | |
| INVENTOR(S) | : Li et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 808 days.

Signed and Sealed this
Eighteenth Day of November, 2014

Michelle K. Lee
*Deputy Director of the United States Patent and Trademark Office*